US007763718B2

(12) United States Patent
Jakobsen et al.

(10) Patent No.: US 7,763,718 B2
(45) Date of Patent: *Jul. 27, 2010

(54) SOLUBLE T CELL RECEPTORS

(75) Inventors: Bent Karsten Jakobsen, Abingdon (GB); Meir Glick, Morristown, NJ (US)

(73) Assignee: Immunocore Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/926,391

(22) Filed: Oct. 29, 2007

(65) Prior Publication Data

US 2008/0153131 A1 Jun. 26, 2008

Related U.S. Application Data

(62) Division of application No. 10/486,924, filed as application No. PCT/GB02/03986 on Aug. 30, 2002, now Pat. No. 7,329,731.

(60) Provisional application No. 60/404,182, filed on Aug. 16, 2002.

(30) Foreign Application Priority Data

Aug. 31, 2001 (GB) .................................. 0121187.9
Aug. 16, 2002 (GB) .................................. 0219146.8

(51) Int. Cl.
*C07H 21/04* (2006.01)
*C12P 21/06* (2006.01)
*C12N 1/20* (2006.01)
*C12N 15/00* (2006.01)

(52) U.S. Cl. ................ 536/23.5; 435/320.1; 435/252.3; 435/69.1

(58) Field of Classification Search ....................... None
See application file for complete search history.

(56) References Cited

U.S. PATENT DOCUMENTS

| 6,008,026 | A | * | 12/1999 | Day | ............................ | 435/96 |
| 6,080,840 | A | | 6/2000 | Slanetz | | |
| 6,147,203 | A | | 11/2000 | Pastan | | |
| 2007/0082362 | A1 | | 4/2007 | Jakobsen | | |

FOREIGN PATENT DOCUMENTS

| WO | WO 94 29350 | 12/1994 |
| WO | WO 96 21028 | 7/1996 |
| WO | WO 99 60119 | 11/1999 |
| WO | WO 99 60120 | 11/1999 |
| WO | WO 01 22084 | 3/2001 |

OTHER PUBLICATIONS

Reiter et al.: "Construction of a functional disulfide-stabilized TCR Fv indicated that antibody and TCR Fv frameworks are very similar in structure."; Immunity; vol. 2, No. 3; Mar. 3, 1995; pp. 281-287; XP009004075.

Garboczi et al.: "Structure of the complex between human T-cell receptor, viral peptide and HLA-A2."; Nature; vol. 384, No. 6605; Nov. 14, 1996; pp. 134-141; XP001097273.

Golden et al., "High-level production of a secreted, heterodimeric αβ murine T-cell receptor in *Escherichia coli*"; Journal of Immunological Methods; vol. 206, No. 1-2; Aug. 7, 1997; pp. 163-169; XP004093129.

Malloy et al., "Production of soluble single-chain T-cell receptor fragments in *Escherichia coli trxB* mutants"; Molecular Immunology; vol. 35, 1998; pp. 73-81.

Garboczi et al., Assembly, Specific Binding, and Crystallization of a Human TCR-αβ with an Antigenic Tax Peptide from Human T Lymphotropic Virus Type 1 and the Class I MHC Molecule HLA-A2[1]; Journal of Immunology; vol. 157, No. 12; 1996; pp. 5403-5410.

Chang et al., "A general method for facilitating heterodimeric pairing between two proteins: Application to expression of α and β T-cell receptor extracellular segments"; Proc. Natl.Acad.Sci; vol. 91; Nov. 1994; pp. 11408-11412.

Davodeau et al., "Secretion of Disulfide-linked Human T-cell Receptor γδ Heterodimers"; The Journal of Biological Chemistry; vol. 268, No. 21; Jul. 25, 1993; pp. 15455-15460.

Brinkman et al.: "A recombinant immunotoxin containing a disulfide-stabilized Fv fragment"; Proc. Natl. Acad. Sci; vol. 90; Aug. 1993; pp. 7538-7542.

Reiter et al;.: "Stabilization of the Fv Fragments in Recombinant Immunotoxins by Disulfide Bonds Engineered into Conserved Framework Regions"; Biochemisty; vol. 33; 1994; pp. 5451-5459.

T Cell Receptor Factsbook; 2001; Le Franc & Le Franc; Academic Press—Book Reference; pp. 3-13.

Schatz: "Use of Peptide Libraries to Map the Substrate Specificity of a Peptide-Modifying Enzyme: A 13 Residue Consensus Peptide Specifies Biotinylation in *Escherichia coli*"; Biotechnology; vol. 11, Oct. 1993; pp. 1138-1143.

Marsh et al., HLA Factsbook; Barclay (ED) Academic Press)-Book Reference; pp. 79-83, 2000.

Altamirano et al.: "Oxidative refolding chromatography: folding of the scorpion toxin Cn5"; Nature Biotechnology; vol. 17; Feb. 1999; pp. 187-191.

Altamirano et al.: "Refolding chromatography with immobilized mini-chaperones"; Proc. Natl. Acad. Sci; vol. 94, Apr. 1997; pp. 3576-3578.

O'Callaghan et al.: "BirA Enzyme: Production and application in the study of membrane receptor-ligand interactions by site-specific biotinylation"; Analytical Biochemistry; vol. 266; 1999; pp. 9-15.

Ding et al.: "Two Human T Cell Receptors Bind in a Similar Diagonal Mode to the HLA-A2/Tax Peptide Complex Using Difference TCR Amino Acids"; Immunity; vol. 8; Apr. 1998; pp. 403-411.

GB Search Report; Aug. 5, 2002; one page.

(Continued)

*Primary Examiner*—Amy E Juedes
(74) *Attorney, Agent, or Firm*—Banner & Witcoff, Ltd.

(57) ABSTRACT

The present invention provides a soluble T cell receptor (sTCR), which comprises (i) all or part of a TCR α chain, except the transmembrane domain thereof, and (ii) all or part of a TCR β chain, except the transmembrane domain thereof. (i) and (ii) each comprise a functional variable domain and at least a part of the constant domain of the TCR chain, and are linked by a disulphide bond between constant domain residues which is not present in native TCR.

9 Claims, 81 Drawing Sheets

OTHER PUBLICATIONS

Tyle, "Review: Iontophoretic Devices for Drug Delivery," *Pharmaceutical Res*. 3, 318-26, 1986.
Gietz et al.: "Transformation of Yeast by Lithium Acetate/Single-Stranded Carrier DNA/Polyethylene Glycol Method," Methods in Enzymology; vol. 350; 2002; pp. 87-96.

Non-final rejection mailed Jun. 22, 2009 in U.S. Appl. No. 10/532,879, 17 pages.
Final rejection mailed May 29, 2009 in U.S. Appl. No. 10/544,448, 8 pages.

* cited by examiner

Figure 1
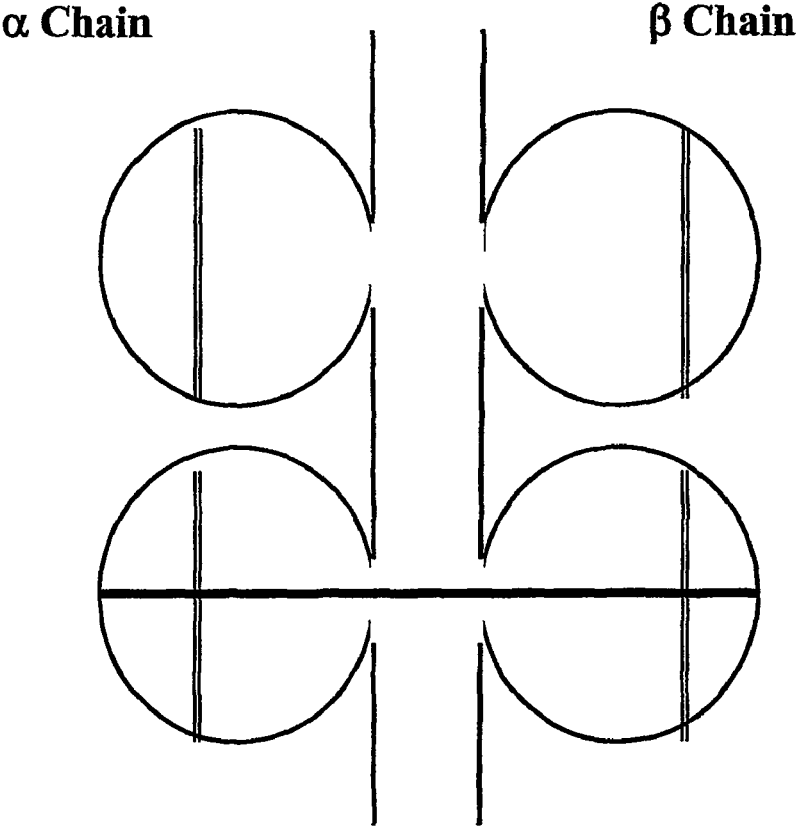
═══════ Native intra-chain disulphide bond
▬▬▬▬▬▬ Non-native interchain disulphide bond
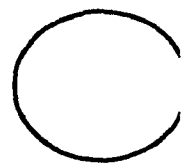 TCR domain

Figure 2a atgcagaaggaagtggagcagaactctggacccctcagtgttccagagggagccattg
cctctctcaactgcacttacagtgaccgaggttcccagtccttcttctggtacagaca
atattctgggaaaagccctgagttgataatgtccatatactccaatggtgacaaagaa
gatggaaggtttacagcacagctcaataaagccagccagtatgtttctctgctcatca
gagactcccagcccagtgattcagccacctacctctgtgccgttacaactgacagctg
ggggaaattgcagtttggagcagggacccaggttgtggtcacccagatatccagaac
cctgaccctgccgtgtaccagctgagagactaaatccagtgacaagtctgtctgcc
tattcaccgatttgattctcaaacaaatgtgtcacaaagtaaggattctgatgtgta
tatcacagacaaa▓▓gtgctagacatgaggtctatggacttcaagagcaacagtgct
gtggcctggagcaacaaatctgactttgcatgtgcaaacgccttcaacaacagcatta
ttccagaagacaccttcttccccagcccagaaagttcctaa

Figure 2b atgaacgctggtgtcactcagaccccaaaattccaggtcctgaagacaggacagagca
tgacactgcagtgtgcccaggatatgaaccatgaatacatgtcctggtatcgacaaga
cccaggcatggggctgaggctgattcattactcagttggtgctggtatcactgaccaa
ggagaagtccccaatggctacaatgtctccagatcaaccacagaggatttcccgctca
ggctgctgtcggctgctccctcccagacatctgtgtacttctgtgccagcaggccggg
actagcgggagggcgaccagagcagtacttcgggccgggcaccaggctcacggtcaca
gaggacctgaaaaacgtgttcccacccgaggtcgctgtgtttgagccatcagaagcag
agatctcccacacccaaaaggccacactggtgtgcctggccacaggcttctaccccga
ccacgtggagctgagctggtgggtgaatgggaaggaggtgcacagtgggtc▓▓▓aca
gacccgcagcccctcaaggagcagcccgccctcaatgactccagatacgctctgagca
gccgcctgagggtctcggccaccttctggcaggaccccgcaaccacttccgctgtca
agtccagttctacgggctctcggagaatgacgagtggacccaggatagggccaaaccc
gtcacccagatcgtcagcgccgaggcctggggtagagcagactaa

Figure 3a

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDK<u>C</u>VL DMRSMDFKSN SAVAWSNKSD FACANAFNNS IIPEDTFFPS
PESS*

Figure 3b

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG V<u>C</u>TDPQPLKE QPALNDSRYA LSSRLRVSAT
FWQDPRNHFR CQVQFYGLSE NDEWTQDRAK PVTQIVSAEA WGRAD*

Figure 8a atgcagaaggaagtggagcagaactctggacccctcagtgttccagagggagccattg
cctctctcaactgcacttacagtgaccgaggttcccagtccttcttctggtacagaca
atattctgggaaaagccctgagttgataatgtccatatactccaatggtgacaaagaa
gatggaaggtttacagcacagctcaataaagccagccagtatgtttctctgctcatca
gagactcccagcccagtgattcagccacctacctctgtgccgttacaactgacagctg
ggggaaattgcagtttggagcagggacccaggttgtggtcacccagatatccagaac
cc▒ga▒cctgccgtgtaccagctgagagactctaaatccagtgacaagtctgtctgcc
tattcaccgattttgattctcaaacaaatgtgtcacaagtaaggattctgatgtgta
tatcacagacaaatgtgtgctagacatgaggtctatggacttcaagagcaacagtgct
gtggcctggagcaacaaatctgactttgcatgtgcaaacgccttcaacaacagcatta
ttccagaagacaccttcttccccagcccagaaagttcctaa

Figure 8b atgcaactactagaacaaagtcctcagtttctaagcatccaagagggagaaaatctca
ctgtgtactgcaactcctcaagtgttttttccagcttacaatggtacagacaggagcc
tggggaaggtcctgtcctcctggtgacagtagttacgggtggagaagtgaagaagctg
aagagactaacctttcagtttggtgatgcaagaaaggacagttctctccacatcactg
cggcccagcctggtgatacaggcctctacctctgtgcaggagcgggaagccaaggaaa
tctcatctttggaaaaggcactaaactctctgtaaaccaaatatccagaacccggat
cctgccgtgtaccagctgagagactctaaatccagtgacaagtctgtctgcctattca
ccgattttgattctcaaacaaatgtgtcacaagtaaggattctgatgtgtatatcac
agacaaatgtgtgctagacatgaggtctatggacttcaagagcaacagtgctgtggcc
tggagcaacaaatctgactttgcatgtgcaaacgccttcaacaacagcattattccag
aagacaccttcttccccagcccagaaagttcctaa

Figure 8c atggtggatggtggaatcactcagtccccaaagtacctgttcagaaaggaaggacaga
atgtgaccctgagttgtgaacagaatttgaaccacgatgccatgtactggtaccgaca
ggacccagggcaagggctgagattgatctactactcacagatagtaaatgactttcag
aaaggagatatagctgaagggtacagcgtctctcgggagaagaaggaatcctttcctc
tcactgtgacatcggcccaaaagaacccgacagctttctatctctgtgccagtagttc
gaggagctcctacgagcagtacttcgggccgggcaccaggctcacggtcacagaggac
ctgaaaaacgtgttccacccgaggtcgctgtgtttgagccatcagaagcagagatct
cccacacccaaaaggccacactggtgtgcctggccacaggcttctaccccgaccacgt
ggagctgagctggtgggtgaatgggaaggaggtgcacagtggggtctgcacagacccg
cagcccctcaaggagcagcccgccctcaatgactccagatacagcctgagcagccgcc
tgagggtctcggccaccttctggcagaaccccgcaaccacttccgctgtcaagtcca
gttctacgggctctcggagaatgacgagtggacccaggatagggccaaacctgtcacc
cagattgtcagcgccgaggcctggggtagagcagactaa

Figure 9a

MQLLEQSPQFLSIQEGENLTVYCNSSSVFSSLQWYRQEP
GEGPVLLVTVVTGGEVKKLKRLTFQFGDARKDSSLHIT
AAQPGDTGLYLCAGAGSQGNLIFGKGTKLSVKPNIQNP
DPAVYQLRDSKSSDKSVCLFTDFDSQTNVSQSKDSDVY
ITDKCVLDMRSMDFKSNSAVAWSNKSDFACANAFNNSI
IPEDTFFPSPESS Stop

Figure 9b

MVDGGITQSPKYLFRKEGQNVTLSCEQNLNHDAMYWY
RQDPGQGLRLIYYSQIVNDFQKGDIAEGYSVSREKKESF
PLTVTSAQKNPTAFYLCASSSRSSYEQYFGPGTRLTVTE
DLKNVFPPEVAVFEPSEAEISHTQKATLVCLATGFYPDH
VELSWWVNGKEVHSGVCTDPQPLKEQPALNDSRYSLSS
RLRVSATFWQNPRNHFRCQVQFYGLSENDEWTQDRAK
PVTQIVSAEAWGRAD Stop

Figure 14a atgcaggaggygacacagattcctgcagctctgagtgtcccagaaggagaaaacttgg
ttctcaactgcagtttcactgatagcgctatttacaacctccagtggtttaggcagga
ccctgggaaaggtctcacatctctgttgcttattcagtcaagtcagagagagcaaaca
agtggaagacttaatgcctcgctggataaatcatcaggacgtagtactttatacattg
cagcttctcagcctggtgactcagccacctacctctgtgctgtgaggcccacatcagg
aggaagctacatacctacatttggaagaggaaccagccttattgttcatccgtatatc
cagaaccctgacctgccgtgtaccagctgagagactctaaatccagtgacaagtctg
tctgcctattcaccgattttgattctcaaacaaatgtgtcacaaagtaaggattctga
tgtgtatatcacagacaaatgtgtgctagacatgaggtctatggacttcaagagcaac
agtgctgtggcctggagcaacaaatctgactttgcatgtgcaaacgccttcaacaaca
gcattattccagaagacaccttcttccccagcccagaaagttcctaa

Figure 14b atgggtgtcactcagacccaaaattccaggtcctgaagacaggacagagcatgacac
tgcagtgtgcccaggatatgaaccatgaatacatgtcctggtatcgacaagacccagg
catggggctgaggctgattcattactcagttggtgctggtatcactgaccaaggagaa
gtccccaatggctacaatgtctccagatcaaccacagaggatttcccgctcaggctgc
tgtcggctgctcctcccagacatctgtgtacttctgtgccagcagttacgtcgggaa
caccggggagctgttttttggagaaggctctaggctgaccgtactggaggacctgaaa
aacgtgttcccacccgaggtcgctgtgtttgagccatcagaagcagagatctcccaca
cccaaaaggccacactggtgtgcctggccacaggcttctaccccgaccacgtggagct
gagctggtgggtgaatgggaaggaggtgcacagtggggtctgcacagacccgcagccc
ctcaaggagcagcccgccctcaatgactccagatacgctctgagcagccgcctgaggg
tctcggccaccttctggcaggaccccgcaaccacttccgctgtcaagtccagttcta
cgggctctcggagaatgacgagtggacccaggatagggccaaacccgtcacccagatc
gtcagcgccgaggcctggggtagagcagactaa

Figure 15a

MQEXTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGGSYIPTFGRGTSLIVHPYI
QNPDPAVYQLRDSKSSDKSVCLFTDFDSQTNVSQSKDS
DVYITDKCVLDMRSMDFKSNSAVAWSNKSDFACANAF
NNSIIPEDTFFPSPESS Stop

Figure 15b

MGVTQTPKFQVLKTGQSMTLQCAQDMNHEYMSWYRQ
DPGMetGLRLIHYSVGAGITDQGEVPNGYNVSRSTTEDF
PLRLLSAAPSQTSVYFCASSYVGNTGELFFGEGSRLTVL
EDLKNVFPPEVAVFEPSEAEISHTQKATLVCLATGFYPD
HVELSWWVNGKEVHSGVCTDPQPLKEQPALNDSRYAL
SSRLRVSATFWQDPRNHFRCQVQFYGLSENDEWTQDRA
KPVTQIVSAEAWGRAD Stop

Figure 20a atgcaggaggygacacagattcctgcagctctgagtgtcccagaaggagaaaacttgg
ttctcaactgcagtttcactgatagcgctatttacaacctccagtggtttaggcagga
ccctgggaaaggtctcacatctctgttgcttattcagtcaagtcagagagagcaaaca
agtggaagacttaatgcctcgctggataaatcatcaggacgtagtactttatacattg
cagcttctcagcctggtgactcagccacctacctctgtgctgtgaggcccacatcagg
aggaagctacatacctacatttggaagaggaaccagccttattgttcatccgtatatc
cagaaccctgaccctgccgtgtaccagctgagagactctaaatccagtgacaagtctg
tctgcctattcaccgatttgattctcaaacaaatgtgtcacaaagtaaggattctga
tgtgtatatcacagacaaa▒▒▒gtgctagacatgaggtctatggacttcaagagcaac
agtgctgtggcctggagcaacaaatctgactttgcatgtgcaaacgccttcaacaaca
gcattattccagaagacaccttcttccccagcccagaaagttcctgttaa

Figure 20b atgggtgtcactcagaccccaaaattccaggtcctgaagacaggacagagcatgacac
tgcagtgtgcccaggatatgaaccatgaatacatgtcctggtatcgacaagacccagg
catggggctgaggctgattcattactcagttggtgctggtatcactgaccaaggagaa
gtccccaatggctacaatgtctccagatcaaccacagaggatttcccgctcaggctgc
tgtcggctgctccctcccagacatctgtgtacttctgtgccagcagttacgtcgggaa
caccggggagctgttttttggagaaggctctaggctgaccgtactggaggacctgaaa
aacgtgttcccacccgaggtcgctgtgtttgagccatcagaagcagagatctcccaca
cccaaaaggccacactggtgtgcctggccacaggcttctaccccgaccacgtggagct
gagctggtgggtgaatgggaaggaggtgcacagtggggtc▒▒▒acagacccgcagccc
ctcaaggagcagcccgccctcaatgactccagatacgctctgagcagccgcctgaggg
tctcggccaccttctggcaggaccccgcaaccacttccgctgtcaagtccagttcta
cgggctctcggagaatgacgagtggacccaggatagggccaaacccgtcacccagatc
gtcagcgccgaggcctggggtagagcagactgttaa

Figure 21a

MQEXTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGGSYIPTFGRGTSLIVHPYI
QNPDPAVYQLRDSKSSDKSVCLFTDFDSQTNVSQSKDS
DVYITDKCVLDMRSMDFKSNSAVAWSNKSDFACANAF
NNSIIPEDTFFPSPESSC Stop

Figure 21b

MGVTQTPKFQVLKTGQSMTLQCAQDMNHEYMSWYRQ
DPGMGLRLIHYSVGAGITDQGEVPNGYNVSRSTTEDFP
LRLLSAAPSQTSVYFCASSYVGNTGELFFGEGSRLTVLE
DLKNVFPPEVAVFEPSEAEISHTQKATLVCLATGFYPDH
VELSWWVNGKEVHSGVCTDPQPLKEQPALNDSRYALSS
RLRVSATFWQDPRNHFRCQVQFYGLSENDEWTQDRAK
PVTQIVSAEAWGRADC Stop

Figure 33a atgaaggaggtggagcagaattctggacccctcagtgttccagagggagccattg
cctctctcaactgcacttacagtgaccgaggttcccagtccttcttctggtacag
acaatattctgggaaaagccctgagttgataatgttcatatactccaatggtgac
aaagaagatggaaggtttacagcacagctcaataaagccagccagtatgtttctc
tgctcatcagagactcccagcccagtgattcagccacctacctctgtgccgtgaa
ggggggtctggggttaccagaaagttacctttggaactggaacaaagctccaa
gtcatcccaaatatccagaacccggatcctgccgtgtaccagctgagagactcta
aatccagtgacaagtctgtctgcctattcaccgattttgattctcaaacaaatgt
gtcacaaagtaaggattctgatgtgtatatcacagacaaatgtgtgctagacatg
aggtctatggacttcaagagcaacagtgctgtggcctggagcaacaaatctgact
tgcatgtgcaaacgccttcaacaacagcattattccagaagaccttcttccc
cagcccagaaagttcctaa

Figure 33b atgggcgtcatgcagaacccaagacacctggtcaggaggaggggacaggaggcaa
gactgagatgcagcccaatgaaaggacacagtcatgtttactggtatcggcagct
cccagaggaaggtctgaaattcatggtttatctccagaaagaaaatatcatagat
gagtcaggaatgccaaaggaacgatttctgctgaatttcccaaagagggcccca
gcatcctgaggatccagcaggtagtgcgaggagattcggcagcttatttctgtgc
cagctcaccacagacaggggcacagatacgcagtatttggcccaggcacccgg
ctgacagtgctcgaggacctgaaaaacgtgttcccacccgaggtcgctgtgtttg
agccatcagaagcagagatctcccacacccaaaaggccacactggtgtgcctggc
cacaggcttctaccccgaccacgtggagctgagctggtgggtgaatgggaaggag
gtgcacagtggggtctgcacagacccgcagcccctcaaggagcagcccgccctca
atgactccagatacgctctgagcagccgcctgagggtctcggccaccttctggca
ggaccccgcaaccacttccgctgtcaagtccagttctacgggctctcggagaat
gacgagtggacccaggatagggccaaacccgtcacccagatcgtcagcgccgagg
cctggggtagagcagactaa

Figure 34a

MKEVEQNSGPLSVPEGAIASLNCTYSDRGSQSFFWYRQYS
GKSPELIMFIYSNGDKEDGRFTAQLNKASQYVSLLIRDSQP
SDSATYLCAVKGGSGGYQKVTFGTGTKLQVIPNIQNPDPA
VYQLRDSKSSDKSVCLFTDFDSQTNVSQSKDSDVYITDKC
VLDMRSMDFKSNSAVAWSNKSDFACANAFNNSIIPEDTFF
PSPESS Stop

Figure 34b

MGVMQNPRHLVRRRGQEARLRCSPMKGHSHVYWYRQLP
EEGLKFMVYLQKENIIDESGMPKERFSAEFPKEGPSILRIQ
QVVRGDSAAYFCASSPQTGGTDTQYFGPGTRLTVLEDLKN
VFPPEVAVFEPSEAEISHTQKATLVCLATGFYPDHVELSW
WVNGKEVHSGVCTDPQPLKEQPALNDSRYALSSRLVSAT
FWQDPRNHFRCQVQFYGLSENDEWTQDRAKPVTQIVSAE
AWGRAD Stop

Figure 39a – T48→C α chain atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctggggaaattgcagtttggagcagggacccaggttgtggtc
accccagatatccagaaccctgacctgccgtgtaccagctgagagactctaaat
ccagtgacaagtctgtctgcctattcaccgattttgattctcaaacaaatgtgtc
acaaagtaaggattctgatgtgtatatcacagacaaatgtgtgctagacatgagg
tctatggacttcaagagcaacagtgctgtggcctggagcaacaaatctgactttg
catgtgcaaacgccttcaacaacagcattattccagaagacaccttcttccccag
cccagaaagttcctaa

Figure 39b – T48→C α chain

MQ
K₁EVEQNSGPL SVPEGAIASL NCTYSDRGSQ SFFWYRQYSG KSPELIMSIY SNGDKEDGRF
TAQLNKASQY VSLLIRDSQP SDSATYLCAV TTDSWGKLQF GAGTQVVVTP DIQNPDPAVY
QLRDSKSSDK SVCLFTDFDS QTNVSQSKDS DVYITDK<u>C</u>VL DMRSMDFKSN SAVAWSNKSD
FACANAFNNS IIPEDTFFPS PESS*

Figure 40a – T45→C alpha chain DNA Sequence

Atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctggggaaattgcagtttggagcagggacccaggttgtggtc
accccagatatccagaaccctgacctgccgtgtaccagctgagagactctaaat
ccagtgacaagtctgtctgcctattcaccgattttgattctcaaacaaatgtgtc
acaaagtaaggattctgatgtgtatatctgtgacaaaactgtgctagacatgagg
tctatggacttcaagagcaacagtgctgtggcctggagcaacaaatctgactttg
catgtgcaaacgccttcaacaacagcattattccagaagacaccttcttccccag
cccagaaagttcctaa

Figure 40b – T45→C alpha chain Amino Acid Sequence

MQ
K₁EVEQNSGPL SVPEGAIASL NCTYSDRGSQ SFFWYRQYSG KSPELIMSIY SNGDKEDGRF
TAQLNKASQY VSLLIRDSQP SDSATYLCAV TTDSWGKLQF GAGTQVVVTP DIQNPDPAVY
QLRDSKSSDK SVCLFTDFDS QTNVSQSKDS DVYI<u>C</u>DKTVL DMRSMDFKSN SAVAWSNKSD
FACANAFNNS IIPEDTFFPS PESS*

Figure 41a – S61→C alpha chain DNA Sequence

Atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtaccagctgagagactctaaat
ccagtgacaagtctgtctgcctattcaccgatttgattctcaaacaaatgtgtc
acaaagtaaggattctgatgtgtatatcacagacaaaactgtgctagacatgagg
tctatggacttcaagagcaac▓▓gctgtggcctggagcaacaaatctgactttg
catgtgcaaacgccttcaacaacagcattattccagaagacaccttcttcccag
cccagaaagttcctaa

Figure 41b – S61→C alpha chain Amino Acid Sequence

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDKTVL DMRSMDFKSN <u>C</u>AVAWSNKSD FACANAFNNS IIPEDTFFPS PESS*

Figure 42a – L50→C alpha chain DNA Sequence

Atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtaccagctgagagactctaaat
ccagtgacaagtctgtctgcctattcaccgatttgattctcaaacaaatgtgtc
acaaagtaaggattctgatgtgtatatcacagacaaaactgtg▓▓gacatgagg
tctatggacttcaagagcaacagtgctgtggcctggagcaacaaatctgactttg
catgtgcaaacgccttcaacaacagcattattccagaagacaccttcttcccag
cccagaaagttcctaa

Figure 42b – L50→C alpha chain Amino Acid Sequence

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDKTV<u>C</u> DMRSMDFKSN SAVAWSNKSD FACANAFNNS IIPEDTFFPS PESS*

Figure 43a – Y10→C α chain atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtgccagctgagagactctaaat
ccagtgacaagtctgtctgcctattcaccgattttgattctcaaacaaatgtgtc
acaaagtaaggattctgatgtgtatatcacagacaaaactgtgctagacatgagg
tctatggacttcaagagcaacagtgctgtggcctggagcaacaaatctgactttg
catgtgcaaacgccttcaacaacagcattattccagaagacaccttcttccccag
cccagaaagttcctaa

Figure 43b – Y10→C α chain

MQ
$K_1$EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVC QLRDSKSSDK SVCLFTDFDS QTNVSQSKDS
DVYITDKTVL DMRSMDFKSN SAVAWSNKSD FACANAFNNS IIPEDTFFPS PESS*

Figure 44a – S15→C α chain atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtaccagctgagagactgtaaat
ccagtgacaagtctgtctgcctattcaccgattttgattctcaaacaaatgtgtc
acaaagtaaggattctgatgtgtatatcacagacaaaactgtgctagacatgagg
tctatggacttcaagagcaacagtgctgtggcctggagcaacaaatctgactttg
catgtgcaaacgccttcaacaacagcattattccagaagacaccttcttccccag
cccagaaagttcctaa

Figure 44b – S15→C α chain

MQ
$K_1$EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDCKSSDK SVCLFTDFDS QTNVSQSKDS
DVYITDKTVL DMRSMDFKSN SAVAWSNKSD FACANAFNNS IIPEDTFFPS PESS*

Figure 45a – L12→C α chain

```
atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactccagcccagtgattcagccacctctgtgccgt
tacaactgacagctgggggaaattgcagtttggagcagggacccaggttgtggtc
accccagatatccagaaccctgaccctgccgtgtaccagcggagagactctaaat
ccagtgacaagtctgtctgcctattcaccgatttgattctcaaacaaatgtgtc
acaaagtaaggattctgatgtgtatatcacagacaaaactgtgctagacatgagg
tctatggacttcaagagcaacagtgctgtggcctggagcaacaaatctgactttg
catgtgcaaacgccttcaacaacagcattattccagaagacacccttcttccccag
cccagaaagttcctaa
```

Figure 45b – L12→C α chain

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QCRDSKSSDK SVCLFTDFDS QTNVSQSKDS
DVYITDKTVL DMRSMDFKSN SAVAWSNKSD FACANAFNNS IIPEDTFFPS PESS*

Figure 46a – V22→C α chain

```
atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactccagcccagtgattcagccacctctgtgccgt
tacaactgacagctgggggaaattgcagtttggagcagggacccaggttgtggtc
accccagatatccagaaccctgaccctgccgtgtaccagctgagagactctaaat
ccagtgacaagtcttgctgcctattcaccgatttgattctcaaacaaatgtgtc
acaaagtaaggattctgatgtgtatatcacagacaaaactgtgctagacatgagg
tctatggacttcaagagcaacagtgctgtggcctggagcaacaaatctgactttg
catgtgcaaacgccttcaacaacagcattattccagaagacacccttcttccccag
cccagaaagttcctaa
```

Figure 46b – V22→C α chain

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SCCLFTDFDS QTNVSQSKDS
DVYITDKTVL DMRSMDFKSN SAVAWSNKSD FACANAFNNS IIPEDTFFPS PESS*

Figure 47a – M52→C α chain

```
atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtaccagctgagagactctaaat
ccagtgacaagtctgtctgcctattcaccgattttgattctcaaacaaatgtgtc
acaaagtaaggattctgatgtgtatatcacagacaaaactgtgctagactgtagg
tctatggacttcaagagcaacagtgctgtggcctggagcaacaaatctgactttg
catgtgcaaacgccttcaacaacagcattattccagaagacaccttcttccccag
cccagaaagttcctaa
```

Figure 47b – M52→C α chain

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDKTVL DCRSMDFKSN SAVAWSNKSD FACANAFNNS IIPEDTFFPS PESS*

Figure 48a – Y43→C α chain

```
atgcagaaggaagtggagcagaactctggacccctcagtgttccagagggagcca
ttgcctctctcaactgcacttacagtgaccgaggttcccagtccttcttctggta
cagacaatattctgggaaaagccctgagttgataatgtccatatactccaatggt
gacaaagaagatggaaggtttacagcacagctcaataaagccagccagtatgttt
ctctgctcatcagagactcccagcccagtgattcagccacctacctctgtgccgt
tacaactgacagctgggggaaattgcagtttggagcagggacccaggttgtggtc
accccagatatccagaaccctgaccctgccgtgtaccagctgagagactctaaat
ccagtgacaagtctgtctgcctattcaccgattttgattctcaaacaaatgtgtc
acaaagtaaggattctgatgtgtgtatcacagacaaaactgtgctagacatgagg
tctatggacttcaagagcaacagtgctgtggcctggagcaacaaatctgactttg
catgtgcaaacgccttcaacaacagcattattccagaagacaccttcttccccag
cccagaaagttcctaa
```

Figure 48b – Y43→C α chain

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVCITDKTVL DMRSMDFKSN SAVAWSNKSD FACANAFNNS IIPEDTFFPS PESS*

Figure 49a – Ser57→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctcctcccagacatctgtgtacttctg
tgccagcaggccgggactagcgggagggcgaccagagcagtacttcgggccgggc
accaggctcacggtcacagaggacctgaaaaacgttcccacccgaggtcgctg
tgtttgagccatcagaagcagagatctcccacacccaaaaggccacactggtgtg
cctggccacaggcttctaccccgaccacgtggagctgagctggtgggtgaatggg
aaggaggtgcacagtggggtcggacagacccgcagcccctcaaggagcagccg
ccctcaatgactccagatacgctctgagcagccgcctgagggtctcggccacctt
ctggcaggaccccgcaaccacttccgctgtcaagtccagttctacgggctctcg
gagaatgacgagtggacccaggatagggccaaaccgtcacccagatcgtcagcg
ccgaggcctggggtagagcagactaa
```

Figure 49b Ser57→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VCTDPQPLKE QPALNDSRYA LSSRLRVSAT
FWQDPRNHFR CQVQFYGLSE NDEWTQDRAK PVTQIVSAEA WGRAD*

Figure 50a – Ser77→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctcctcccagacatctgtgtacttctg
tgccagcaggccgggactagcgggagggcgaccagagcagtacttcgggccgggc
accaggctcacggtcacagaggacctgaaaaacgttcccacccgaggtcgctg
tgtttgagccatcagaagcagagatctcccacacccaaaaggccacactggtgtg
cctggccacaggcttctaccccgaccacgtggagctgagctggtgggtgaatggg
aaggaggtgcacagtggggtcagcacagacccgcagcccctcaaggagcagccg
ccctcaatgactccagatacgctctgtgtagccgcctgagggtctcggccacctt
ctggcaggaccccgcaaccacttccgctgtcaagtccagttctacgggctctcg
gagaatgacgagtggacccaggatagggccaaaccgtcacccagatcgtcagcg
ccgaggcctggggtagagcagactaa
```

Figure 50b Ser77→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VSTDPQPLKE QPALNDSRYA LCSRLRVSAT
FWQDPRNHFR CQVQFYGLSE NDEWTQDRAK PVTQIVSAEA WGRAD*

Figure 51a – Ser17→C β chain atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcgggagggcgaccagagcagtacttcgggccgggc
accaggctcacggtcacagaggacctgaaaaacgttcccacccgaggtcgctg
tgtttgagcca▓▓▓gaagcagagatctcccacacccaaaaggccacactggtgtg
cctggccacaggcttctaccccgaccacgtggagctgagctggtgggtgaatggg
aaggaggtgcacagtggggtcagcacagacccgcagcccctcaaggagcagccg
ccctcaatgactccagatacgctctgagcagccgcctgagggtctcggccacctt
ctggcaggaccccgcaaccacttccgctgtcaagtccagttctacggctctcg
gagaatgacgagtggacccaggatagggccaaacccgtcacccagatcgtcagcg
ccgaggcctggggtagagcagactaa

Figure 51b Ser17→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PCEAEISHTQ KATLVCLATG
FYPDHVELSW WVNGKEVHSG VSTDPQPLKE QPALNDSRYA LSSRLRVSAT
FWQDPRNHFR CQVQFYGLSE NDEWTQDRAK PVTQIVSAEA WGRAD*

Figure 52a – Val 13→C β chain atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcgggagggcgaccagagcagtacttcgggccgggc
accaggctcacggtcacagaggacctgaaaaacgttcccacccgaggtcgct▓
▓▓tttgagccatcagaagcagagatctcccacacccaaaaggccacactggtgtg
cctggccacaggcttctaccccgaccacgtggagctgagctggtgggtgaatggg
aaggaggtgcacagtggggtcagcacagacccgcagcccctcaaggagcagccg
ccctcaatgactccagatacgctctgagcagccgcctgagggtctcggccacctt
ctggcaggaccccgcaaccacttccgctgtcaagtccagttctacggctctcg
gagaatgacgagtggacccaggatagggccaaacccgtcacccagatcgtcagcg
ccgaggcctggggtagagcagactaa

Figure 52 Val 13→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVA<u>C</u>FE PSEAEISHTQ KATLVCLATG
FYPDHVELSW WVNGKEVHSG VSTDPQPLKE QPALNDSRYA LSSRLRVSAT
FWQDPRNHFR CQVQFYGLSE NDEWTQDRAK PVTQIVSAEA WGRAD*

Figure 53a – Asp 59→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcgggagggcgaccagagcagtacttcgggccgggc
accaggctcacggtcacagaggacctgaaaaacgtgttcccacccgaggtcgctg
tgtttgagccatcagaagcagagatctcccacacccaaaaggccacactggtgtg
cctggccacaggcttctaccccgaccacgtggagctgagctggtgggtgaatggg
aaggaggtgcacagtggggtcagcaca██ccgcagcccctcaaggagcagcccg
ccctcaatgactccagatacgctctgagcagccgcctgagggtctcggccacctt
ctggcaggaccccgcaaccacttccgctgtcaagtccagttctacgggctctcg
gagaatgacgagtggacccaggatagggccaaaccgtcacccagatcgtcagcg
ccgaggcctggggtagagcagactaa
```

Figure 53b Asp 59→C β chain

```
M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VSTCPQPLKE QPALNDSRYA LSSRLRVSAT
FWQDPRNHFR CQVQFYGLSE NDEWTQDRAK PVTQIVSAEA WGRAD*
```

Figure 54a – Arg 79→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcgggagggcgaccagagcagtacttcgggccgggc
accaggctcacggtcacagaggacctgaaaaacgtgttcccacccgaggtcgctg
tgtttgagccatcagaagcagagatctcccacacccaaaaggccacactggtgtg
cctggccacaggcttctaccccgaccacgtggagctgagctggtgggtgaatggg
aaggaggtgcacagtggggtcagcacagacccgcagcccctcaaggagcagcccg
ccctcaatgactccagatacgctctgagcagc██ctgagggtctcggccacctt
ctggcaggaccccgcaaccacttccgctgtcaagtccagttctacgggctctcg
gagaatgacgagtggacccaggatagggccaaaccgtcacccagatcgtcagcg
ccgaggcctggggtagagcagactaa
```

Figure 54b Arg 79→C β chain

```
M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VSTDPQPLKE QPALNDSRYA LSSCLRVSAT
FWQDPRNHFR CQVQFYGLSE NDEWTQDRAK PVTQIVSAEA WGRAD*
```

Figure 55a – Phe 14→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctcctcccagacatctgtgtacttctg
tgccagcaggccgggactagcgggagggcgaccagagcagtacttcgggccgggc
accaggctcacggtcacagaggacctgaaaaacgtgttcccacccgaggtcgctg
tg[cgt]gagccatcagaagcagagatctcccacacccaaaaggccacactggtgtg
cctggccacaggcttctaccccgaccacgtggagctgagctggtgggtgaatggg
aaggaggtgcacagtggggtcagcacagacccgcagcccctcaaggagcagccg
ccctcaatgactccagatacgctctgagcagccgcctgagggtctcggccacctt
ctggcaggaccccgcaaccacttccgctgtcaagtccagttctacggctctcg
gagaatgacgagtggacccaggatagggccaaacccgtcacccagatcgtcagcg
ccgaggcctggggtagagcagactaa
```

Figure 55b Phe 14→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVC̱E PSEAEISHTQ KATLVCLATG
FYPDHVELSW WVNGKEVHSG VSTDPQPLKE QPALNDSRYA LSSRLRVSAT
FWQDPRNHFR CQVQFYGLSE NDEWTQDRAK PVTQIVSAEA WGRAD*

Figure 56a – Gly 55→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctcctcccagacatctgtgtacttctg
tgccagcaggccgggactagcgggagggcgaccagagcagtacttcgggccgggc
accaggctcacggtcacagaggacctgaaaaacgtgttcccacccgaggtcgctg
tgtttgagccatcagaagcagagatctcccacacccaaaaggccacactggtgtg
cctggccacaggcttctaccccgaccacgtggagctgagctggtgggtgaatggg
aaggaggtgcacagt[tgt]gtcagcacagacccgcagcccctcaaggagcagccg
ccctcaatgactccagatacgctctgagcagccgcctgagggtctcggccacctt
ctggcaggaccccgcaaccacttccgctgtcaagtccagttctacggctctcg
gagaatgacgagtggacccaggatagggccaaacccgtcacccagatcgtcagcg
ccgaggcctggggtagagcagactaa
```

Figure 56b Gly 55→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSC̱ VSTDPQPLKE QPALNDSRYA LSSRLRVSAT
FWQDPRNHFR CQVQFYGLSE NDEWTQDRAK PVTQIVSAEA WGRAD*

Figure 57a – Leu 63→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcggagggcgaccagagcagtacttcgggccgggc
accaggctcacggtcacagaggacctgaaaaacgtgttcccacccgaggtcgctg
tgtttgagccatcagaagcagagatctccacacccaaaaggccacactggtgtg
cctggccacaggcttctaccccgaccacgtggagctgagctggtgggtgaatggg
aaggaggtgcacagtggggtcagcacagaccgcagccctgcaaggagcagcccg
ccctcaatgactccagatacgctctgagcagccgcctgagggtctcggccacctt
ctggcaggaccccgcaaccacttccgctgtcaagtccagttctacgggctctcg
gagaatgacgagtggacccaggatagggccaaacccgtcacccagatcgtcagcg
ccgaggcctggggtagagcagactaa
```

Figure 57b Leu 63→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VSTDPQPCKE QPALNDSRYA LSSRLRVSAT
FWQDPRNHFR CQVQFYGLSE NDEWTQDRAK PVTQIVSAEA WGRAD*

Figure 58a – Glu 15→C β chain

```
atgaacgctggtgtcactcagaccccaaaattccaggtcctgaagacaggacaga
gcatgacactgcagtgtgcccaggatatgaaccatgaatacatgtcctggtatcg
acaagacccaggcatggggctgaggctgattcattactcagttggtgctggtatc
actgaccaaggagaagtccccaatggctacaatgtctccagatcaaccacagagg
atttcccgctcaggctgctgtcggctgctccctcccagacatctgtgtacttctg
tgccagcaggccgggactagcggagggcgaccagagcagtacttcgggccgggc
accaggctcacggtcacagaggacctgaaaaacgtgttcccacccgaggtcgctg
tgttttgtccatcagaagcagagatctccacacccaaaaggccacactggtgtg
cctggccacaggcttctaccccgaccacgtggagctgagctggtgggtgaatggg
aaggaggtgcacagtggggtcagcacagaccgcagccctcaaggagcagcccg
ccctcaatgactccagatacgctctgagcagccgcctgagggtctcggccacctt
ctggcaggaccccgcaaccacttccgctgtcaagtccagttctacgggctctcg
gagaatgacgagtggacccaggatagggccaaacccgtcacccagatcgtcagcg
ccgaggcctggggtagagcagactaa
```

Figure 58b Glu 15→C β chain

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFC PSEAEISHTQ KATLVCLATG
FYPDHVELSW WVNGKEVHSG VSTDPQPLKE QPALNDSRYA LSSRLRVSAT
FWQDPRNHFR CQVQFYGLSE NDEWTQDRAK PVTQIVSAEA WGRAD*

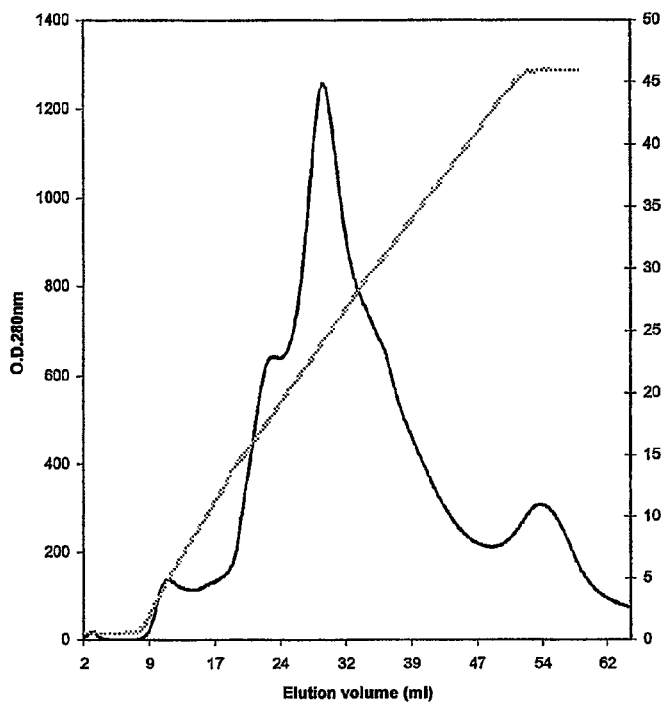
Figure 63: AE column Met52/Gly55
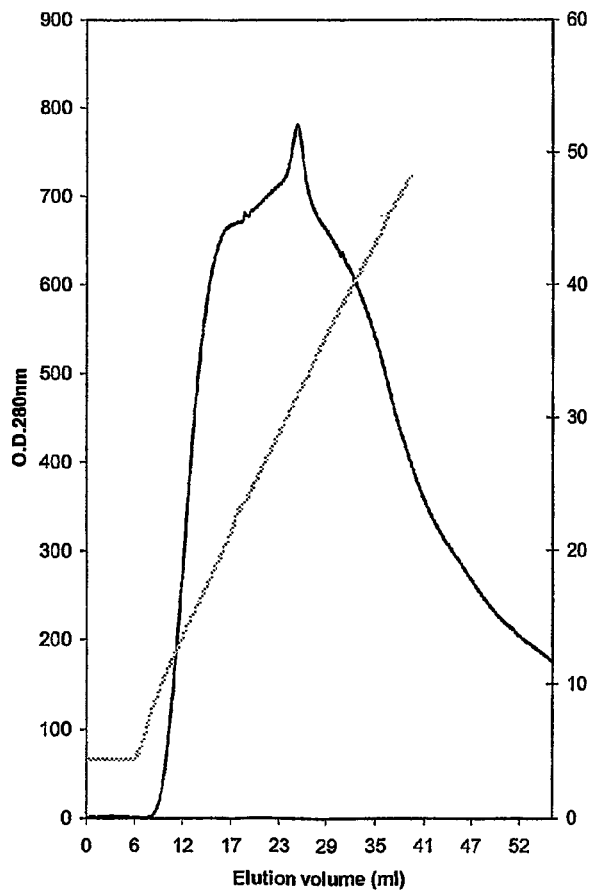
Figure 64: AE column Ser15/Glu15

SDS PAGE Thr48/Ser57

SDS PAGE Thr45/Ser77

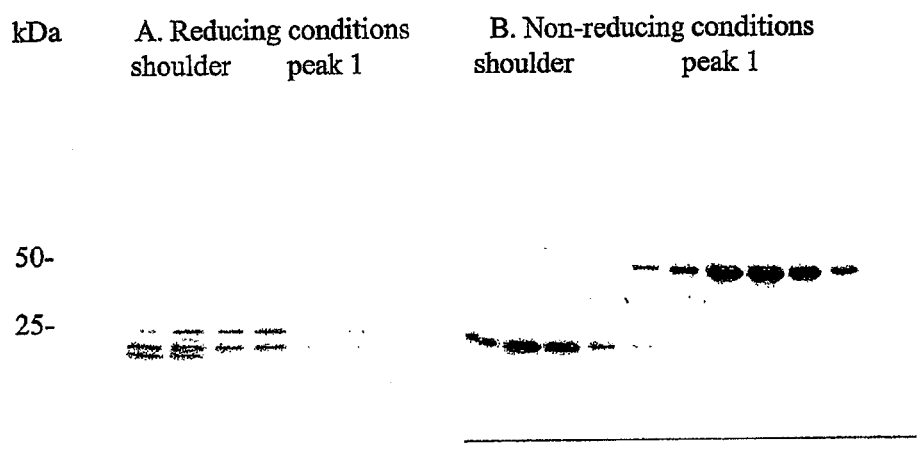
Figure 69: SDS PAGE Met52/Gly55
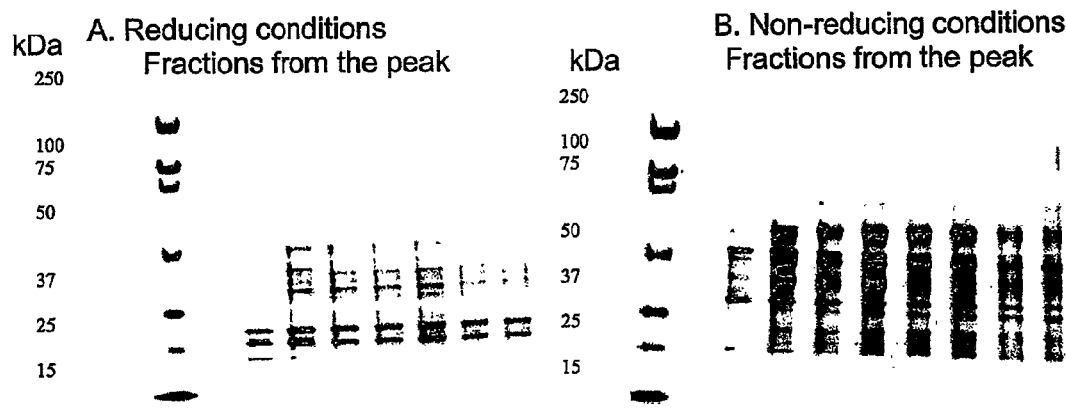
Figure 70: SDS PAGE Ser 15/Glu 15

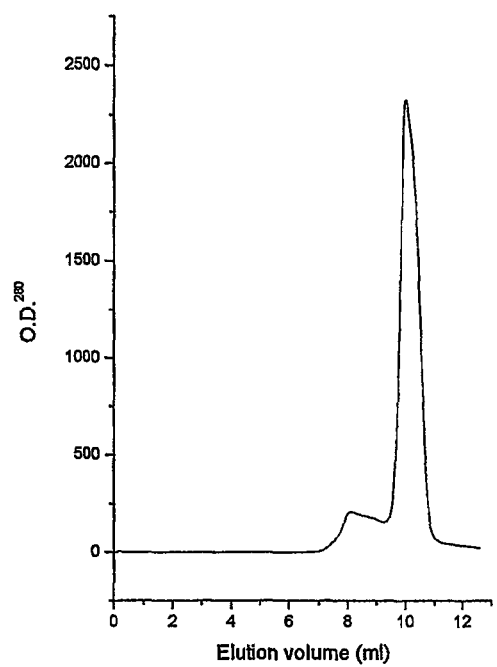
Figure 71: SEC Thr48/Ser57
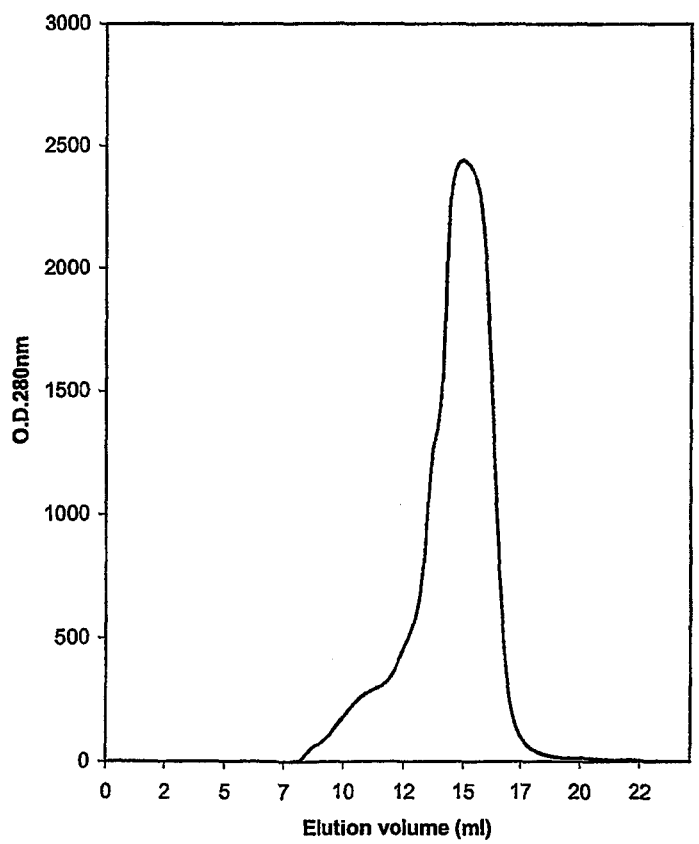
Figure 72: SEC Thr45/Ser77 (200 HR column)

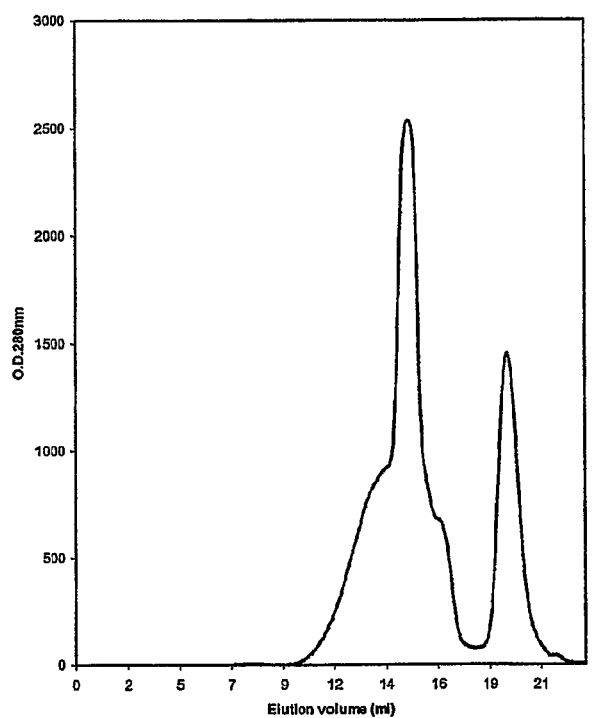
Figure 75 SEC Met 52 / Gly 55 (200 HR Column)
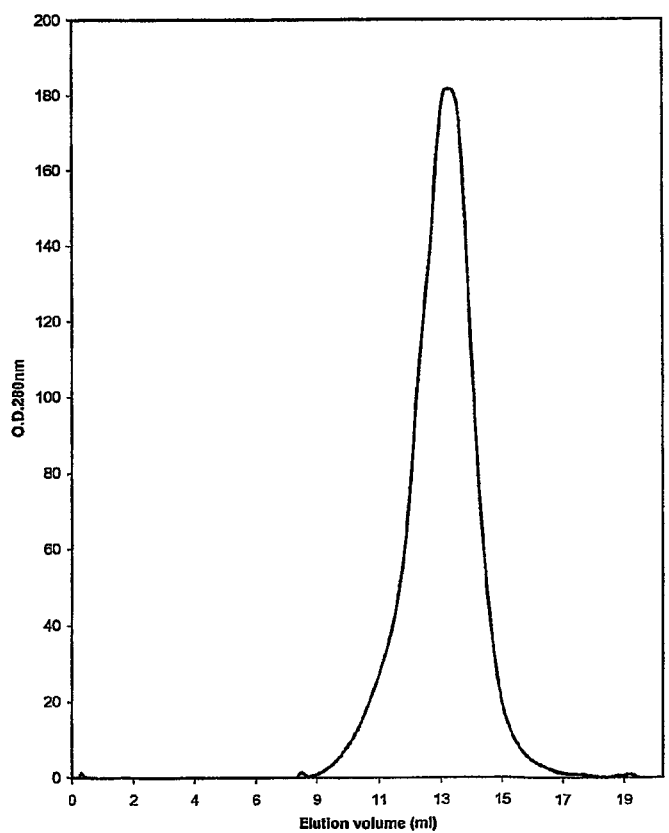
Figure 76: SEC Ser 15/Glu 15 (200 HR Column)

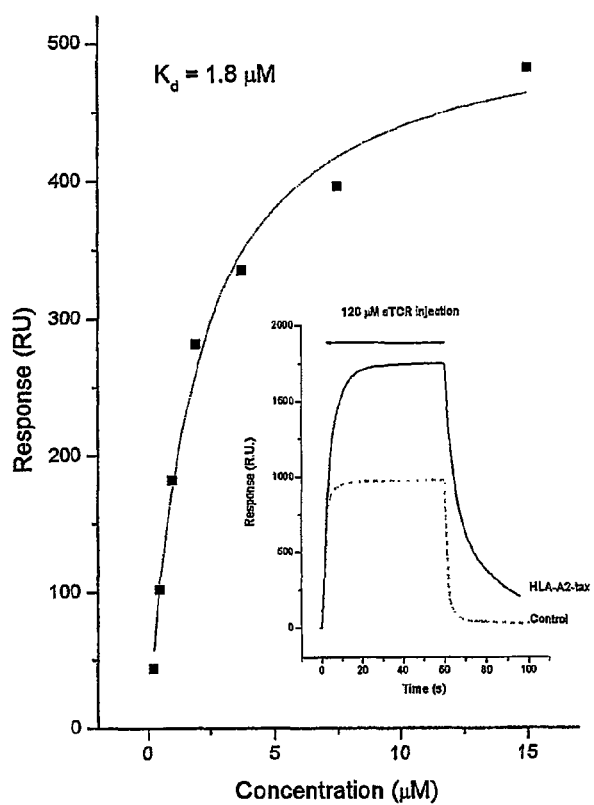
Figure 77: Thr 48/Ser 57
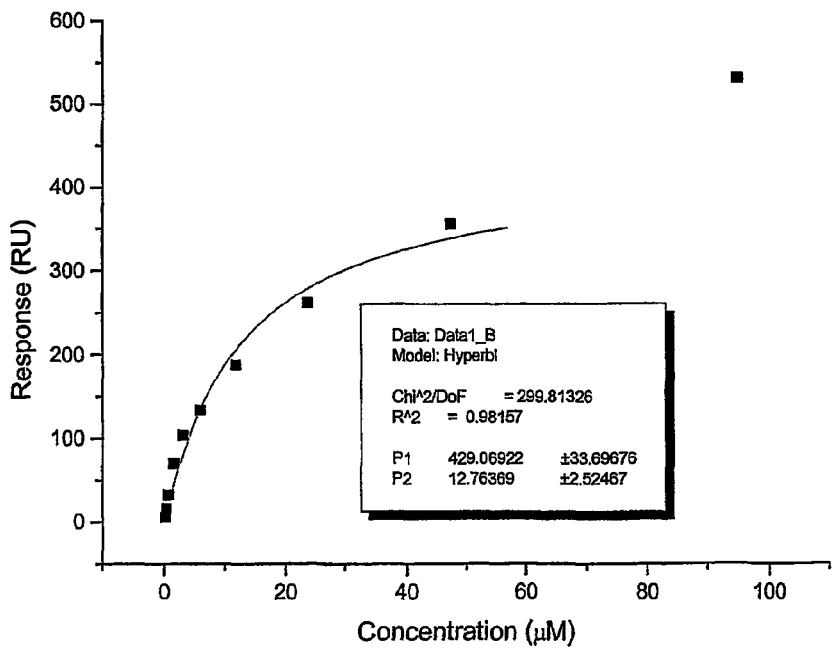
Figure 78: Thr 45/Ser 77

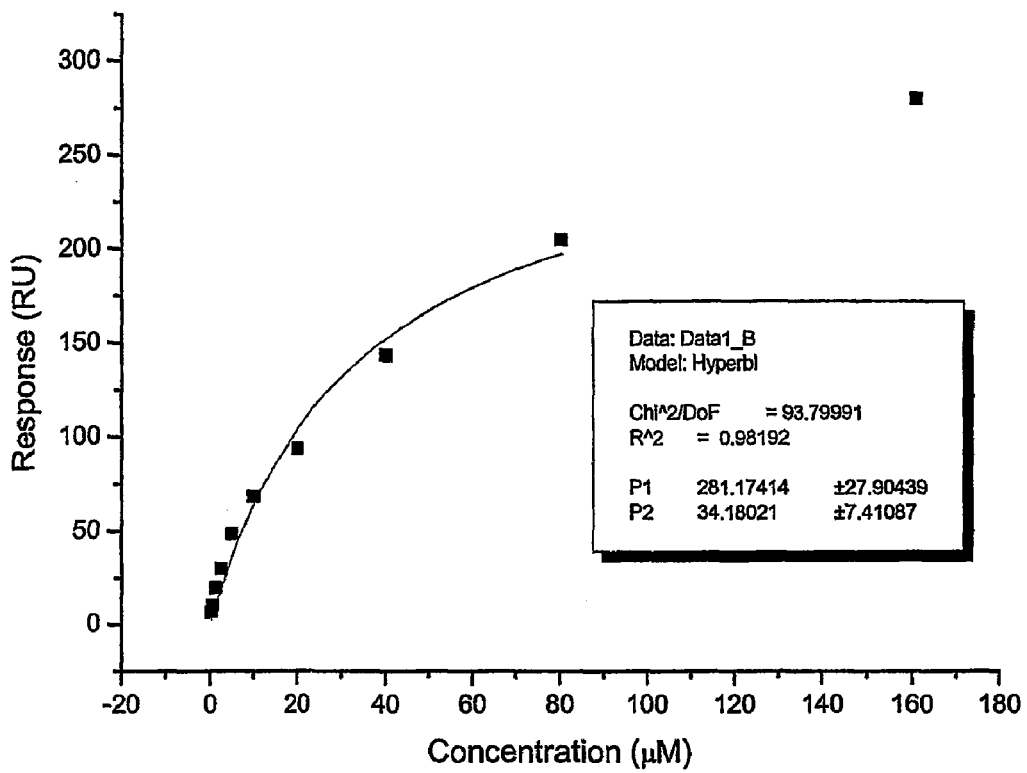
Figure 79: Tyr 10/Ser 17
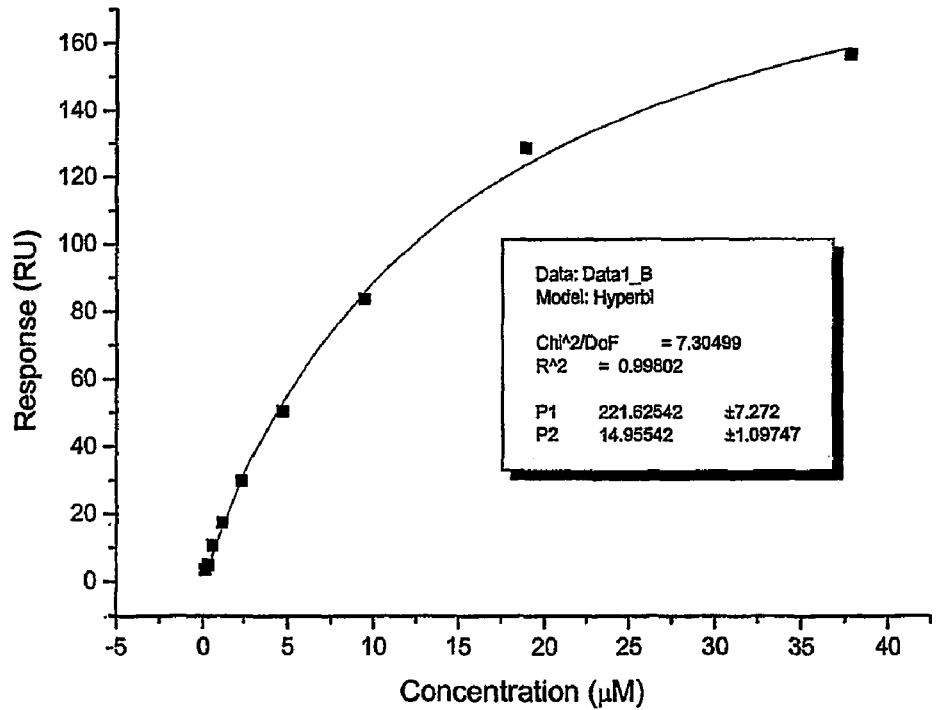
Figure 80: Thr 45/Asp 59

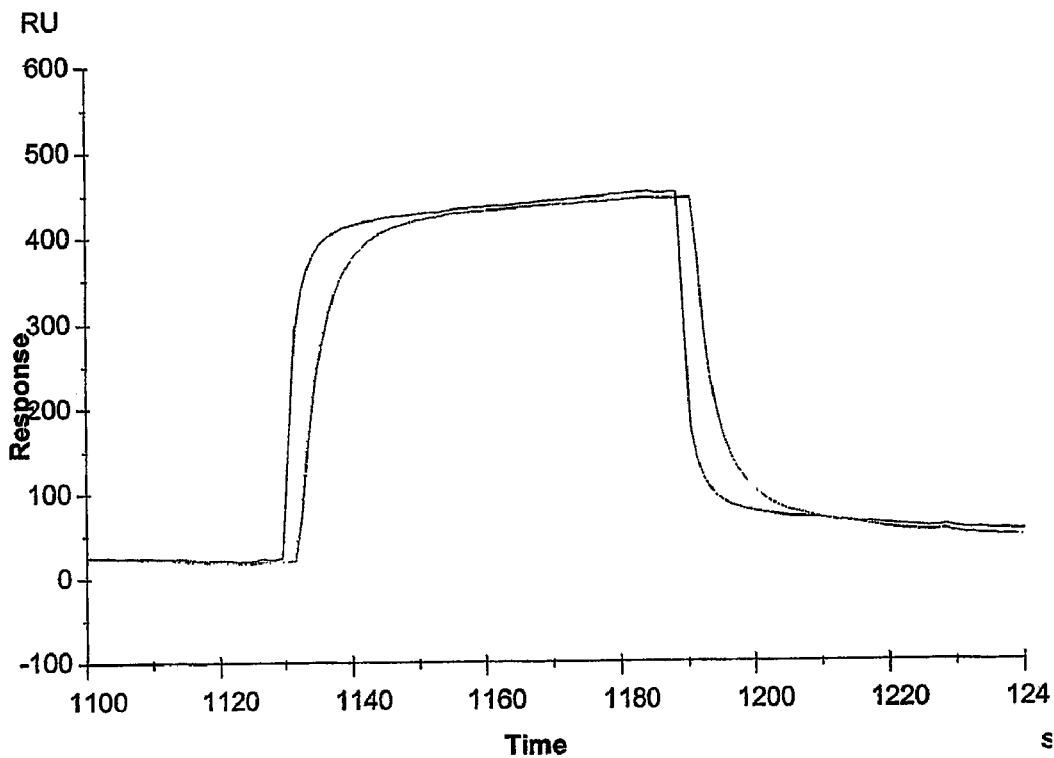
Figure 81: Met 52/Gly 55
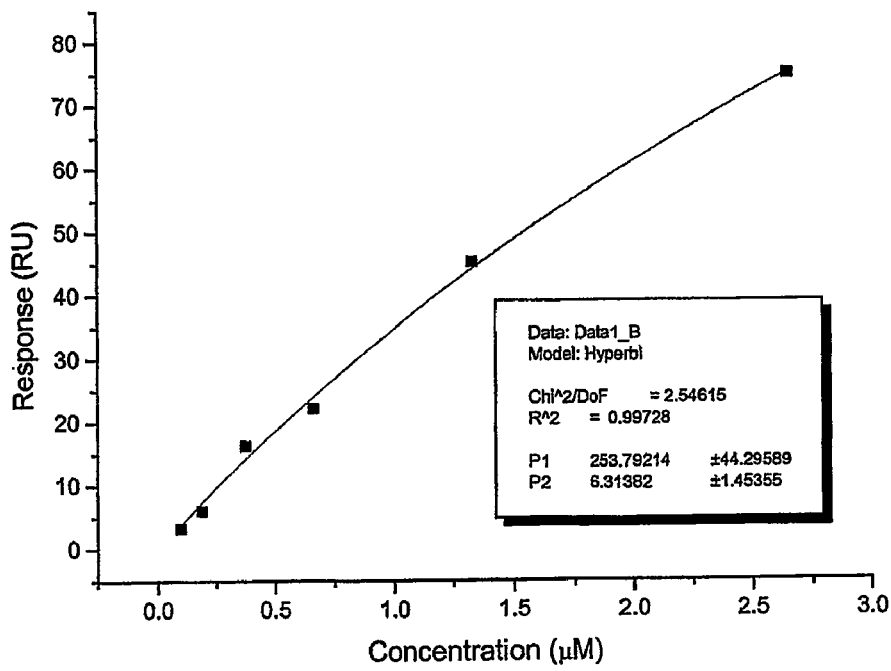
Figure 82: Ser 15/Glu 15

Figure 85a atgggtgtcactcagaccccaaaattccaggtcctgaagacaggacagagcatgaca
ctgcagtgtgcccaggatatgaaccatgaatacatgtcctggtatcgacaagaccca
ggcatggggctgaggctgattcattactcagttggtgctggtatcactgaccaagga
gaagtccccaatggctacaatgtctccagatcaaccacagaggatttcccgctcagg
ctgctgtcggctgctccctcccagacatctgtgtacttctgtgccagcagttacgtc
gggaacaccggggagctgttttttggagaaggctctaggctgaccgtactggaggac
ctgaaaaacgtgttcccacccgaggtcgctgtgtttgagccatcagaagcagagatc
tcccacacccaaaaggccacactggtgtgcctggccacaggcttctaccccgaccac
gtggagctgagctggtgggtgaatgggaaggaggtgcacagtggggtctgcacagac
ccgcagcccctcaaggagcagcccgccctcaatgactccagatacgctctgagcagc
cgcctgagggtctcggccaccttctggcaggaccccgcaaccacttccgctgtcaa
gtccagttctacgggctctcggagaatgacgagtggacccaggatagggccaaaccc
gtcacccagatcgtcagcgccgaggcctggggtagagcagacggatccggtggtggt
ctgaacgatatttttgaagctcagaaaatcgaatggcattaa

Figure 85b

M G V T Q T P K F Q V L K T G Q S M T L Q C A Q D M N H E Y M
S W Y R Q D P G M G L R L I H Y S V G A G I T D Q G E V P N G
Y N V S R S T T E D F P L R L L S A A P S Q T S V Y F C A S S
Y V G N T G E L F F G E G S R L T V L E D L K N V F P P E V A
V F E P S E A E I S H T Q K A T L V C L A T G F Y P D H V E L
S W W V N G K E V H S G V C T D P Q P L K E Q P A L N D S R Y
A L S S R L R V S A T F W Q D P R N H F R C Q V Q F Y G L S E
N D E W T Q D R A K P V T Q I V S A E A W G R A D G S G G G
███████████████████████ Stop

Figure 86a atgggtgtcactcagaccccaaaattccaggtcctgaagacaggacagagcatgaca
ctgcagtgtgcccaggatatgaaccatgaatacatgtcctggtatcgacaagaccca
ggcatggggctgaggctgattcattactcagttggtgctggtatcactgaccaagga
gaagtccccaatggctacaatgtctccagatcaaccacagaggatttcccgctcagg
ctgctgtcggctgctccctcccagacatctgtgtacttctgtgccagcagttacgtc
gggaacaccggggagctgttttttggagaaggctctaggctgaccgtactggaggac
ctgaaaaacgtgttcccacccgaggtcgctgtgtttgagccatcagaagcagagatc
tcccacacccaaaaggccacactggtgtgcctggccacaggcttctaccccgaccac
gtggagctgagctggtgggtgaatgggaaggaggtgcacagtggggtctgcacagac
ccgcagcccctcaaggagcagcccgccctcaatgactccagatacgctctgagcagc
cgcctgagggtctcggccaccttctggcaggaccccgcaaccacttccgctgtcaa
gtccagttctacgggctctcggagaatgacgagtggacccaggatagggccaaaccc
gtcacccagatcgtcagcgccgaggcctggggtagagcagacggatccggtggtggt
catcatcaccatcatcactaa

Figure 86b

```
M G V T Q P K F Q V L K T G Q S M T L Q C A Q D M N H E Y M
S W Y R Q D P G M G L R L I H Y S V G A G I T D Q G E V P N G
Y N V S R S T T E D F P L R L L S A A P S Q T S V Y F C A S S
Y V G N T G E L F F G E G S R L T V L E D L K N V F P P E V A
V F E P S E A E I S H T Q K A T L V C L A T G F Y P D H V E L
S W W V N G K E V H S G V C T D P Q P L K E Q P A L N D S R Y
A L S S R L R V S A T F W Q D P R N H F R C Q V Q F Y G L S E
N D E W T Q D R A K P V T Q I V S A E A W G R A D G S G G G
HHHHHH Stop
```

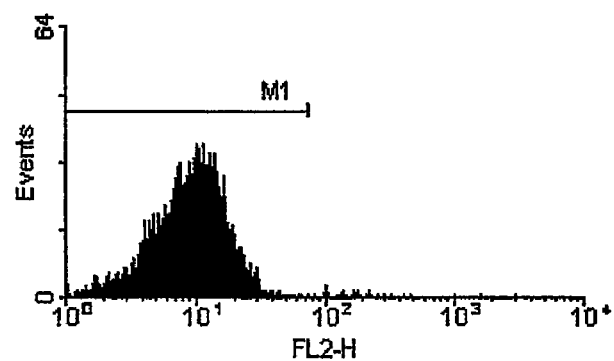
Figure 91a. PP LCL NYESO 0 TCR 5μg
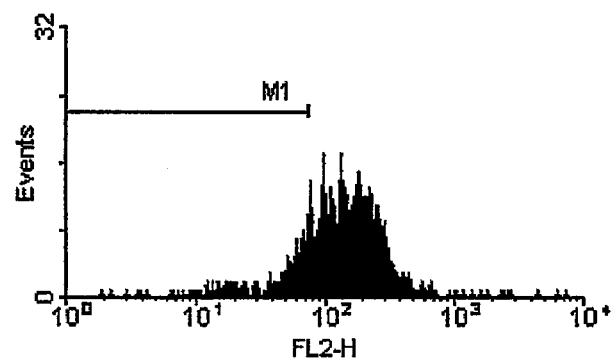
Figure 91b. PP LCL NYESO $10^{-4}$M TCR 5μg
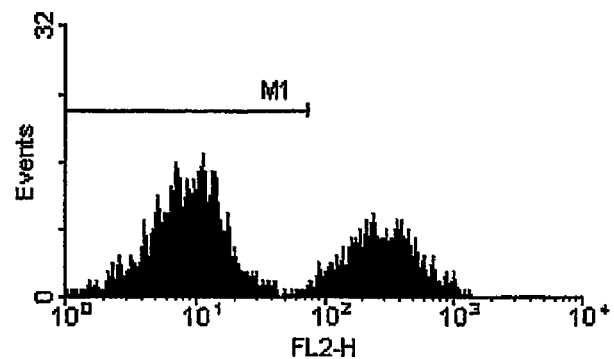
Figure 91c. PP LCL NYESO $10^{-5}$M TCR 5μg

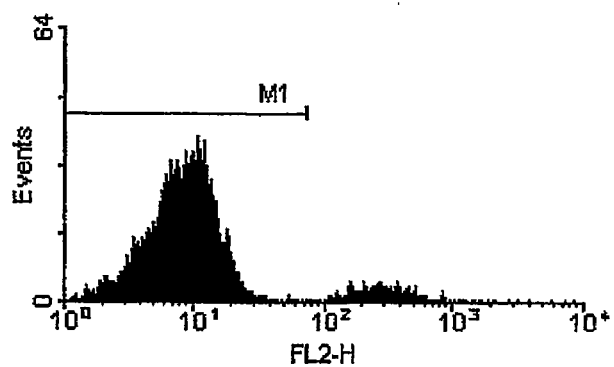
Figure 91d. PP LCL NYESO $10^{-6}$M TCR 5µg
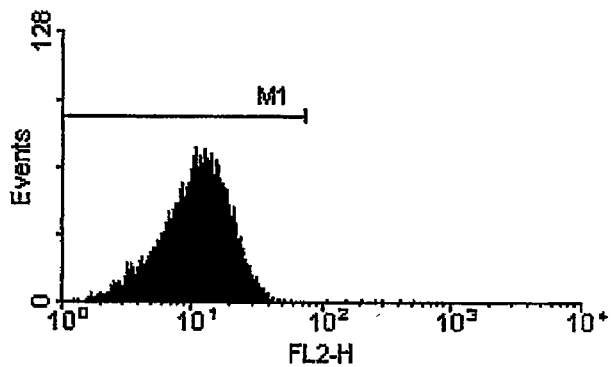
Figure 91e. PP LCL NYESO 0 TCR 10µg
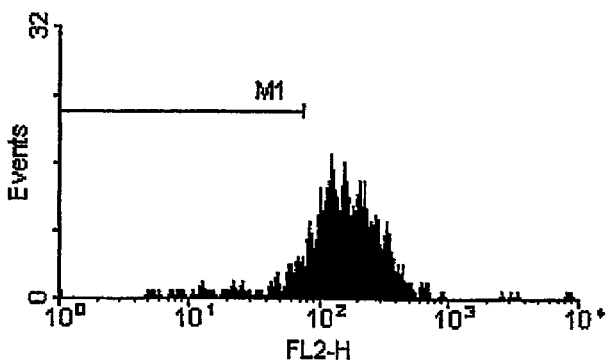
Figure 91f. PP LCL NYESO $10^{-4}$M TCR 10µg

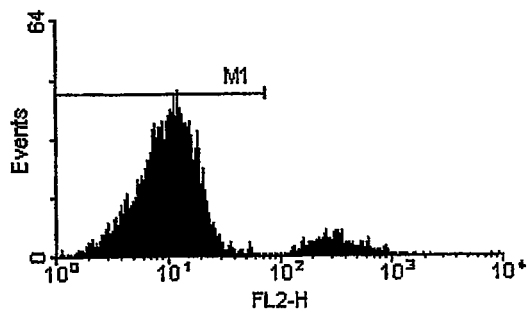

Figure 91g. PP LCL NYESO $10^{-5}$M TCR 10μg

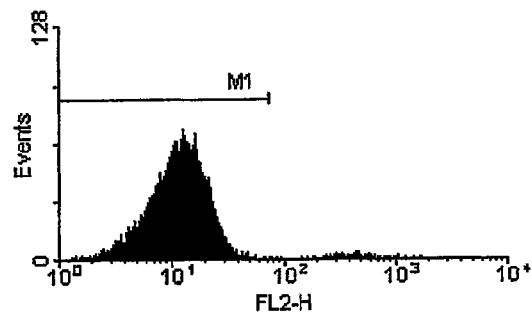

Figure 91h. PP LCL NYESO $10^{-6}$M TCR 10μg

```
atgaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttcccg
ctcaggctgctgtcggctgctcctcccagacatctgtgtacttctgtgccagcagg
ccgggactagcgggagggcgaccagagcagtacttcgggccgggcaccaggctcacg
gtcacagaggacctgaacaaggtgttccacccgaggtcgctgtgtttgagccatca
gaagcagagatctcccacacccaaaaggccacactggtgtgcctggccacaggcttc
ttccccgaccacgtggagctgagctggtgggtgaatgggaaggaggtgcacagtggg
gtctgcacagacccgcagcccctcaaggagcagcccgccctcaatgactccagatac
tctctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa
```

Figure 92

Figure 96
A
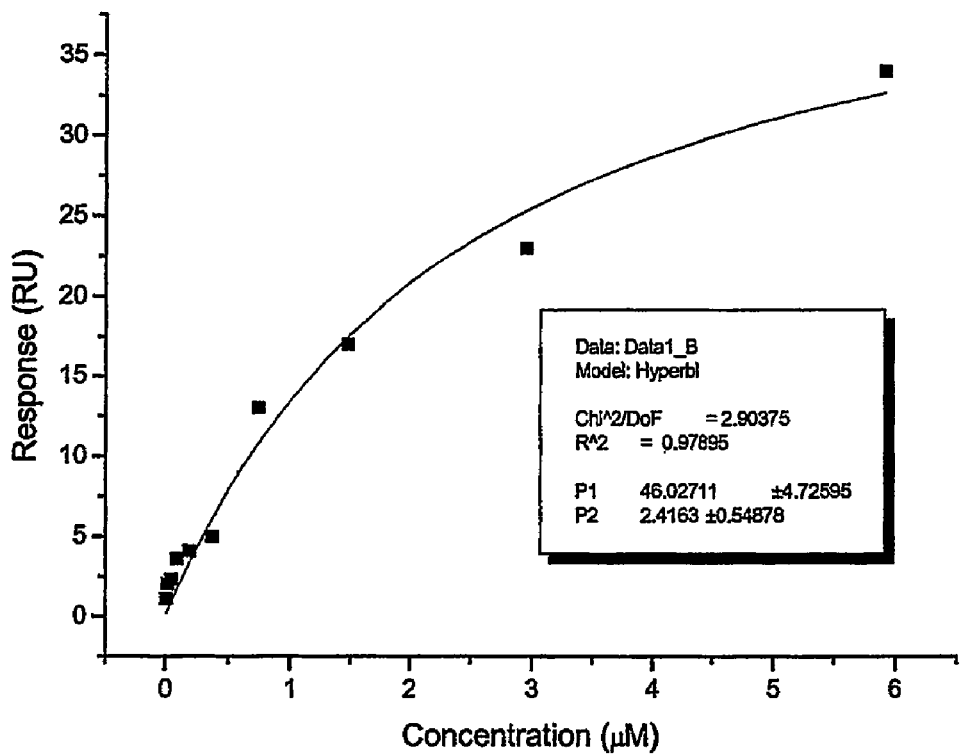
B
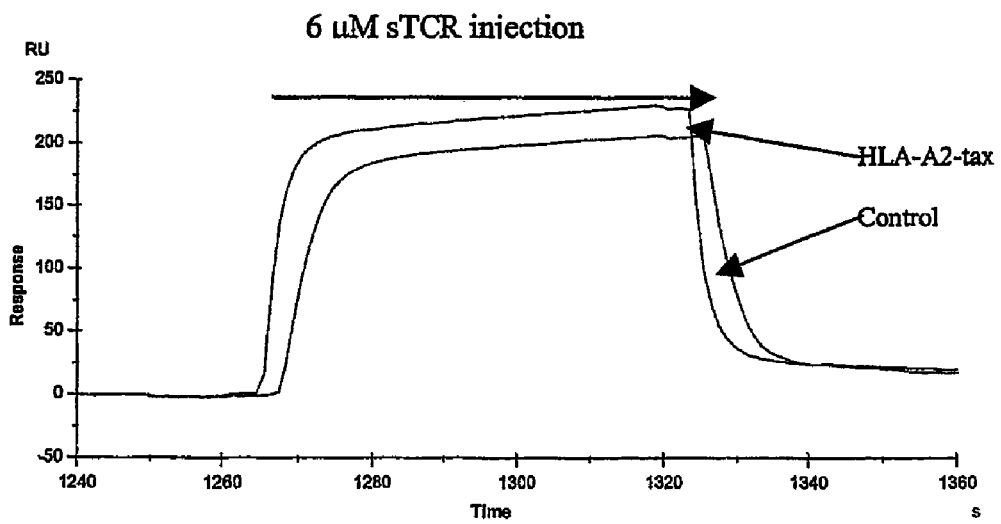

Figure 97

```
atgaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttcccg
ctcaggctgctgtcggctgctccctcccagacatctgtgtacttctgtgccagcagg
ccgggactagcgggagggcgaccagagcagtacttcgggccgggcaccaggctcacg
gtcacagaggacctgaaaaacgtgttcccacccgaggtcgctgtgtttgagccatca
gaagcagagatctcccacacccaaaaggccacactggtgtgcctggccacaggcttc
taccccgaccacgtggagctgagctggtgggtgaatgggaaggaggtgcacagtggg
gtctgcacagacccgcagcccctcaaggagcagccgccctcaatgactccagatac
tgtctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa
```

A. Reducing conditions  B. Non-reducing conditions

KDa  peak 1      peak 2       peak 1      peak 2

Figure 101
A
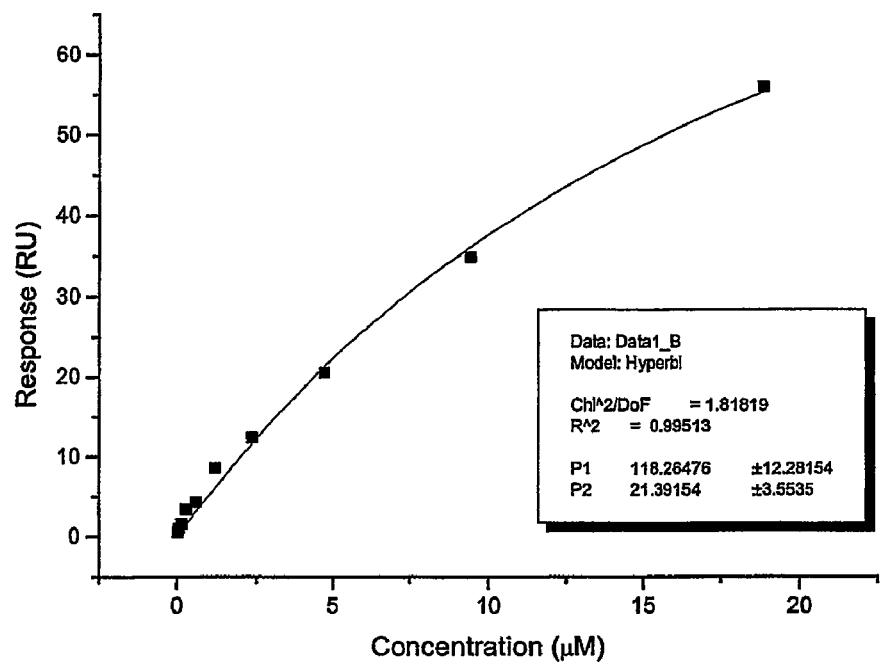
B
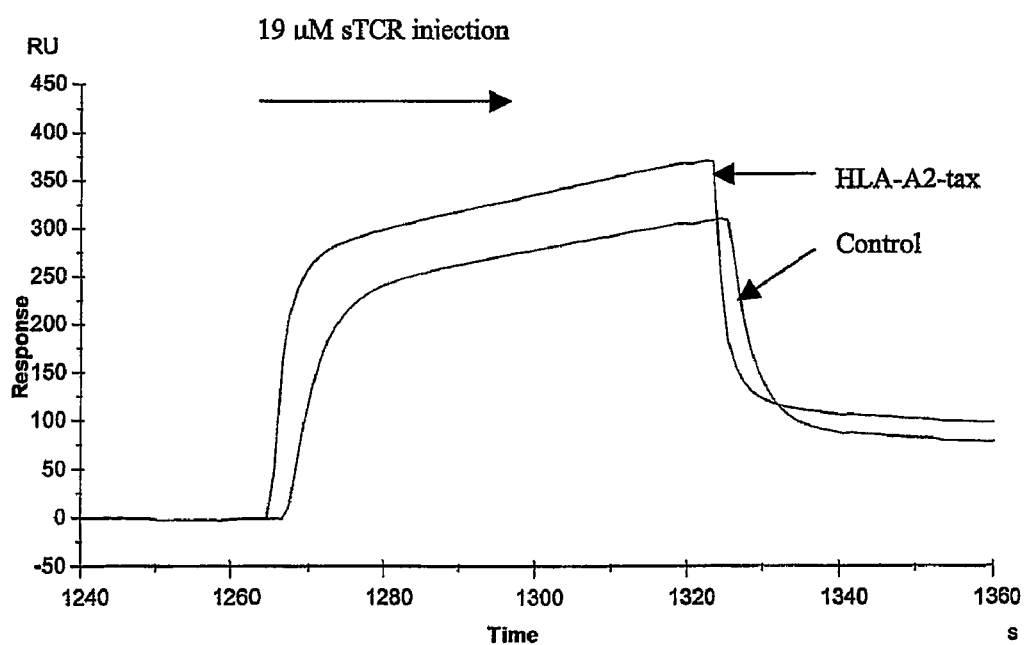

Figure 102

```
atgaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttcccg
ctcaggctgctgtcggctgctccctcccagacatctgtgtacttctgtgccagcagg
ccgggactagcgggagggcgaccagagcagtacttcgggccgggcaccaggctcacg
gtcacagaggacctgaaaaacgtgttcccacccgaggtcgctgtgtttgagccatca
gaagcagagatctcccacacccaaaaggccacactggtgtgcctggccacaggcttc
tacccgaccacgtggagctgagctggtgggtgaatgggaaggaggtgcacagtggg
gtctgcacagacccgcagcccctcaaggagcagcccgccctcaatgactccagatac
tctctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa
```

Figure 106
A
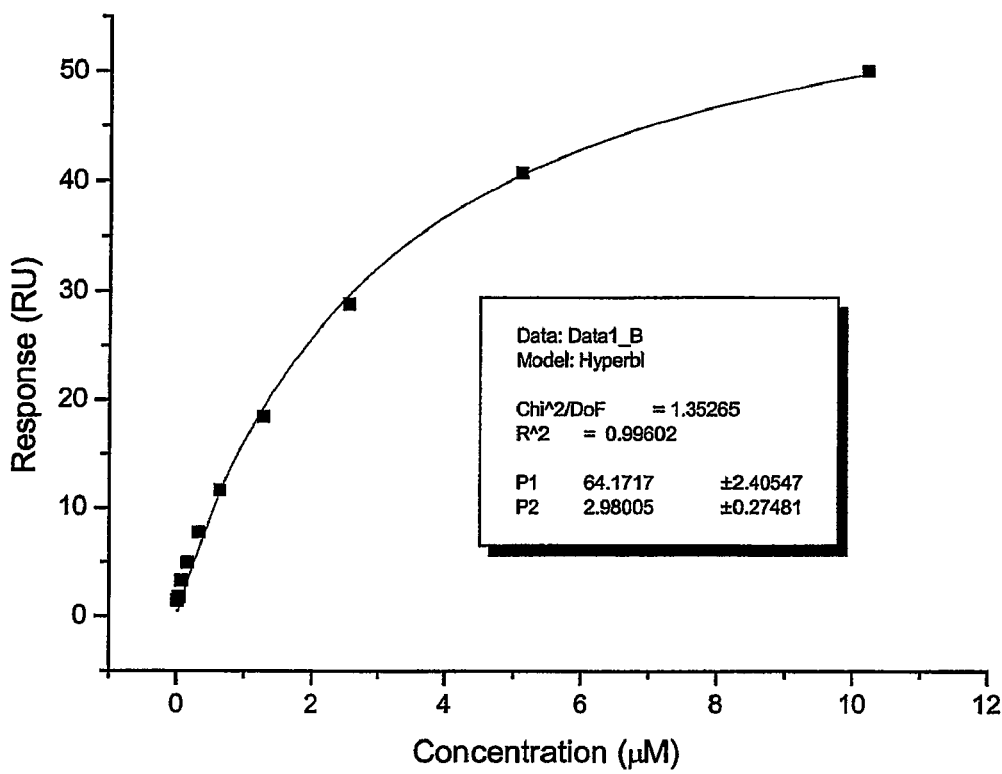
B
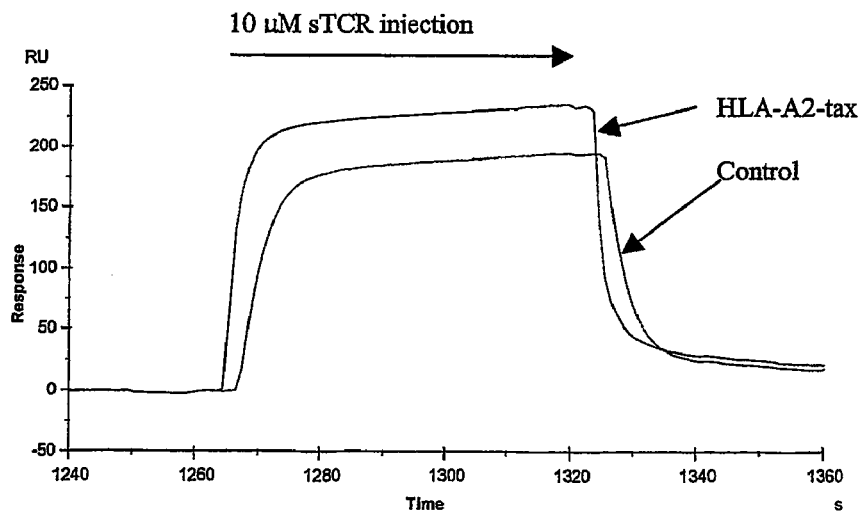

Figure 107

```
   1 GAATTCACCA TGGATCCTAG GGCCCACAAG CTTACGCGTC GACCCGGGTA TCCGTATGAT GTGCCTGACT ACGCATGATA TCTCGAGCTC AGCTAGCTAA
 101 CTGAATAAGG AACAATGAAC GTTTTTCCTT TCTCTTGTTC CTAGTATTAA TGACTGACCG ATACATCCCT TTTTTTTTTT GTCTTTGTCT AGTTCCAGCT
 201 TTTGTTCCCT TTAGTGAGGG TTAATTCAAT TCACTGGCCG TCGTTTTACA ACGTCGTGAC TGGGAAAACC CTGGCGTTAC CCAACTTAAT CGCCTTGCAG
 301 CACATCCCCC TTTCGCCAGC TGGCGTAATA GCGAAGAGGC CCGCACCGAT CCCCAGCGCA AACAGTGCGG CAGCCTGAAT GGCGAATGGC GCGACGCGCC
 401 CTGTAGCGGC GCATTAAGCG CGGCGGGTGT GGTGGTTACG CGCAGCGTGA CCGCTACACT TGCCAGCGCC CTAGCGCCCG CTCCTTTCGC TTTCTTCCCT
 501 TCCTTTCTCG CCACGTTCGC CGGCTTTCCC CGTCAAGCTC TAAATCGGGG GCTCCCTTTA GGGTTCCGAT TTAGTGTTTT ACGGCACCTC GACCCCAAAA
 601 AACTTGATTA GGGTGATGGT TCACGTAGTG GGCCATCGCC CTGATAGACG GTTTTTCGCC CTTTGACGTT GGAGTCCACG TTCTTTAATA GTGGACTCTT
 701 GTTCCAAACT GGAACAACAC TCAACCCTAT CTCGGTCTAT TCTTTTGATT TATAAGGGAT TTTGCCGATT TCGGCCTATT GGTTAAAAAA TGAGCTGATT
 801 TAACAAAAAT TTAACGCGAA TTTTAACAAA ATATTAACGT TTACAATTTC CTGATGCGGT ATTTTCTCCT TACGCATCTG TGCGGTATTT CACACCGCAT
 901 AGGGTAATAA CTGATATAAT TAAATTGAAG CTCTAATTTG TGAGTTTAGT ATACATGCAT ATTTCTTCCT TACAGTTTTT TAGTTTTGCT GGCCGTATCT
1001 TCTCAAATAT GCTTCCCAGC CTGCTTTTCT GTAACGTTCA CCCTGTACCT TAGCATCCCT AATAGTCCTC AATAGTCCTC TTCCAACAAT AATAATGTCA
1101 GATCCGTAGA AGACCACATC ATCCACGGTT CTATACTGTT GACCCAATGC GTCTCCCTTG TCATCTAAAC CCACACCGGG TGTCATAATC AACCAATCGT
1201 AACCTTCATC TCTTCCACCC ATGTCTCTTT GAGCAATAAC AGCCAATAACA AAATCTTTGT CGCTCTTCGC AATGTCAACA GTACCCTTAG TATATTCTCC
1301 AGTAGATAGG GAGCCCTTGC ATGACAATTC TGCTAACATC AAAAGGCCTC TAGGTTCCTT TGTTACTTCT CTGCCGCCCT GCTTCAAACC GCTAACAATA
1401 CCTGGCCCCA GCACACCGTG TGCATTCGTA ATGTCTGCCC ATTCTGCTAT TCTGTATACA CCCGCAGAGT ACTGCAATTT GACTGTATTA CCAATGTCAG
1501 CAAATTTTCT GTCTTCGAAG AGTAAAAAAT TGTACTTTGGC GGATAATGCC TTTAGCGGCT TAACTGTGCC CTCCATCGAA AAATCAGTCA ATATATCCAC
1601 ATGTGTTTTT AGTAAACAAA TTTTGGGACC ACTAACTCCA GTAAATTCCTT GGTGGTACGA ACACACAAA AAGCACACAA GTTTGTTTGC
1701 TTTTCGTGCA TGATATTAAA TAGCTTGGTA GCAACAGGAC TAGGATGAGT AGCAGCACGT TCCTTATATG TAGCTTTTGA CATGATTTAT CTTCGTTTCC
1801 TGCAGGTTTT TGTTCTGTGC AGTTGGGTTA AGAATACTGG GCAATTTCAT GTTTTCTTCAA AAAGAAACCG GCTATATAT ACCAATCTAA GTCTGTCTC
1901 CTTCCTTCGT TCTTCCTTCT GTTCGGAGAT TACCGAATCA AAAAAATTTC AAAAGAAACG AAATCAAAAA AAAGAATAAA ACCGCTGAAC TGAATTGAAT
2001 TGAAAAGCTG TGGTATGGTG CACTCTCAGT ACAATCTGCT CTGATGCCGC ATAGTTAAGC CAGCCCCGAC ACCCGCTGAC GCGCCCTGAC
2101 GGGCTTGTCT GCTCCCGGCA TCCGCTTACA GACAAGCTGT GACCGTCTCC GGGAGCTGCA TGTGTCAGAG GTTTTCACCG TCATCACCGA AACGCGCGAG
2201 ACGAAAGGGC CTCGTGATAC GCCTATTTTT ATAGGTTAAT GTCATGATAA TAATGGTTTC TGCTTGCCT GTAACTTACA TCTTGTTACA ACGCGCCTCGT
2301 ATCTTTTAAT GATGGAATAA TTTGGGAATT TACTCTGTGT TTATTTATTT TCTAAATGTG GTATTGGATT TACATATA TTAGAAAGTA AATAAAGAAG GTAGAAGAGT
2401 TACGGAATGA AGAAAAAAAA ATAAACAAAG GTTTAAAAAA TACTGAGTT TCCAACGGCT CACAGAAAAG TAATGCAGTG AAGAAAGCA GATTAAATGA
2501 ATATACATTC GATTAACGAT AAGTAAAATG TAAAATCACA GGATTTTCGT CTACACAGAC AATGGCAT AATTGGCAT AATTTCTTTT
2601 GAGCAGGAAG AGCAAGATAA AAGGTAGTAT TTGTTGGCGA TCCCCCTAGA GTCTTTTACA TCTTCGGAAA ACAAAACTA CCCAGGTGGC ACTTTTCGGG
2701 TTTACTTTCT ATTTTTAATT TATATATTTA TATTAAAAA TTTAAATTAT AATTATTTT ATAGCACGTG AGAAAGGA ATGAAGCG TAAATGCTTC AATAATATTG
2801 GAAATGTGCG CGGAACCCCT CGGAACTGTA ATTTGTTTAT TTTTCTAAT ACATTCAAAT ATGTATCCGC TCATGAGACA ATAACCGTGA CTCACCAGA AACGCTGGTG
2901 AAAAGGAAG AGTATGAGTA TTCAACATTT CCGTGTCGCC CTTATTCCCT TTTTGCGGC CATTGCGG GATCTC ATTTTGCCTT ACTGAGTCGA AGTTGGTA CCCGAAGAAC
3001 AAAGTAAAG ATGCTGAAGA TCAGTTGGGT GCACGAGTGG GTTACATCGA ACTGGATCT GCCGGGCAA CATCTTACGG CGGGTATTG ACTGGATTG TCCCGTATTG GGAGTCGTTG
3101 GTTTTCCAAT GATGAGCACT TTTAAAGTTC TGCTATGTGG CGCGGTATTA TCCCGTATTG CGCGGTATTA ATGCATGAC AGAGCAACTC GCTCGCCGCA TACACTATTC
3201 TCAGAATGAC TTGGTTGAGT ACTCACCAGT CACAGAAAAG CATCTTACGG ATGGCATGAC AGTAAGAGAA TTATGCAGTG CTGCCATAAC CATGAGTGAT
3301 AACACTGCGG CCAACTTACT TCTGACAACG ATCGGAGGAC CGAAGGAGCT AACCGCTTTT TTGCACAACA TGGGGGATCA TGTAACTCGC CTTGATCGTT
3401 GGGAACCGGA GCTGAATGAA GCCATACCAA AACAATTAAT AGACTGGATG GAGGCGGATA AAGTTGCAGG ACCACTTCTG CGCTCGGCCC TTCCGGCTGG
3501 ACTTACTCTA GCTTCCCGGC AACAATTAAT AGACTGGATG GAGGCGGATA AAGTTGCAGG ACCACTTCTG CGCTCGGCCC TTCCGGCTGG CTGGTTTATT
3601 GCTGATAAAT CTGGAGCCGG TGAGCGTGGG TCTCGCGGTA TCATTGCAGC ACTGGGGCCA GATGGTAAGC CCTCCCGTAT CGTAGTTATC TACACGACGG
3701 GGAGTCAGGC AACTATGGAT GAACGAAATA GACAGATCGC TGAGATAGGT GCCTCACTGA TTAAGCATTG GTAACTGTCA GACCAAGTTT ACTCATATAT
```

Figure 107 continued

```
3801 ACTTTAGATT GATTTAAAAC TTCATTTTTA ATTTAAAAGG ATCTAGGTGA AGATCCTTTT TGATAATCTC ATGACCAAAA TCCCTTAACG TGAGTTTTCG
3901 TTCCACTGAG CGTCAGACCC CGTAGAAAAG ATCAAAGGAT CTTCTTGAGA TCCTTTTTTT CTGCGCGTAA TCTGCTGCTT GCAAACAAAA AAACCACCGC
4001 TACCAGCGGT GGTTTGTTTG CCGGATCAAG AGCTACCAAC TCTTTTTCCG AAGGTAACTG GCTTCAGCAG AGCGCAGATA CCAAATACTG TCCTTCTAGT
4101 GTAGCCGTAG TTAGGCCACC ACTTCAAGAA CTCTGTAGCA CCGCCTACAT ACCTCGCTCT GCTAATCCTG TTACCAGTGG CTGCTGCCAG TGGCGATAAG
4201 TCGTGTCTTA CCGGGTTGGA CTCAAGACGA TAGTTACCGG ATAAGGCGCA GCGGTCGGGC TGAACGGGGG GTTCGTGCAC ACAGCCCAGC TTGGAGCGAA
4301 CGACCTACAC CGAACTGAGA TACCTACAGC GTGAGCTATG AGAAAGCGCC ACGCTTCCCG AAGGGAGAAA GGCGGACAGG TATCCGGTAA GCGGCAGGGT
4401 CGGAACAGGA GAGCGCACGA GGGAGCTTCC AGGGGGAAAC GCCTGGTATC TTTATAGTCC TGTCGGGTTT CGCCACCTCT GACTTGAGCG TCGATTTTTG
4501 TGATGCTCGT CAGGGGGGCG GAGCCTATGG AAAAACGCCA GCAACGCGGC CTTTTTACGG TTCCTGGCCT TTTGCTGGCC TTTTGCTCAC ATGTTCTTTC
4601 CTGCGTTATC CCCTGATTCT GTGGATAACC GTATTACCGC CTTTGAGTGA GCTGATACCG CTCGCCGCAG CCGAACGACC GAGCGCAGCG AGTCAGTGAG
4701 CGAGGAAGCG GAAGAGCGCC CAATACGCAA ACCGCCTCTC CCCGCGCGTT GGCCGATTCA TTAATGCAGC TGGCACGACA GGTTTCCCGA CTGGAAAGCG
4801 GGCAGTGAGC GCAACGCAAT TAATGTGAGT TAGCTCACTC ATTAGGCACC CCAGGCTTTA CACTTTATGC TTCCGGCTCG TATGTTGTGT GGAATTGTGA
4901 GCGGATAACA ATTTCACACA GGAAACAGCT ATGACCATGA TTACGCCAAG CTCGAAATAC CTCGAATACC CTCGAATC AGGGCGAATT ACATGATCCC CCGGCCGTCG
5001 AGCTTGATGG CATCGTGGTG TCACGCTCGT CGTTTGGTAT GGCTTCATTC AGCTCCGGTT CCCAACGATC AAGGCGAGTT ACATGATCCC CCATGTTGTG
5101 AAAAAAGCG GTTAGCTCTT CATCCCCGTA ATGCTTTTCT GAAGTAAGTT TACTCAACCA AGTCATTCTG AGAATAGTGT ATGCGGCGAC CGAGTTGCTC TTGCCCGGCG
5201 ACTGTCATGC CATCCGTAAG ATGCTTTTCT CGGTCCTTTCT GTGACTGGTG AGTCATTCTG AGAATAGTGT ATGCGGCGAC CGAGTTGCTC TTGCCCGGCG
5301 TCAACACGGG ATAATACCGC GCCACATAGC AGAACTTTAA AAGTGCTCAT CATTGGAAAA CGTTCTTCGG GGCGAAAACT CTCAAGGATC TTACCGCTGT
5401 TGAGATCCAG TTCGATGTAA CCCCACTCGTG GAAATGTTGA ATACTCATAC TCTTCCTTTT TCAATATTAT TGAAGCATTT TCCGGAGCAA GAAGCAAAAA
5501 TGCCGCAAAA AAGGGAATAA GGGCGACACG GAAATGTTGA ATACTCATAC AGGGGTTCCG CGCACATTTC CCCGAAAAGT GCCACCTGAC GTCTAAGAAA CCATTATTAT
5601 AGCGGATACAT ATTTGAATGT ATTTAGAAAA ATAAACAAAT AGGGGTTCCG TTTCGTCTTC AAGAATTGGG GATCTTCGTA TCTTCAGATT CCCTCATGGA
5701 CATGACATTA ACCTATAAAA ATAGGCGTAT CACGAGGCCC TTTCGTCTTC AGAGACTTTA TTCAGGCACT GATGGACATA TTCAGGACTT CCAATGTTCC
5801 GAAGTGCGGC AGATGTATAT GACAGAGTCG CCAGTTTCCA AAATGGTTTA TCCTGAGGAC CGTGCTACCC AAATGGACTG ATTGTGAGGG AGACCAGAG ATGTTGTGT
5901 CCTAGTTACA CATGGTATTT ATTCCAGAGT CGAATCCATC AATAGATACG TCCTGAGGAC CGTGCTACCC AAATGGACTG ATTGTGAGGG AGACTAACT ACATAGTGTT
6001 GTAATGGTGA TGGAACTGAA CTTACTTAGA ATAATGCCAT TTTTTTGAGT CTACTTATTC TATAATAATC CTAGTTAGT GTGAGCGGGA TTTAAACTGT GAGGACCTCA
6101 TAAAGATTAC GGATATTTAA ACACTTCTGA CGGTATCACC CTACTTATTC TATAATAATC CTACTTATTA CTACTTAGG AACCCATCAG GTTGGTGGAA GATTACCCGT TCTAAGACTT
6201 ATACATTCAG ACACTTCTGA TCTATTGATG TTACACTCGG AGCATAATTT AGGAGTTTAG TGAACTTGCA ACATTACTA TTTTCCCTTC TTACGTAAAT ATTTTTCTTT AATTAAAGCA
6301 TTCAGCTTCC TCTATTCGGA TATAAAGGGC AGCATAATTT AGGAGTTTAG TGAACTTGCA ACATTACTA TTTTCCCTTC TTACGTAAAT ATTTTTCTTT AATTAAAGCA
6401 AICACACAAT TCTCTCGGAT TATAAAGGGC AGCATAATTT AGGAGTTTAG TGAACTTGCA ACATTACTA TTTTCCCTTC TTACGTAAAT ATTTTTCTTT TAATTCTAA
6501 TAACAGGGAA TATAAAGGGC AGCATAATTT TGTTTGTATT CTTTTTCTTGC TTAAATCTAT AACTACAAAA AACACATACA G
6601 ATCAATCTTT TTCAATTTTT TGTTTGTATT CTTTTTCTTGC TTAAATCTAT AACTACAAAA AACACATACA G
```

Figure 108

```
   1 GAATTCACCA TGGATCCTAG GGCCCACAAG CTTACGCGTC GACCCGGGTA TCCGTATGAT GTGCCTGACT ACGCATGATA TCTCGAGCTC AGCTAGCTAA
 101 CTGAATAAGG AACAATGAAC GTTTTTTCCTT TCTCTTGTTC CTAGTATTAA TGACTGACCG ATACATCCCT TTTTTTTTTT GTCTTTGTCT AGCTCCAGCT
 201 TTTGTTCCCT TTAGTGAGGG TTAATTCAAT TCACTGGCCG TCGTTTTACA AGTCGTGAC TGGGAAAACC CTGGCGTTAC CCAACTTAAT CGCCTTGCAG
 301 CACATCCCCC TTTCGCCAGC TGGCGTAATA GCGAAGAGGC CCGCACCGAT CGCCCTTCCC AACAGTTGCG CAGCCTGAAT GGCGAATGGC GCGACGCGCC
 401 CTGTAGCGGC GCATTAAGCG CGGCGGGTGT GGTGGTTACG CGCAGCGTGA CCGCTACACT TGCCAGCGCC CTAGCGCCCG CTCCTTTCGC TTTCTTCCCT
 501 TCCTTTCTCG CCACGTTCGC CGGCTTTCCC CGTCAAGCTC TAAATCGGGG GCTCCCTTTA GGGTTCCGAT TTAGTGCTTT ACGGCACCTC GACCCCAAAA
 601 AACTTGATTA GGGTGATGGT TCACGTAGTG GGCCATCGCC CTGATAGACG GTTTTTCGCC CTTTGACGTT GGAGTCCACG TTCTTTAATA GTGGACTCTT
 701 GTTCCAAACT GGAACAACAC TCAACCCTAT CTCGGTCTAT TCTTTTGATT TATAAGGGAT TTTGCCGATT TCGGCCTATT GGTTAAAAAA TGAGCTGATT
 801 TAACAAAAAT TTAACGCGAA TTTTAACAAA ATATTAACGT TTACAATTTC CTGATGCGGT ATTTTCTCCT TACGCATCTG TGCGGTATTT CACACCGCAT
 901 AGATCCGTCG AGTTCAAGAG AAAAAAAAG AAGAAAAAG CATTCATAGG GAAAGCGCGC CTCGTTCAGA ATGACACGTA TAGAATGATG CATTACCTTG
1001 TCATCTTCAG TATCATACTG TTCGTATACA TACTTACTGA CATTCATAGG TATACATGTA TATATATCGT ATGCTGCAGC TTTAAATAAT
1101 CGGTGTCACT ACATAAGAAC ACCTTTGGTG GAGGGAACAT CGTTGGTTCC CTCGTTCTC GTGGCTTCTC CGCAAGAGCC TTGAACGCAC
1201 TCTCACTACG GTGATGATCA TTCTTGCCTC GCAGGAACAAGT AACGTGGAGG GTAATTCTGC TTGCCTCTGC AAAACTTTCA AGAAAATGCG GGATCATCTC
1301 GCAAGAGAGA TCTCCTACTT TCTCCCTTTG CAAACCAAGT TCGACAACTG CGTACGGCCT GTTCGAAAGA TCTACCACCG CTCTGGAAAG TGCCTCATCC
1401 AAAGGCGCAA ATCCTGATCC AAACCTTTTT ACTCCACGCG CCAGTAGGGC CTCTTTAAAT GCTGACCGA GAGCAATCCC GCAGTCTTCA GTGGTGTGAT
1501 GGTCGTCTAT GTGTAAGTCA CCAATGCACT CAACGATTAG CGACCAGCCG GAATGCTTGG CCAGACCATG TATCATATGG TCCAGAAACC CTATACCTGT
1601 GTGGACGTTA ATCACTTGCG ATTGTGTGGG CTGTTCTGCT ACTGGTTCTG GGCTTTCTGC CCTCTCTTTC GAGTGCTCTA TTGCCTTTGC ACCAGCTTT
1701 AAAGAGACGT CAATCTGAAT CTTGGTTTCA ATTACCGAGC GTATAATTCA GTATAATTAAT GCCAATCG CTAAGAAAAA AAAAGAGTCA TCCGCTAGGG
1801 TTAGTATATT CTTCGAAGGA ATCACATTAC ATTACCGAGG CATAAAAAA TATAGAGTGT ACTAGAGAG ATGCCAATCG CTAAGAAAAA AAAGAGTCA
1901 GAAAAAAAAA AATGAAAATC AATTAAAATT ATTACCGAGG CATAAAAAA TATAGAGTGT ACTAGAGAG ATGCCAAGAGTA AAAAGAGTCA TCCGCTAGGG
2001 TGTTATGACT TCCCTGACTA ATGCCGTGTT CTAAACGATAC CTGGCAGTGA ACACCCTTG TCACCAAGCT ACGGCCCCTG CTTAAACCG GAATTATGG TGCACTCTCA
2101 GTACAATCTG CTCTGATGCC GCATAGTTAA GCCAGCCCG ACACCCCA AGGTTTTAC CGTCATCACC GAAACGCGCG AGACGAAAGG ACGGGCTTGT CTGCTCCCGG CATCCGCTTA
2201 CAGACAAGCT GTGACCGTCT CCGGGAGCTG CATGTGTCAG AGGTTTTCAC CGTCATCACC GAAACGCGCG AGACGAAAGG GCCTCGTGAT ACGCCTATT
2301 TTATAGGTTA ATGTCATGAT AATAATGGTT TCTTAGACG CTGTAACTTA TAAATAAAGA CAGCGCCTC GTACGCCTC GTATCTTTA ATGATGGAAT AATTGGGAA
2401 TTTACTCTGT GTTTATTTAT TTTTATGTT TGTATTTGGA TTTTAGAAAG ACAATTGGG ATTAATACAT AGAAGAAAAA GAAGAAAAAA AATAAACAA
2501 AGGTTTAAAA AATTTCAACA CAGGATTTTC GTGTGTGGTC TTCTACACAG ACAAGATGAA ACAATTCGGC ATTAATAACT AGAGCAGGA AGAGCAAGAT AAAAGTAGT
2601 TGTAAAATCA CAGGATTTTC GTGTGTGGTC TTCTACACAG ACAAGATGAA ACAATTCGGC ATTAATAACT TTAATTTTCT TTTTTACTTT CTATTTTTAA TTTATATATT
2701 ATTTGTTGGC GATCCCCCTA GAGTCTTTTA CATCTTCGGA AAACAAAAAC TATTTTTTCT GACCCAGGTG GCACTTTTCG CGCGGAACCC CTATTTGTTT
2801 TATATTAAAA AATTTAAATT ATAATTATTT TTATAGCACG TGATGAAAAG GACCCAGGTG GCACTTTTCG CGCGGAACCC CTATTTGTTT
2901 ATTTTCTAA ATACATTCAA ATATGTATCC GCTCATGAGA CAATAACCCT GATAAATGCT TCAATAATAT TGAAAAAGGA AGAGTATGAG TATTCAACAT
3001 TTCCGTGTCG CCCTTATTCC CTTTTTTGCG GCATTTTGCC TTCCTGTTTT TGCTCACCCA GAAACGCTGG TGAAAGTAAA AGATGCTGAA GATCAGTTGG
3101 GTGCACGAGT GGGTTACATC GAACTGGATC TCAACAGCGG TAAGATCCTT GAGAGTTTTC GCCCCGAAGA ACGTTTTTCCA ACTTGGTTGA CTTTAAAGT
3201 TCTGCTATGT GGCGCGGTAT TATCCCGTAT TGACGCCGGG CAAGAGCAAC TCGGTCGCCG CATACACTAT TCTCAGAATG ACTTGGTTGA GTACTCACCA
3301 GTCACAGAAA AGCATCTTAC ACGGATGGCA TGACAGTAAG AGAATTATGC AGTGCTGCCA TAACCATGAG TGATAACACT GCGGCCAACTTA CTTCTGACAA
3401 CGATCGGAGG ACCGAAGGAG CTAACCGCTT TTTTTGGACAA AGTAGACTTA CATCGGGGAT CATGTAACTC GCCTTGATCG TTGGGAACCG GAGCTGAATG AAGCCATACC
3501 AAACGACGAG CGTGACACCA CGATGCCTGT AGCAATGGCA ACAACGTTGC GCAAACTATT AACTGGCGAA CTACTTACTC TAGCTTCCCG GCAACAATTA
3601 ATAGACTGGA TGGAGGCGGA TAAAGTTGCA GGACCACTTC TGCGCTCGGC CCTTCCGGCT GGCTGGTTTA TTGCTGATAA ATCTGGAGCC GGTGAGCGTG
3701 GGTCTCGCGG TATCATTGCA GCACTGGGGC CAGATGGTAA GCCCTCCCGT ATCGTAGTTA TCTACACGAC GGGAGTCAG GCAACTATGG ATGAACGAAA
```

Figure 108 continued

```
3801  TAGACAGATC GCTGAGATAG GTGCCTCACT GATTAAGCAT TGGTAACTGT CAGACCAAGT TTACTCATAT ATACTTTAGA TTGATTTAAA ACTTCATTTT
3901  TAATTTAAAA GGATCTAGGT GAAGATCCTT TTTGATAAATC TTTCTGCGCGT TCATGACCAA AATCCCTTAA CGTGAGTTTT CGTTCCACTG AGCGTCAGAC CCCGTAGAAA
4001  AGATCAAAGG ATCTTCTTGA GATCCTTTTT TTCTGCGCGT AATCTGCTGC TTGCAAACAA AAAAACCACC GCTACCAGCG GTGGTTTGTT TGCCGGATCA
4101  AGAGCTACCA ACTCTTTTTC CGAAGGTAAC TGGCTTCAGC AGAGCGCAGA TACCAAATAC TGTCCTTCTA GTGTAGCCGT AGTTAGGCCA CCACTTCAAG
4201  AACTCTGTAG CACCGCCTAC ATACCTCGCT CTGCTAATCC TGTTACCAGT GGCTGCTGCC ACACAGCCCA GCTTGGAGCG AGTCGTGTCT TACCGGGTTG GACTCAAGAC
4301  GATAGTTACC GGATAAGGCG CAGCGGTCGG GCTGAACGGG GGGTTCGTGC ACACAGCCCA GCTTGGAGCG AACGACCTAC ACCGAACTGA GATACCTACA
4401  GCGTGAGCTA TGAGAAAGCG CCACGCTTCC CGAAGGGAGA AAGGCGGACA GGTATCCGGT AAGCGGCAGG GTCGAACAG GAGAGCGCAC GAGGGAGCTT
4501  CCAGGGGGAA ACGCCTGGTA TCTTTATAGT CCTGTCGGGT TTCGCCACCT CTGACTTGAG CGTCGATTTT TGTGATGCTC GTCAGGGGGG CGGAGCCTAT
4601  GGAAAAACGC CAGCAACGCG GCCTTTTTAC GGTTCCTGGC CTTTTGCTGG CCTTTTGCTC ACATGTTCTT TCCTGCGTTA TCCCCTGATT CTGTGGATAA
4701  CCGTATTACC GCCTTTGAGT GAGCTGATAC CGCTCGCCGC AGCCGAACGA CCGAGCGCAG CGAGTCAGTG AGCGAGGAAG CGGAAGAGCG CCCAATACGC
4801  AAACGCCTC TCCCCGCGCG TTGGCCGATT CATTAATGCA GCTGGCACGA CAGGTTTCCC GACTGGAAAG CGGGCAGTGA GCGCAACGCA ATTAATGTGA
4901  GTTACCTCAC TCATTAGGCA CCCCAGGCTT TACACTTTAT GCTTCCGGCT CCTATGTTGT GTGGAATTGT GAGCGGATAA CAATTTCACA CAGGAAACAG
5001  CTATGACCAT GATTACGCCA AGCTCGAAAT ACGACTCACT ATAGGGCGAA TTGGGTACCG GGCCGGCCGT CCCCATGTTG TTACATGATC TAACATGATC
5101  GTCGTTTGGT ATGGCTTCAT TCAGCTCCGG TTCCAACGA TCAAGGCGAG CATGGTTATG TTACATGATC CCCATGTTG CATAATTCTC TTACTTAGCTC TTCGGTCCTC
5201  CGATCGTGT CAGAAGTAAG TTGGCCGCAG TGTTATCACT CATGGTTATG GTATGCGGCG ACCGAGTTGC TCTTGCCCGG CGTCAACACG GCGAATACG AGATGCTTT
5301  CTGTGACTGG TGTACTCAAC CAAGTCATTC TGAGAATAGT GGGGCGAAAA TCTTCAAGGA TCTTACCGCT GTTGAGATCC AGTTCGATGT ACCCACTG
5401  GCAGAACTTT AAAAGTGCTC ATCATTGGAA AACGTTCTTC GTTTCTGGGT GCAGAAAAAC AGGAAGGCAA AATGCCGCAA AAAAGGGAAT AAGGGCGACA
5501  TGCACCCAAC TGATCTTCAG CATCTTTTAC TTTCACTGA TTTCAATATT ATTGAAGCAT TTATCAGGGT TATTGTCTCA TGAGCGGATAC ATATTTGAAT GTATTAGAA
5601  CGGAAATGTT GAATACTCAT ACTCTTCCTT TTTCAATATT TCCCCGAAAA GTGCCACCTG ACGTCTAAGA AACCATTATT ATCATGACAT TAACCTATAA AAATAGGCGT
5701  AAATAAACAA ATAGGGGTTC CGCGCACATT TCCCCGAAAA TGTGGTCATT TATGGTCATT AGTTCCTGTC TCTTCGTCT CAAGAATTG CGCGCACATT TCAGCTCCGG GGATCTACG GGGATCTACG TTCCCATG GCAGATGTAT ATGACAGAGT
5801  ATCACGAGGC CCTTTCGTCT CAAGAATTG CGCGCACATT TCAGCTCCGG GGATCTACG TATGGTCATT AGGCAAGAGA GAAGACCCAG AGATGTTGTT GTCCTAGTTA CACATGGTAT TTATTCCAGA
5901  CGCCAGTTTC CAAGAGACTT TATTCAGGCA CTTGCCATGA TACGAAGAGT CCTCCATGA TTGAATCGTT TACCAATGTT CCTAACGGGA GCGTAATAGTG GATGGAACTG GACGAATCCA
6001  GTATTCCTGA TGAAATGGTT TAGAATGGTT ACCGTGCTAC CCAAATGGAC TCCTACGTTA TGATTGTGAG TGTGTGAGCGG AGGTTGGTGG AGGATTACCC CCTCTATTGA GACGTATCA
6101  TCAATAGATA CGTCCTGAGG ATTTTTTGA GTTATAAATAA ATTATATCTA GGAACCCATC ATCTTCAGTG GCATGTGAGA AAGGAGCCTA GTTCTAAGAC CAATACATTC AACGTTACTTA
6201  GAATAATGCC ATTTTTTTGA CCAGTTTTTA ATCTTCAGTG TGCTAATGCA AAGGAGCCTA TTCTCCGAAA TTAATTAAAG CAATCACACA ATTCTCTCGG ATACCACCTC
6301  CCCTACTTAT TCCCCTTGAG ACCAGGGTGT TGTTACGCA TGCTAATGCA AAGGAGCCTA TCTCTCAGAA TTAATTAAAG CAATCACACA ATTCTCTCGG ATACCACCTC
6401  GGACACCCT TTTCTGGCAT GACAGGTGGT AGTGAACTTG CAACATTTAC TATTTTCCCT TCTTACGTAA TTTTAAATCT ATATTTCCT TTTCAATTT TTTGTTGTA
6501  GGTTGAAACT GACAGGTGGT AGTGAACTTG GCTTAAATCT ATAACTACAA AAAACACATA CAG
```

Figure 109

```
          MetArg PheProSer IlePheThr AlaValLeuPhe AlaAlaSer SerAlaLeu AlaAlaAlaProVal AsnThrThr ThrGluAsp GluThrAlaGln·
  1   GAATTC[highlighted sequence]
      ·IleProAla GluAlaVal IleGlyTyrLeu AspLeuGlu GlyAlaVal GlyAspPhe AspValAlaVal LeuProPhe SerAsnSer ThrAsnAsnGly LeuLeuPhe·
101   [highlighted sequence]
      ·IleAsnThr ThrIleAlaSer IleAlaAla LysGluGlu GlyValSerLeu AspLysArg GluAlaGlu AlaGlnGluVal ThrGlnIle ProAlaAla
201   [highlighted sequence]                                              CAGGAGG TGACACAGAT TCCTGCAGCT
      LeuSerValPro GluGlyGlu LeuAsnCysSer PheThrAsp SerAlaIle TyrAsnLeuGln TrpPheArg GlnAspPro GlyLysGlyLyLeu·
301   CTGAGTGTCC CAGAAGGAGA AAACTTGGTT CTCAACTGCA GTTTCACTGA TAGCGCTATT TACAACCTCC AGTGGTTTAG GCAGGACCCT GGGAAAGTC
      ·ThrSerLeu LeuLeuIle GlnSerSerGln ArgGluGln ThrSerGly ArgLeuAsnAla SerLeuAsp LysSerSer GlyArgSerThr LeuTyrIle·
401   TCACATCTCT GTTGCTTATT CAGTCAAGTC AGAGAGAGCA AACAAGTGGA ACTTAATG TCCTCGCTGGA TAAATCATCA GGACGTAGTA CTTTATACAT
      ·AlaAlaSer GlnProGlyAsp SerAlaThr TyrLeuCys AlaValArgPro ThrSerGly GlySerTyr IleProThrPhe GlyArgGly ThrSerLeu
501   TGCAGCTTCT CAGCCTGGTG ACTCAAGCCAC CTACCTCTGT GCTGTGAGGC CCACATCAGG AGGAAGCTAC ATACCTACAT TTGGAAGAGG AACCAGCCTT
      IleValHisPro TyrIleGln AsnProAsp ProAlaValTyr GlnLeuArg SerSerAspLys LeuPheThr AspPheAspSer·
601   ATTGTTCATC CGTATATCCA GAACCCGGAT CCTGCCGTGT ACCAGTTGAG AGACTCTAAA TCCAGTGACA AGTCTGTCTG CCTATTCACC GATTTTGATT
      ·GlnThrAsn ValSerGln IleThrArg IleThrTyr LysCysValLeu AspMetArg SerMetAsp PheLysSerAsn SerAlaVal·
701   CTCAAACAAA TGTGTCACAA AGTAAGGATT CTGATGTGTA TATCACAGAC AAATGTGTGC TAGACATGAG GTCTATGGAC TTCAAGAGCA ACAGTGCTGT
      ·AlaTrpSer AsnLysSerAsp PheAlaCys AlaAsnAla PheAsnAsnSer IleIlePro GluAspThr PhePheProSer ProGluSer Ser***
801   GGCCTGGAGC AACAAATCTG ACTTTGCATG TGCAAACGCC TTCAACAACA GCATTATTCC AGAAGACACC TTCTTCCCCA GCCCAGAAAG TTCCTAACTC
901   GAG
```

The pre-pro mating factor alpha sequence is highlighted. *BamHI* site is underlined.

Figure 110

```
     MetArg PheProSer IlePheThr AlaValLeuPhe AlaAlaSer SerAlaLeu AlaAlaProVal AsnThrThr ThrGluAsp GluThrAlaGln
  1  GAATTCATGAGATTTCCTTCAATTTTTACTGCAGTTTTATTCGCAGCATCCTCCGCATTAGCTGCTCCAGTCAACACTACAACAGAAGATGAAACGGCACAA
     ..IleProAla GluAlaVal IleGlyTyrLeu AspLeuGlu GlyAspPhe AspValAlaVal LeuProPhe SerAsnSer ThrAsnAsnGly LeuLeuPhe
101  ATTCCGGCTGAAGCTGTCATCGGTTACTTAGATTTAGAAGGGGATTTCGATGTTGCCGTTTTGCCATTTTCCAACAGCACAAATAACGGGTTATTATTT
     .IleAsnThr ThrIleAlaSer IleAlaAla LysGluGlu GlyValSerLeu GlyValSerLeu AlaGlyAla LysLysArg GluAlaGlu AlaGlyValThr GlnThrPro LysPheGln
201  ATAAATACTACTATTGCGTCAATTGCAGCTAAAGAAGAAGGTGTATCACTTGATAAAAGAGAGGCTGAAGCTGGGGTCA CTCAGACCCC AAAATTCCAG
     ValLeuLysThr GlyGlnSer MetThrLeu GlnCysAlaGln AspMetAsn HisGluTyr MetSerTrpTyr ArgGlnAsp ProGlyMet GlyLeuArgLeu
301  GTCCTGAAGA CAGGACAGAG CATGACACTG CAGTGTGCCC AGGATATGAA CCATGAATAC ATGTCCTGGT ATCGACAAGA CCCAGGCATG GGGCTGAGGC
     ..IleHisTyr SerValGly AlaGlyIleThr AspGlnGly GluValPro AsnGlyTyrAsn ValSerArg SerThrThr GluAspPhePro LeuArgLeu
401  TGATTCATTA CTCAGTTGGT GCTGGTATCA CTGACCAAGG AGAAGTCCCA AATGGCTACA ATGTCTCCAG AGAACCACA GAGGATTTCC CGCTCAGGCT
     .LeuSerAla AlaProSerGln ThrSerVal TyrPheCys AlaSerSerTyr ValGlyAsn ThrGlyGlu LeuPhePheGly GluGlySer ArgLeuThr
501  GCTGTCGGCT GCTCCCTCCC AGACATCTGT GTACTTCTGT GCCAGCAGTT ACGTCGGGAA CACCGGGGAG CTGTTTTTTG GAGAAGGCTC TAGGCTGACC
     ValLeuGluArg ProLysAsn ValPhePro AspHisValAla ValPheGlu ProSerGlu AlaGluIleSer HisThrGln LysValCysLeu LeuValCysLeu
601  GTACTGGAGG ACCTGAAAAA CGTGTTCCCA CCCGAGGTCG CTGTGTTTGA GCCATCAGAA GCAGAGATCT CCCACACCCA AAAGGCCACA CTGGTGTGCC
     ..AlaThrGly PheTyrPro AspHisValGlu LeuSerTrp TrpValAsn GlyLysGluVal HisSerGly ValCysThr AspProGlnPro LeuLysGlu
701  TGGCCACAGG CTTCTACCCC GACCACGTGG AGCTGAGCTG GTGGGTGAAT GGGAAGGAGG TGCACAGTGG GGTCTGCACA GACCCGCAGC CCCTCAAGGA
     .GlnProAla LeuAsnAspSer ArgTyrAla LeuSerSer ArgLeuArgVal SerAlaThr PheTrpGln AspProArgAsn HisPheArg CysGlnVal
801  GCAGCCCGCC CTCAATGACT CCAGATACGC TCTGAGCAGC CGCTGAGGG TCTCGGCCAC CTTCTGGCAG GACCCCCGCA ACCACTTCCG CTGTCAAGTC
     GlnPheTyrGly LeuSerGlu AsnAspGlu TrpThrGlnAsp ArgAlaLys ProValThr GlnIleValSer AlaGluAla TrpGlyArg AlaAsp***
901  CAGTTCTACG GGCTCTCGGA GAATGACGAG TGGACCCAGG ATAGGGCCAA ACCCGTCACC CAGATCGTCA GCGCCGAGGC CTGGGGTAGA GCAGACTAAC
1001 TCGAG
```

The pre-pro mating factor alpha sequence is highlighted.

Figure 111

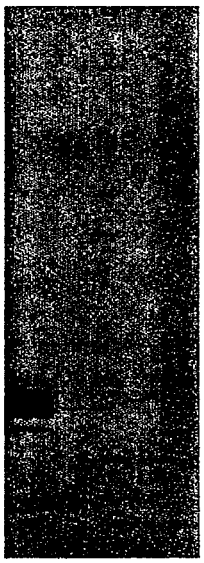

Figure 112 ggatccagcatggtgtgtctgaagctccctggaggctcctgcatgacagcgctgaca
gtgacactgatggtgctgagctccccactggctttgtccggagacaccggtggcgga
tctctagttccacgcggtagtggaggcggtggttccggagacacgcgttagtaggtc
gacggaggcggtgggggtagaatcgcccggctggaggaaaaagtgaaaaccttgaaa
gctcagaactcggagctggcgtccacggccaacatgctcagggaacaggtggcacag
cttaaacagaaagtcatgaactactaggatcc

Figure 113

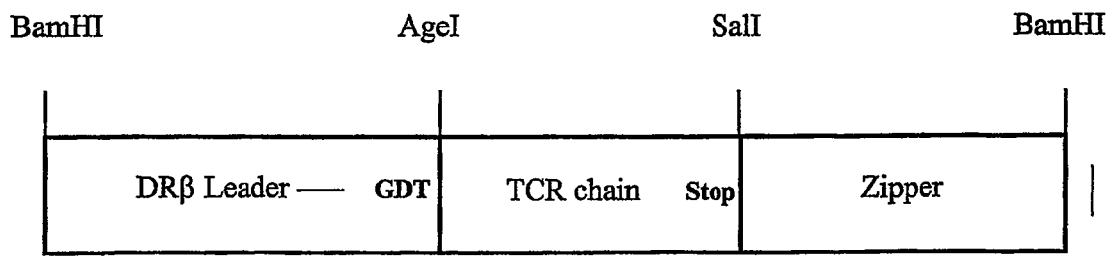

Figure 114 ggatccagcatggtgtgtctgaagctccctggaggctcctgcatgacagcgctgaca
gtgacactgatggtgctgagctccccactggctttgtccggagacaccggagacacc
ggacagaaggaagtggagcagaactctggacccctcagtgttccagagggagccatt
gcctctctcaactgcacttacagtgaccgaggttcccagtccttcttctggtacaga
caatattctgggaaaagccctgagttgataatgtccatatactccaatggtgacaaa
gaagatggaaggtttacagcacagctcaataaagccagccagtatgtttctctgctc
atcagagactccagcccagtgattcagccacctacctctgtgccgttacaactgac
agctgggggaaattgcagtttggagcagggacccaggttgtggtcacccagatatc
cagaaccctgaccctgccgtgtaccagctgagagactctaaatccagtgacaagtct
gtctgcctattcaccgatttgattctcaaacaaatgtgtcacaaagtaaggattct
gatgtgtatatcacagacaaatgtgctagacatgaggtctatggacttcaagagc
aacagtgctgtggcctggagcaacaaatctgactttgcatgtgcaaacgccttcaac
aacagcattattccagaagacaccttcttccccagcccagaaagttcctaagtcgac
ggaggcggtggggtagaatcgcccggctggaggaaaaagtgaaaaccttgaaagct
cagaactcggagctggcgtccacggccaacatgctcagggaacaggtggcacagctt
aaacagaaagtcatgaactactaggatcc

Figure 115 ggatccagcatggtgtgtctgaagctccctggaggctcctgcatgacagcgctgaca
gtgacactgatggtgctgagctccccactggctttgtccggagacaccggagacacc
ggaaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttccg
ctcaggctgctgtcggctgctccctcccagacatctgtgtacttctgtgccagcagg
ccgggactagcggggagggcgaccagagcagtacttcgggccgggcaccaggctcacg
gtcacagaggacctgaaaaacgtgttccacccgaggtcgctgtgtttgagccatca
gaagcagagatctcccacacccaaaaggccacactggtgtgcctggccacaggcttc
tacccgaccacgtggagctgagctggtgggtgaatgggaaggaggtgcacagtggg
gtctgcacagacccgcagcccctcaaggagcagcccgccctcaatgactccagatac
gctctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa
gtcgacggaggcggtggggtagaatcgcccggctggaggaaaaagtgaaaaccttg
aaagctcagaactcggagctggcgtccacggccaacatgctcagggaacaggtggca
cagcttaaacagaaagtcatgaactactaggatcc

SOLUBLE T CELL RECEPTORS

This application is a division of Ser. No. 10/486,924 filed Sep. 1, 2004, which is a national stage application of PCT/GB02/03986 filed Aug. 30, 2002, which was published in English on Mar. 13, 2003 and which claims the benefit of GB 0121187.9 filed Aug. 31, 2001, GB 0219146.8 filed Aug. 16, 2002, and Ser. No. 60/404,182 filed Aug. 16, 2002.

This application incorporates by reference the contents of a 142 KB text file created Jan. 29, 2008 and named "substitute_11926391 _sequence _listing," which is the sequence listing for this application.

The present invention relates to soluble T cell receptors (TCRs).

As is described in WO 99/60120, TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MHC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The TCR is a heterodimeric cell surface protein of the immunoglobulin superfamily which is associated with invariant proteins of the CD3 complex involved in mediating signal transduction. TCRs exist in αβ and γδ forms, which are structurally similar but T cells expressing them have quite distinct anatomical locations and probably functions. The extracellular portion of the receptor consists of two membrane-proximal constant domains, and two membrane-distal variable domains bearing polymorphic loops analogous to the complementarity determining regions (CDRs) of antibodies. It is these loops which form the binding site of the TCR molecule and determine peptide specificity. The MHC class I and class II ligands are also immunoglobulin superfamily proteins but are specialised for antigen presentation, with a polymorphic peptide binding site which enables them to present a diverse array of short peptide fragments at the APC cell surface.

Soluble TCRs are useful, not only for the purpose of investigating specific TCR-pMHC interactions, but also potentially as a diagnostic tool to detect infection, or to detect autoimmune disease markers. Soluble TCRs also have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an auto-immune peptide antigen.

Proteins which are made up of more than one polypeptide subunit and which have a transmembrane domain can be difficult to produce in soluble form because, in many cases, the protein is stabilised by its transmembrane region. This is the case for the TCR, and is reflected in the scientific literature which describes truncated forms of TCR, containing either only extracellular domains or extracellular and cytoplasmic domains, which can be recognised by TCR-specific antibodies (indicating that the part of the recombinant TCR recognised by the antibody has correctly folded), but which cannot be produced at a good yield, which are not stable at low concentrations and/or which cannot recognise MHC-peptide complexes. This literature is reviewed in WO 99/60120.

A number of papers describe the production of TCR heterodimers which include the native disulphide bridge which connects the respective subunits (Garboczi, et al., (1996), *Nature* 384(6605): 134-41; Garboczi, et al., (1996), *J Immunol* 157(12): 5403-10; Chang et al., (1994), *PNAS USA* 91: 11408-11412; Davodeau et al., (1993), *J. Biol. Chem.* 268 (21): 15455-15460; Golden et al., (1997), *J. Imm. Meth.* 206: 163-169; U.S. Pat. No. 6,080,840). However, although such TCRs can be recognised by TCR-specific antibodies, none were shown to recognise its native ligand at anything other than relatively high concentrations and/or were not stable.

In WO 99/60120, a soluble TCR is described which is correctly folded so that it is capable of recognising its native ligand, is stable over a period of time, and can be produced in reasonable quantities. This TCR comprises a TCR α or γ chain extracellular domain dimerised to a TCR β or δ chain extracellular domain respectively, by means of a pair of C-terminal dimerisation peptides, such as leucine zippers. This strategy of producing TCRs is generally applicable to all TCRs.

Reiter et al, *Immunity*, 1995, 2:281-287, details the construction of a soluble molecule comprising disulphide-stabilised TCR α and β variable domains, one of which is linked to a truncated form of *Pseudomonas* exotoxin (PE38). One of the stated reasons for producing this molecule was to overcome the inherent instability of single-chain TCRs. The position of the novel disulphide bond in the TCR variable domains was identified via homology with the variable domains of antibodies, into which these have previously been introduced (for example see Brinkmann, et al. (1993), *Proc. Natl. Acad. Sci. USA* 90: 7538-7542, and Reiter, et al. (1994) *Biochemistry* 33: 5451-5459). However, as there is no such homology between antibody and TCR constant domains, such a technique could not be employed to identify appropriate sites for new inter-chain disulphide bonds between TCR constant domains.

Given the importance of soluble TCRs, it would be desirable to provide an alternative way of producing such molecules.

According to a first aspect, the present invention provides a soluble T cell receptor (sTCR), which comprises (i) all or part of a TCR α chain, except the transmembrane domain thereof, and (ii) all or part of a TCR β chain, except the transmembrane domain thereof, wherein (i) and (ii) each comprise a functional variable domain and at least a part of the constant domain of the TCR chain, and are linked by a disulphide bond between constant domain residues which is not present in native TCR.

In another aspect, the invention provides a soluble αβ-form T cell receptor (sTCR), wherein a covalent disulphide bond links a residue of the immunoglobulin region of the constant domain of the α chain to a residue of the immunoglobulin region of the constant domain of the β chain.

The sTCRs of the present invention have the advantage that they do not contain heterologous polypeptides which may be immunogenic, or which may result in the sTCR being cleared quickly from the body. Furthermore, TCRs of the present invention have a three-dimensional structure which is highly similar to the native TCRs from which they are derived and, due to this structural similarity, they are not likely to be immunogenic. sTCRs in accordance with the invention may be for recognising Class I MHC-peptide complexes or Class II MHC-peptide complexes.

TCRs of the present invention are soluble. In the context of this application, solubility is defined as the ability of the TCR to be purified as a mono disperse heterodimer in phosphate buffered saline (PBS) (KCL 2.7 mM, KH$_2$PO$_4$ 1.5 mM, NaCl 137 mM and Na$_2$PO4 8 mM, pH 7.1-7.5. Life Technologies, Gibco BRL) at a concentration of 1 mg/ml and for >90% of said TCR to remain as a mono disperse heterodimer after incubation at 25° C. for 1 hour. In order to assess the solubility of the TCR, it is first purified as described in Example 2. Following this purification, 100 μg of the TCR is analysed by analytical size exclusion chromatography e.g. using a Pharmacia Superdex 75 HR column equilibrated in PBS. A further 100 μg of the TCR is incubated at 25° C. for 1 hour and then analysed by size exclusion chromatography as before. The size exclusion traces are then analysed by integration and the areas under the peaks corresponding to the mono disperse heterodimer are compared. The relevant peaks may be identified by comparison with the elution position of protein standards of known molecular weight. The mono disperse heterodimeric soluble TCR has a molecular weight of approximately 50 kDa. As stated above, the TCRs of the present invention are soluble. However, as explained in more detail below, the TCRs can be coupled to a moiety such that the resulting complex is insoluble, or they may be presented on the surface of an insoluble solid support.

The numbering of TCR amino acids used herein follows the IMGT system described in The T Cell Receptor Factsbook, 2001, LeFranc & LeFranc, Academic Press. In this system, the α chain constant domain has the following notation: TRAC*01, where "TR" indicates T Cell Receptor gene; "A" indicates α chain gene; C indicates constant region; and "*01" indicates allele 1. The β chain constant domain has the following notation: TRBC1*01. In this instance, there are two possible constant region genes "C1" and "C2". The translated domain encoded by each allele can be made up from the genetic code of several exons; therefore these are also specified. Amino acids are numbered according to the exon of the particular domain in which they are present.

The extracellular portion of native TCR consists of two polypeptides (αβ or γδ) each of which has a membrane-proximal constant domain, and a membrane-distal variable domain (see FIG. 1). Each of the constant and variable domains includes an intra-chain disulphide bond. The variable domains contain the highly polymorphic loops analogous to the complementarity determining regions (CDRs) of antibodies. CDR3 of the TCR interacts with the peptide presented by MHC, and CDRs 1 and 2 interact with the peptide and the MHC. The diversity of TCR sequences is generated via somatic rearrangement of linked variable (V), diversity (D), joining (J), and constant genes. Functional α chain polypeptides are formed by rearranged V-J-C regions, whereas β chains consist of V-D-J-C regions. The extracellular constant domain has a membrane proximal region and an immunoglobulin region. The membrane proximal region consists of the amino acids between the transmembrane domain and the membrane proximal cysteine residue. The constant immunoglobulin domain consists of the remainder of the constant domain amino acid residues, extending from the membrane proximal cysteine to the beginning of the joining region, and is characterised by the presence of an immunoglobulin-type fold. There is a single α chain constant domain, known as Cα1 or TRAC*01, and two different β constant domains, known as Cβ1 or TRBC1*01 and Cβ2 or TRBC2*01. The difference between these different β constant domains is in respect of amino acid residues 4, 5 and 37 of exon 1. Thus, TRBC1*01 has 4N, 5K and 37 in respect thereof, and TRBC2*01 has 4K, 5N and 37Y in exon 1 thereof. The extent of each of the TCR extracellular domains is somewhat variable.

In the present invention, the disulphide bond is introduced between residues located in the constant domains (or parts thereof) of the respective chains. The respective chains of the TCR comprise sufficient of the variable domains thereof to be able to interact with its pMHC complex. Such interaction can be measured using a BIAcore 3000™ or BIAcore 2000™ instrument as described in Example 3 herein or in WO99/6120 respectively.

In one embodiment, the respective chains of the sTCR of the invention also comprise the intra-chain disulphide bonds thereof. The TCR of the present invention may comprise all of the extracellular constant Ig region of the respective TCR chains, and preferably all of the extracellular domain of the respective chains, i.e. including the membrane proximal region. In native TCR, there is a disulphide bond linking the conserved membrane proximal regions of the respective chains. In one embodiment of the present invention, this disulphide bond is not present. This may be achieved by mutating the appropriate cysteine residues (amino acid 4, exon 2 of the TRAC*01 gene and amino acid 2 of both the TRBC1*01 and TRBC2*01 genes respectively) to another amino acid, or truncating the respective chains so that the cysteine residues are not included. A preferred soluble TCR according to the invention comprises the native α and β TCR chains truncated at the C-terminus such that the cysteine residues which form the native interchain disulphide bond are excluded, i.e. truncated at the residue 1, 2, 3, 4, 5, 6, 7, 8, 9 or 10 residues N-terminal to the cysteine residues. It is to be noted however that the native inter-chain disulphide bond may be present in TCRs of the present invention, and that, in certain embodiments, only one of the TCR chains has the native cysteine residue which forms the native interchain disulphide bond. This cysteine can be used to attach moieties to the TCR.

However, the respective TCR chains may be shorter. Because the constant domains are not directly involved in contacts with the peptide-MHC ligands, the C-terminal truncation point may be altered substantially without loss of functionality.

Alternatively, a larger fragment of the constant domains may be present than is preferred herein, i.e. the constant domains need not be truncated just prior to the cysteines forming the interchain disulphide bond. For instance, the entire constant domain except the transmembrane domain (i.e. the extracellular and cytoplasmic domains) could be included. It may be advantageous in this case to mutate one or more of the cysteine residues forming the interchain disulphide bond in the cellular TCR to another amino acid residue which is not involved in disulphide bond formation, or to delete one or more of these residues.

The signal peptide may be omitted if the soluble TCR is to be expressed in prokaryotic cells, for example *E. coli*, since it does not serve any purpose in the mature TCR for its ligand binding ability, and may in some circumstances prevent the formation of a functional soluble TCR. In most cases, the cleavage site at which the signal peptide is removed from the mature TCR chains is predicted but not experimentally determined. Engineering the expressed TCR chains such that they are a few, i.e. up to about 10 for example, amino acids longer or shorter at the N-terminal end may have no significance for the functionality (i.e. the ability to recognise pMHC) of the soluble TCR. Certain additions which are not present in the original protein sequence could be added. For example, a short tag sequence which can aid in purification of the TCR chains could be added, provided that it does not interfere with the correct structure and folding of the antigen binding site of the TCR.

For expression in *E. coli*, a methionine residue may be engineered onto the N-terminal starting point of the predicted mature protein sequence in order to enable initiation of translation.

Far from all residues in the variable domains of TCR chains are essential for antigen specificity and functionality. Thus, a significant number of mutations can be introduced in this domain without affecting antigen specificity and functionality. Far from all residues in the constant domains of TCR chains are essential for antigen specificity and functionality. Thus, a significant number of mutations can be introduced in this region without affecting antigen specificity.

The TCR β chain contains a cysteine residue which is unpaired in the cellular or native TCR. It is preferred if this cysteine residue is removed or mutated to another residue to avoid incorrect intrachain or interchain pairing. Substitutions of this cysteine residue for another residue, for example serine or alanine, can have a significant positive effect on refolding efficiencies in vitro.

The disulphide bond may be formed by mutating non-cysteine residues on the respective chains to cysteine, and causing the bond to be formed between the mutated residues. Residues whose respective β carbons are approximately 6 Å (0.6 nm) or less, and preferably in the range 3.5 Å (0.35 nm) to 5.9 Å (0.59 nm) apart in the native TCR are preferred, such that a disulphide bond can be formed between cysteine residues introduced in place of the native residues. It is preferred if the disulphide bond is between residues in the constant immunoglobulin region, although it could be between residues of the membrane proximal region. Preferred sites where cysteines can be introduced to form the disulphide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 48 | Ser 57 | 0.473 |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

One sTCR of the present invention is derived from the A6 Tax TCR (Garboczi et al, *Nature*, 1996, 384(6605): 134-141). In one embodiment, the sTCR comprises the whole of the TCR α chain which is N-terminal of exon 2, residue 4 of TRAC*01 (amino acid residues 1-182 of the α chain according to the numbering used in Garboczi et al) and the whole of the TCR β chain which is N-terminal of exon 2, residue 2 of both TRBC1*01 and TRCB2*01 (amino acid residues 1-210 of the β chain according to the numbering used in Garboczi et al). In order to form the disulphide bond, threonine 48 of exon 1 in TRAC*01 (threonine 158 of the α chain according to the numbering used in Garboczi et al) and serine 57 of exon 1 in both TRBC1*01 and TRBC2*01 (serine 172 of the β chain according to the numbering used in Garboczi et al) may each be mutated to cysteine. These amino acids are located in β strand D of the constant domain of α and β TCR chains respectively.

It is to be noted that, in FIGS. 3a and 3b, residue 1 (according to the numbering used in Garboczi et al) is K and N respectively. The N-terminal methionine residue is not present in native A6 Tax TCR and, as mentioned above, is sometimes present when the respective chains are produced in bacterial expression systems.

Now that the residues in human TCRs which can be mutated into cysteine residues to form a new interchain disulphide bond have been identified, those of skill in the art will be able to mutate any TCR in the same way to produce a soluble form of that TCR having a new interchain disulphide bond. In humans, the skilled person merely needs to look for the following motifs in the respective TCR chains to identify the residue to be mutated (the shaded residue is the residue for mutation to a cysteine).

α Chain Thr 48: DSDVYITDKTVLDMRSMDFK (amino acids 39-58 of exon 1 of the TRAC*01 gene) (SEQ ID NO: 1)

α Chain Thr 45: QSKDSDVYITDKTVLDMRSM (amino acids 36-55 of exon 1 of the TRAC*01 gene) (SEQ ID NO: 2)

α Chain Tyr 10: DIQNPDPAVYQLRDSKSSDK (amino acids 1-20 of exon 1 of the TRAC*01 gene) (SEQ ID NO: 3)

α Chain Ser 15: DPAVYQLRDSKSSDKSVCLF (amino acids 6-25 of exon 1 of the TRAC*01 gene) (SEQ ID NO: 4)

β Chain Ser 57: NGKEVHSGVSTDPQPLKEQP (amino acids 48-67 of exon 1 of the TRBC1*01 & TRBC2*01 genes) (SEQ ID NO: 5)

β Chain Ser 77: ALNDSRYALSSRLRVSATFW (amino acids 68-87 of exon 1 of the TRBC1*01 & TRBC2*01 genes) (SEQ ID NO: 6)

β Chain Ser 17: PPEVAVFEPSEAEISHTQKA (amino acids 8-27 of exon 1 of the TRBC1*01 & TRBC2*01 genes) (SEQ ID NO: 7)

β Chain Asp 59: KEVHSGVSTDPQPLKEQPAL (amino acids 50-69 of exon 1 of the TRBC1*01 & TRBC2*01 genes gene) (SEQ ID NO: 8)

| | | |
|---|---|---|
| β Chain Glu 15: | VFPPEVAVFPPSEAEISHTQ | (amino acids 6-25 of exon 1 of the TRBC1*01 & TRBC2*01 genes) (SEQ ID NO: 9) |

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, ClustalW, available on the European Bioinformatics Institute website can be used to compare the motifs above to a particular TCR chain sequence in order to locate the relevant part of the TCR sequence for mutation.

The present invention includes within its scope human disulphide-linked αβ TCRs, as well as disulphide-linked αβ TCRs of other mammals, including, but not limited to, mouse, rat, pig, goat and sheep. As mentioned above, those of skill in the art will be able to determine sites equivalent to the above-described human sites at which cysteine residues can be introduced to form an inter-chain disulphide bond. For example, the following shows the amino acid sequences of the mouse Cα and Cβ soluble domains, together with motifs showing the murine residues equivalent to the human residues mentioned above that can be mutated to cysteines to form a TCR interchain disulphide bond (where the relevant residues are shaded):

species and the inter-chain disulphide bond being between residues in said respective all or part of the constant domain not present in native TCR. In one embodiment, the first and second TCRs are human. In other words, the disulphide bond-linked constant domains act as a framework on to which variable domains can be fused. The resulting TCR will be substantially identical to the native TCR from which the first TCR is obtained. Such a system allows the easy expression of any functional variable domain on a stable constant domain framework.

The constant domains of the A6 Tax sTCR described above, or indeed the constant domains of any of the mutant αβ TCRs having a new interchain disulphide bond described above, can be used as framework onto which heterologous variable domains can be fused. It is preferred if the fusion protein retains as much of the conformation of the heterologous variable domains as possible. Therefore, it is preferred that the heterologous variable domains are linked to the constant domains at any point between the introduced cysteine residues and the N terminus of the constant domain. For the A6 Tax TCR, the introduced cysteine residues on the α and β chains are preferably located at threonine 48 of exon 1 in TRAC*01 (threonine 158 of the α chain according to the Mouse Cα soluble domain:
PYIQNPEPAVYQLKDPRSQDSTLCLFTDFDSQINVPKTMESGTFITDKTVLDMKAMDS
KSNGAIAWSNQTSFTCQDIFKETNATYPSSDVP (SEQ ID NO: 10)
Mouse Cβ soluble domain:
EDLRNVTPPKVSLFEPSKAEIANKQKATLVCLARGFFPDHVELSWWVNGREVHSGVST
DPQAYKESNYSYCLSSRLRVSATFWHNPRNHFRCQVQFHGLSEEDKWPEGSPKPVTQN
ISAEAWGRAD (SEQ ID NO: 11)

| | | |
|---|---|---|
| Murine equivalent of human α Chain Thr 48: | ESGTFITDKTVLDMKAMDSK | (SEQ ID NO: 12) |
| Murine equivalent of human α Chain Thr 45: | KTMESGTFITDKTVLDMKAM | (SEQ ID NO: 13) |
| Murine equivalent of human α Chain Tyr 10: | YIQNPEPAVYQLKDPRSQDS | (SEQ ID NO: 14) |
| Murine equivalent of human α Chain Ser 15: | AVYQLKDPRSQDSTLCLFTD | (SEQ ID NO: 15) |
| Murine equivalent of human β Chain Ser 57: | NGREVHSGVSTDPQAYKESN | (SEQ ID NO: 16) |
| Murine equivalent of human β Chain Ser 77: | KESNYSYCLSSRLRVSATFW | (SEQ ID NO: 17) |
| Murine equivalent of human β Chain Ser 17: | PPKVSLFEPSKAEIANKQKA | (SEQ ID NO: 18) |
| Murine equivalent of human β Chain Asp 59: | REVHSGVSTDPQAYKESNYS | (SEQ ID NO: 19) |
| Murine equivalent of human β Chain Glu 15: | VTPPKVSLFEPSKAEIANKQ | (SEQ ID NO: 20) |

In a preferred embodiment of the present invention, (i) and (ii) of the TCR each comprise the functional variable domain of a first TCR fused to all or part of the constant domain of a second TCR, the first and second TCRs being from the same species and serine 57 of exon 1 in both TRBC1*01 and TRBC2*01 (serine 172 of the β chain according to the numbering used in Garboczi et al) respectively. Therefore it is preferred if the heterologous α and β chain variable domain attachment points are between residues 48 (159 according to the numbering used in Garboczi et al) or 58 (173 according to the numbering used in Garboczi et al) and the N terminus of the α or β constant domains respectively.

The residues in the constant domains of the heterologous α and β chains corresponding to the attachment points in the A6 Tax TCR can be identified by sequence homology. The fusion protein is preferably constructed to include all of the heterologous sequence N-terminal to the attachment point.

As is discussed in more detail below, the sTCR of the present invention may be derivatised with, or fused to, a moiety at its C or N terminus. The C terminus is preferred as this is distal from the binding domain. In one embodiment, one or both of the TCR chains have a cysteine residue at its C and/or N terminus to which such a moiety can be fused.

A soluble TCR (which is preferably human) of the present invention may be provided in substantially pure form, or as a purified or isolated preparation. For example, it may be provided in a form which is substantially free of other proteins.

A plurality of soluble TCRs of the present invention may be provided in a multivalent complex. Thus, the present invention provides, in one aspect, a multivalent T cell receptor (TCR) complex, which comprises a plurality of soluble T cell receptors as described herein. Each of the plurality of soluble TCRs is preferably identical.

In another aspect, the invention provides a method for detecting MHC-peptide complexes which method comprises:
(i) providing a soluble T cell receptor or a multivalent T cell receptor complex as described herein;
(ii) contacting the soluble T cell receptor or multivalent TCR complex with the MHC-peptide complexes; and
(iii) detecting binding of the soluble T cell receptor or multivalent TCR complex to the MHC-peptide complexes.

In the multivalent complex of the present invention, the TCRs may be in the form of multimers, and/or may be present on or associated with a lipid bilayer, for example, a liposome.

In its simplest form, a multivalent TCR complex according to the invention comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Structures which are a good deal larger than TCR tetramers may be used in tracking or targeting cells expressing specific MHC-peptide complex. Preferably the structures are in the range 10 nm to 10 μm in diameter. Each structure may display multiple TCR molecules at a sufficient distance apart to enable two or more TCR molecules on the structure to bind simultaneously to two or more MHC-peptide complexes on a cell and thus increase the avidity of the multimeric binding moiety for the cell.

Suitable structures for use in the invention include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present invention. For example, the label or other moiety may be included in a mixed molecule multimer. An example of such a multimeric molecule is a tetramer containing three TCR molecules and one peroxidase molecule. This could be achieved by mixing the TCR and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

Alternative means of biotinylating the TCR may be possible. For example, chemical biotinylation may be used. Alternative biotinylation tags may be used, although certain amino acids in the biotin tag sequence are essential (Schatz, (1993). *Biotechnology NY* 11(10): 1138-43). The mixture used for biotinylation may also be varied. The enzyme requires Mg-ATP and low ionic strength, although both of these conditions may be varied e.g. it may be possible to use a higher ionic strength and a longer reaction time. It may be possible to use a molecule other than avidin or streptavidin to form multimers of the TCR. Any molecule which binds biotin in a multivalent manner would be suitable. Alternatively, an entirely different linkage could be devised (such as polyhistidine tag to chelated nickel ion (Quiagen Product Guide 1999, Chapter 3 "Protein Expression, Purification, Detection and Assay" p. 35-37). Preferably, the tag is located towards the C-terminus of the protein so as to minimise the amount of steric hindrance in the interaction with peptide-MHC complexes.

One or both of the TCR chains may be labelled with a detectable label, for example a label which is suitable for diagnostic purposes. Thus, the invention provides a method for detecting MHC-peptide complexes which method comprises contacting the MHC-peptide complexes with a TCR or multimeric TCR complex in accordance with the invention which is specific for the MHC-peptide complex; and detecting binding of the TCR or multimeric TCR complex to the MHC-peptide complex. In tetrameric TCR formed using biotinylated heterodimers, fluorescent streptavidin (commercially available) can be used to provide a detectable label. A fluorescently-labelled tetramer is suitable for use in FACS analysis, for example to detect antigen presenting cells carrying the peptide for which the TCR is specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant regions of the α and β chain, respectively.

The TCR (or multivalent complex thereof) of the present invention may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present invention may have enhanced binding capability for a pMHC compared to a non-multimeric T cell receptor heterodimer. Thus, the multivalent TCR complexes according to the invention are particularly useful for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the MHC-peptide complexes and having the therapeutic agent associated therewith.

In particular, the soluble TCR or multivalent TCR complex can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to T cell receptors or multivalent TCR complexes specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Examples include ricin, diphtheria toxin, pseudomonas bacterial exotoxin A, DNAase and RNAase;

radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213;

prodrugs, such as antibody directed enzyme pro-drugs;

immuno-stimulants, i.e. moieties which stimulate immune response. Examples include cytokines such as IL-2, chemokines such as IL-8, platelet factor 4, melanoma growth stimulatory protein, etc, antibodies or fragments thereof, complement activators, xenogeneic protein domains, allogeneic protein domains, viral/bacterial protein domains and viral/bacterial peptides.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

Examples of suitable MHC-peptide targets for the TCR according to the invention include, but are not limited to, viral epitopes such as HTLV-1 epitopes (e.g. the Tax peptide restricted by HLA-A2; HTLV-1 is associated with leukemia), HIV epitopes, EBV epitopes, CMV epitopes; melanoma epitopes (e.g. MAGE-1 HLA-A1 restricted epitope) and other cancer-specific epitopes (e.g. the renal cell carcinoma associated antigen G250 restricted by HLA-A2); and epitopes associated with autoimmune disorders, such as rheumatoid arthritis. Further disease-associated pMHC targets, suitable for use in the present invention, are listed in the HLA Factbook (Barclay (Ed) Academic Press), and many others are being identified.

A multitude of disease treatments can potentially be enhanced by localising the drug through the specificity of soluble TCRs.

Viral diseases for which drugs exist, e.g. HIV, SIV, EBV, CMV, would benefit from the drug being released or activated in the near vicinity of infected cells. For cancer, the localisation in the vicinity of tumours or metastasis would enhance the effect of toxins or immunostimulants. In autoimmune diseases, immunosuppressive drugs could be released slowly, having more local effect over a longer time-span while minimally affecting the overall immuno-capacity of the subject. In the prevention of graft rejection, the effect of immunosuppressive drugs could be optimised in the same way. For vaccine delivery, the vaccine antigen could be localised in the vicinity of antigen presenting cells, thus enhancing the efficacy of the antigen. The method can also be applied for imaging purposes.

The soluble TCRs of the present invention may be used to modulate T cell activation by binding to specific pMHC and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986). Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas. Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurised aerosols, nebulizers or insufflators. Pharmaceutical compositions adapted for vaginal administration may be presented as pessaries, tampons, creams, gels, pastes, foams or spray formulations. Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substances of the present invention can vary between wide limits, depending upon the disease or disorder to be treated, the age and condition of the individual to be treated, etc. and a physician will ultimately determine appropriate dosages to be used. The dosage may be repeated as often as appropriate. If side effects develop the amount and/or frequency of the dosage can be reduced, in accordance with normal clinical practice.

Gene cloning techniques may be used to provide a sTCR of the invention, preferably in substantially pure form. These techniques are disclosed, for example, in J. Sambrook et al *Molecular Cloning* 2nd Edition, Cold Spring Harbor Laboratory Press (1989). Thus, in a further aspect, the present invention provides a nucleic acid molecule comprising a sequence encoding a chain of the soluble TCR of the present invention, or a sequence complementary thereto. Such nucleic acid sequences may be obtained by isolating TCR-encoding nucleic acid from T-cell clones and making appropriate mutations (by insertion, deletion or substitution).

The nucleic acid molecule may be in isolated or recombinant form. It may be incorporated into a vector and the vector may be incorporated into a host cell. Such vectors and suitable hosts form yet further aspects of the present invention.

The invention also provides a method for obtaining a TCR chain, which method comprises incubating such a host cell under conditions causing expression of the TCR chain and then purifying the polypeptide.

The soluble TCRs of the present invention may obtained by expression in a bacterium such as *E. coli* as inclusion bodies, and subsequent refolding in vitro.

Refolding of the TCR chains may take place in vitro under suitable refolding conditions. In a particular embodiment, a TCR with correct conformation is achieved by refolding solubilised TCR chains in a refolding buffer comprising a solubilising agent, for example urea. Advantageously, the urea may be present at a concentration of at least 0.1M or at least 1M or at least 2.5M, or about 5M. An alternative solubilising agent which may be used is guanidine, at a concentration of between 0.1M and 8M, preferably at least 1M or at least 2.5M. Prior to refolding, a reducing agent is preferably employed to ensure complete reduction of cysteine residues. Further denaturing agents such as DTT and guanidine may be used as necessary. Different denaturants and reducing agents may be used prior to the refolding step (e.g. urea, β-mercaptoethanol). Alternative redox couples may be used during refolding, such as a cystamine/cysteamine redox couple, DTT or β-mercaptoethanol/atmospheric oxygen, and cysteine in reduced and oxidised forms.

Folding efficiency may also be increased by the addition of certain other protein components, for example chaperone proteins, to the refolding mixture. Improved refolding has been achieved by passing protein through columns with immobilised mini-chaperones (Altamirano, et al. (1999). *Nature Biotechnology* 17: 187-191; Altamirano, et al. (1997). *Proc Natl Acad Sci USA* 94(8): 3576-8).

Alternatively, soluble TCR the present invention may obtained by expression in a eukaryotic cell system, such as insect cells.

Purification of the TCR may be achieved by many different means. Alternative modes of ion exchange may be employed or other modes of protein purification may be used such as gel filtration chromatography or affinity chromatography.

Soluble TCRs and multivalent TCR complexes of the present invention also find use in screening for agents, such as small chemical compounds, which have the ability to inhibit the binding of the TCR to its pMHC complex. Thus, in a further aspect, the present invention provides a method for screening for an agent which inhibits the binding of a T cell receptor to a peptide-MHC complex, comprising monitoring the binding of a soluble T cell receptor of the invention with a peptide-MHC complex in the presence of an agent; and selecting agents which inhibit such binding.

Suitable techniques for such a screening method include the Surface Plasmon Resonance-based method described in WO 01/22084. Other well-known techniques that could form the basis of this screening method are Scintillation Proximity Analysis (SPA) and Amplified Luminescent Proximity Assay.

Agents selected by screening methods of the invention can be used as drugs, or as the basis of a drug development programme, being modified or otherwise improved to have characteristics making them more suitable for administration as a medicament. Such medicaments can be used for the treatment of conditions which include an unwanted T cell response component. Such conditions include cancer (e.g. renal, ovarian, bowel, head & neck, testicular, lung, stomach, cervical, bladder, prostate or melanoma), autoimmune disease, graft rejection and graft versus host disease.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIG. 1 is a schematic diagram of a soluble TCR with an introduced inter-chain di-sulphide bond in accordance with the invention;

FIGS. 2*a* and 2*b* show respectively the nucleic acid sequences of the α (SEQ ID NO:107) and β (SEQ ID NO:108) chains of a soluble A6 TCR, mutated so as to introduce a cysteine codon. The shading indicates the introduced cysteine codon;

FIG. 3*a* shows the A6 TCR α chain extracellular amino acid sequence (SEQ ID NO:128), including the $T_{48}{\rightarrow}C$ mutation (underlined) used to produce the novel disulphide inter-chain bond, and FIG. 3*b* shows the A6 TCR β chain extracellular amino acid sequence (SEQ ID NO:109), including the $S_{57}{\rightarrow}C$ mutation (underlined) used to produce the novel disulphide inter-chain bond;

FIG. 4 is a trace obtained after anion exchange chromatography of soluble A6 TCR, showing protein elution from a POROS 50HQ column using a 0-500 mM NaCl gradient, as indicated by the dotted line;

FIG. 5—A. Reducing SDS-PAGE (Coomassie-stained) of fractions from column run in FIG. 4, as indicated. B. Non-reducing SDS-PAGE (Coomassie-stained) of fractions from column run in FIG. 4, as indicated. Peak 1 clearly contains mainly non-disulphide linked β-chain, peak 2 contains TCR heterodimer which is inter-chain disulphide linked, and the shoulder is due to *E. coli* contaminants, mixed in with the inter-chain disulphide linked sTCR, which are poorly visible on this reproduction;

Figure 10:
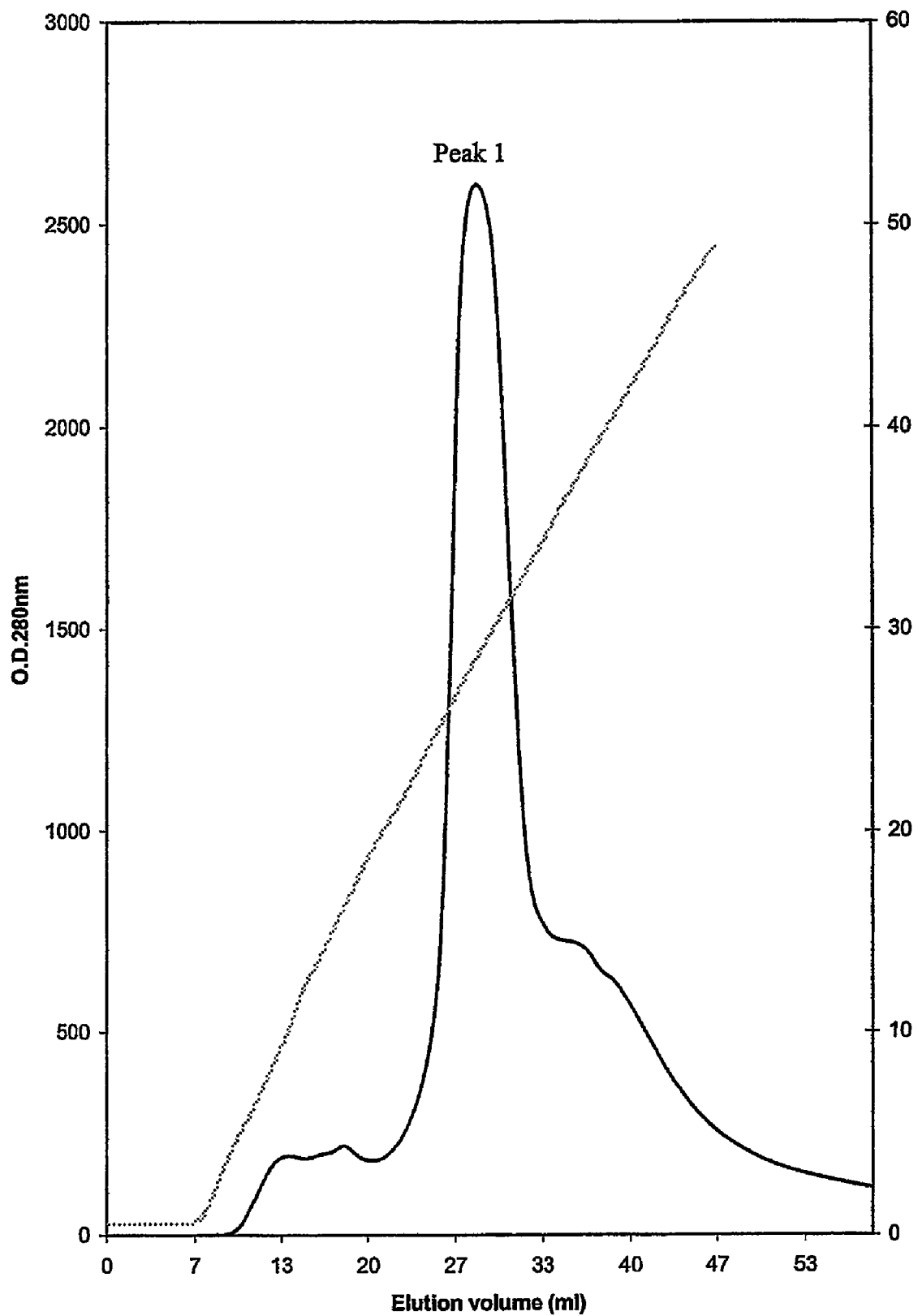

FIG. 8*a* shows the A6 TCR α chain sequence (SEQ ID NO:107) including novel cysteine residue mutated to incorporate a BamH1 restriction site. Shading indicates the mutations introduced to form the BamH1 restriction site. FIGS. 8*b* and 8*c* show the DNA sequence of α (SEQ ID NO:111) and β (SEQ ID NO:112) chain of the JM22 TCR mutated to include additional cysteine residues to form a non-native disulphide bond;

FIGS. 9*a* and 9*b* show respectively the JM22 TCR α (SEQ ID NO:113) and β (SEQ ID NO:114) chain extracellular amino acid sequences produced from the DNA sequences of FIGS. 8*a* and 8*b*;

FIG. 10 is a trace obtained after anion exchange chromatography of soluble disulphide-linked JM22 TCR showing protein elution from a POROS 50HQ column using a 0-500 mM NaCl gradient, as indicated by the dotted line;

FIG. 11*a* shows a reducing SDS-PAGE (Coomassie-stained) of fractions from column run in FIG. 10, as indicated and FIG. 11*b* shows a non-reducing SDS-PAGE (Coomassie-stained) of fractions from column run in FIG. 10, as indicated. Peak 1 clearly contains TCR heterodimer which is inter-chain disulphide linked.

Figure 12:
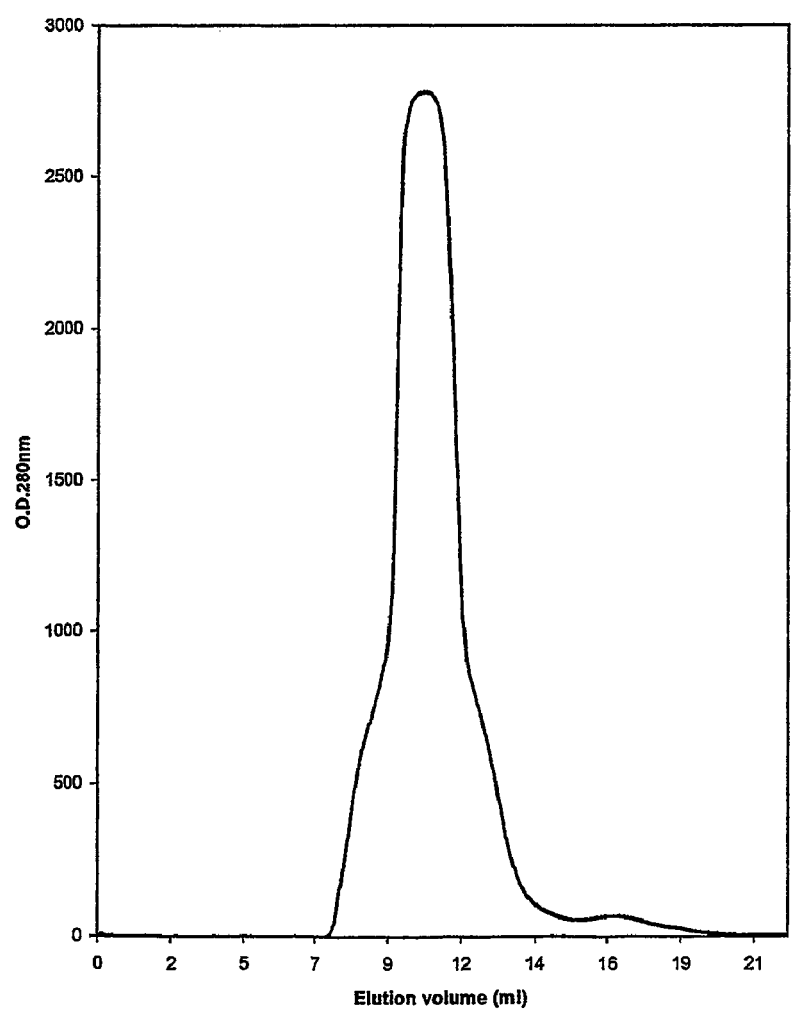

FIG. 12 is a trace obtained from size-exclusion chromatography of pooled fractions from peak 1 in FIG. 10. The protein elutes as a single major peak, corresponding to the heterodimer. Yield is 80%;

FIG. 13—A. BIAcore response curve of the specific binding of disulphide-linked JM22 soluble TCR to HLA-Flu complex. B. Binding response compared to control for a single injection of disulphide-linked JM22 soluble TCR;

FIGS. 14*a* and 14*b* show the DNA sequence of α (SEQ ID NO:115) and β (SEQ ID NO:116) chain of the NY-ESO mutated to include additional cysteine residues to form a non-native disulphide bond;

FIGS. 15*a* and 15*b* show respectively the NY-ESO TCR α (SEQ ID NO:117) and β (SEQ ID NO:118) chain extracellular amino acid sequences produced from the DNA sequences of FIGS. 14*a* and 14*b*

Figure 16:
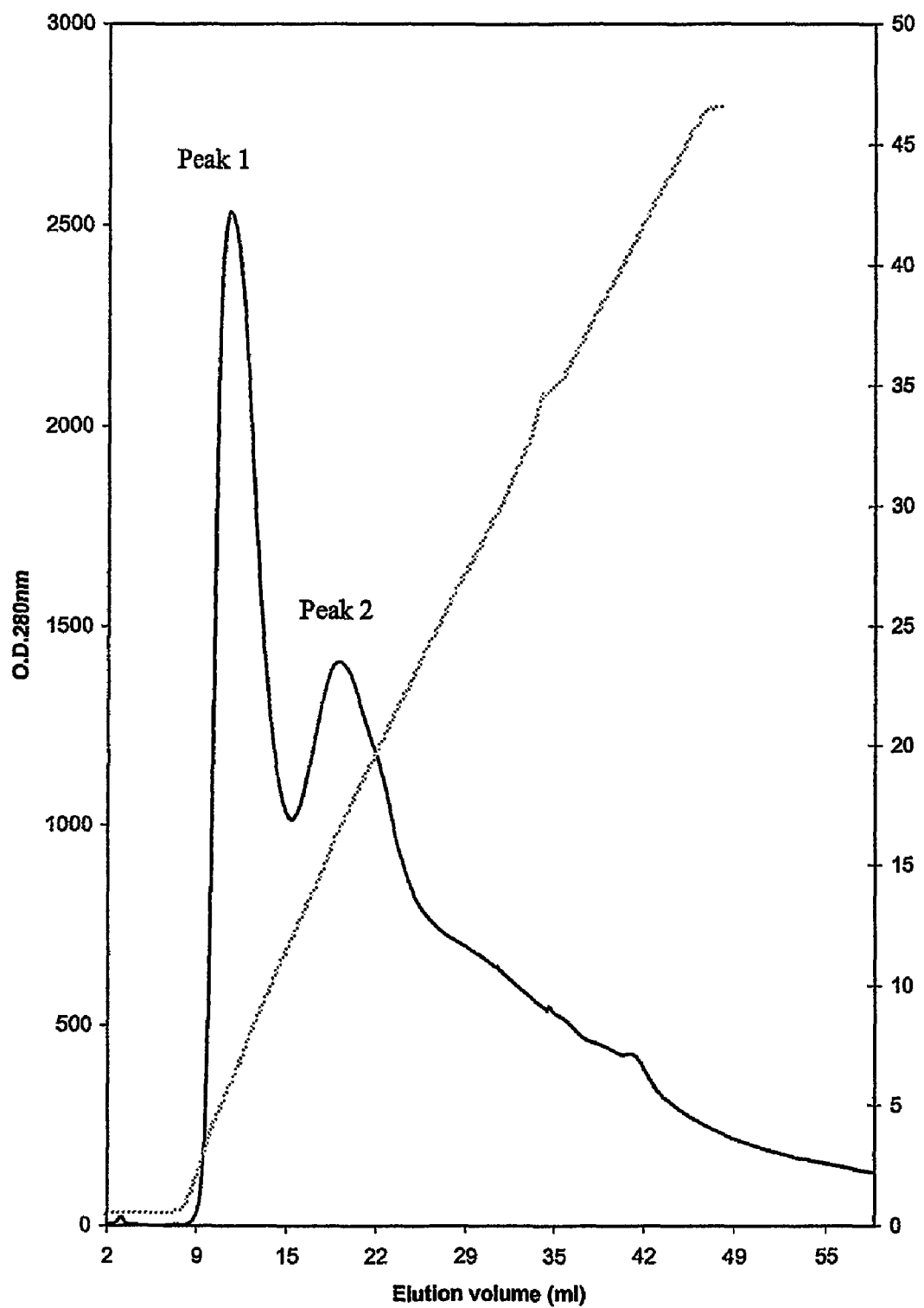
Figure 17:
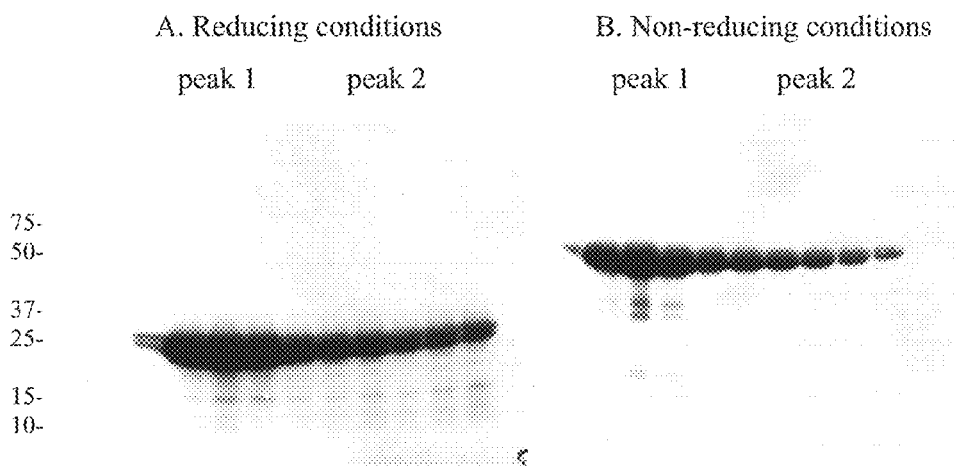
Figure 18:
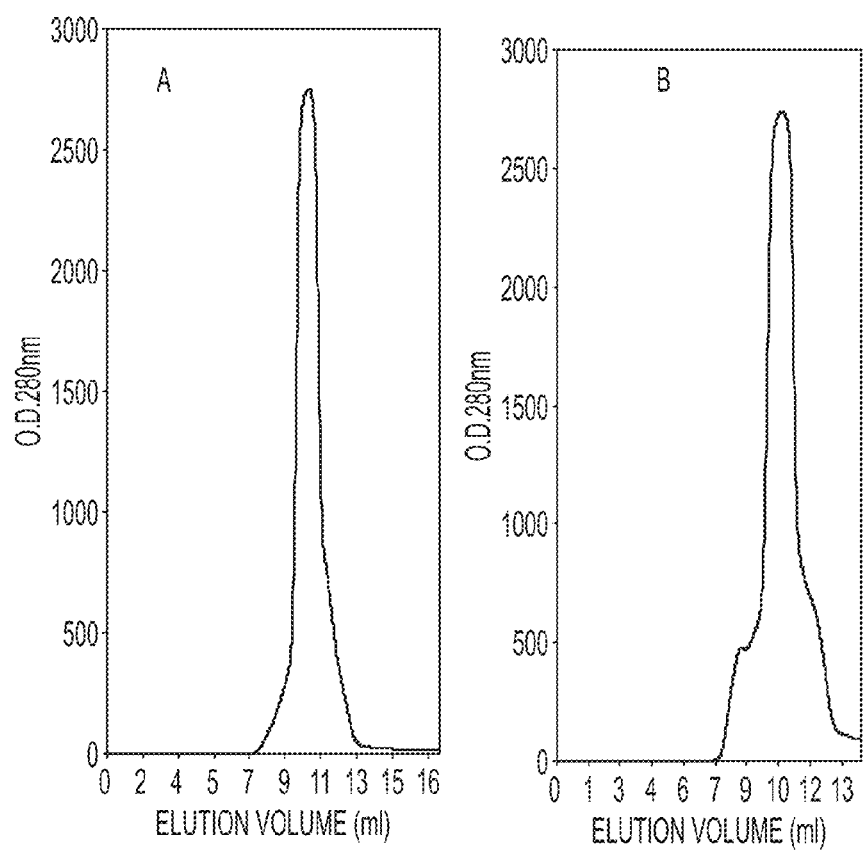
Figure 19A:
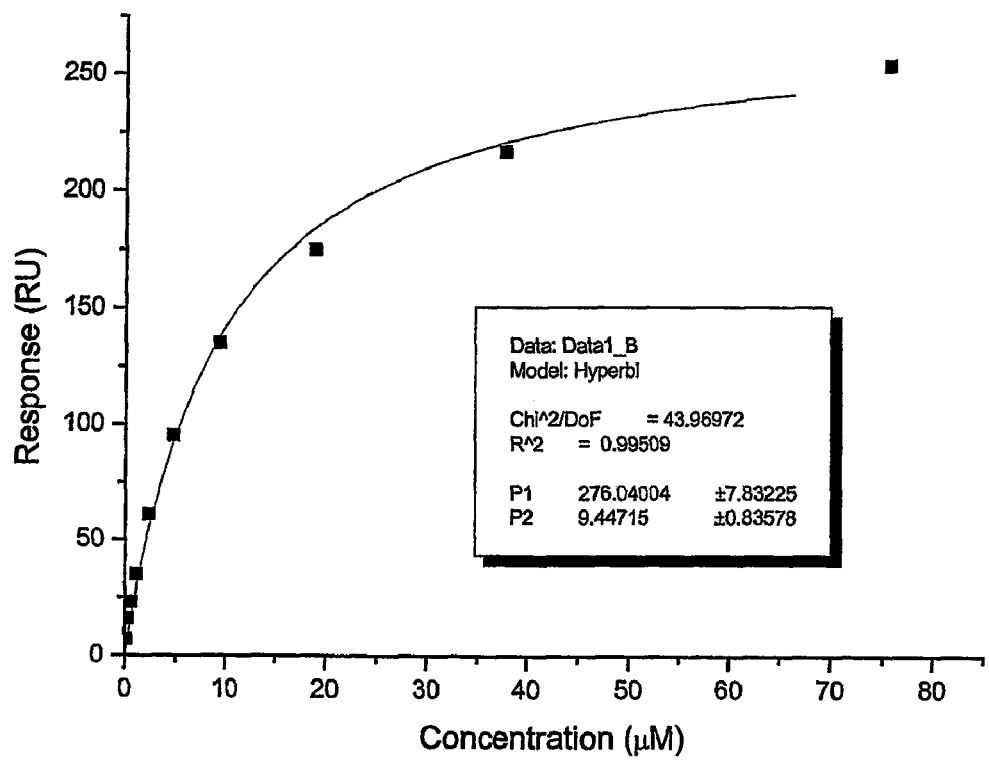
Figure 19B:
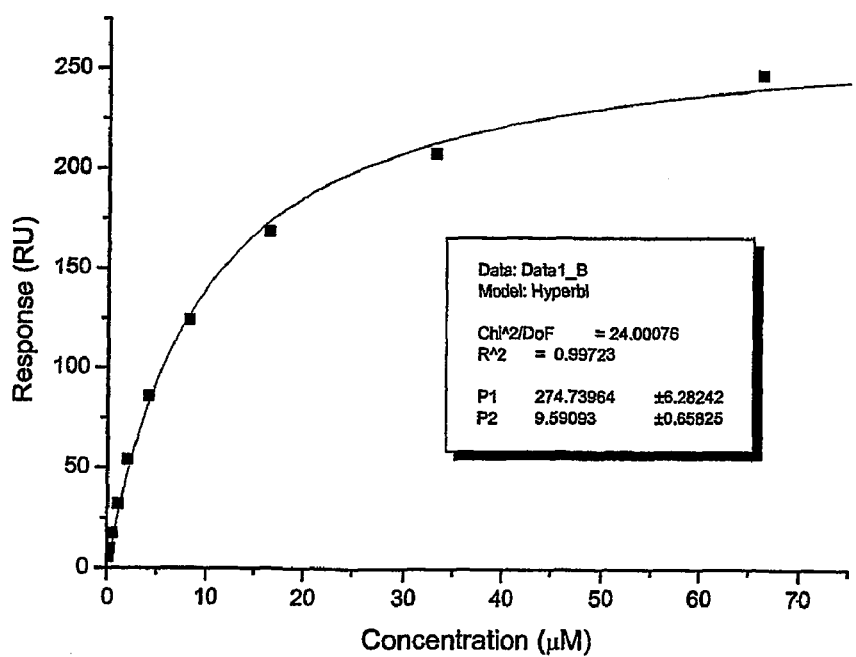
Figure 22:
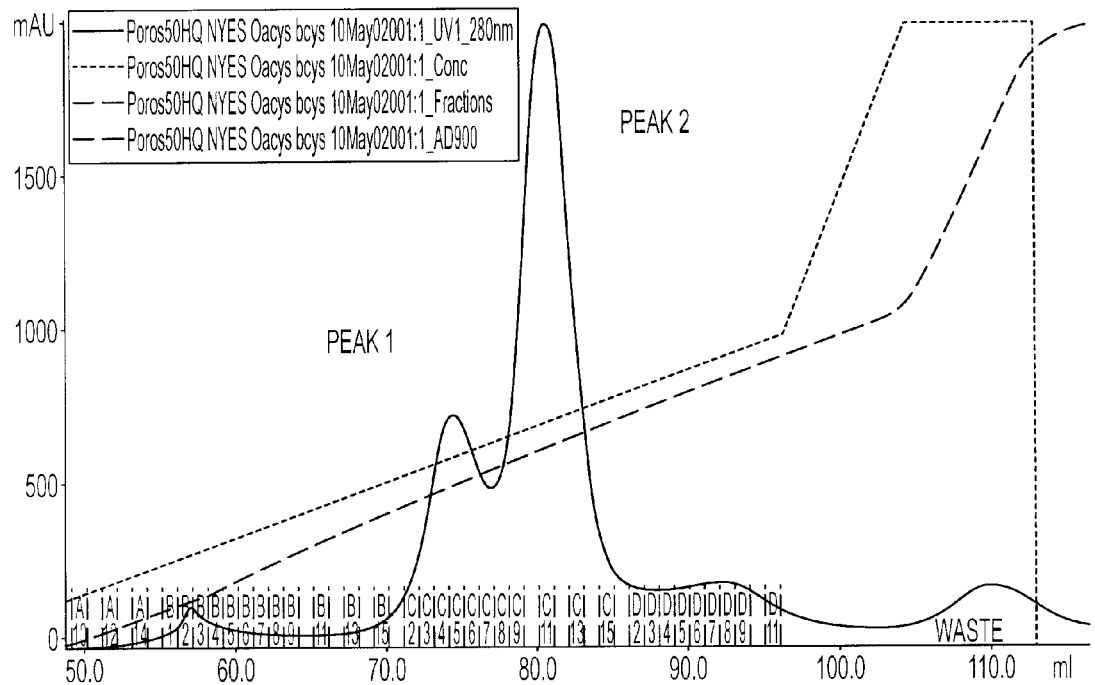
Figure 23:
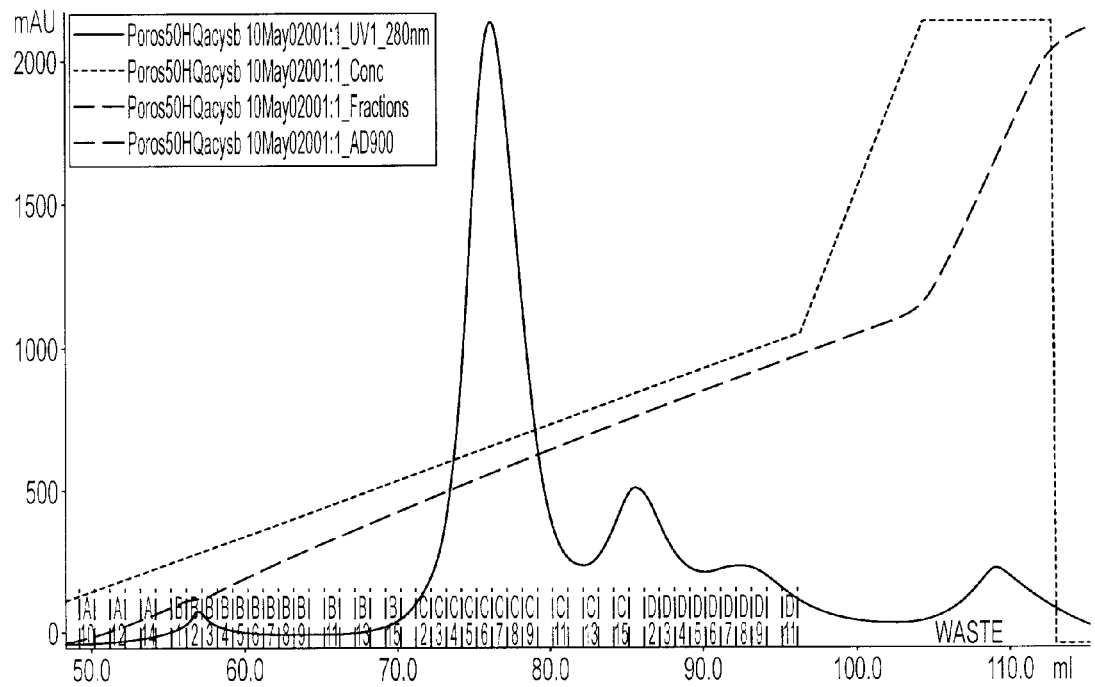
Figure 24:
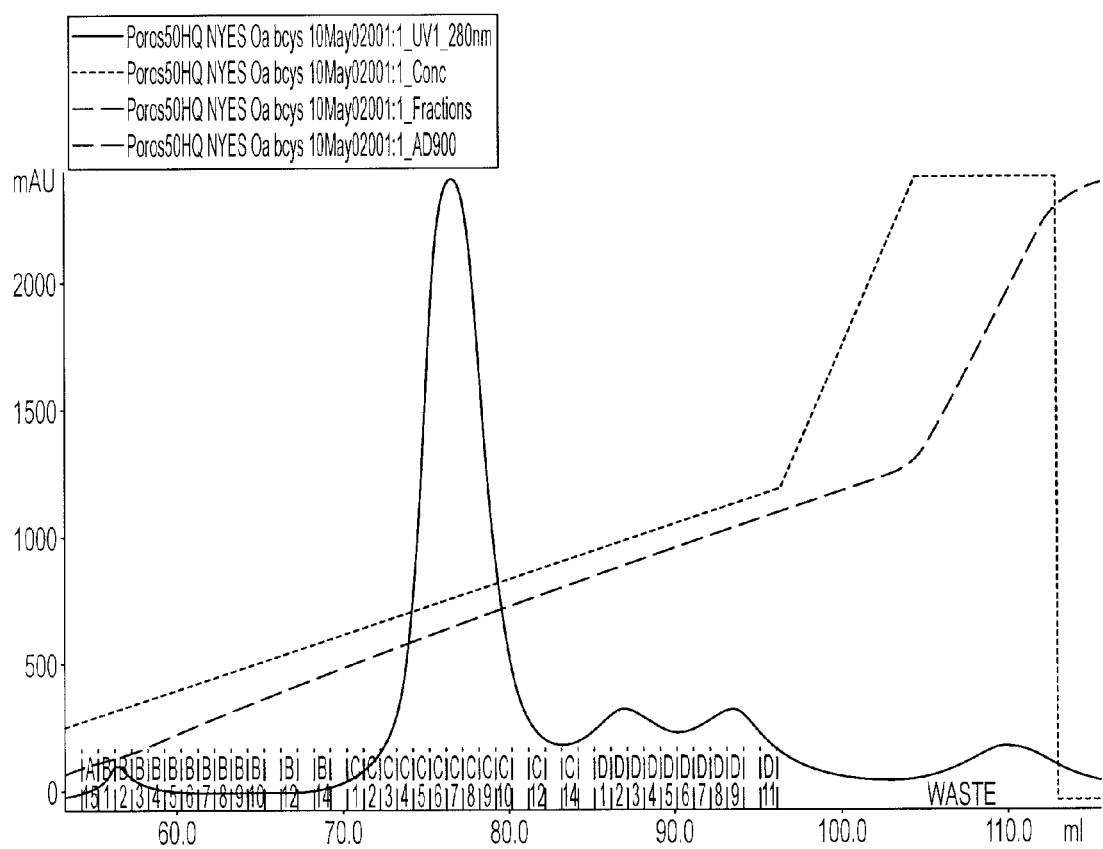
Figure 25:
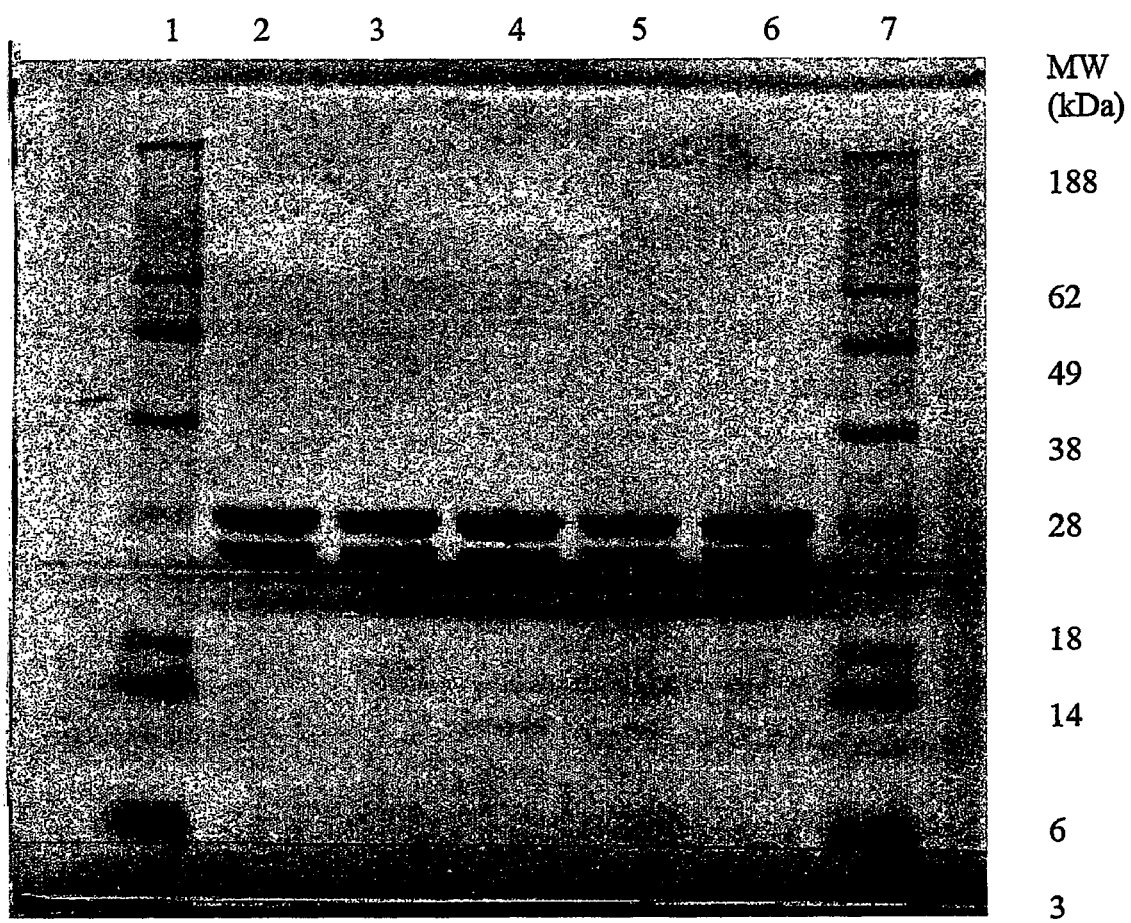
Figure 26:
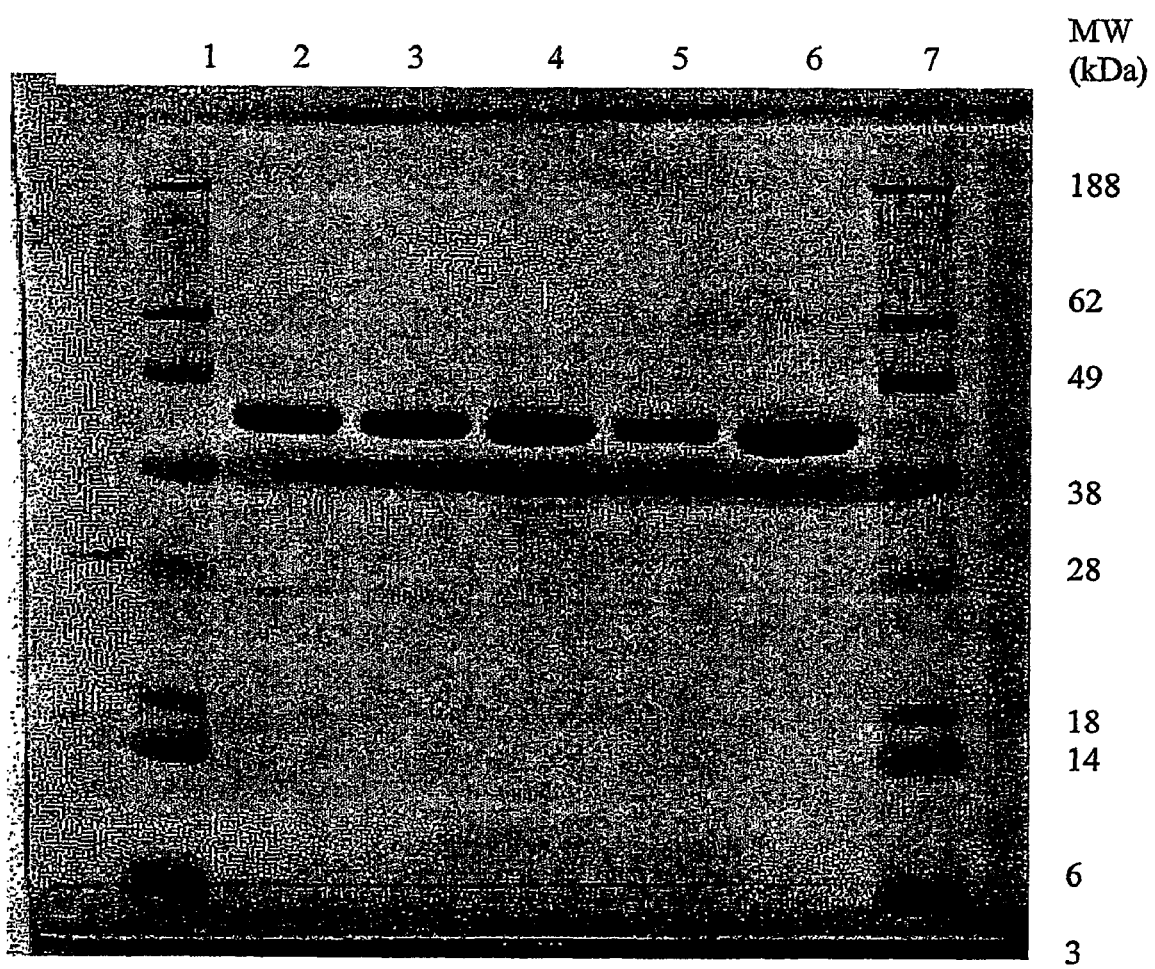
Figure 27:
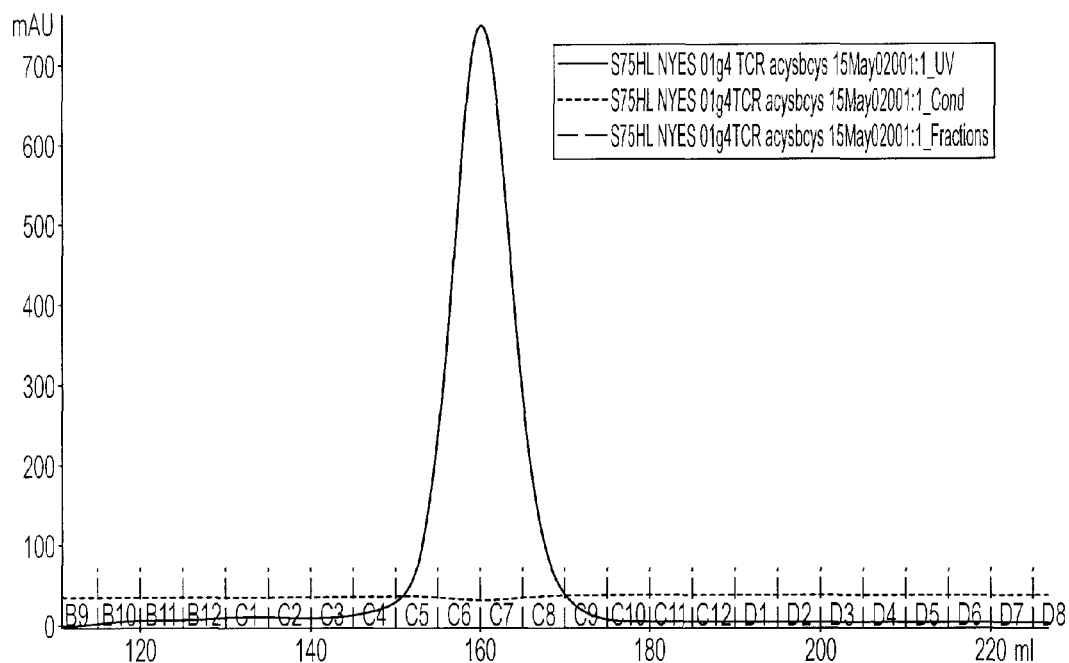
Figure 28:
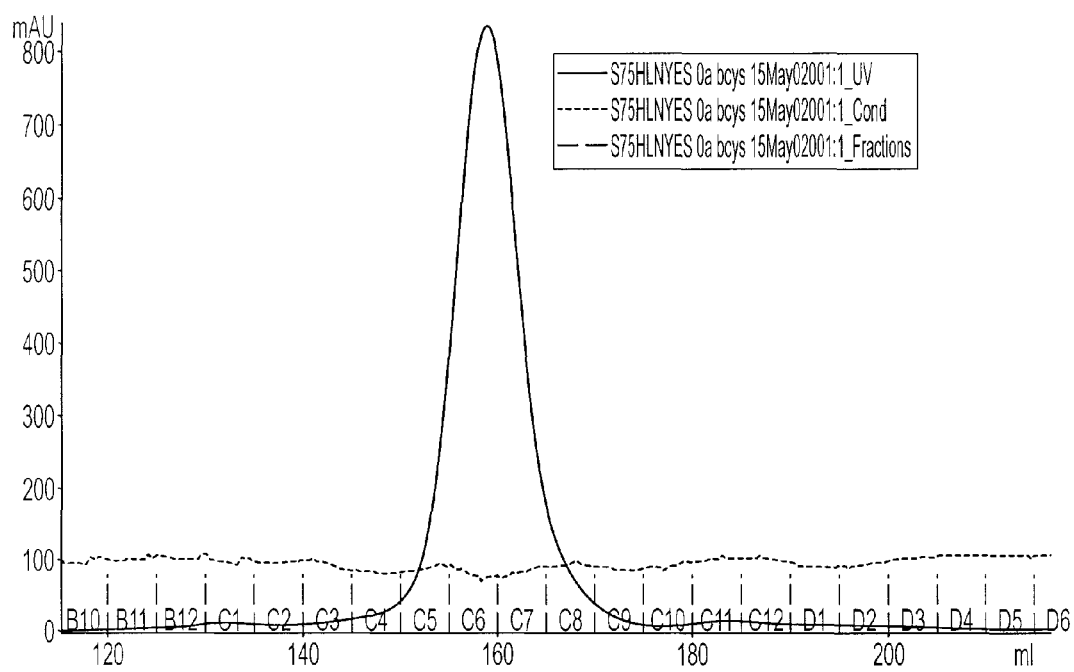
Figure 29:
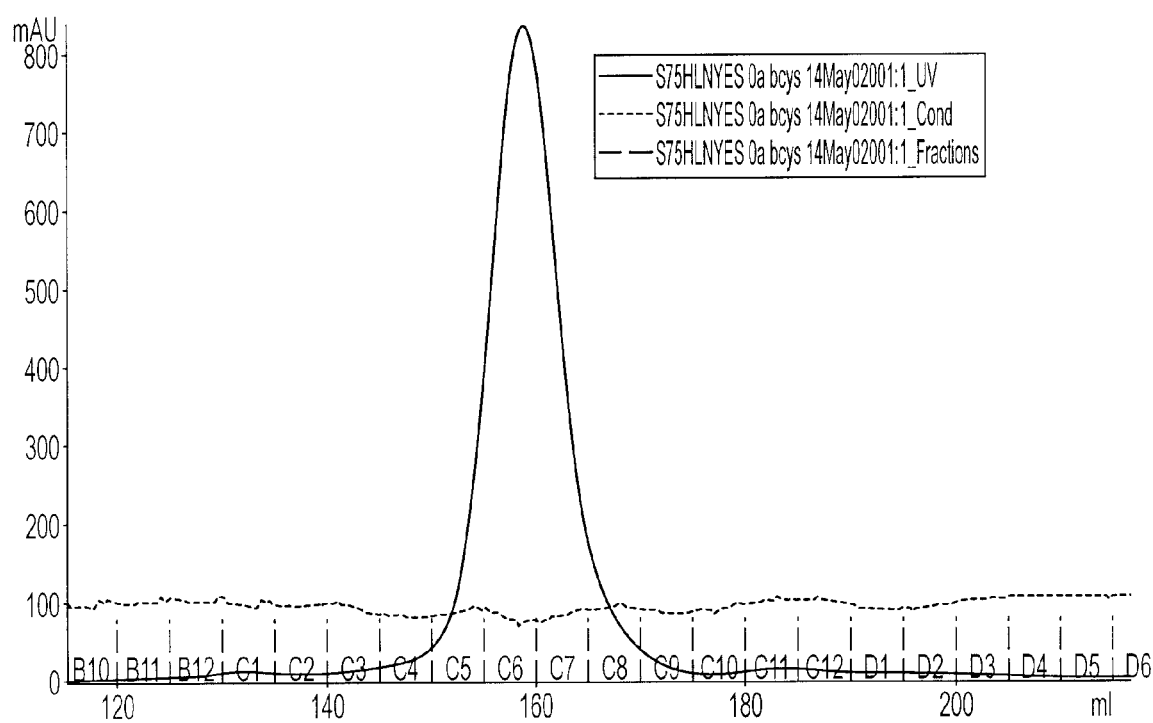
Figure 30:
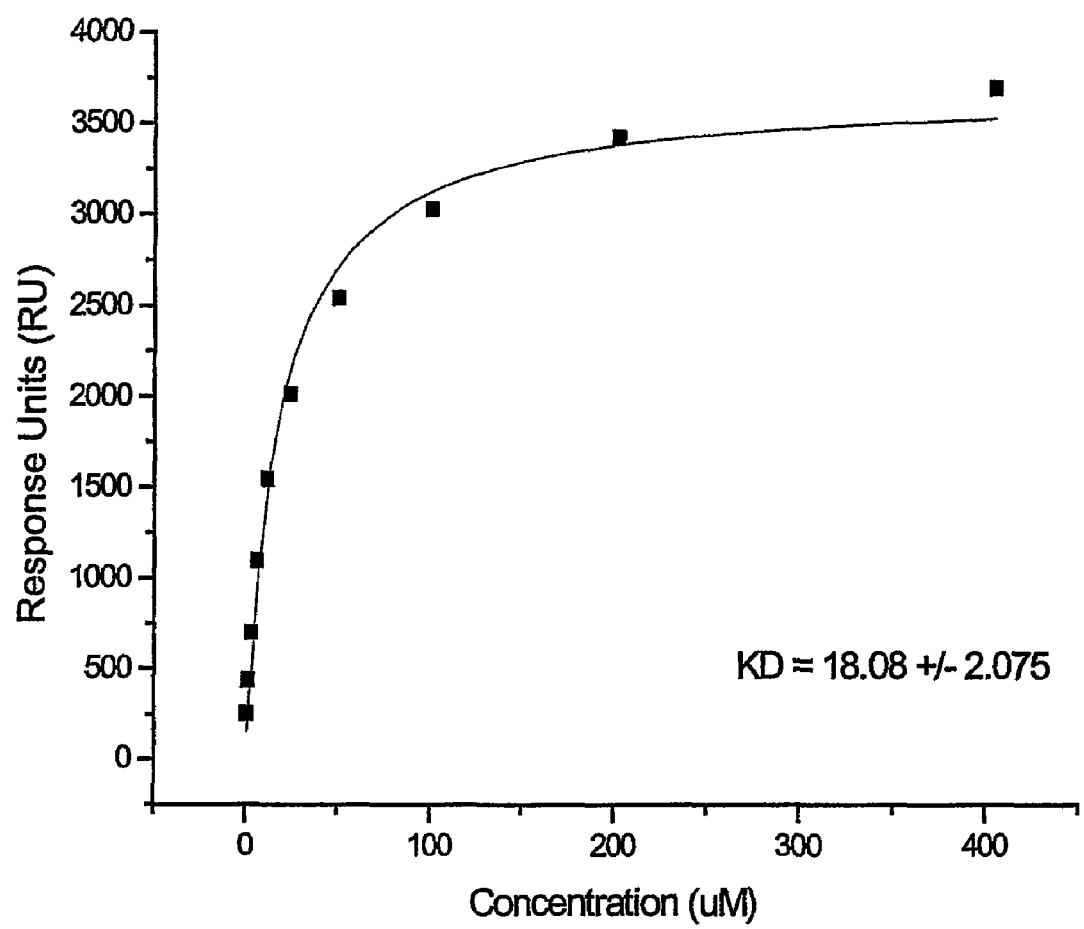
Figure 31:
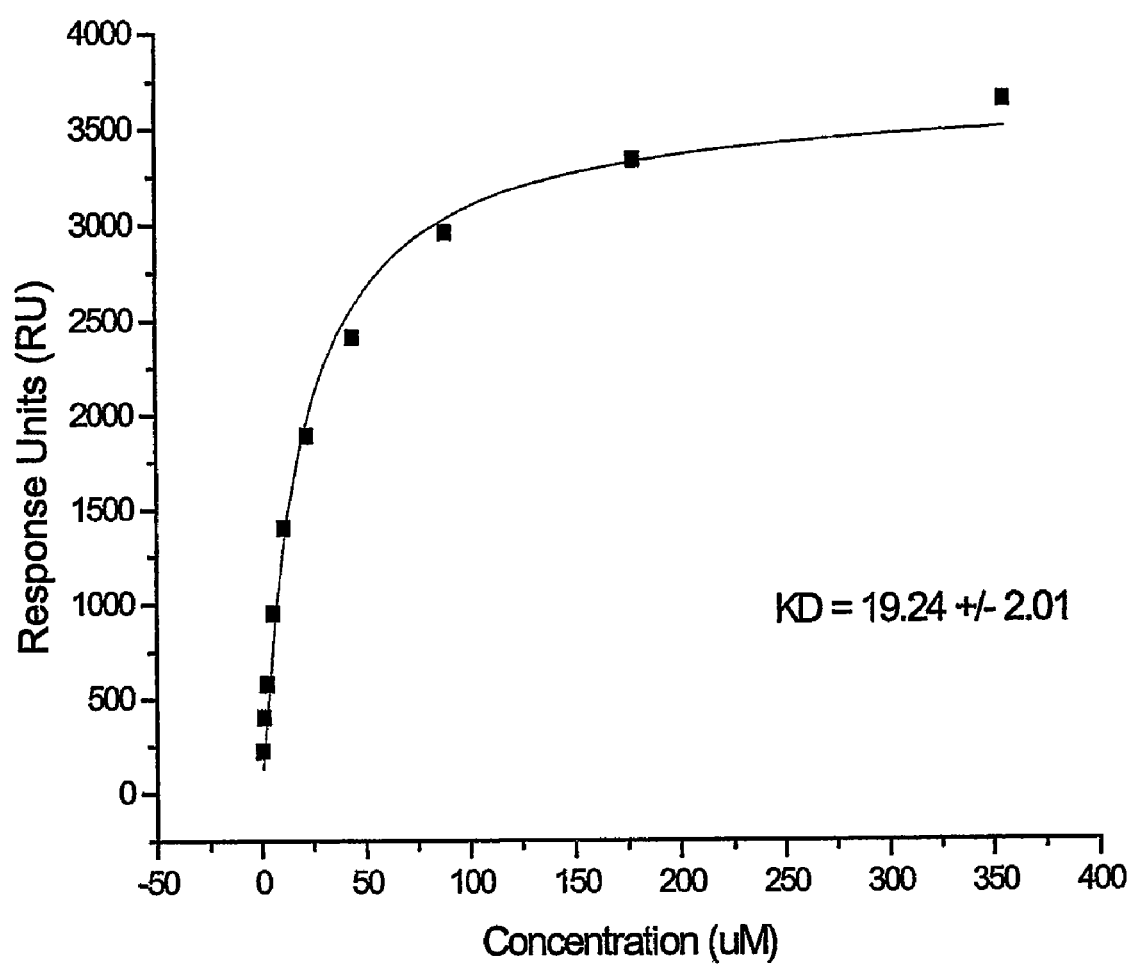
Figure 32:
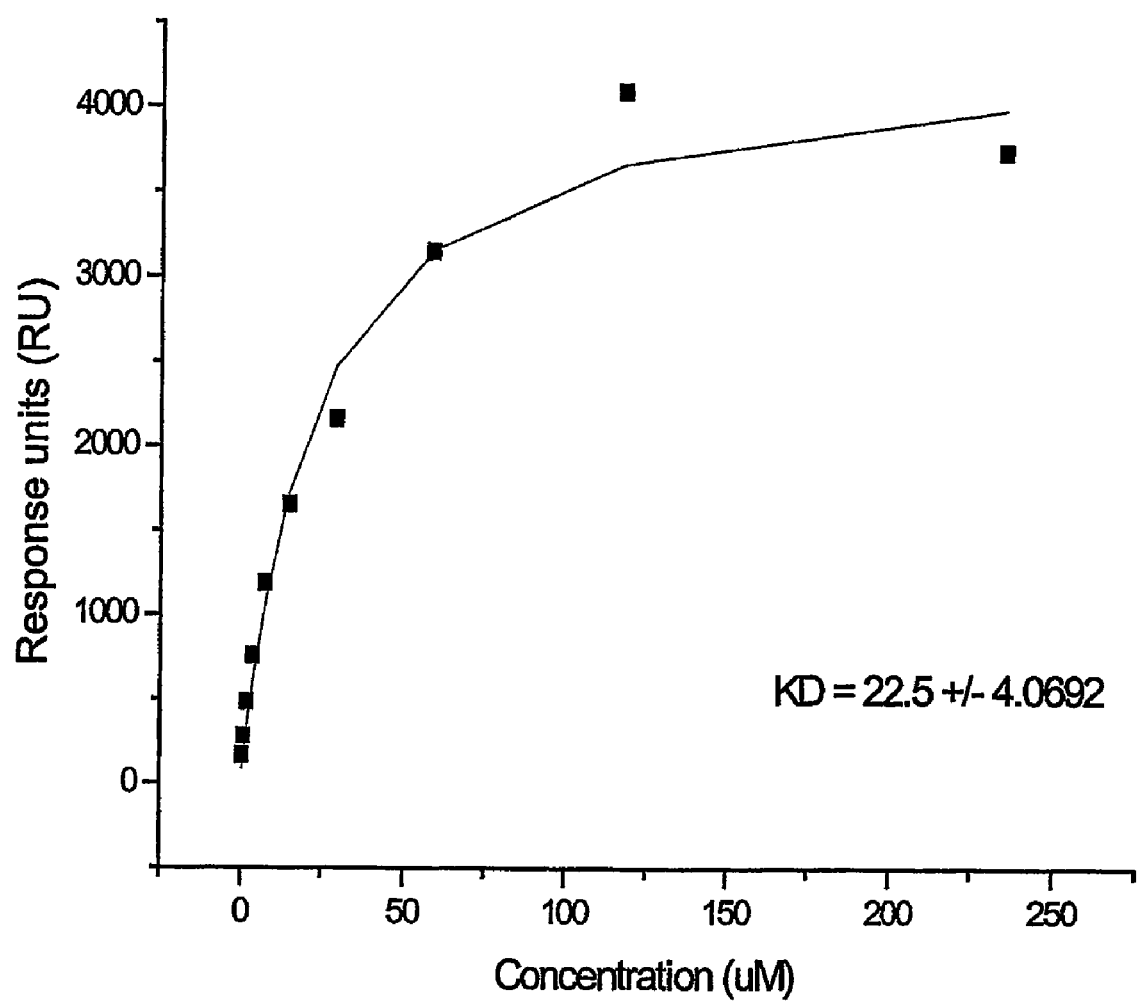
Figure 35:
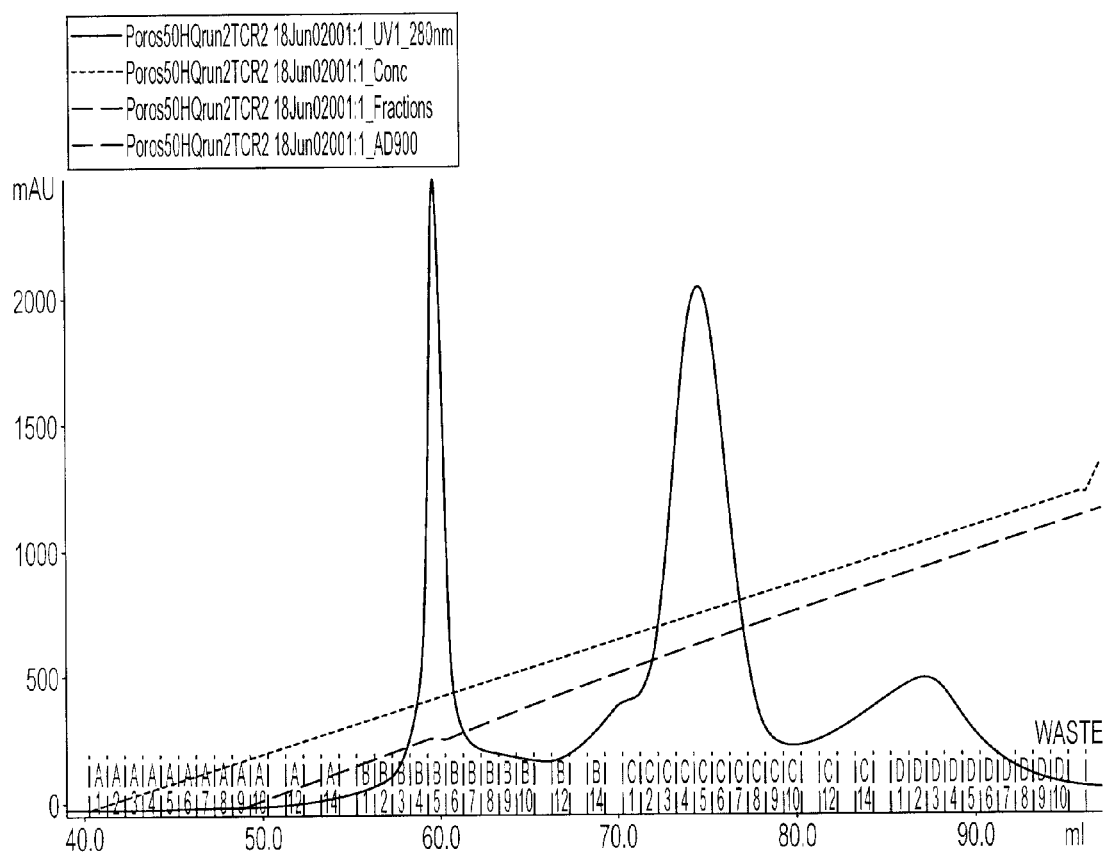
Figure 36:
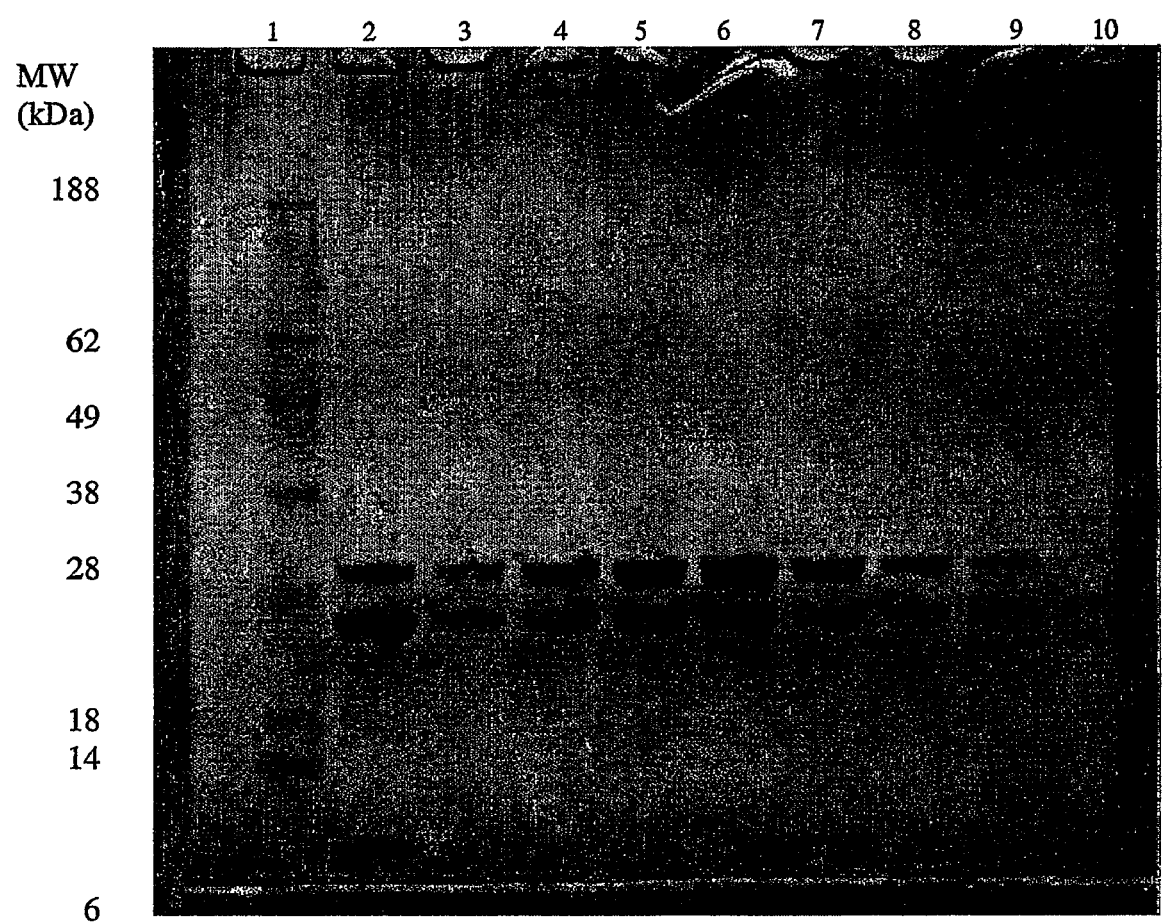
Figure 37:
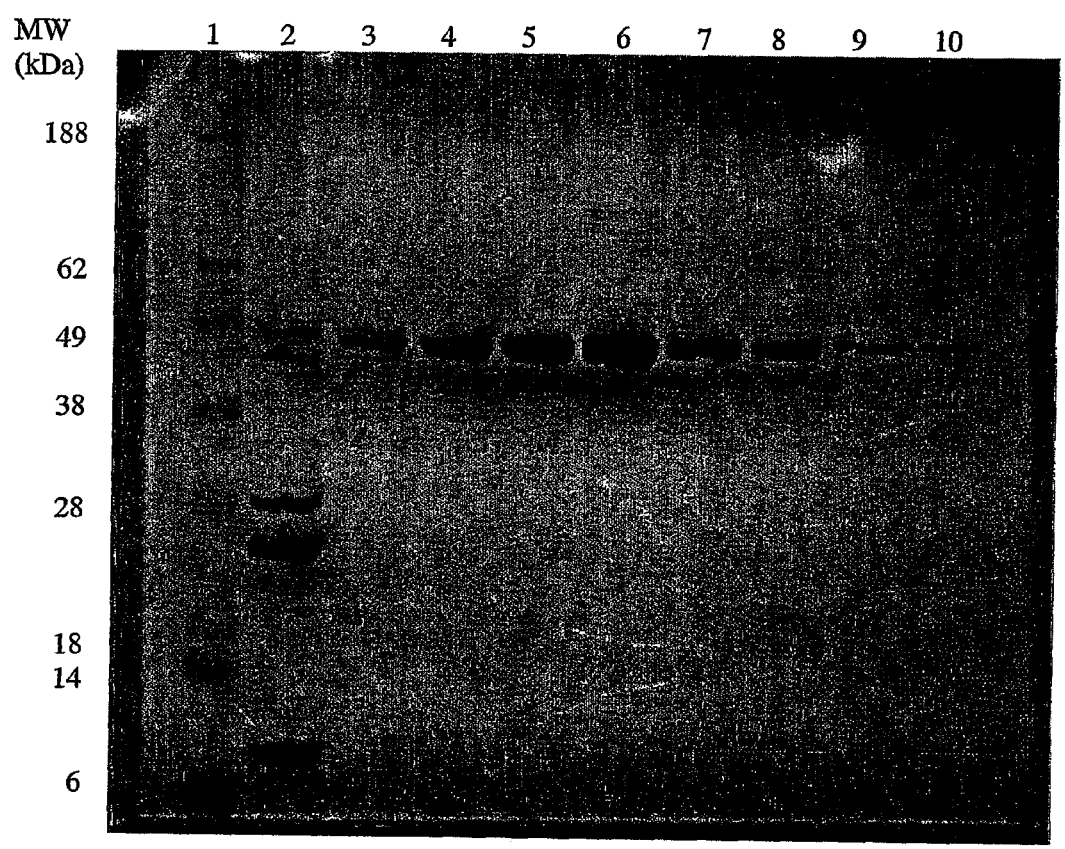
Figure 38:
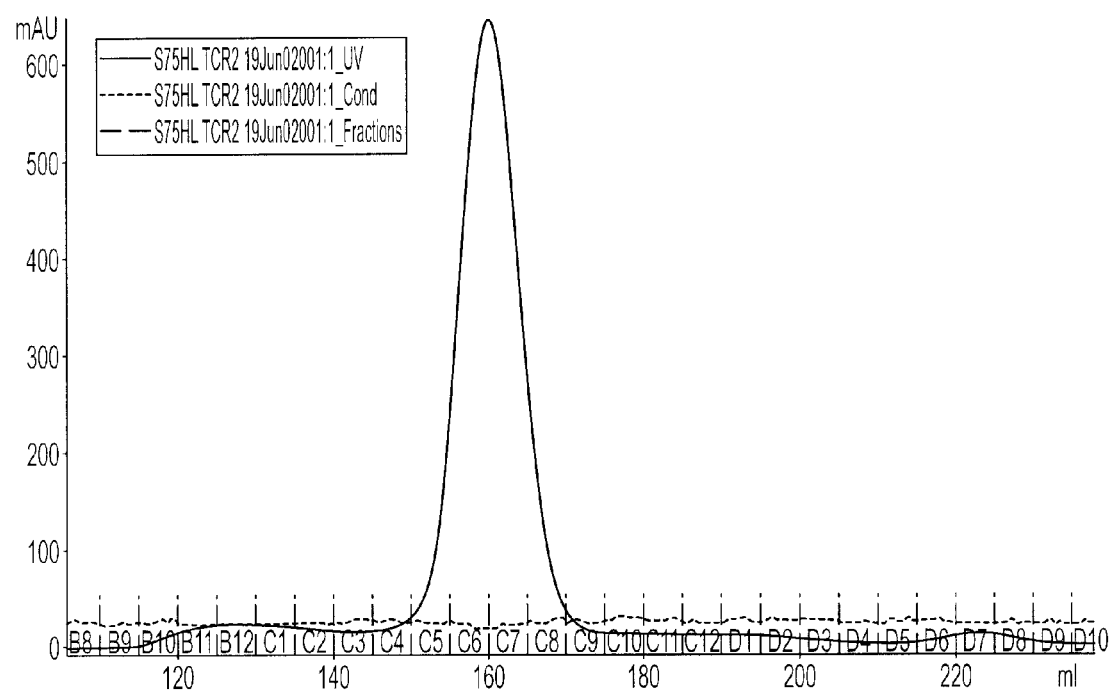
Figure 59:
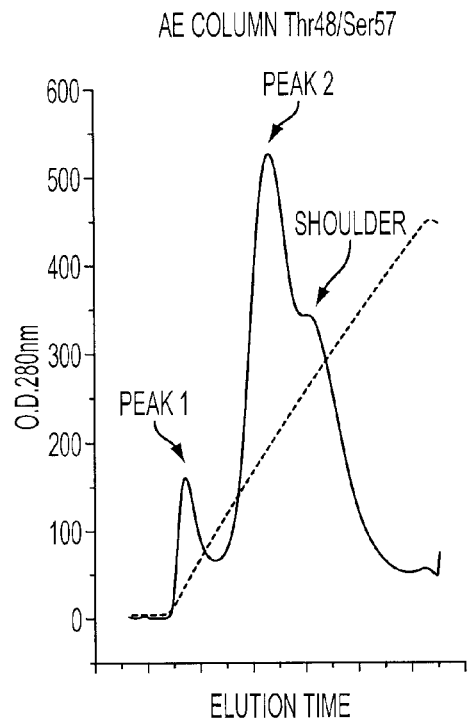
Figure 60:
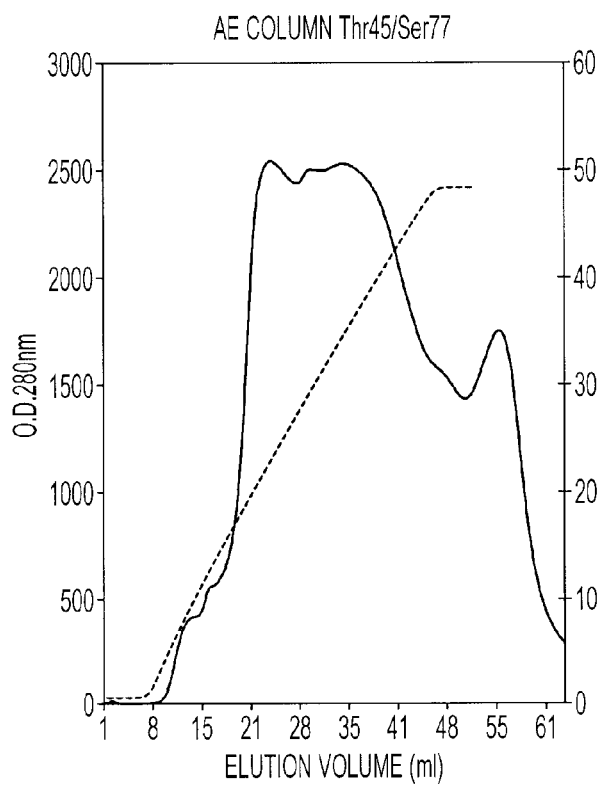
Figure 61:
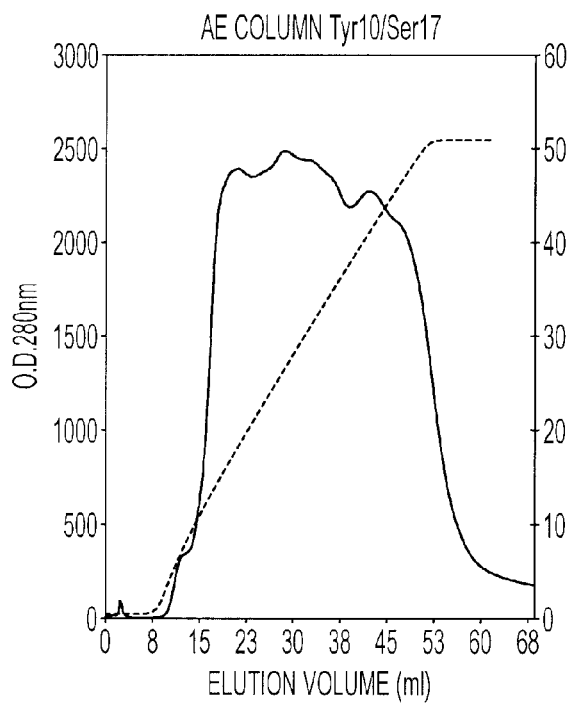
Figure 65:
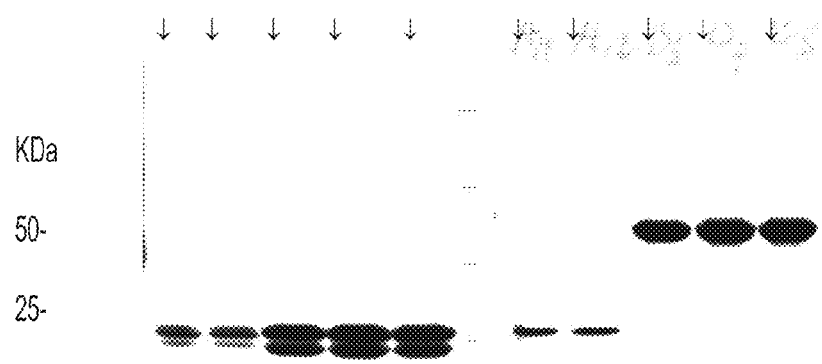
Figure 66:
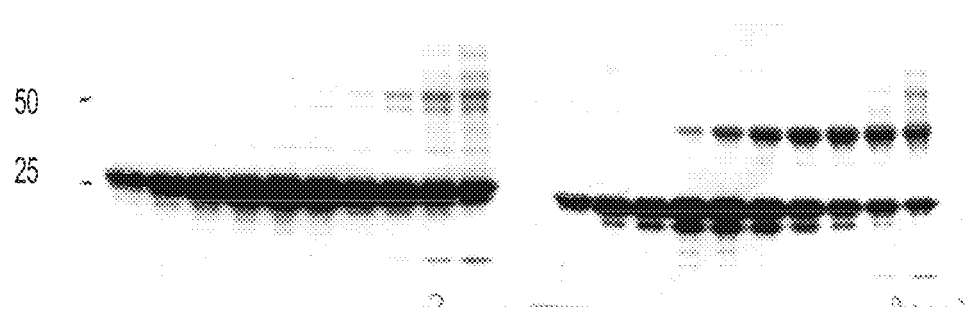
Figure 67:
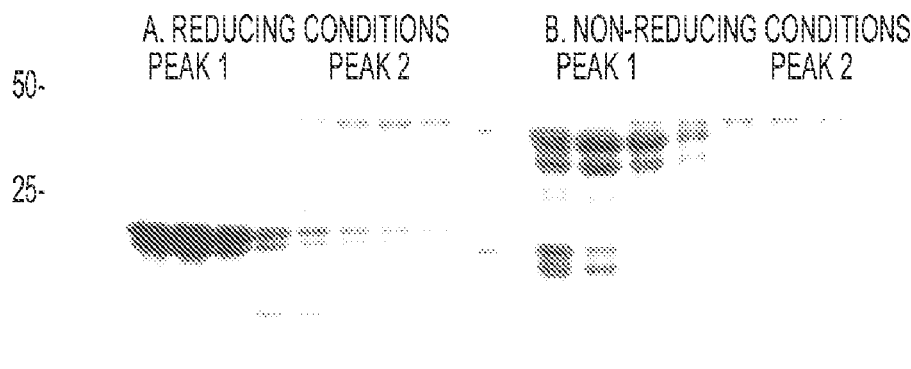
Figure 68:
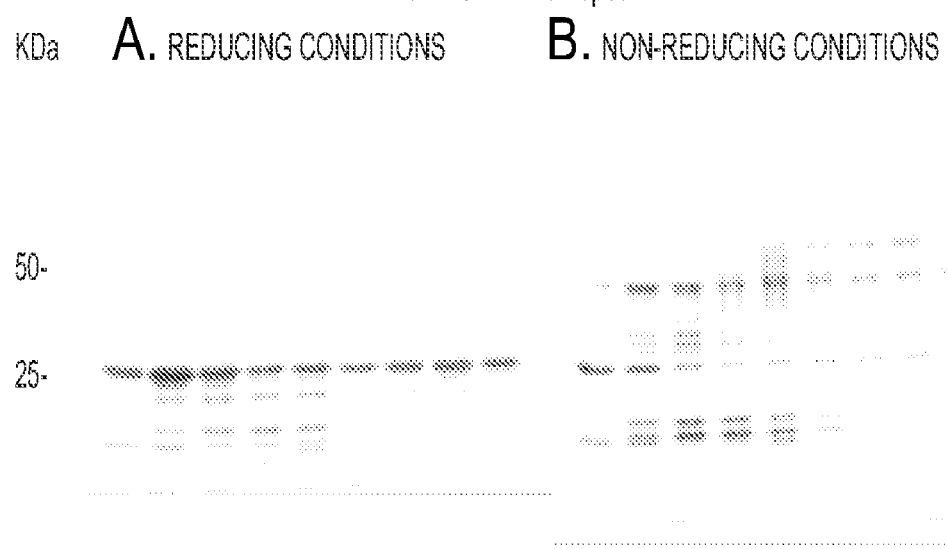

FIG. 16 is a trace obtained from anion exchange chromatography of soluble NY-ESO disulphide-linked TCR showing protein elution from a POROS 50HQ column using a 0-500 mM NaCl gradient, as indicated by the dotted line;

FIG. 17—A. Reducing SDS-PAGE (Coomassie-stained) of fractions from column run in FIG. 16, as indicated. B. Non-reducing SDS-PAGE (Coomassie-stained) of fractions from column run in FIG. 16, as indicated. Peak 1 and 2 clearly contain TCR heterodimer which is inter-chain disulphide linked;

FIG. 18. Size-exclusion chromatography of pooled fractions from peak 1 (A) and peak 2 (B) in FIG. 17. The protein elutes as a single major peak, corresponding to the heterodimer;

FIG. 19 shows a BIAcore response curve of the specific binding of disulphide-linked NY-ESO soluble TCR to HLA-NYESO complex. A. peak 1, B. peak 2;

FIGS. 20*a* and 20*b* show respectively the DNA sequences of the α (SEQ ID NO:119) and β (SEQ ID NO:120) chains of a soluble NY-ESO TCR, mutated so as to introduce a novel cysteine codon (indicated by shading). The sequences include the cysteine involved in the native disulphide inter-chain bond (indicated by the codon in bold);

FIGS. 21a and 21b show respectively the NY-ESO TCR α (SEQ ID NO:121) and β (SEQ ID NO:122) chain extracellular amino acid sequences produced from the DNA sequences of FIGS. 20a and 21b;

FIG. 22 shows a trace obtained from anion exchange chromatography of soluble NY-ESO TCRα$^{cys}$ β$^{cys}$ showing protein elution from a POROS 50HQ column using a 0-500 mM NaCl gradient, as indicated by the dotted line;

FIG. 23 shows a trace obtained from anion exchange chromatography of soluble NY-ESO TCRα$^{cys}$ showing protein elution from a POROS 50HQ column using a 0-500 mM NaCl gradient, as indicated by the dotted line;

FIG. 24 shows a trace obtained from anion exchange chromatography of soluble NY-ESO TCRβ$^{cys}$ showing protein elution from a POROS 50HQ column using a 0-500 mM NaCl gradient, as indicated by the dotted line;

FIG. 25 shows a reducing SDS-PAGE (Coomassie-stained) of NY-ESO TCRα$^{cys}$ β$^{cys}$, TCRα$^{cys}$, and TCRβ$^{cys}$ fractions from anion exchange column runs in FIGS. 22-24 respectively. Lanes 1 and 7 are MW markers, lane 2 is NYESOdsTCR1g4 α-cys β peak (EB/084/033); lane 3 is NYESOdsTCR1g4 α-cys β small peak (EB/084/033), lane 4 is NYESOdsTCR1g4 α β-cys (EB/084/034), lane 5 is NYESOdsTCR1g4 α-cys β-cys small peak (EB/084/035), and lane 6 is NYESOdsTCR1g4 α-cys β-cys peak (EB/084/035);

FIG. 26 shows a non-reducing SDS-PAGE (Coomassie-stained) of NY-ESO TCRα$^{cys}$ β$^{cys}$, TCRα$^{cys}$, and TCRβ$^{cys}$ fractions from anion exchange column runs in FIGS. 22-24 respectively. Lanes 1 and 7 are MW markers, lane 2 is NYESOdsTCR1g4 α-cys β peak (EB/084/033); lane 3 is NYESOdsTCR1g4 α-cys β small peak (EB/084/033), lane 4 is NYESOdsTCR1g4 α β-cys (EB/084/034), lane 5 is NYESOdsTCR1g4 α-cys β-cys small peak (EB/084/035), and lane 6 is NYESOdsTCR1g4 α-cys β-cys peak (EB/084/035);

FIG. 27 is a trace obtained from size exclusion exchange chromatography of soluble NY-ESO TCRα$^{cys}$ β$^{cys}$ showing protein elution of pooled fractions from FIG. 22. The protein elutes as a single major peak, corresponding to the heterodimer;

FIG. 28 is a trace obtained from size exclusion exchange chromatography of soluble NY-ESO TCRα$^{cys}$ showing protein elution of pooled fractions from FIG. 22. The protein elutes as a single major peak, corresponding to the heterodimer;

FIG. 29 is a trace obtained from size exclusion exchange chromatography of soluble NY-ESO TCRβ$^{cys}$ showing protein elution of pooled fractions from FIG. 22. The protein elutes as a single major peak, corresponding to the heterodimer;

FIG. 30 is a BIAcore response curve of the specific binding of NY-ESO TCRα$^{cys}$ β$^{cys}$ to HLA-NY-ESO complex;

FIG. 31 is a BIAcore response curve of the specific binding of NY-ESO TCRα$^{cys}$ to HLA-NY-ESO complex;

FIG. 32 is a BIAcore response curve of the specific binding of NY-ESO TCRβ$^{cys}$ to HLA-NY-ESO complex;

FIGS. 33a and 33b show respectively the DNA sequences of the α (SEQ ID NO:123) and β (SEQ ID NO:124) chains of a soluble AH-1.23 TCR, mutated so as to introduce a novel cysteine codon (indicated by shading). The sequences include the cysteine involved in the native disulphide inter-chain bond (indicated by the codon in bold);

FIGS. 34a and 34b show respectively the AH-1.23 TCR α (SEQ ID NO:125) and β (SEQ ID NO:126) chain extracellular amino acid sequences produced from the DNA sequences of FIGS. 33a and 33b;

FIG. 35 is a trace obtained from anion exchange chromatography of soluble AH-1.23 TCR showing protein elution from a POROS 50HQ column using a 0-500 mM NaCl gradient, as indicated by the dotted line;

FIG. 36 is a reducing SDS-PAGE (10% Bis-Tris gel, Coomassie-stained) of AH-1.23 TCR fractions from anion exchange column run in FIG. 35. Proteins examined are the anion exchange fractions of TCR 1.23 S—S from refold 3. Lane 1 is MW markers, lane 2 is B4, lane 3 is C2, lane 4 is C3, lane 5 is C4, lane 6 is C5, lane 7 is C6, lane 8 is C7, lane 9 is C8, and lane 10 is C9;

FIG. 37 is a non-reducing SDS-PAGE (10% Bis-Tris gel, Coomassie-stained) of AH-1.23 TCR fractions from anion exchange column run in FIG. 35. Proteins examined are the anion exchange fractions of TCR 1.23 S—S from refold 3. Lane 1 is MW markers, lane 2 is B4, lane 3 is C2, lane 4 is C3, lane 5 is C4, lane 6 is C5, lane 7 is C6, lane 8 is C7, lane 9 is C8, and lane 10 is C9;

FIG. 38 is a trace obtained from size exclusion exchange chromatography of soluble AH-1.23 TCR showing protein elution of pooled fractions from FIG. 35. The protein elutes as a single major peak, corresponding to the heterodimer;

FIGS. 39a and 39b show respectively the DNA (SEQ ID NO:127) and amino acid (SEQ ID NO:128) sequences of the α chain of a soluble A6 TCR, mutated so as to introduce a novel cysteine at residue 48 in exon 1 of TRAC*01. The shaded nucleotides indicate the introduced novel cysteine codon and the underlined amino acid indicates the introduced cysteine;

FIGS. 40a and 40b show respectively the DNA (SEQ ID NO:129) and amino acid (SEQ ID NO:130) sequences of the α chain of a soluble A6 TCR, mutated so as to introduce a novel cysteine at residue 45 in exon 1 of TRAC*01. The shaded nucleotides indicate the introduced novel cysteine codon and the underlined amino acid indicates the introduced cysteine;

FIGS. 41a and 41b show respectively the DNA (SEQ ID NO:131) and amino acid (SEQ ID NO:132) sequences of the α chain of a soluble A6 TCR, mutated so as to introduce a novel cysteine at residue 61 in exon 1 of TRAC*01. The shaded nucleotides indicate the introduced novel cysteine codon and the underlined amino acid indicates the introduced cysteine;

FIGS. 42a and 42b show respectively the DNA (SEQ ID NO:133) and amino acid (SEQ ID NO:134) sequences of the α chain of a soluble A6 TCR, mutated so as to introduce a novel cysteine at residue 50 in exon 1 of TRAC*01. The shaded nucleotides indicate the introduced novel cysteine codon and the underlined amino acid indicates the introduced cysteine;

FIGS. 43a and 43b show respectively the DNA (SEQ ID NO:135) and amino acid (SEQ ID NO:136) sequences of the α chain of a soluble A6 TCR, mutated so as to introduce a novel cysteine at residue 10 in exon 1 of TRAC*01. The shaded nucleotides indicate the introduced novel cysteine codon and the underlined amino acid indicates the introduced cysteine;

FIGS. 44a and 44b show respectively the DNA (SEQ ID NO:137) and amino acid (SEQ ID NO:138) sequences of the α chain of a soluble A6 TCR, mutated so as to introduce a novel cysteine at residue 15 in exon 1 of TRAC*01. The shaded nucleotides indicate the introduced novel cysteine codon and the underlined amino acid indicates the introduced cysteine;

FIGS. 45a and 45b show respectively the DNA (SEQ ID NO:139) and amino acid (SEQ ID NO:140) sequences of the α chain of a soluble A6 TCR, mutated so as to introduce a novel cysteine at residue 12 in exon 1 of TRAC*01. The shaded nucleotides indicate the introduced novel cysteine codon and the underlined amino acid indicates the introduced cysteine;

FIGS. 46a and 46b show respectively the DNA (SEQ ID NO:141) and amino acid (SEQ ID NO:142) sequences of the α chain of a soluble A6 TCR, mutated so as to introduce a novel cysteine at residue 22 in exon 1 of TRAC*01. The shaded nucleotides indicate the introduced novel cysteine codon and the underlined amino acid indicates the introduced cysteine;

FIGS. 47a and 47b show respectively the DNA (SEQ ID NO:143) and amino acid (SEQ ID NO:144) sequences of the α chain of a soluble A6 TCR, mutated so as to introduce a novel cysteine at residue 52 in exon 1 of TRAC*01. The shaded nucleotides indicate the introduced novel cysteine codon and the underlined amino acid indicates the introduced cysteine;

FIGS. 48a and 48b show respectively the DNA (SEQ ID NO:145) and amino acid (SEQ ID NO:146) sequences of the α chain of a soluble A6 TCR, mutated so as to introduce a novel cysteine at residue 43 in exon 1 of TRAC*01. The shaded nucleotides indicate the introduced novel cysteine codon and the underlined amino acid indicates the introduced cysteine;

FIGS. 49a and 49b show respectively the DNA (SEQ ID NO:147) and amino acid (SEQ ID NO:148) sequences of the α chain of a soluble A6 TCR, mutated so as to introduce a novel cysteine at residue 57 in exon 1 of TRAC*01. The shaded nucleotides indicate the introduced novel cysteine codon and the underlined amino acid indicates the introduced cysteine;

FIGS. 50a and 50b show respectively the DNA (SEQ ID NO:149) and amino acid (SEQ ID NO:150) sequences of the β chain of a soluble A6 TCR, mutated so as to introduce a novel cysteine at residue 77 in exon 1 of TRBC2*01. The shaded nucleotides indicate the introduced novel cysteine codon and the underlined amino acid indicates the introduced cysteine;

FIGS. 51a and 51b show respectively the DNA (SEQ ID NO:151) and amino acid (SEQ ID NO:152) sequences of the β chain of a soluble A6 TCR, mutated so as to introduce a novel cysteine at residue 17 in exon 1 of TRBC2*01. The shaded nucleotides indicate the introduced novel cysteine codon and the underlined amino acid indicates the introduced cysteine;

FIGS. 52a and 52b show respectively the DNA (SEQ ID NO:153) and amino acid (SEQ ID NO:154) sequences of the β chain of a soluble A6 TCR, mutated so as to introduce a novel cysteine at residue 13 in exon 1 of TRBC2*01. The shaded nucleotides indicate the introduced novel cysteine codon and the underlined amino acid indicates the introduced cysteine;

FIGS. 53a and 53b show respectively the DNA (SEQ ID NO:155) and amino acid (SEQ ID NO:156) sequences of the β chain of a soluble A6 TCR, mutated so as to introduce a novel cysteine at residue 59 in exon 1 of TRBC2*01. The shaded nucleotides indicate the introduced novel cysteine codon and the underlined amino acid indicates the introduced cysteine;

FIGS. 54a and 54b show respectively the DNA (SEQ ID NO:157) and amino acid (SEQ ID NO:158) sequences of the β chain of a soluble A6 TCR, mutated so as to introduce a novel cysteine at residue 79 in exon 1 of TRBC2*01. The shaded nucleotides indicate the introduced novel cysteine codon and the underlined amino acid indicates the introduced cysteine;

FIGS. 55a and 55b show respectively the DNA (SEQ ID NO:159) and amino acid (SEQ ID NO:160) sequences of the β chain of a soluble A6 TCR, mutated so as to introduce a novel cysteine at residue 14 in exon 1 of TRBC2*01. The shaded nucleotides indicate the introduced novel cysteine codon and the underlined amino acid indicates the introduced cysteine;

FIGS. 56a and 56b show respectively the DNA (SEQ ID NO:161) and amino acid (SEQ ID NO:162) sequences of the β chain of a soluble A6 TCR, mutated so as to introduce a novel cysteine at residue 55 in exon 1 of TRBC2*01. The shaded nucleotides indicate the introduced novel cysteine codon and the underlined amino acid indicates the introduced cysteine;

FIGS. 57a and 57b show respectively the DNA (SEQ ID NO:163) and amino acid (SEQ ID NO:164) sequences of the β chain of a soluble A6 TCR, mutated so as to introduce a novel cysteine at residue 63 in exon 1 of TRBC2*01. The shaded nucleotides indicate the introduced novel cysteine codon and the underlined amino acid indicates the introduced cysteine;

FIGS. 58a and 58b show respectively the DNA (SEQ ID NO:165) and amino acid (SEQ ID NO:166) sequences of the β chain of a soluble A6 TCR, mutated so as to introduce a novel cysteine at residue 15 in exon 1 of TRBC2*01. The shaded nucleotides indicate the introduced novel cysteine codon and the underlined amino acid indicates the introduced cysteine;

FIGS. 59-64 are traces obtained from anion exchange chromatography of soluble A6 TCR containing a novel disulphide inter-chain bond between: residues 48 of exon 1 of TRAC*01 and 57 of exon 1 of TRBC2*01; residues 45 of exon 1 of TRAC*01 and 77 of exon 1 of TRBC2*01; residues 10 of exon 1 of TRAC*01 and 17 of exon 1 of TRBC2*01; residues 45 of exon 1 of TRAC*01 and 59 of exon 1 of TRBC2*01; residues 52 of exon 1 of TRAC*01 and 55 of exon 1 of TRBC2*01; residues 15 of exon 1 of TRAC*01 and 15 of exon 1 of TRBC2*01, respectively, showing protein elution from a POROS 50 column using a 0-500 mM NaCl gradient, as indicated by the dotted line;

FIGS. 65a and 65b are, respectively, reducing and non-reducing SDS-PAGE (Coomassie-stained) of soluble A6 TCR containing a novel disulphide inter-chain bond between residues 48 of exon 1 of TRAC*01 and 57 of exon 1 of TRBC2*01, fractions run were collected from anion exchange column run in FIG. 59;

FIGS. 66a and 66b are, respectively, reducing and non-reducing SDS-PAGE (Coomassie-stained) of soluble A6 TCR containing a novel disulphide inter-chain bond between residues 45 of exon 1 of TRAC*01 and 77 of exon 1 of TRBC2*01, fractions run were collected from anion exchange column run in FIG. 60;

FIGS. 67a and 67b are, respectively, reducing and non-reducing SDS-PAGE (Coomassie-stained) of soluble A6 TCR containing a novel disulphide inter-chain bond between residues 10 of exon 1 of TRAC*01 and 17 exon 1 of TRBC2*01, fractions run were collected from anion exchange column run in FIG. 61;

FIGS. 68a and 68b are, respectively, reducing and non-reducing SDS-PAGE (Coomassie-stained) of soluble A6

Figure 62:
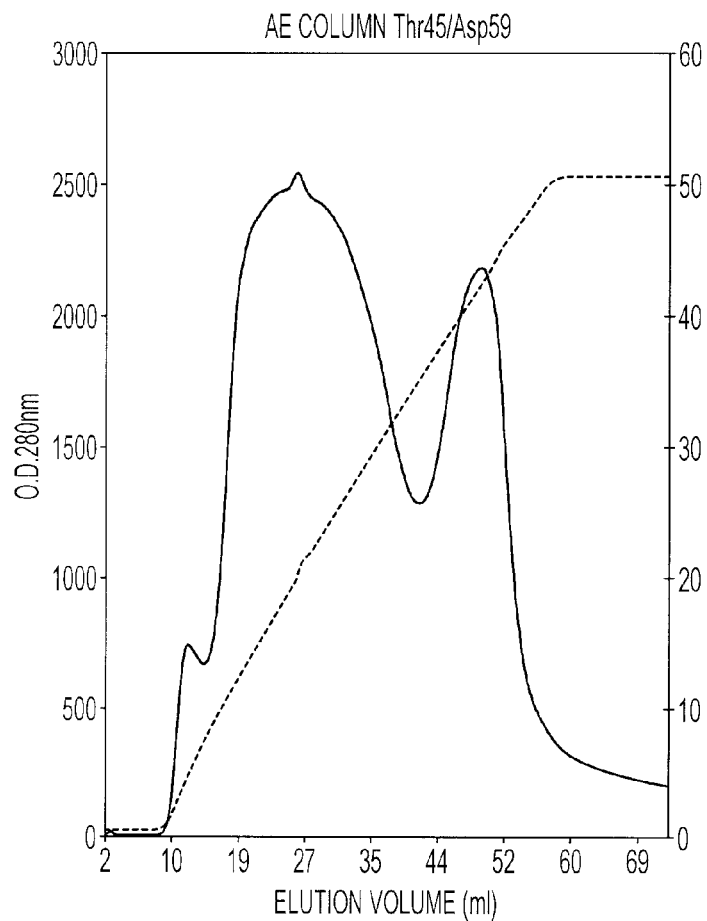
Figure 73:
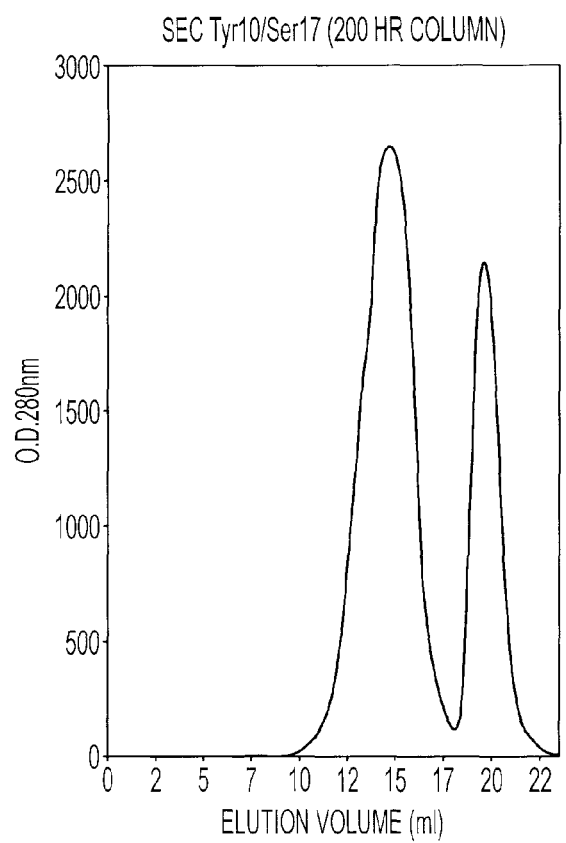
Figure 74:
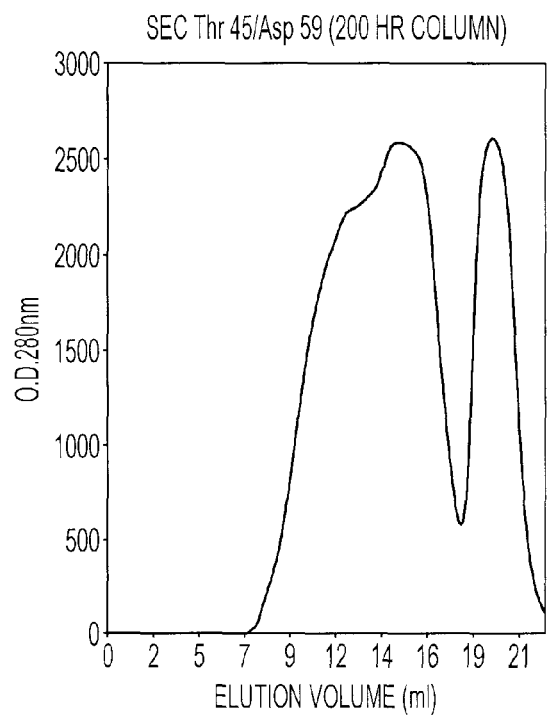

TCR containing a novel disulphide inter-chain bond between residues 45 of exon 1 of TRAC*01 and 59 of exon 1 of TRBC2*01, fractions run were collected from anion exchange column run in FIG. 62;

FIGS. 69*a* and 69*b* are, respectively, reducing and non-reducing SDS-PAGE (Coomassie-stained) of soluble A6 TCR containing a novel disulphide inter-chain bond between residues 52 of exon 1 of TRAC*01 and 55 of exon 1 of TRBC2*01, fractions run were collected from anion exchange column run in FIG. 63;

FIGS. 70*a* and 70*b* are, respectively, reducing and non-reducing SDS-PAGE (Coomassie-stained) of soluble A6 TCR containing a novel disulphide inter-chain bond between residues 15 of exon 1 of TRAC*01 and 15 of exon 1 of TRBC2*01, fractions run were collected from anion exchange column run in FIG. 64;

FIG. 71 is a trace obtained from size exclusion chromatography of soluble A6 TCR containing a novel disulphide inter-chain bond between residues 48 of exon 1 of TRAC*01 and 57 of exon 1 of TRBC2*01, showing protein elution from a Superdex 200 HL gel filtration column. Fractions run were collected from anion exchange column run in FIG. 59;

FIG. 72 is a trace obtained from size exclusion chromatography of soluble A6 TCR containing a novel disulphide inter-chain bond between residues 45 of exon 1 of TRAC*01 and 77 of exon 1 of TRBC2*01, showing protein elution from a Superdex 200 HL gel filtration column. Fractions run were collected from anion exchange column run in FIG. 60;

FIG. 73 is a trace obtained from size exclusion chromatography of soluble A6 TCR containing a novel disulphide inter-chain bond between residues 10 of exon 1 of TRAC*01 and 17 of exon 1 of TRBC2*01, showing protein elution from a Superdex 200 HL gel filtration column. Fractions run were collected from anion exchange column run in FIG. 61;

FIG. 74 is a trace obtained from size exclusion chromatography of soluble A6 TCR containing a novel disulphide inter-chain bond between residues 45 of exon 1 of TRAC*01 and 59 of exon 1 of TRBC2*01, showing protein elution from a Superdex 200 HL gel filtration column. Fractions run were collected from anion exchange column run in FIG. 62;

FIG. 75 is a trace obtained from size exclusion chromatography of soluble A6 TCR containing a novel disulphide inter-chain bond between residues 52 of exon 1 of TRAC*01 and 55 of exon 1 of TRBC2*01, showing protein elution from a Superdex 200 HL gel filtration column. Fractions run were collected from anion exchange column run in FIG. 63;

FIG. 76 is a trace obtained from size exclusion chromatography of soluble A6 TCR containing a novel disulphide inter-chain bond between residues 15 of exon 1 of TRAC*01 and 15 of exon 1 of TRBC2*01, showing protein elution from a Superdex 200 HL gel filtration column. Fractions run were collected from anion exchange column run in FIG. 64; and FIGS. 77-80 are BIAcore response curves showing, respectively, binding of soluble A6 TCR containing a novel disulphide inter-chain bond between: residues 48 of exon 1 of TRAC*01 and 57 of exon 1 of TRBC2*01; residues 45 of exon 1 of TRAC*01 and 77 of exon 1 of TRBC2*01; residues 10 of exon 1 of TRAC*01 and 17 of exon 1 of TRBC2*01; and residues 45 of exon 1 of TRAC*01 and 59 of exon 1 of TRBC2*01 to HLA-A2-tax pMHC.

Figure 83A:
Figure 83B:
Figure 84:
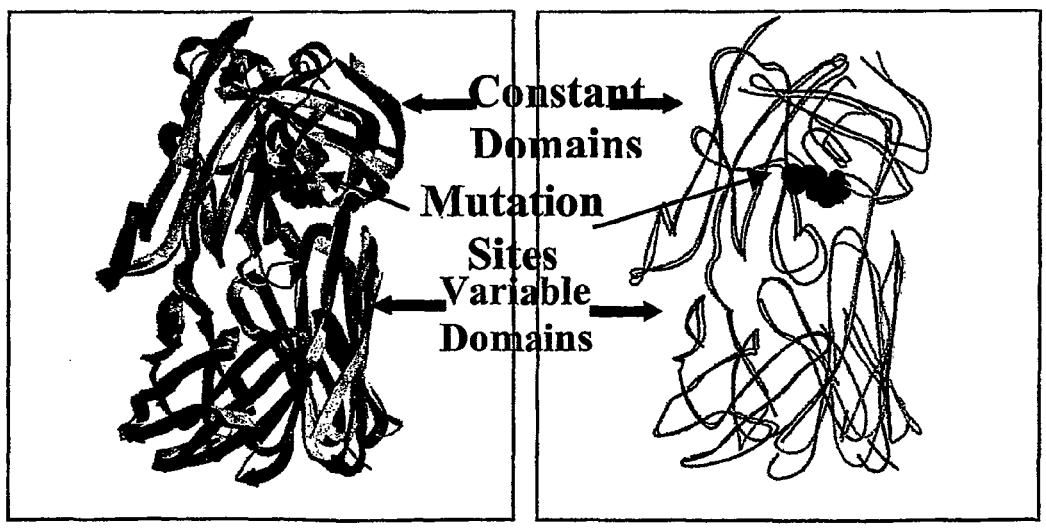
Figure 87:
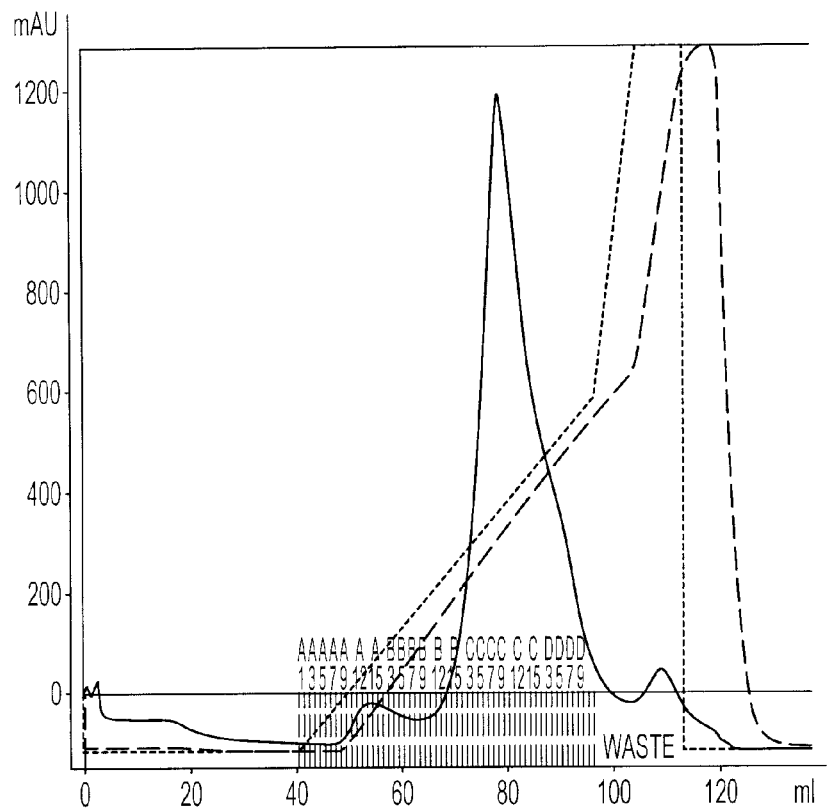
Figure 88:
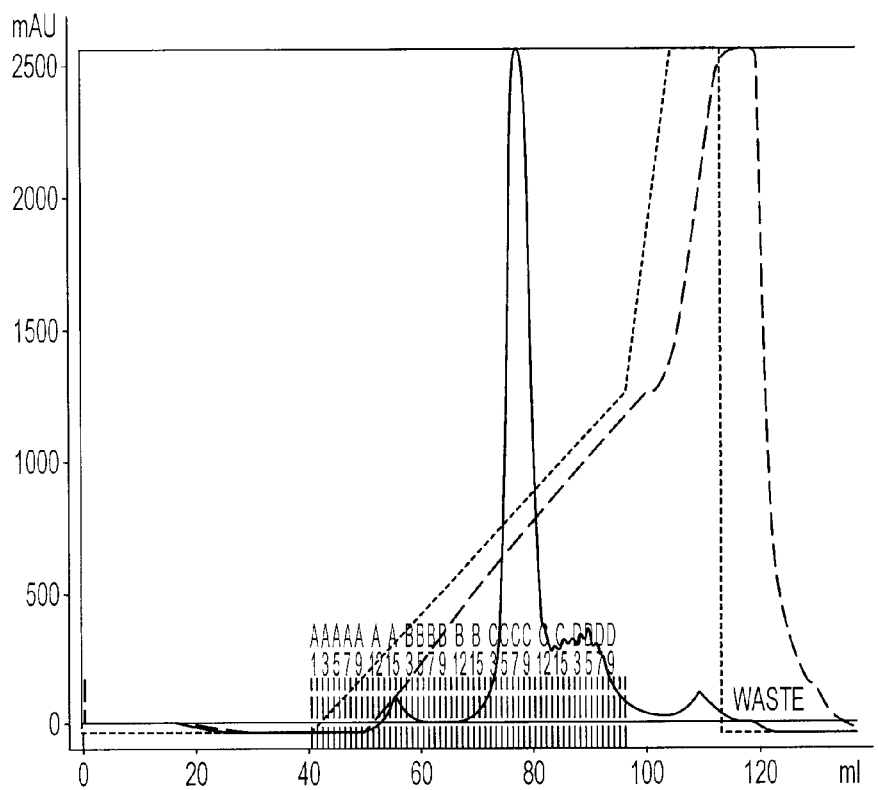
Figure 89:
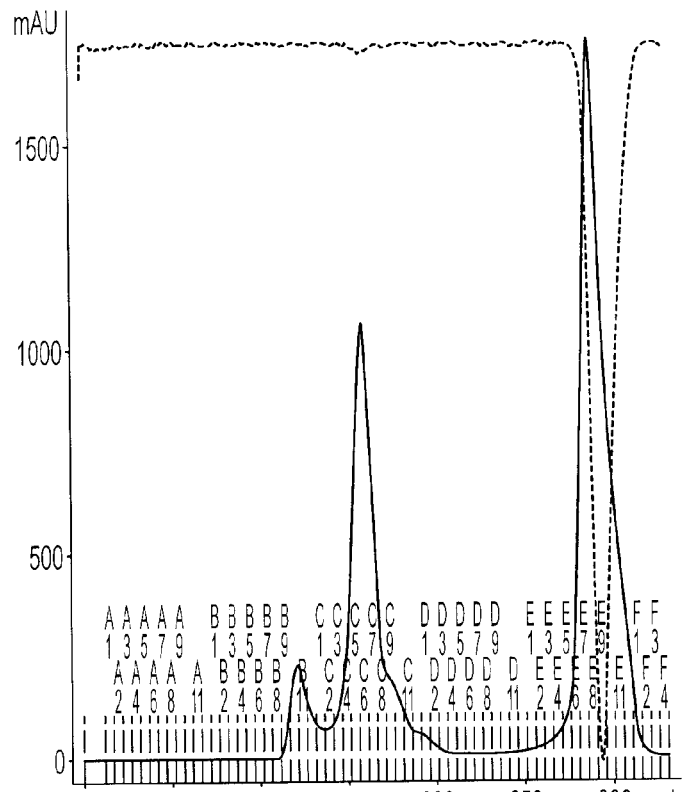
Figure 90:
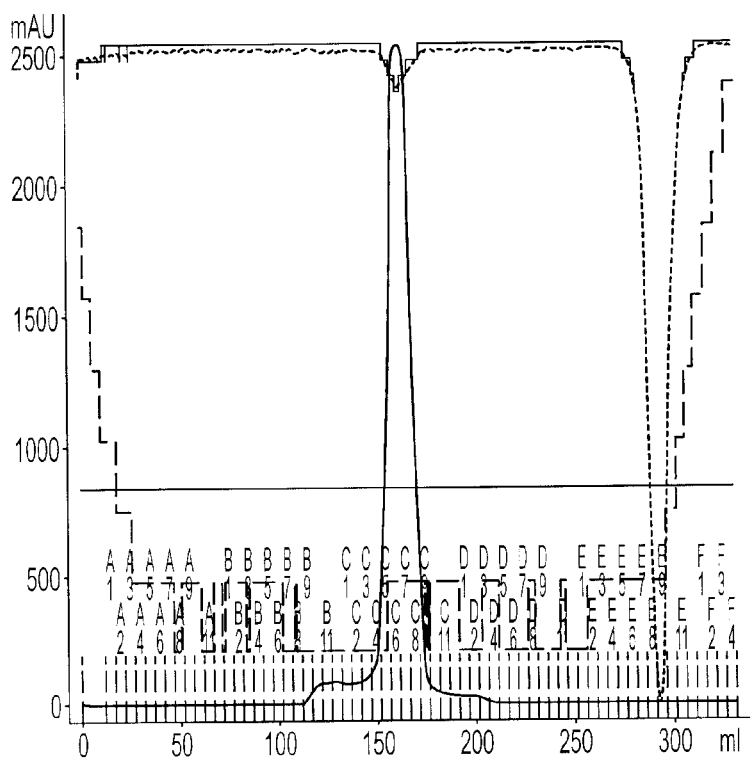
Figure 93:
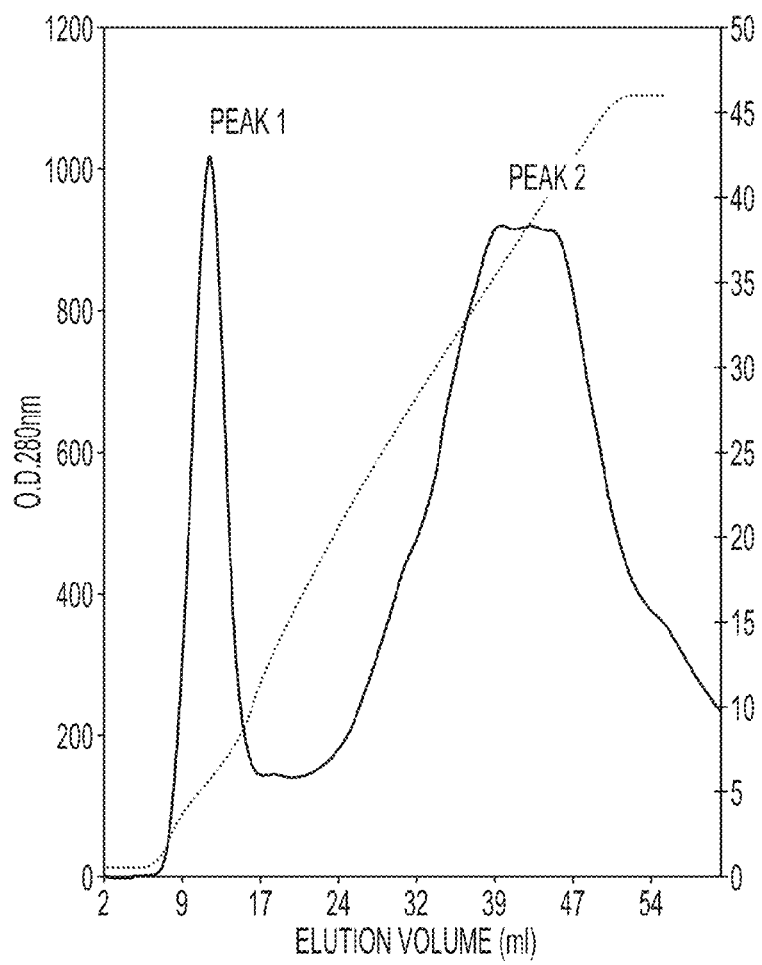
Figure 94:
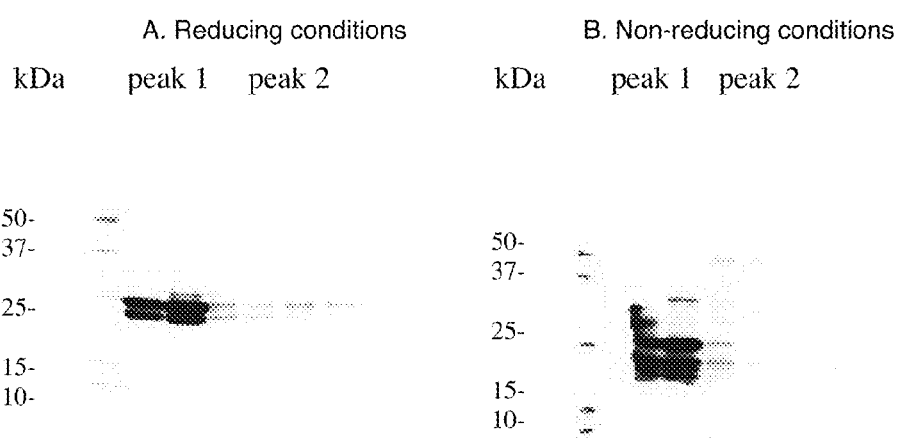
Figure 95:
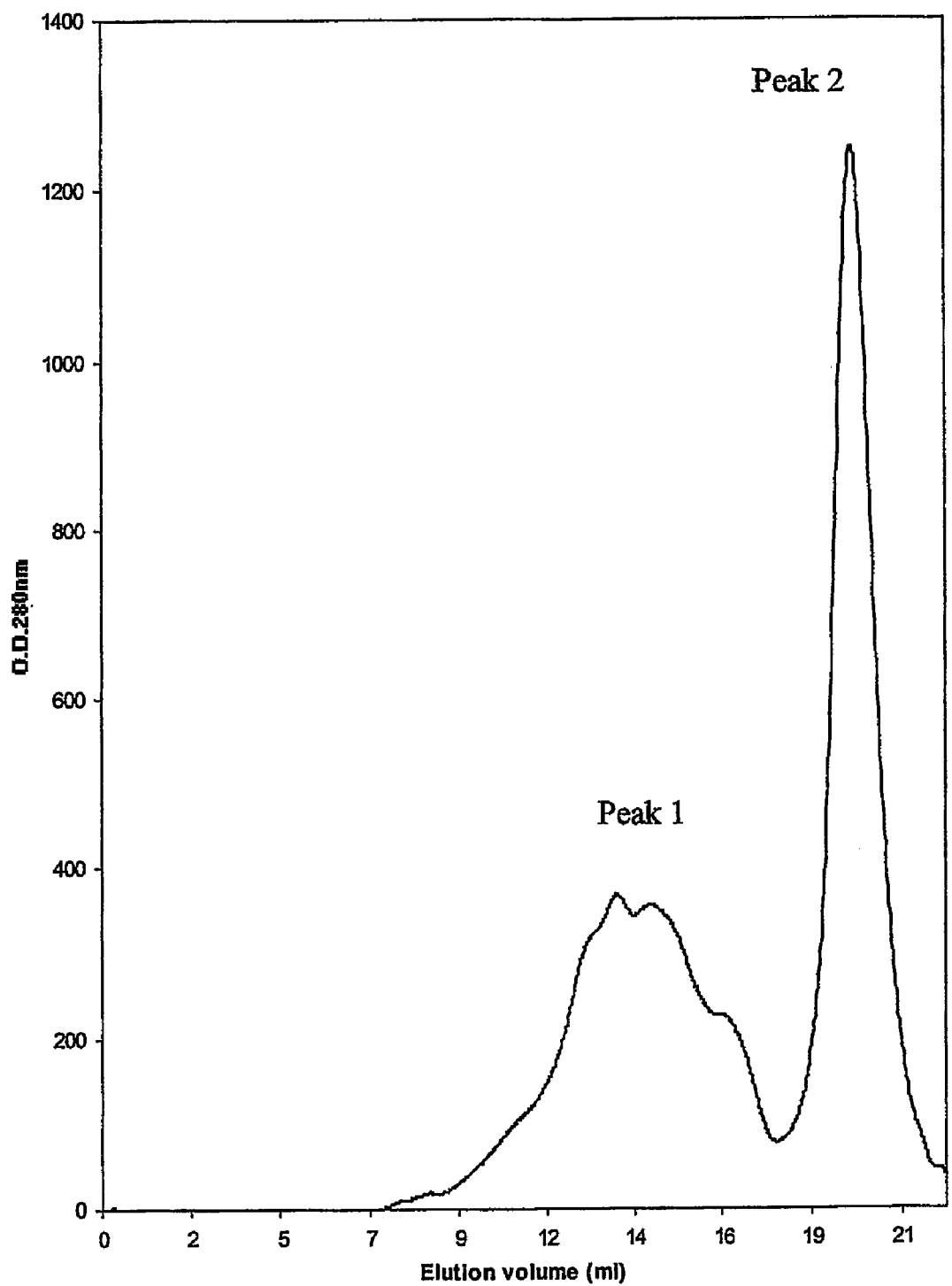
Figure 98:
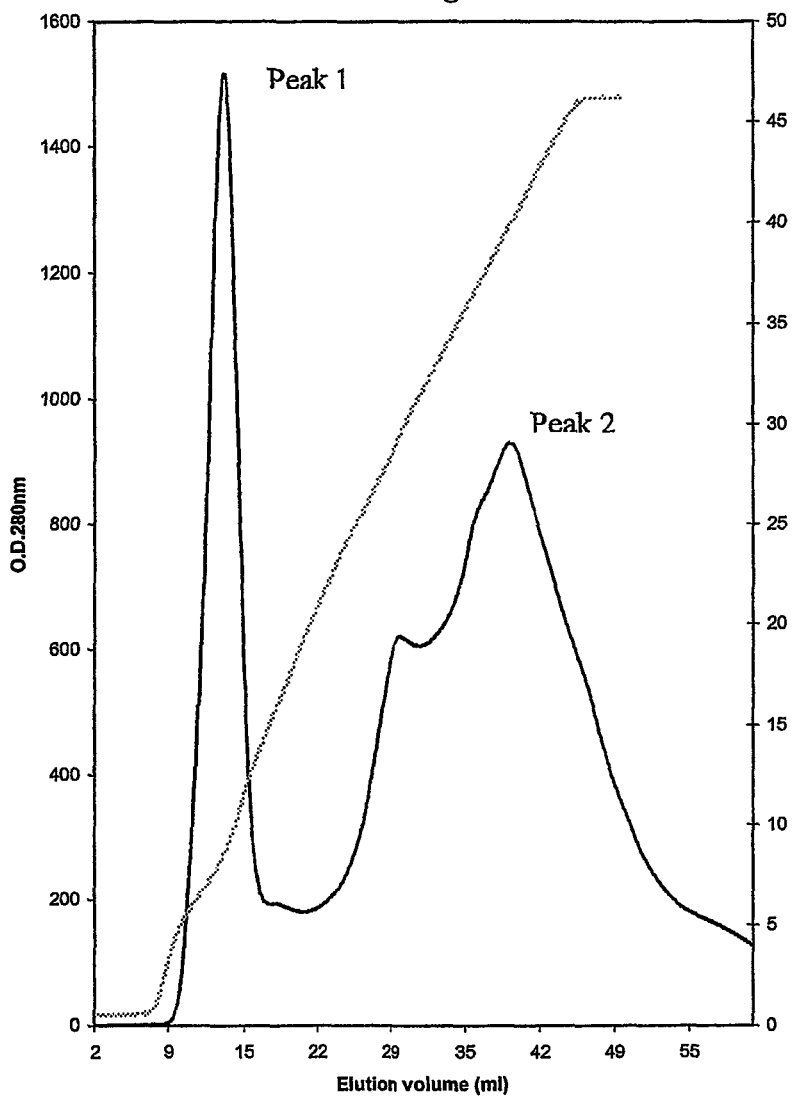
Figure 99:
Figure 100:
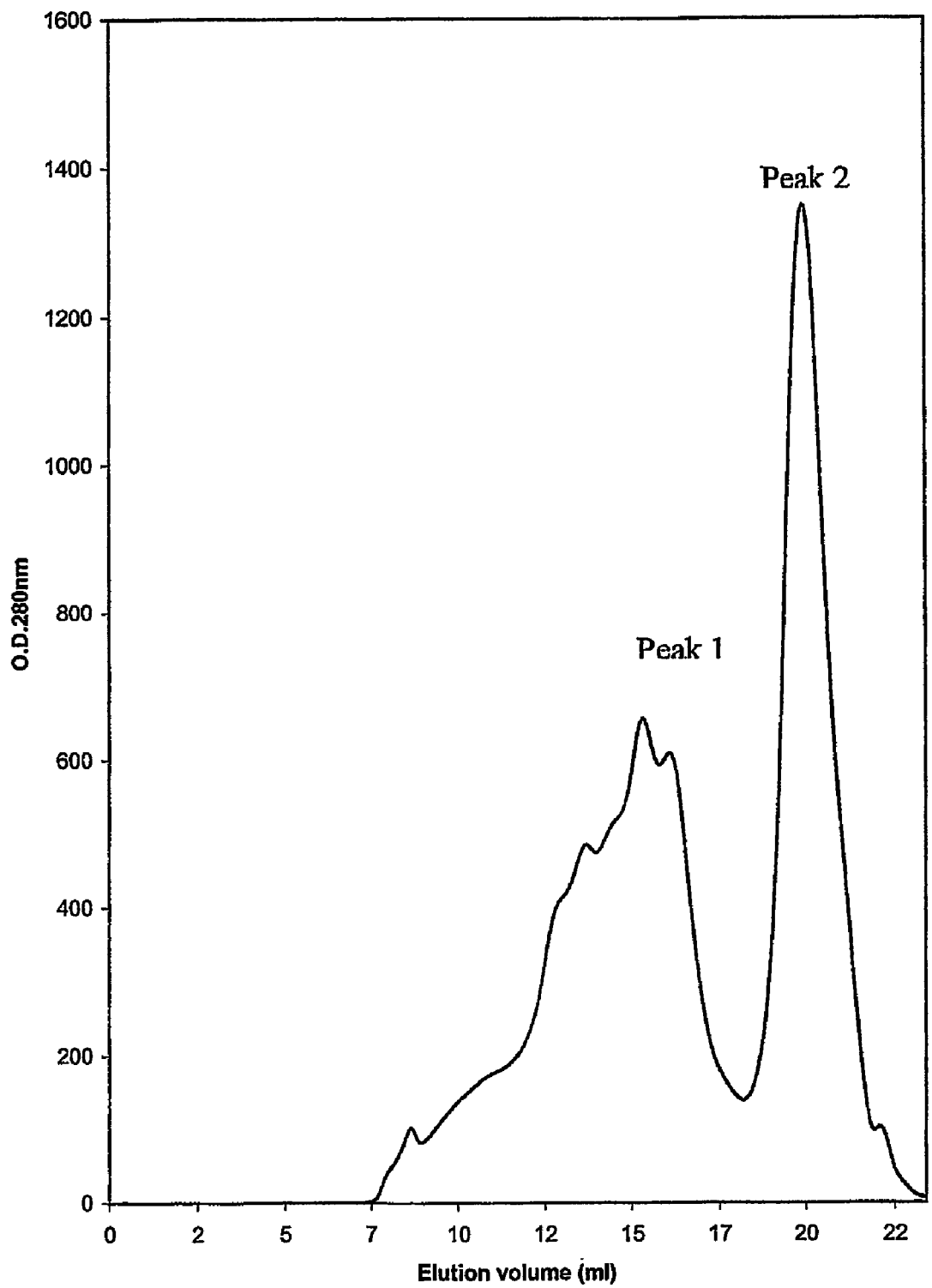
Figure 103:
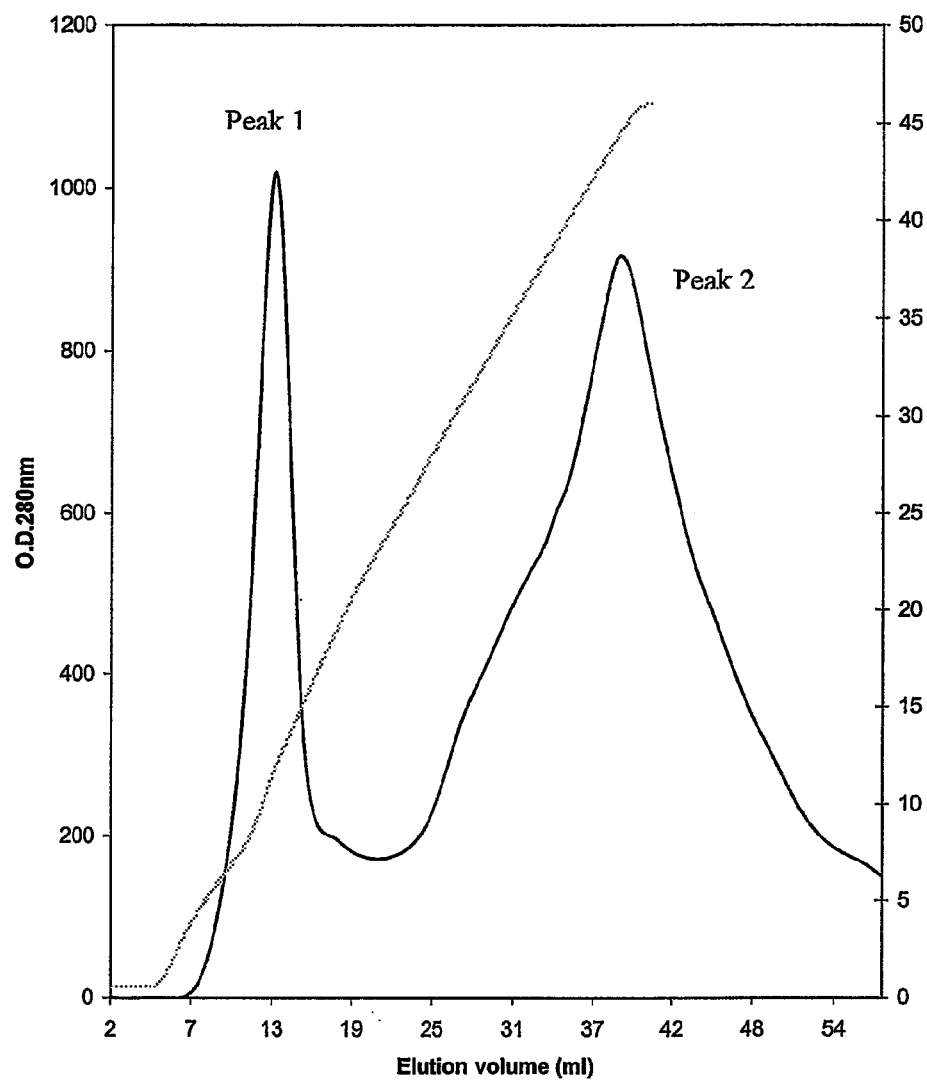
Figure 104:
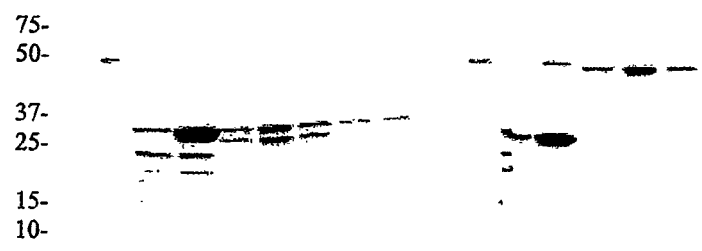
Figure 105:
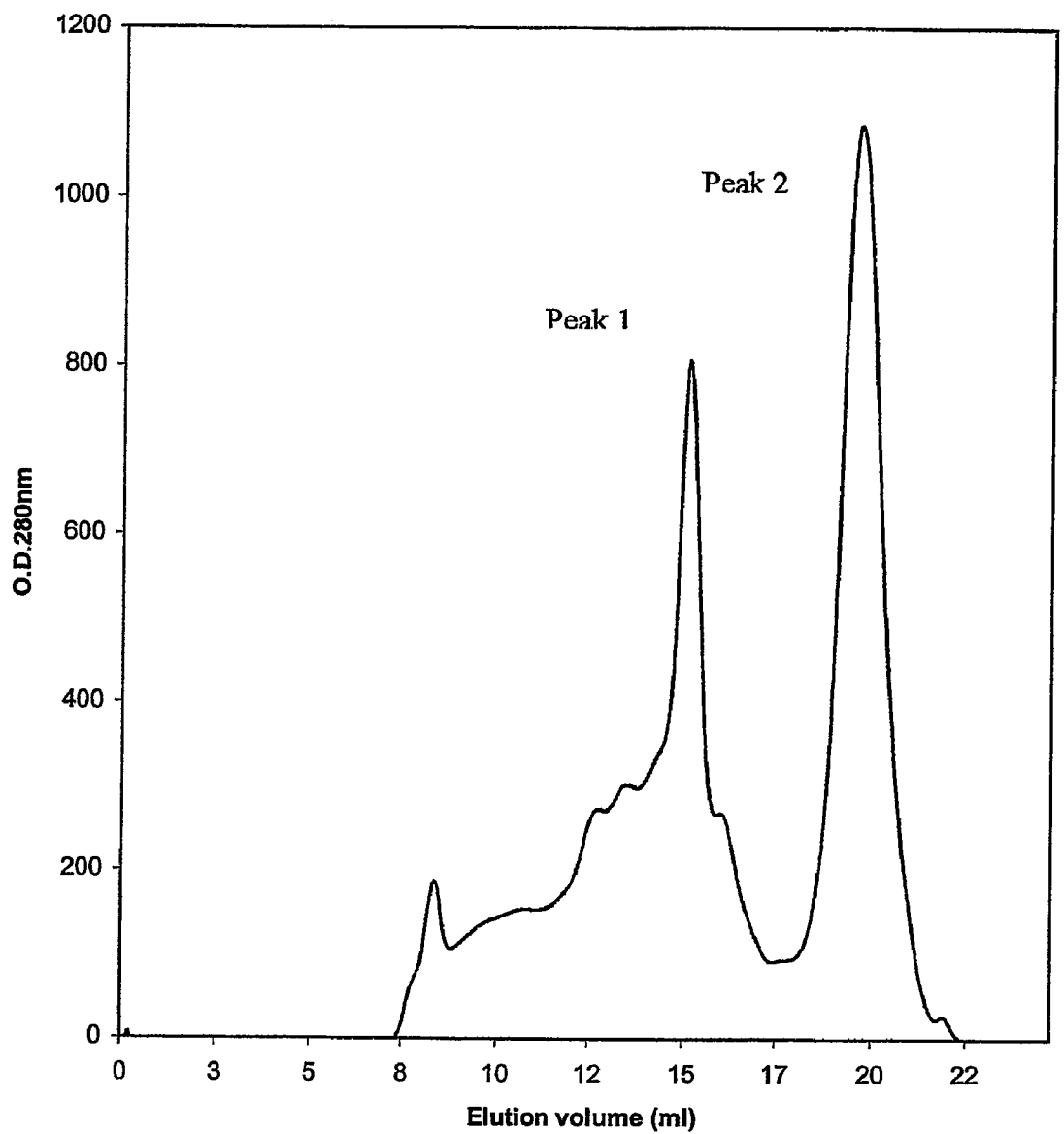
Figure 116:
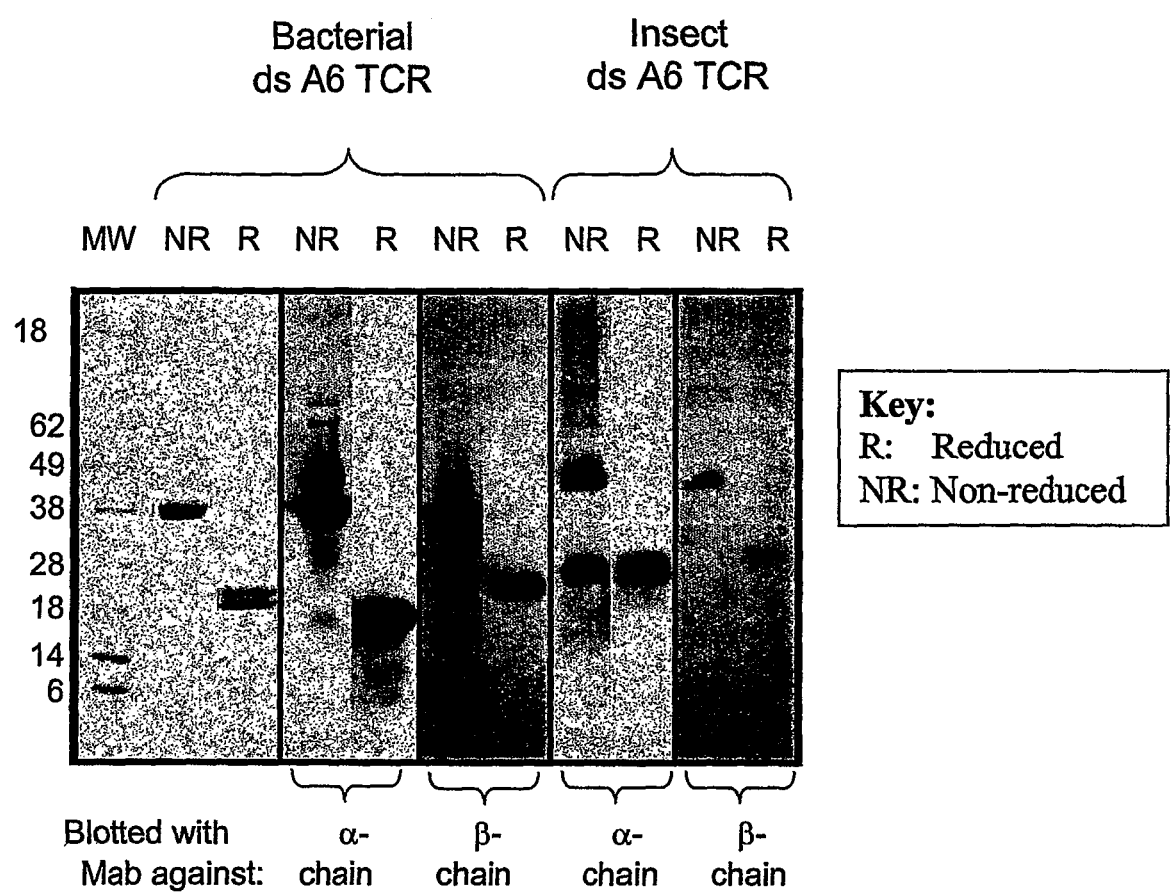

FIG. 81 is a BIAcore trace showing non-specific binding of soluble A6 TCR containing a novel disulphide inter-chain bond between residues 52 of exon 1 of TRAC*01 and 55 of exon 1 of TRBC2*01 to HLA-A2-tax and to HLA-A2-NY-ESO pMHC;

FIG. 82 is a BIAcore response curve showing binding of soluble A6 TCR containing a novel disulphide inter-chain bond between residues 15 of exon 1 of TRAC*01 and 15 of exon 1 of TRBC2*01 to HLA-A2-tax pMHC;

FIG. 83*a* is an electron density map around the model with 1BD2 sequence (Chain A Thr164, Chain B Ser 174). Map contoured at 1.0, 2.0 and 3.0 σ. FIG. 83*b* is an electron density map after refinement with Cys in the two positions A164 and B174. The map is contoured at the same σ levels as for FIG. 83*a*;

FIG. 84 compares the structures of 1BD2 TCR with an NY-ESO TCR of the present invention by overlaying said structures in ribbon and coil representations;

FIGS. 85*a* and 85*b* show the DNA (SEQ ID NO:167) and amino acid sequences (SEQ ID NO:168) respectively of the P chain of the NY-ESO TCR incorporating a biotin recognition site. The biotin recognition site is highlighted;

FIGS. 86*a* and 86*b* show the DNA (SEQ ID NO:169) and amino acid (SEQ ID NO:170) sequences respectively of the P chain of the NY-ESO TCR incorporating the hexa-hisitidine tag. The hexa-hisitidine tag is highlighted;

FIG. 87 illustrates the elution of soluble NY-ESO TCR containing a novel disulphide bond and a biotin recognition sequence from a POROS 50HQ anion exchange column using a 0-500 mM NaCl gradient, as indicated by the dotted line;

FIG. 88 illustrates the elution of soluble NY-ESO TCR containing a novel disulphide bond and a hexa-histidine tag from a POROS 50HQ anion exchange columns using a 0-500 mM NaCl gradient, as indicated by the dotted line;

FIG. 89 is a protein elution profile from gel filtration chromatography of pooled fractions from the NY-ESO-biotin tagged anion exchange column run illustrated by FIG. 87;

FIG. 90 is a protein elution profile from gel filtration chromatography of pooled fractions from the NY-ESO-hexa-histidine tagged anion exchange column run illustrated by FIG. 88;

FIGS. 91*a-h* are FACS histograms illustrating the staining intensity produced from 25,000 events for HLA-A2 positive EBV transformed B cell line (PP LCL) incubated with the following concentrations of NY-ESO peptide and fluorescent NY-ESO TCR tetramers respectively: NYESO 0 TCR 5 µg, NYESO $10^{-4}$M TCR 5 µg, NYESO $10^{-5}$M TCR 5 µg, NYESO $10^{-6}$M TCR 5 µg, NYESO 0 TCR 10 µg, NYESO $10^{-4}$M TCR 10 µg, NYESO $10^{-5}$M TCR 10 µg, NYESO $10^{-6}$M TCR 10 µg;

FIG. 92 is the DNA sequence (SEQ ID NO:165) of the beta-chain of A6 TCR incorporating the TRBC1*01 constant region;

FIG. 93 is an anion exchange chromatography trace of soluble A6 TCR incorporating the TRBC1*01 constant region showing protein elution from a POROS 50HQ column using a 0-500 mM NaCl gradient, as indicated by the dotted line;

FIG. 94—A. Reducing SDS-PAGE (Coomassie-stained) of fractions from column run in FIG. 93, as indicated. B. Non-reducing SDS-PAGE (Coomassie-stained) of fractions from column run in FIG. 93, as indicated;

FIG. 95—Size-exclusion chromatography of pooled fractions from peak 2 in FIG. 93. Peak 1 contains TCR heterodimer which is inter-chain disulphide linked;

FIG. 96—A. BIAcore analysis of the specific binding of disulphide-linked A6 soluble TCR to HLA-Flu complex. B. Binding response compared to control for a single injection of disulphide-linked A6 soluble TCR;

FIG. 97 shows the nucleic acid sequence (SEQ ID NO:165) of the mutated beta chain of the A6 TCR incorporating the 'free' cysteine;

FIG. 98-A*nion* exchange chromatography of soluble A6 TCR incorporating the 'free' cysteine showing protein elution from a POROS 50HQ column using a 0-500 mM NaCl gradient, as indicated by the dotted line;

FIG. 99—A. Reducing SDS-PAGE (Coomassie-stained) of fractions from column run in FIG. 98, as indicated. B. Non-reducing SDS-PAGE (Coomassie-stained) of fractions from column run in FIG. 98, as indicated;

FIG. 100—Size-exclusion chromatography of pooled fractions from peak 2 in FIG. 98. Peak 1 contains TCR heterodimer which is inter-chain disulphide linked;

FIG. 101—A. BIAcore analysis of the specific binding of disulphide-linked A6 soluble TCR incorporating the 'free' cysteine to HLA-Flu complex. B. Binding response compared to control for a single injection of disulphide-linked A6 soluble TCR;

FIG. 102 shows the nucleic acid sequence (SEQ ID NO:173) of the mutated beta chain of the A6 TCR incorporating a serine residue mutated in for the 'free' cysteine;

FIG. 103—Anion exchange chromatography of soluble A6 TCR incorporating a serine residue mutated in for the 'free' cysteine showing protein elution from a POROS 50HQ column using a 0-500 mM NaCl gradient, as indicated by the dotted line;

FIG. 104—A. Reducing SDS-PAGE (Coomassie-stained) of fractions from column run in FIG. 103, as indicated. B. Non-reducing SDS-PAGE (Coomassie-stained) of fractions from column run in FIG. 103, as indicated. Peak 2 clearly contains TCR heterodimer which is inter-chain disulphide linked;

FIG. 105—Size-exclusion chromatography of pooled fractions from peak 2 in FIG. 103. Peak 1 contains TCR heterodimer which is inter-chain disulphide linked;

FIG. 106—A. BIAcore analysis of the specific binding of disulphide-linked A6 soluble TCR incorporating a serine residue mutated in for the 'free' cysteine to HLA-Flu complex. B. Binding response compared to control for a single injection of disulphide-linked A6 soluble TCR;

FIG. 107 shows the nucleotide sequence of pYX112 (SEQ ID NO:174);

FIG. 108 shows the nucleotide sequence of pYX122 (SEQ ID NO:175);

FIG. 109 shows the DNA (SEQ ID NO:177) and protein (SEQ ID NO:178) sequences of pre-pro mating factor alpha fused to TCR α chain;

FIG. 110 shows the DNA (SEQ ID NO:179) and protein (SEQ ID NO:178) sequence of pre-pro mating factor alpha fused to TCR β chain;

FIG. 111 shows a Western Blot of soluble TCR expressed in *S. cerevisiae* strain SEY6210. Lane C contains 60 ng of purified soluble NY-ESO TCR as a control. Lanes 1 and 2 contain the proteins harvested from the two separate TCR transformed yeast cultures;

FIG. 112 shows the nucleic acid sequence (SEQ ID NO:180) of the KpnI to EcoRI insert of the pEX172 plasmid. The remainder of the plasmid is pBlueScript II KS−;

FIG. 113 is a schematic diagram of the TCR chains for cloning into baculovirus;

FIG. 114 shows the nucleic acid sequence (SEQ ID NO:181) of disulphide A6 α TCR construct as a BamHI insert for insertion into pAcAB3 expression plasmid;

FIG. 115 shows the disulphide A6 β TCR construct (SEQ ID NO:182) as a BamHI for insertion into pAcAB3 expression plasmid; and FIG. 116 shows a Coomassie stained gel and Western Blot against the bacterially-produced disulphide A6 TCR and the Insect disulphide A6 TCR.

In all of the following examples, unless otherwise stated, the soluble TCR chains produced are truncated immediately C-terminal to the cysteine residues which form the native interchain disulphide bond.

Example 1

Design of Primers and Mutagenesis of A6 Tax TCR α and β Chains

For mutating A6 Tax threonine 48 of exon 1 in TRAC*01 to cysteine, the following primers were designed (mutation shown in lower case):

```
                                        (SEQ ID NO:21)
    5'-C ACA GAC AAA tgT GTG CTA GAC AT (SEQ ID NO:22)
    5'-AT GTC TAG CAC Aca TTT GTC TGT G
```

For mutating A6 Tax serine 57 of exon 1 in both TRBC1*01 and TRBC2*01 to cysteine, the following primers were designed (mutation shown in lower case):

```
                                        (SEQ ID NO:23)
    5'-C AGT GGG GTC tGC ACA GAC CC (SEQ ID NO:24)
    5'-GG GTC TGT GCa GAC CCC ACT G
```

PCR Mutagenesis:

Expression plasmids containing the genes for the A6 Tax TCR α or β chain were mutated using the α-chain primers or the β-chain primers respectively, as follows.

100 ng of plasmid was mixed with 5 μl 10 mM dNTP, 25 μl 10×Pfu-buffer (Stratagene), 10 units Pfu polymerase (Stratagene) and the final volume was adjusted to 240 μl with $H_2O$. 48 μl of this mix was supplemented with primers diluted to give a final concentration of 0.2 μM in 50 μl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 μl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University. The respective mutated nucleic acid and amino acid sequences are shown in FIGS. 2*a* and 3*a* for the α chain and FIGS. 2*b* and 3*b* for the β chain.

Example 2

Expression, Refolding and Purification of Soluble TCR

The expression plasmids containing the mutated α-chain and β-chain respectively were transformed separately into *E. coli* strain BL21pLysS, and single ampicillin-resistant colonies were grown at 37° C. in TYP (ampicillin 100 μg/ml)

medium to $OD_{600}$ of 0.4 before inducing protein expression with 0.5 mM IPTG. Cells were harvested three hours post-induction by centrifugation for 30 minutes at 400 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Figure 4:
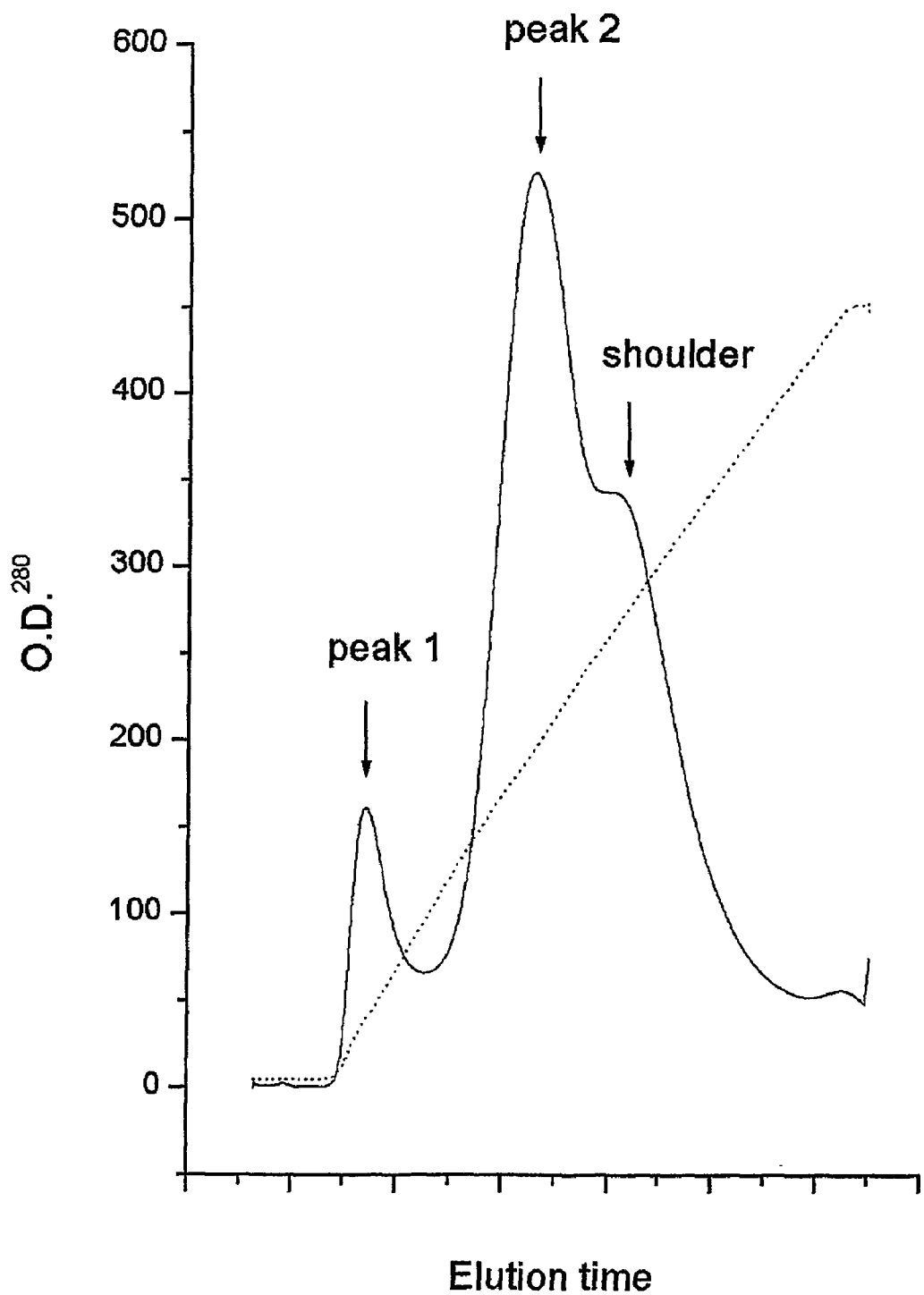
Figure 5:
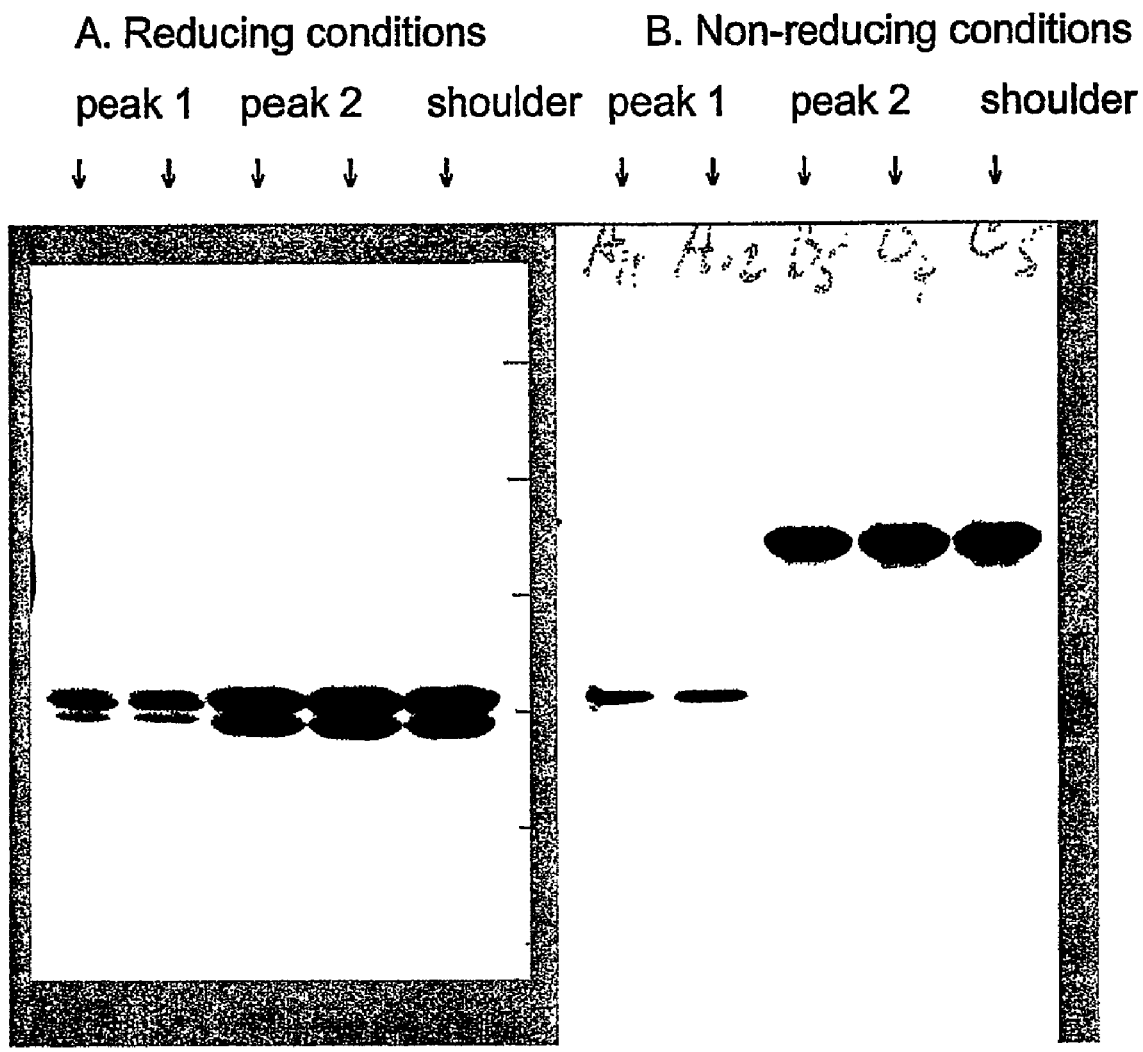
Figure 6:
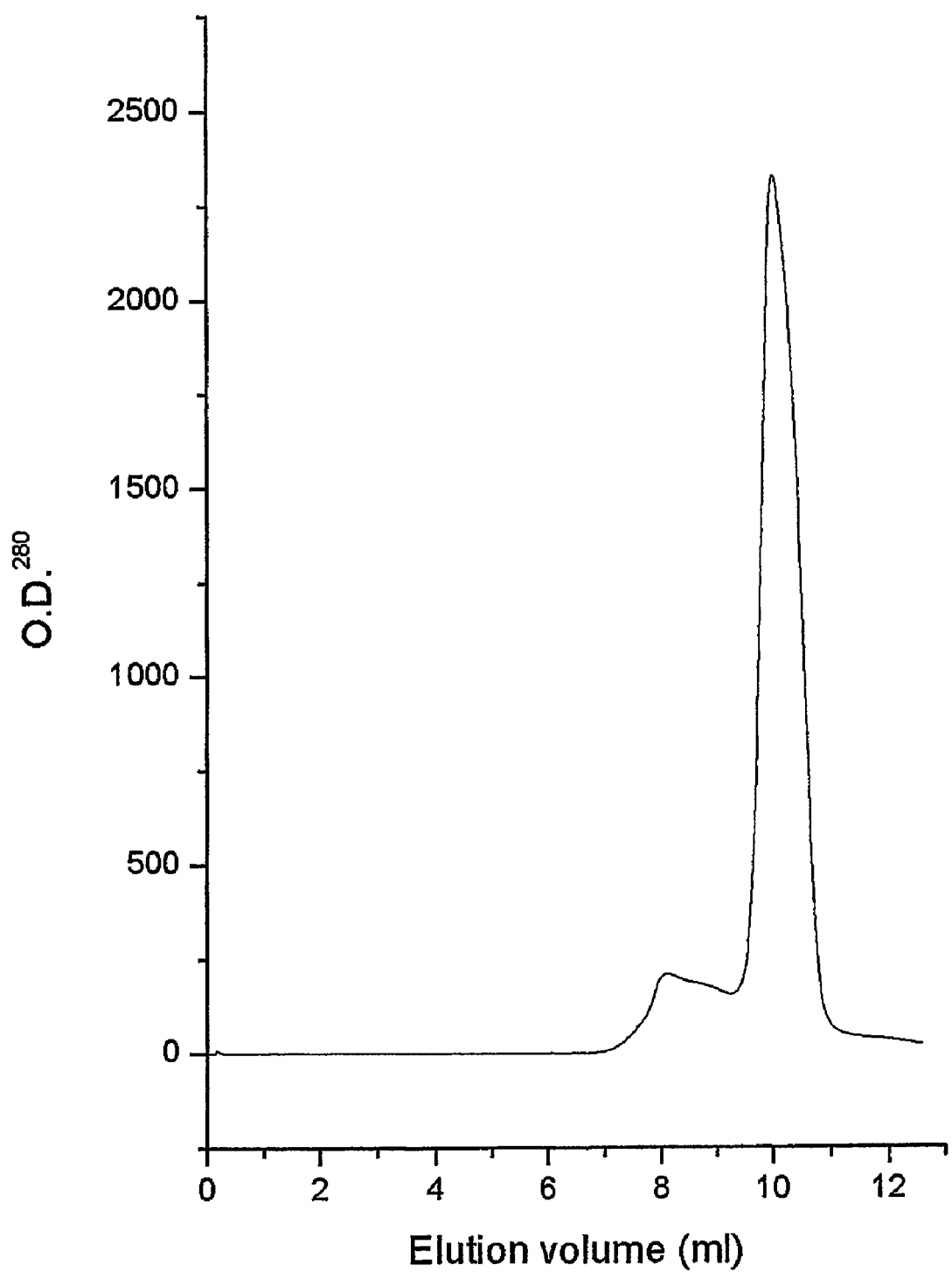
FIG. 6 is a trace obtained from size-exclusion chromatography of pooled fractions from peak 1 in FIG. 5. The protein elutes as a single major peak, corresponding to the heterodimer.

Approximately 30 mg (i.e. 1 μmole) of each solubilised inclusion body chain was thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The solution was left for 24 hrs. The refold was then dialysed twice, firstly against 10 liters of 100 mM urea, secondly against 10 liters of 100 mM urea, 10 mM Tris pH 8.0. Both refolding and dialysis steps were carried out at 6-8° C.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia) as in FIG. 4. Peak fractions were stored at 4° C. and analysed by Coomassie-stained SDS-PAGE (FIG. 5) before being pooled and concentrated. Finally, the sTCR was purified and characterised using a Superdex 200HR gel filtration column (FIG. 6) pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

Example 3

BIAcore Surface Plasmon Resonance Characterisation of sTCR Binding to Specific pMHC A surface plasmon resonance biosensor (BIAcore 3000™) was used to analyse the binding of a sTCR to its peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

Biotinylated class I HLA-A2-peptide complexes were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-heavy chain was expressed with a C-terminal biotinylation tag which replaces the transmembrane and cytoplasmic domains of the protein in an appropriate construct. Inclusion body expression levels of ~75 mg/liter bacterial culture were obtained. The HLA light-chain or β2-microglobulin was also expressed as inclusion bodies in *E. coli* from an appropriate construct, at a level of ~500 mg/liter bacterial culture.

*E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2m into 0.4 M L-Arginine-HCl, 100 mM Tris pH 8.1, 3.7 mM cystamine, mM cysteamine, 4 mg/ml peptide (e.g. tax 11-19), by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. HLA-A2-peptide complex eluted at approximately 250 mM NaCl, and peak fractions were collected, a cocktail of protease inhibitors (Calbiochem) was added and the fractions were chilled on ice.

Biotinylation tagged HLA complexes were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 μg/ml BirA enzyme (purified according to O'Callaghan et al. (1999) *Anal. Biochem.* 266: 9-15). The mixture was then allowed to incubate at room temperature overnight.

Biotinylated HLA complexes were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated HLA complexes eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated HLA complexes were stored frozen at −20° C. Streptavidin was immobilised by standard amine coupling methods.

Figure 7:
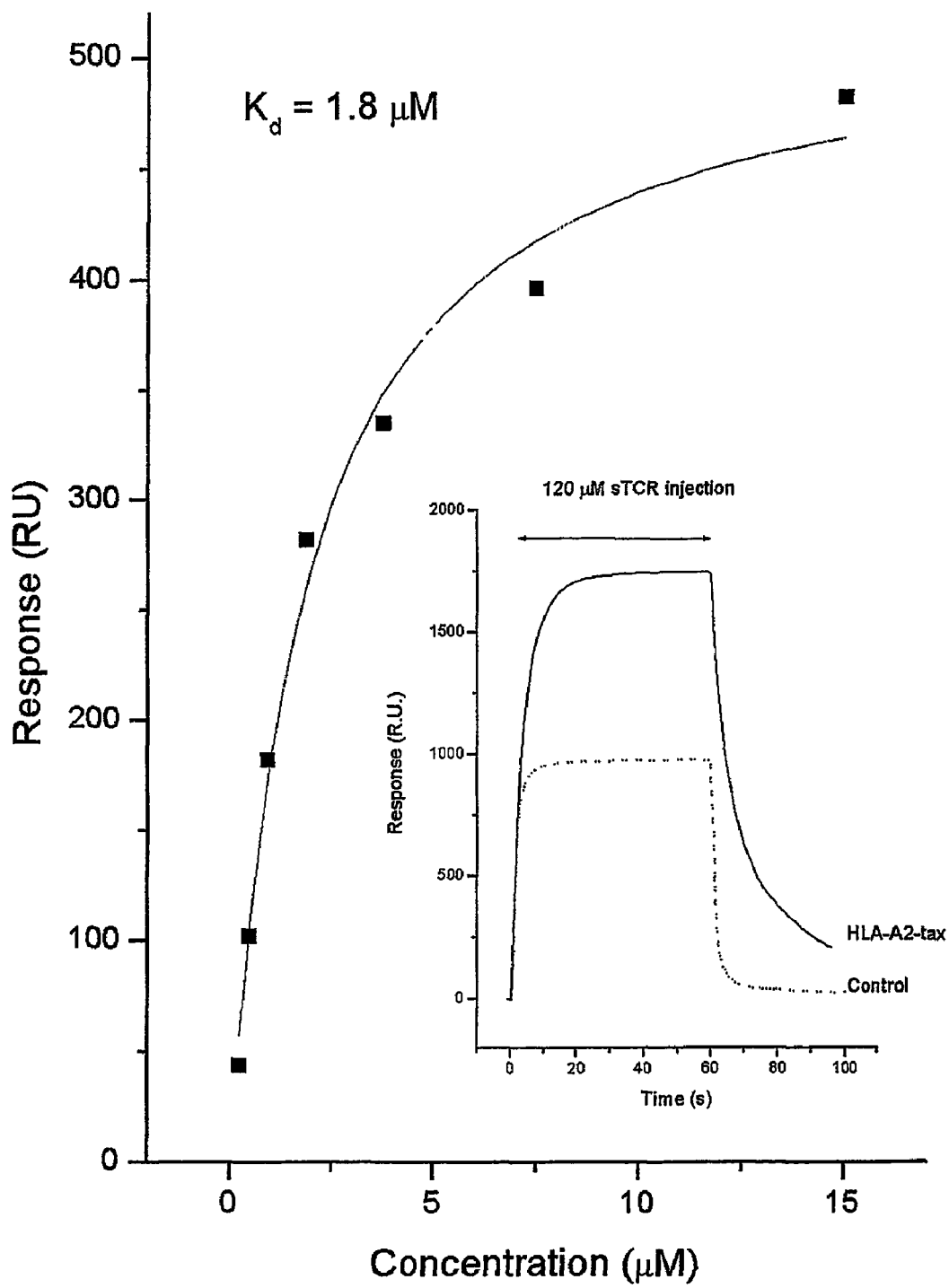
FIG. 7 is a BIAcore response curve of the specific binding of disulphide-linked A6 soluble TCR to HLA-A2-tax complex. Insert shows binding response compared to control for a single injection of disulphide-linked A6 soluble TCR.

The interactions between A6 Tax sTCR containing a novel inter-chain bond and its ligand/MHC complex or an irrelevant HLA-peptide combination, the production of which is described above, were analysed on a BIAcore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing sTCR over the surfaces of the different flow cells at a constant flow rate, measuring the SPR response in doing so. Initially, the specificity of the interaction was verified by passing sTCR at a constant flow rate of 5 µl min-1 over two different surfaces; one coated with ~5000 RU of specific peptide-HLA complex, the second coated with ~5000 RU of non-specific peptide-HLA complex (FIG. 7 insert). Injections of soluble sTCR at constant flow rate and different concentrations over the peptide-HLA complex were used to define the background resonance. The values of these control measurements were subtracted from the values obtained with specific peptide-HLA complex and used to calculate binding affinities expressed as the dissociation constant, Kd (Price & Dwek, Principles and Problems in Physical Chemistry for Biochemists ($2^{nd}$ Edition) 1979, Clarendon Press, Oxford), as in FIG. 7.

The Kd value obtained (1.8 µM) is close to that reported for the interaction between A6 Tax sTCR without the novel disulphide bond and pMHC (0.91 µM—Ding et al, 1999, *Immunity* 11:45-56).

Example 4

Production of Soluble JM22 TCR Containing a Novel Disulphide Bond

The β chain of the soluble A6 TCR prepared in Example 1 contains in the native sequence a BglII restriction site (AAGCTT) suitable for use as a ligation site. PCR mutagenesis was carried as detailed below to introduce a BamH1 restriction site (GGATCC) into the α chain of soluble A6 TCR, 5' of the novel cysteine codon. The sequence described in FIG. 2a was used as a template for this mutagenesis. The following primers were used:

```
                |BamHI |
5'-ATATCCAGAACCCgGAtCCTGCCGTGTA-3'     (SEQ ID NO:25)

5'-TACACGGCAGGAaTCcGGGTTCTGGATAT-3'    (SEQ ID NO:26)
```

100 ng of plasmid was mixed with 5 µl 10 mM dNTP, 25 µl 10×Pfu-buffer (Stratagene), 10 units Pfu polymerase (Stratagene) and the final volume was adjusted to 240 µl with $H_2O$. 48 µl of this mix was supplemented with primers diluted to give a final concentration of 0.2 µM in 50 µl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 µl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University. The mutations introduced into the α chain were "silent", therefore the amino acid sequence of this chain remained unchanged from that detailed in FIG. 3a. The DNA sequence for the mutated α chain is shown in FIG. 8a.

In order to produce a soluble JM22 TCR incorporating a novel disulphide bond, A6 TCR plasmids containing the α chain BamH1 and β chain BglII restriction sites were used as templates. The following primers were used:

```
                       | NdeI |
5'-GGAGATATACATATGCAACTACTAGAACAA-3'     (SEQ ID NO:27)
5'-TACACGGCAGGATCCGGGTTCTGGATATT-3'      (SEQ ID NO:28)
                 | BamHI|

|NdeI |
5'-GGAGATATACATATGGTGGATGGTGGAATC-3'     (SEQ ID NO:29)
5'-CCCAAGCTTAGTCTGCTCTACCCCAGGCCTCGGC-3' (SEQ ID NO:30)
            |BglII|
```

JM22 TCR α and β-chain constructs were obtained by PCR cloning as follows. PCR reactions were performed using the primers as shown above, and templates containing the JM22 TCR chains. The PCR products were restriction digested with the relevant restriction enzymes, and cloned into pGMT7 to obtain expression plasmids. The sequence of the plasmid inserts were confirmed by automated DNA sequencing. FIGS. 8b and 8c show the DNA sequence of the mutated α and β chains of the JM22 TCR respectively, and FIGS. 9a and 9b show the resulting amino acid sequences.

Figure 11:
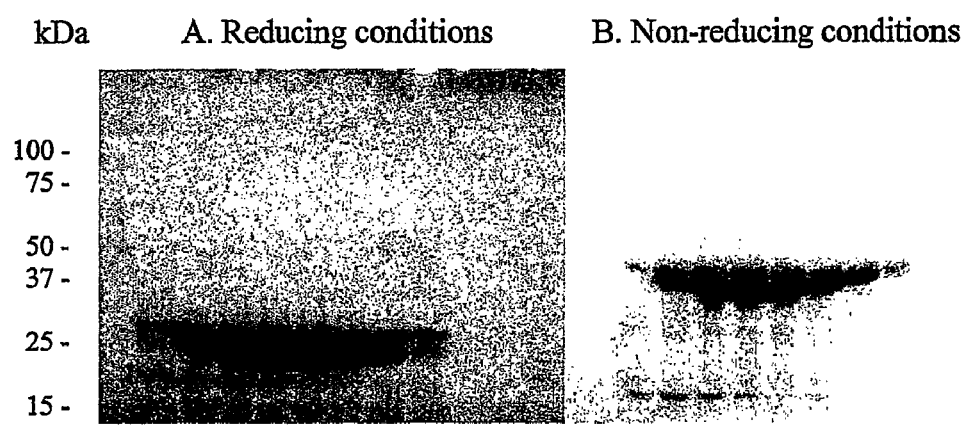

The respective TCR chains were expressed, co-refolded and purified as described in Examples 1 and 2. FIG. 10 illustrates the elution of soluble disulphide-linked JM22 TCR protein elution from a POROS 50HQ column using a 0-500 mM NaCl gradient, as indicated by the dotted line. FIG. 11 shows the results of both reducing SDS-PAGE (Coomassie-stained) and non-reducing SDS-PAGE (Coomassie-stained) gels of fractions from the column run illustrated by FIG. 10. Peak 1 clearly contains TCR heterodimer which is inter-chain disulphide linked. FIG. 12 shows protein elution from a size-exclusion column of pooled fractions from peak 1 in FIG. 10.

Figure 13A:
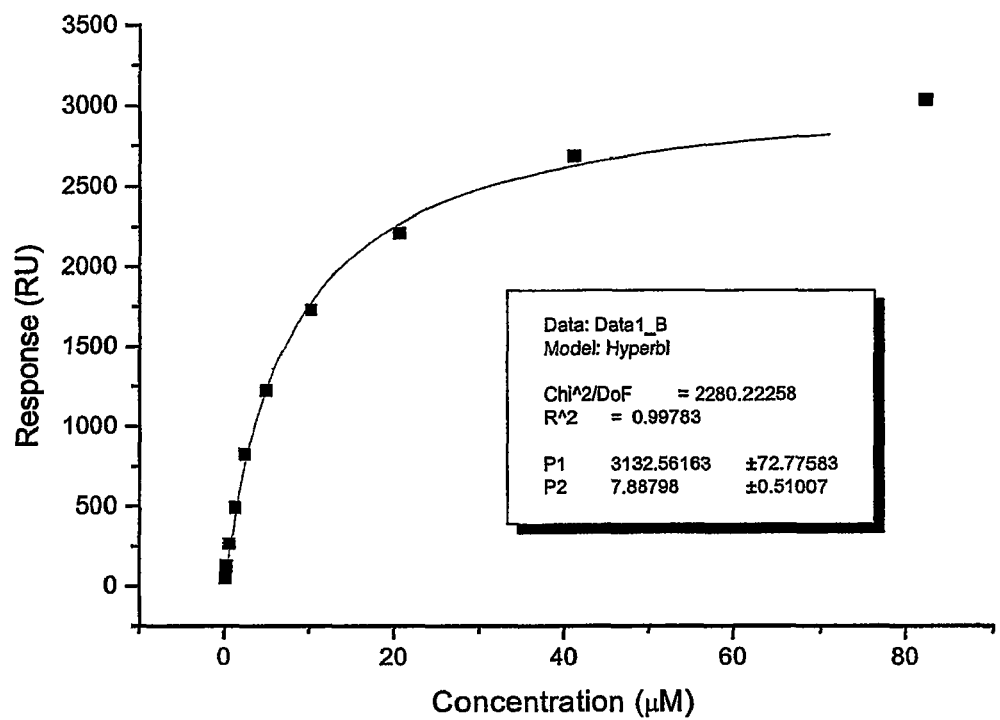
Figure 13B:
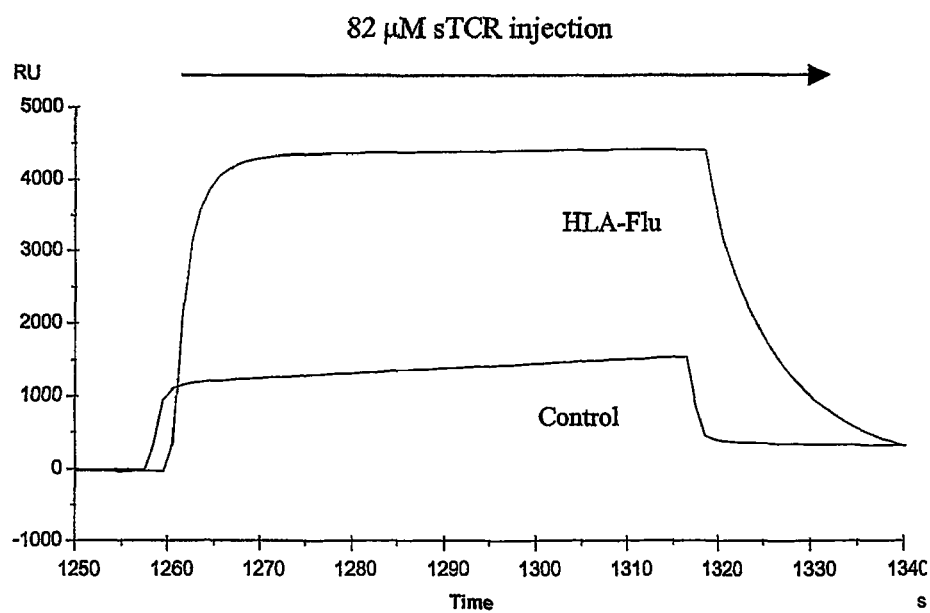

A BIAcore analysis of the binding of the JM22 TCR to pMHC was carried out as described in Example 3. FIG. 13a shows BIAcore analysis of the specific binding of disulphide-linked JM22 soluble TCR to HLA-Flu complex. FIG. 13b shows the binding response compared to control for a single injection of disulphide-linked JM22 soluble TCR. The Kd of this disulphide-linked TCR for the HLA-flu complex was determined to be 7.9±0.51 µM Example 5

Production of Soluble NY-ESO TCR Containing a Novel Disulphide Bond cDNA encoding NY-ESO TCR was isolated from T cells supplied by Enzo Cerundolo (Institute of Molecular Medicine, University of Oxford) according to known techniques.

cDNA encoding NY-ESO TCR was produced by treatment of the mRNA with reverse transcriptase.

In order to produce a soluble NY-ESO TCR incorporating a novel disulphide bond, A6 TCR plasmids containing the α chain BamHI and β chain BglII restriction sites were used as templates as described in Example 4. The following primers were used:

```
         | NdeI |
5'-GGAGATATACATATGCAGGAGGTGACACAG-3'          (SEQ ID NO:31)
5'-TACACGGCAGGATCCGGGTTCTGGATATT-3'           (SEQ ID NO:32)
         | BamHI|

|NdeI |
5'-GGAGATATACATATGGGTGTCACTCAGACC-3'          (SEQ ID NO:33)
5'-CCCAAGCTTAGTCTGCTCTACCCCAGGCCTCGGC-3'      (SEQ ID NO:34)
      |BglII|
```

NY-ESO TCR α and β-chain constructs were obtained by PCR cloning as follows. PCR reactions were performed using the primers as shown above, and templates containing the NY-ESO TCR chains. The PCR products were restriction digested with the relevant restriction enzymes, and cloned into pGMT7 to obtain expression plasmids. The sequence of the plasmid inserts were confirmed by automated DNA sequencing. FIGS. 14a and 14b show the DNA sequence of the mutated α and β chains of the NY-ESO TCR respectively, and FIGS. 15a and 15b show the resulting amino acid sequences.

The respective TCR chains were expressed, co-refolded and purified as described in Examples 1 and 2, except for the following alterations in protocol:

Denaturation of soluble TCRs; 30 mg of the solubilised TCR β-chain inclusion body and 60 mg of the solubilised TCR α-chain inclusion body was thawed from frozen stocks. The inclusion bodies were diluted to a final concentration of 5 mg/ml in 6M guanidine solution, and DTT (2M stock) was added to a final concentration of 10 mM. The mixture was incubated at 37° C. for 30 min.

Refolding of soluble TCRs: 1 L refolding buffer was stirred vigorously at 5° C.±3° C. The redox couple (2-mercaptoethylamine and cystamine (to final concentrations of 6.6 mM and 3.7 mM, respectively) were added approximately 5 minutes before addition of the denatured TCR chains. The protein was then allowed to refold for approximately 5 hours±15 minutes with stirring at 5° C.±3° C.

Dialysis of refolded soluble TCRs: The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C.±3° C. for another 20-22 hours.

FIG. 16 illustrates the elution of soluble NY-ESO disulphide-linked TCR protein elution from a POROS 50HQ column using a 0-500 mM NaCl gradient, as indicated by the dotted line. FIG. 17 shows the results of both reducing SDS-PAGE (Coomassie-stained) and non-reducing SDS-PAGE (Coomassie-stained) gels of fractions from the column run illustrated by FIG. 16. Peaks 1 and 2 clearly contain TCR heterodimer which is inter-chain disulphide linked. FIG. 18 shows size-exclusion chromatography of pooled fractions from peak 1 (A) and peak 2 (B) in FIG. 17. The protein elutes as a single major peak, corresponding to the heterodimer.

A BIAcore analysis of the binding of the disulphide-linked NY-ESO TCR to pMHC was carried out as described in Example 3. FIG. 19 shows BIAcore analysis of the specific binding of disulphide-linked NY-ESO soluble TCR to HLA-NYESO complex. A. peak 1, B. peak 2.

The Kd of this disulphide-linked TCR for the HLA-NY-ESO complex was determined to be 9.4±0.84 µM.

Example 6

Production of Soluble NY-ESO TCR Containing a Novel Disulphide Inter-chain Bond, and at Least One of the Two Cysteines Required to Form the Native Disulphide Inter-chain Bond In order to produce a soluble NY-ESO TCR incorporating a novel disulphide bond and at least one of the cysteine residues involved in the native disulphide inter-chain bond, plasmids containing the α chain BamHI and β chain BglII restriction sites were used as a framework as described in Example 4. The following primers were used:

```
            | NdeI |
5'-GGAGATATACATATGCAGGAGGTGACACAG-3'          (SEQ ID NO:35)
5'-CCCAAGCTTAACAGGAACTTTCTGGGCTGGGGAAGAA-3'   (SEQ ID NO:36)
         | HindIII|

| NdeI |
5'-GGAGATATACATATGGGTGTCACTCAGACC-3'          (SEQ ID NO:37)
5'-CCCAAGCTTAACAGTCTGCTCTACCCCAGGCCTCGGC-3'   (SEQ ID NO:38)
         |BglII |
```

NY-ESO TCR α and β-chain constructs were obtained by PCR cloning as follows. PCR reactions were performed using the primers as shown above, and templates containing the NY-ESO TCR chains. The PCR products were restriction digested with the relevant restriction enzymes, and cloned into pGMT7 to obtain expression plasmids. The sequence of the plasmid inserts were confirmed by automated DNA sequencing. FIGS. 20a and 20b show the DNA sequence of the mutated α and β chains of the NY-ESO TCR respectively, and FIGS. 21a and 21b show the resulting amino acid sequences.

To produce a soluble NY-ESO TCR containing both a non-native disulphide inter-chain bond and the native disulphide inter-chain bond, DNA isolated using both of the above primers was used. To produce soluble NY-ESO TCRs with a non-native disulphide inter-chain bond and only one of the cysteine residues involved in the native disulphide inter-chain bond, DNA isolated using one of the above primers together with the appropriate primer from Example 5 was used.

The respective TCR chains were expressed, co-refolded and purified as described in Example 5.

FIGS. 22-24 illustrate the elution of soluble NY-ESO TCRα$^{cys}$ β$^{cys}$ PCs (i.e. with non-native and native cysteines in both chains), TCRα$^{cys}$ (with non-native cysteines in both chains but the native cysteine in the α chain only), and TCR-β$^{cys}$ (with non-native cysteines in both chains but the native cysteine in the β chain only) protein elution from POROS 50HQ anion exchange columns using a 0-500 mM NaCl gradient, as indicated by the dotted line. FIGS. 25 and 26 respectively show the results of reducing SDS-PAGE (Coomassie-stained) and non-reducing SDS-PAGE (Coomassie-stained) gels of fractions from the NY-ESO TCRα$^{cys}$ β$^{cys}$, TCRα$^{cys}$, and TCRβ$^{cys}$ column runs illustrated by FIGS. 22-24. These clearly indicate that TCR heterodimers which are inter-chain disulphide linked have been formed. FIGS. 27-29 are protein elution profiles from gel filtration chromatography of pooled fractions from the NY-ESO TCRα$^{cys}$ β$^{cys}$, TCRα$^{cys}$, and TCRβ$^{cys}$ anion exchange column runs illustrated by FIGS. 22-24 respectively. The protein elutes as a single major peak, corresponding to the TCR heterodimer.

A BIAcore analysis of sTCR binding to pMHC was carried out as described in Example 3. FIGS. 30-32 show BIAcore analysis of the specific binding of NY-ESO TCRα$^{cys}$ β$^{cys}$, TCRα$^{cys}$, and TCRβ$^{cys}$ respectively to HLA-NYESO complex.

TCRα$^{cys}$ β$^{cys}$ had a $K_d$ of 18.08±2.075 μM, TCRα$^{cys}$ had a $K_d$ of 19.24±2.01 μM, and TCRβ$^{cys}$ had a $K_d$ of 22.5±4.0692 μM.

Example 7

Production of Soluble AH-1.23 TCR Containing a Novel Disulphide Inter-chain Bond cDNA encoding AH-1.23 TCR was isolated from T cells supplied by Hill Gaston (Medical School, Addenbrooke's Hospital, Cambridge) according to known techniques. cDNA encoding NY-ESO TCR was produced by treatment of the mRNA with reverse transcriptase.

In order to produce a soluble AH-1.23 TCR incorporating a novel disulphide bond, TCR plasmids containing the α chain BamHI and β chain BglII restriction sites were used as a framework as described in Example 4. The following primers were used:

```
        | NdeI |
5'-GGGAAGCTTACATATGAAGGAGGTGGAGCAGAATTCTGG-3'    (SEQ ID NO:39)
5'-TACACGGCAGGATCCGGGTTCTGGATATT-3'              (SEQ ID NO:40)
              |BamHI|

| NdeI |
5'-TTGGAATTCACATATGGGCGTCATGCAGAACCCAAGACAC-3'   (SEQ ID NO:41)
5'-CCCAAGCTTAGTCTGCTCTACCCCAGGCCTCGGC-3'         (SEQ ID NO:42)
     |BglII|
```

AH-1.23 TCR α and β-chain constructs were obtained by PCR cloning as follows. PCR reactions were performed using the primers as shown above, and templates containing the AH-1.23 TCR chains. The PCR products were restriction digested with the relevant restriction enzymes, and cloned into pGMT7 to obtain expression plasmids. The sequence of the plasmid inserts were confirmed by automated DNA sequencing. FIGS. 33a and 33b show the DNA sequence of the mutated α and β chains of the AH-1.23 TCR respectively, and FIGS. 34a and 34b show the resulting amino acid sequences.

The respective TCR chains were expressed, co-refolded and purified as described in Example 5.

FIG. 35 illustrates the elution of soluble AH-1.23 disulphide-linked TCR protein elution from a POROS 50HQ anion exchange column using a 0-500 mM NaCl gradient, as indicated by the dotted line. FIGS. 36 and 37 show the results of reducing SDS-PAGE (Coomassie-stained) and non-reducing SDS-PAGE (Coomassie-stained) gels respectively of fractions from the column run illustrated by FIG. 35. These gels clearly indicate the presence of a TCR heterodimer which is inter-chain disulphide linked. FIG. 38 is the elution profile from a Superdex 75 HR gel filtration column of pooled fractions from the anion exchange column run illustrated in FIG. 35. The protein elutes as a single major peak, corresponding to the heterodimer.

Example 8

Production of Soluble A6 TCRs Containing a Novel Disulphide Inter-chain Bond at Alternative Positions Within the Immunoglobulin Region of the Constant Domain The following experiments were carried out in order to investigate whether it was possible to form functional soluble TCRs which include a novel disulphide bond in the TCR immunoglobulin region at a position other than between threonine 48 of exon 1 in TRAC*01 and serine 57 of exon 1 in both TRBC1*01/TRBC2*01.

For the mutating the A6 TCR α-chain, the following primers were designed (the numbers in the primer names refer to the position of the amino acid residue to be mutated in exon 1 of TRAC*01, mutated residues are shown in lower case):

```
T48→C Mutation
                                        (SEQ ID NO:43)
5'-CACAGACAAAtgTGTGCTAGACAT-3'

(SEQ ID NO:44)
5'-ATGTCTAGCACAcaTTTGTCTGTG-3'

Y10→C Mutation
                                        (SEQ ID NO:45)
5'-CCCTGCCGTGTgCCAGCTGAGAG-3'
```

-continued (SEQ ID NO:46)
5'-CTCTCAGCTGGcACACGGCAGGG-3'

L12→C Mutation
(SEQ ID NO:47)
5'-CCGTGTACCAGtgcAGAGACTCTAAATC-3'

(SEQ ID NO:48)
5'-GATTTAGAGTCTCTgcaCTGGTACACGG-3'

S15→C Mutation
(SEQ ID NO:49)
5'-CAGCTGAGAGACTgTAAATCCAGTGAC-3'

(SEQ ID NO:50)
5'-GTCACTGGATTTAcAGTCTCTCAGCTG-3'

V22→C Mutation
(SEQ ID NO:51)
5'-CAGTGACAAGTCTtgCTGCCTATTCAC-3'

(SEQ ID NO:52)
5'-GTGAATAGGCAGcaAGACTTGTCACTG-3'

Y43→C Mutation
(SEQ ID NO:53)
5'-GATTCTGATGTGTgTATCACAGACAAAT-3'

(SEQ ID NO:54)
5'-ATTTGTCTGTGATAcACACATCAGAATC-3'

T45→C Mutation
(SEQ ID NO:55)
5'-CTGATGTGTATATCtgtGACAAAACTGTGC-3'

(SEQ ID NO:56)
5'-GCACAGTTTTGTCacaGATATACACATCAG-3'

L50→C Mutation
(SEQ ID NO:57)
5'-AGACAAAACTGTGtgtGACATGAGGTCT-3'

(SEQ ID NO:58)
5'-AGACCTCATGTCacaCACAGTTTTGTCT-3'

M52→C Mutation
(SEQ ID NO:59)
5'-ACTGTGCTAGACtgtAGGTCTATGGAC-3'

(SEQ ID NO:60)
5'-GTCCATAGACCTacaGTCTAGCACAGT-3'

S61→C Mutation
(SEQ ID NO:61)
5'-CTTCAAGAGCAACtGTGCTGTGGCC-3'

(SEQ ID NO:62)
5'-GGCCACAGCACaGTTGCTCTTGAAG-3'

For mutating the TCR A6 β-chain, the following primers were designed (the numbers in the primer names refer to the position of the amino acid residue to be mutated in exon 1 of TRBC2*01. Mutated residues are shown in lower case):

S57→C Mutation
(SEQ ID NO:63)
5'-CAGTGGGGTCtGCACAGACCC-3'

(SEQ ID NO:64)
5'-GGGTCTGTGCagACCCCACTG-3'

V13→C Mutation
(SEQ ID NO:65)
5'-CCGAGGTCGCTtgtTTTGAGCCATCAG-3'

(SEQ ID NO:66)
5'-CTGATGGCTCAAAacaAGCGACCTCGG-3'

-continued

F14→C Mutation
(SEQ ID NO:67)
5'-GGTCGCTGTGtgtGAGCCATCAGA-3'

(SEQ ID NO:68)
5'-TCTGATGGCTCacaCACAGCGACC-3'

S17→C Mutation
(SEQ ID NO:69)
5'-GTGTTTGAGCCATgtGAAGCAGAGATC-3'

(SEQ ID NO:70)
5'-GATCTCTGCTTCacATGGCTCAAACAC-3'

G55→C Mutation
(SEQ ID NO:71)
5'-GAGGTGCACAGTtGtGTCAGCACAGAC-3'

(SEQ ID NO:72)
5'-GTCTGTGCTGACaCaACTGTGCACCTC-3'

D59→C Mutation
(SEQ ID NO:73)
5'-GGGTCAGCACAtgCCCGCAGCCC-3'

(SEQ ID NO:74)
5'-GGGCTGCGGGcaTGTGCTGACCC-3'

L63→C Mutation
(SEQ ID NO:75)
5'-CCCGCAGCCCtgCAAGGAGCAGC-3'

(SEQ ID NO:76)
5'-GCTGCTCCTTGCaGGGCTGCGGG-3'

S77→C Mutation
(SEQ ID NO:77)
5'-AGATACGCTCTGtGCAGCCGCCT-3'

(SEQ ID NO:78)
5'-AGGCGGCTGCaCAGAGCGTATCT-3'

R79→C Mutation
(SEQ ID NO:79)
5'-CTCTGAGCAGCtGCCTGAGGGTC-3'

(SEQ ID NO:80)
5'-GACCCTCAGGCaGCTGCTCAGAG-3'

E15→C Mutation
(SEQ ID NO:81)
5'-GCTGTGTTTtgtCCATCAGAA-3'

(SEQ ID NO:82)
5'-TTCTGATGGacaAAACACAGC-3'

PCR mutagenesis, α and β TCR construct amplification, ligation and plasmid purification was carried out as described in Example 1 using the appropriate combination of the above primers in order to produce soluble TCRs including novel disulphide inter-chain bonds between the following pairs of amino acids:

| TCR α chain | TCR β chain | α Primer used | β Primer used |
|---|---|---|---|
| Thr 48 | Ser 57 | T48→C | S57→C |
| Thr 45 | Ser 77 | T45→C | S77→C |
| Ser 61 | Ser 57 | S61→C | S57→C |
| Leu 50 | Ser 57 | L50→C | S57→C |
| Tyr 10 | Ser 17 | Y10→C | S17→C |
| Ser 15 | Val 13 | S15→C | V13→C |
| Thr 45 | Asp 59 | T45→C | D59→C |
| Leu 12 | Ser 17 | L12→C | S17→C |
| Ser 61 | Arg 79 | S61→C | R79→C |
| Leu 12 | Phe 14 | L12→C | F14→C |
| Val 22 | Phe 14 | V22→C | F14→C |

-continued

| TCR α chain | TCR β chain | α Primer used | β Primer used |
|---|---|---|---|
| Met 52 | Gly 55 | M52→C | G55→C |
| Tyr 43 | Leu 63 | Y43→C | L63→C |
| Ser 15 | Glu 15 | S15→C | E15→C |

FIGS. 39 to 58 show the DNA and amino acid sequences of the mutated A6 TCR chains amplified by the above primers. The codons encoding the mutated cysteines are highlighted.

The respective TCR chains were expressed, co-refolded and purified as described in Example 5. Following purification on POROS 50HQ anion exchange column, the resulting proteins were run on SDS-Page gels in order to assess whether any correctly-refolded soluble TCR had been formed. These gels were also assessed to ascertain the presence or absence of any disulphide-linked protein of the correct molecular weight in the purified material. TCRs under investigation containing the following novel disulphide interchain bonds failed to produce disulphide-linked protein of the correct molecular weight using this bacterial expression system and these were not further assessed. However, alternative prokaryotic or eukaryotic expression systems are available.

| TCR α chain | TCR β chain |
|---|---|
| Ser 61 | Ser 57 |
| Leu 50 | Ser 57 |
| Ser 15 | Val 13 |
| Leu 12 | Ser 17 |
| Ser 61 | Arg 79 |
| Leu 12 | Phe 14 |
| Val 22 | Phe 14 |
| Tyr 43 | Leu 63 |

FIGS. 59 to 64 respectively illustrate the elution of soluble TCRs containing novel disulphide interchain bonds between the following residues: Thr 48-Ser 57, Thr 45-Ser 77, Tyr 10-Ser 17, Thr 45-Asp 59, Met 52-Gly 55 and Ser 15-Glu 15 from a POROS 200HQ anion exchange column using a 0-500 mM NaCl gradient, as indicated by the dotted line. FIGS. 65 to 70 show the results of reducing SDS-PAGE (Coomassie-stained) and non-reducing SDS-PAGE (Coomassie-stained) gels respectively of fractions from the column runs illustrated by FIGS. 59 to 64. These gels clearly indicate the presence of TCR heterodimers that are inter-chain disulphide linked.

FIGS. 71 to 76 are elution profiles from a Superdex 200 HR gel filtration column of pooled fractions from the anion exchange column runs illustrated in FIGS. 59 to 64. A BIAcore analysis of the binding of the TCRs to pMHC was carried out as described in Example 3. FIGS. 77-82 are BIAcore traces demonstrating the ability of the purified soluble TCRs to bind to HLA-A2 tax pMHC complexes.

Thr 48-Ser 57 had a $K_d$ of 7.8 µM, Thr 45-Ser 77 had a $K_d$ of 12.7 µM, Tyr 10-Ser 17 had a $K_d$ of 34 µM, Thr 45-Asp 59 had a $K_d$ of 14.9 µM, and Ser 15-Glu 15 had a $K_d$ of 6.3 µM. Met 52-Gly 55 was capable of binding to its native "target", the HLA-A2 tax complex, although it also bound in a similar manner to an "irrelevant" target, the HLA-A2-NY-ESO complex (see FIG. 81)

Example 9

X-ray Crystallography of the Disulphide-linked NY-ESO T Cell Receptor, Specific for the NY-ESO-HLA-A2 Complex The NY-ESO dsTCR was cloned as described in Example 5, and expressed as follows.

The expression plasmids containing the mutated α-chain and β-chain respectively were transformed separately into E. coli strain BL21 pLysS, and single ampicillin-resistant colonies were grown at 37° C. in TYP (ampicillin 100 µg/ml) medium to $OD_{600}$ of 0.7 before inducing protein expression with 0.5 mM IPTG. Cells were harvested 18 hours post-induction by centrifugation for 30 minutes at 400 rpm in a Beckman J-6B. Cell pellets were resuspended in lysis buffer containing 10 mM Tris-HCl pH 8.1, 10 mM $MgCl_2$, 150 mM NaCl, 2 mM DTT, 10% glycerol. For every 1 L of bacterial culture 100 µl of lysozyme (20 mg/ml) and 100 µl of Dnase I (20 µg/ml) were added. After incubation on ice for 30 minutes, the bacterial suspension was sonicated in 1 minute bursts for a total of 10 minutes using a Milsonix XL2020 sonicator with a standard 12 mm diameter probe. Inclusion body pellets were recovered by centrifugation for 30 minutes at 13000 rpm in a Beckman J2-21 centrifuge (4° C.). Three washes were then carried out in Triton wash buffer (50 mM Tris-HCl pH 8.1, 0.5% Triton-X100, 100 mM NaCl, 10 mM NaEDTA, 0.1% (w/v), 2 mM DTT) to remove cell debris and membrane components. Each time, the inclusion body pellet was homogenised in Triton wash buffer before being pelleted by centrifugation for 15 minutes at 13000 rpm in a Beckman J2-21. Detergent and salt was then removed by a similar wash in Resuspension buffer (50 mM Tris-HCl pH 8.1 100 mM NaCl, 10 mM NaEDTA, 0.1% (w/v) NaAzide, 2 mM DTT). Finally, the inclusion bodies were solubilised in 6 M guanidine buffer (6 M Guanidine-hydrochloride, 50 mM Tris pH 8.1, 100 mM NaCl, 10 mM EDTA, 10 mM DTT), divided into 120 mg aliquots and frozen at −70° C. Inclusion bodies were quantitated by solubilising with 6M guanidine-HCl and measurement with a Bradford dye-binding assay (PerBio).

Approximately 60 mg (i.e. 2.4 µmole) of frozen solubilised alpha chain was mixed with 30 mg (i.e. 1.2 µmole) of frozen solubilised beta chain. The TCR mixture was diluted to a final volume of 18 ml with 6 M guanidine buffer and heated to 37° C. for 30 min to ensure complete chain denaturation. The guanidine solution containing fully reduced and denatured TCR chains was then mixed into 1 liter of cold refolding buffer (100 mM Tris pH 8.1, 400 mM L-Arginine-HCl, 2 mM EDTA, 6.6 mM 2-mercapthoethylamine, 3.7 mM Cystamine, 5M urea) with stirring. The solution was left for 5 hrs in the cold room (5° C.±3° C.) to allow refolding to take place. The refold was then dialysed against 12 liters of water for 18-20 hours, followed by 12 liters of 10 mM Tris pH 8.1 for 18-20 hours (5° C.±3° C.). Spectrapor 1 (Spectrum Laboratories product no. 132670) dialysis membrane that has a molecular weight cut off of 6-8000 kDa was used for this dialysis process. The dialysed protein was filtered through 0.45 µm pore size filters (Schleicher and Schuell, Ref. number, 10 404012) fitted to a Nalgene filtration unit.

The refolded NY-ESO TCR was separated from degradation products and impurities by loading the dialysed refold onto a POROS 50HQ (Applied Biosystems) anion exchange column using an AKTA purifier (Amersham Biotech). A POROS 50 HQ column was pre-equilibrated with 10 column volumes of buffer A (10 mM Tris pH 8.1) prior to loading with protein. The bound protein was eluted with a gradient of 0-500 mM NaCl over 7 column volumes. Peak fractions (1 ml) were analysed on denaturing SDS-PAGE using reducing and non-reducing sample buffer. Peak fractions containing the heterodimeric alpha-beta complex were further purified using a Superdex 75HR gel filtration column pre-equilibrated in 25 mM MES pH 6.5. The protein peak eluting at a relative molecular weight of approximately 50 kDa was pooled, concentrated to 42 mg/ml in Ultrafree centrifugal concentrators (Millipore, part number UFV2BGC40) and stored at −80° C.

Crystallisation of NY-ESO TCR was performed by hanging drop technique at 18° C. using 1 μl of protein solution (8.4 mg/ml) in 5 mM Mes pH 6.5 mixed with an equivalent volume of crystallisation buffer. Crystals appeared under several different conditions using Crystal Screen buffers (Hampton Research). Single cubic crystals (<100 μm) were grown in 30% PEG 4000, 0.1 M Na Citrate pH 5.6, 0.2 M ammonium acetate buffer and used for structure determination.

Crystals of the NY-ESO TCR were flash-frozen and tested for diffraction in the X-ray beam of the Daresbury synchrotron. The crystals diffracted to 0.25 nm (2.5 Å) resolution. One data set was collected and processed to give a 98.6% complete set of amplitudes that were reasonable to around 0.27 nm (2.7 Å), but usable up to 0.25 nm (2.5 Å). The merging R-factor, i.e. the agreement between multiple measurements of crystallographically equivalent reflections, was 10.8% for all the data. This is marginal at the highest resolution shell. The space group was P2₁, with cell dimensions a=4.25 nm (42.5 Å), b=5.95 nm (59.5 Å), c=8.17 nm (81.7 Å), 0=91.5°. The cell dimensions and symmetry meant there were two copies in the cell. The asymmetric unit, au or the minimum volume that needs to be studied, has only 1 molecule, and the other molecule in the cell is generated by the 2₁ symmetry operation. The positioning of the molecule in the au is arbitrary in the y-direction. As long as it is in the correct position in the x-z plane, it can be translated at will in the y-direction. This is referred to as a free parameter, in this 'polar' space group.

The PDB data base has only one entry containing an A/B heterodimeric TCR, 1BD2. This entry also has co-ordinates of the HLA-cognate peptide in complex with the TCR. The TCR chain B was the same in NY-ESO, but chain A had small differences in the C-domain and significant differences in the N-domain. Using the 1BD2 A/B model for molecular replacement, MR, gave an incorrect solution, as shown by extensive overlap with symmetry equivalent molecules. Using the B chain alone gave a better solution, which did not have significant clashes with neighbours. The correlation coefficient was 49%, the crystallographic R-factor 50%, and the nearest approach (centre-of-gravity to c-o-g) was 0.49 nm (49 Å). The rotation and translation operation needed to transform the starting chain B model to the MR equivalent, was applied to chain A. The hybrid MR solution thus generated, packed well in the cell, with minimal clashes.

Electron density maps generally agreed with the model, and allowed its adjustment to match the sequence of the NY-ESO TCR. But the starting model had many gaps, specifically missing side-chains, that are characteristic of poorly ordered portions of the model. Many of the hair-pin loops in between strands had very low density, and were difficult to model. The crystallographic R-factor of the model is 30%. The R-factor is a residual, i.e. it is the difference between the calculated and observed amplitudes.

As FIGS. 83a and 83b demonstrate, the input sequence from 1BD2 do not match up with the density very well. Changing the model for Cys at positions 164 in chain A, and 174 in chain B, followed by further refinement, showed clearly that this sequence assignment is much better fitted to the density. But the differences in terms of size of the side chain are minimal, so there was little perturbation in the model. The electron density in that region is little changed.

The most important aspect of this work is that the new TCR is very similar in structure to the published model (1BD2). The comparison could include all of the TCR, the constant domains, or the small part near the mutation point.

The r.m.s deviation values are listed in the table below. The comparison of structures is shown in FIG. 84.

|  | Chain A Complete | Chain B Complete | Chain A Constant | Chain B Constant | Short Stretch |
|---|---|---|---|---|---|
| r.m.s Displacement | 2.831 | 1.285 | 1.658 | 1.098 | 0.613 |
| Mean Displacement | 2.178 | 1.001 | 1.235 | 0.833 | 0.546 |
| Max Displacement | 9.885 | 6.209 | 6.830 | 4.490 | 1.330 |

(All units are in Å)

The short stretch refers to the single strand from Chain A (A157 to A169) and the single strand from Chain B (B170 to B183) that are now joined by the disulphide bridge. The deviations were calculated for only the main chain atoms.

These results show that the introduction of the disulphide bond has minimal effect on the local structure of the TCR around the bond. Some larger effects are observed when comparing the TCR to the published structure (1BD2) of the A6 TCR, but the increase in RMS displacement is largely due to differences in loop conformations (see FIG. 84). These loops do not form part of the core structure of the TCR, which is formed by a series of β-sheets which form a characteristic Ig fold. The RMS deviation for the whole α-chain is particularly large because of the difference in the sequence of the variable domains between the A6 (1BD2) and the NY-ESO TCRs. However, the A6 and NY-ESO TCRs have the same variable β-domain and the RMS deviations for the whole β-chain show that the structure of this variable domain is also maintained in the TCR with the new disulphide bond. These data therefore indicate that the core structure of the TCR is maintained in the crystal structure of the TCR with the new disulphide bond.

Example 10

Production of Soluble NY-ESO TCRs Containing a Novel Disulphide Inter-Chain Bond, and C-Terminal, Chain Tagging Sites In order to produce a soluble NY-ESO TCR incorporating a novel disulphide bond, A6 TCR plasmids containing the α chain BamHI and β chain BglII restriction sites were used as frameworks as described in Example 4.

NY-ESO TCR β-chain constructs were obtained by PCR cloning as follows. PCR reactions were performed using the primers as shown below, and templates containing the NY-ESO TCR chains.

```
        | NdeI |
Fwd 5'-GGAGATATACATATGGGTGTCACTCAGAAC-3'    (SEQ ID NO:83)
Rev 5'-CCACCGGATCCGTCTGCTCTACCCCAGGC-3'
          | BamHI|
```

(nucleotides 1-29 of SEQ ID NO:84)

The PCR products were restriction digested with the relevant restriction enzymes, and cloned into pGMT7 containing the biotin recognition sequence to obtain expression plasmids. The sequence of the plasmid inserts were confirmed by automated DNA sequencing. FIG. 85a shows the DNA sequence of the β chain of the NY-ESO TCR incorporating the biotin recognition site, and FIG. 85b shows the resulting amino acid sequence.

The α chain construct was produced as described in Example 5. The respective TCR chains were expressed, co-refolded and purified as described in Example 5.

In order to produce a soluble NY-ESO TCR containing a non-native disulphide inter-chain bond and a hexa-histidine tag on the C-terminus of the β chain, the same primers and NY-ESO template were used as above. The PCR products were restriction digested with the relevant restriction enzymes, and cloned into pGMT7 containing the hexa-histidine sequence to obtain expression plasmids. FIG. 86a shows the DNA sequence of the β chain of the NY-ESO TCR incorporating the hexa-histidine tag, and FIG. 86b shows the resulting amino acid sequence.

FIG. 87 illustrates the elution of soluble NY-ESO TCR containing a novel disulphide bond and the biotin recognition sequence from a POROS 50HQ anion exchange column using a 0-500 mM NaCl gradient, as indicated by the dotted line. FIG. 88 illustrates the elution of soluble NY-ESO TCR containing a novel disulphide bond and the hexa-histidine tag from a POROS 50HQ anion exchange columns using a 0-500 mM NaCl gradient, as indicated by the dotted line.

FIGS. 89 and 90 are protein elution profiles from gel filtration chromatography of pooled fractions from the NY-ESO-biotin and NY-ESO-hexa-histidine tagged anion exchange column runs illustrated by FIGS. 87 and 88 respectively. The protein elutes as a single major peak, corresponding to the TCR heterodimer.

A BIAcore analysis of sTCR binding to pMHC was carried out as described in Example 3. The NY-ESO-biotin TCR had a Kd of 7.5 µM, The NY-ESO-hexa-histidine tagged TCR had a Kd of 9.6 µM Example 11

Cell Staining Using Fluorescent Labelled Tetramers of Soluble NY-ESO TCR Containing a Novel Disulphide Inter-chain Bond TCR Tetramer Preparation The NY-ESO soluble TCRs containing a novel disulphide bond and a biotin recognition sequence prepared as in Example 10 were utilised to form the soluble TCR tetramers using required for cell staining. 2.5 ml of purified soluble TCR solution (~0.2 mg/ml) was buffer exchanged into biotinylation reaction buffer (50 mM Tris pH 8.0, 10 mM $MgCl_2$) using a PD-10 column (Pharmacia). The eluate (3.5 ml) was concentrated to 1 ml using a centricon concentrator (Amicon) with a 10 kDa molecular weight cut-off. This was made up to 10 mM with ATP added from stock (0.1 g/ml adjusted to pH 7.0). A volume of a cocktail of protease inhibitors was then added (protease inhibitor cocktail Set 1, Calbiochem Biochemicals), sufficient to give a final protease cocktail concentration of $1/100^{th}$ of the stock solution as supplied, followed by 1 mM biotin (added from 0.2M stock) and 20 µg/ml enzyme (from 0.5 mg/ml stock). The mixture was then incubated overnight at room temperature. Excess biotin was removed from the solution by size exclusion chromatography on a S75 HR column. The level of biotinylation present on the NY-ESO TCR was determined via a size exclusion HPLC-based method as follows. A 50 ul aliquot of the biotinylated NY-ESO TCR (2 mg/ml) was incubated with 50 ul of streptavidin coated agarose beads (Sigma) for 1 hour. The beads were then spun down, and 50 µl of the unbound sample was run on a TSK 2000 SW column (Tosoohaas) using a 0.5 ml/min flow-rate (200 mM Phosphate Buffer pH 7.0) over 30 minutes. The presence of the biotinylated NY-ESO TCR was detected by a UV spectrometer at both 214 nm and 280 nm. The biotinylated NY-ESO was run against a non-bioninylated NY-ESO TCR control. The percentage of biotinylation was calculated by subtracting the peak-area of the biotinylated protein from that of the non-biotinylated protein.

Tetramerisation of the biotinylated soluble TCR was achieved using neutravidin-phycoerythrin conjugate (Cambridge Biosciences, UK). The concentration of biotinylated soluble TCR was measured using a Coomassie protein assay (Pierce), and a ratio of soluble TCR 0.8 mg/mg neutravidin-phycoerthrin conjugate was calculated to achieve saturation of the neutravidin-PE by biotinylated TCR at a ratio of 1:4. 19.5 µl of a 6.15 mg/ml biotinylated NY-ESO soluble TCR solution in phosphate buffered saline (PBS) was added slowly to 150 µl of a 1 mg/ml neutravidin-PE soluble over ice with gentle agitation. 100.5 µl of PBS was then added to this solution to provide a final NY-ESO TCR tetramer concentration of 1 mg/ml.

Staining Protocol

Four aliquots of $0.3 \times 10^6$ HLA-A2 positive EBV transformed B cell line (PP LCL) in 0.5 ml of PBS were incubated with varying concentrations (0, $10^{-4}$, $10^{-5}$ and $10^{-6}$ M) of HLA-A2 NYESO peptide (SLLMWITQC) (SEQ ID NO:106) for 2 h at 37° C. These PP LCL cells were then washed twice in Hanks buffered Saline solution (HBSS) (Gibco, UK).

Each of the four aliquots were divided equally and stained with biotinylated NY-ESO disulphide linked TCR freshly tetramerised with neutravidin-phycoerythrin. Cells were incubated with either 5 or 10 µg of phycoerythrin labelled tetrameric dsTCR complexes on ice for 30 minutes and washed with HBSS. Cells were washed again, re-suspended in HBSS and analysed by FACSVantage. 25,000 events were collected and data analysed using WinMIDI software.

Results

FIGS. 91a-h illustrate as histograms the FACSVantage data generated for each of the samples prepared as described above. The following table lists the percentage of positively stained cells observed for each of the samples:

| Sample | Positive stained Cells (%) |
|---|---|
| 0 NY-ESO peptide, 5 μg TCR | 0.75 |
| $10^{-4}$ M NY-ESO peptide, 5 μg TCR | 84.39 |
| $10^{-5}$ M NY-ESO peptide, 5 μg TCR | 35.29 |
| $10^{-6}$ M NY-ESO peptide, 5 μg TCR | 7.98 |
| 0 NY-ESO peptide, 10 μg TCR | 0.94 |
| $10^{-4}$ M NY-ESO peptide, 10 μg TCR | 88.51 |
| $10^{-5}$ M NY-ESO peptide, 10 μg TCR | 8.25 |
| $10^{-6}$ M NY-ESO peptide, 10 μg TCR | 3.45 |

These data clearly indicate that the proportion of the cells labelled by the NY-ESO TCR tetramers increases in a manner correlated to the concentration of the peptide (SLLM-WITQC) in which they had been incubated. Therefore, these NY-ESO TCR tetramers are moieties suitable for specific cell labelling based on the expression of the HLA-A2 NY-ESO complex.

In the present example, a fluorescent conjugated NY-ESO TCR tetramer has been used. However, similar levels of cell binding would be expected if this label were replaced by a suitable therapeutic moiety.

Example 12

Production of Soluble A6 TCR with a Novel Disulphide Bond Incorporating the Cβ1 Constant Region All of the previous examples describe the production of soluble TCRs with a novel disulphide bond incorporating the Cβ2 constant region. The present example demonstrates that soluble TCRs incorporating the Cβ1 constant region can be produced successfully.

Design of Primers for PCR Stitching of A6 TCR β-Chain V-Domain to Cβ1.

For PCR construct of A6 TCR β-chain V-domain, the following primers were designed:

```
5'-GGAGATATACATATGAACGCTGGTGTCACT-3'
(nucleotides 30-59 of SEQ ID NO:84)

(SEQ ID NO:85)
5'-CCTTGTTCAGGTCCTCTGTGACCGTGAG-3'
```

For PCR construct of Cβ1, the following primers were designed:

```
                                    (SEQ ID NO:86)
5'-CTCACGGTCACAGAGGACCTGAACAAGG-3'

(SEQ ID NO:87)
5'-CCCAAGCTTAGTCTGCTCTACCCCAGGCCTCGGC-3'
```

Beta VTCR construct and Cβ1 construct were separately amplified using standard PCR technology. They were connected to each other using a stitching PCR. Plasmid DNA was purified on a Qiagen mini-prep column according to the manufacturer's instructions and the sequence was verified by automated sequencing at the sequencing facility of Department of Biochemistry, Oxford University. The sequence for A6+Cβ1 is shown in FIG. 92.

Consequently, the A6+Cβ1 chain was paired to A6 alpha TCR by inter-chain disulphide bond after introducing cysteine in C-domain of both chains.

The soluble TCR was expressed and refolded as described in Example 2.

Purification of Refolded Soluble TCR:

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia) as in FIG. 93. Peak fractions were stored at 4° C. and analysed by Coomassie-stained SDS-PAGE (FIG. 94) before being pooled and concentrated. Finally, the sTCR was purified and characterised using a Superdex 200HR gel filtration column (FIG. 95) pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

A BIAcore analysis of the binding of the disulphide-linked A6 TCR to pMHC was carried out as described in Example 3. FIG. 96 shows BIAcore analysis of the specific binding of disulphide-linked A6 soluble TCR to its cognate pMHC.

The soluble A6 TCR with a novel disulphide bond incorporating the Cβ1 constant region had a $K_d$ of 2.42±0.55 μM for its cognate pMHC. This value is very similar to the $K_d$ of 1.8 μM determined for the soluble A6 TCR with a novel disulphide bond incorporating the Cβ2 constant region as determined in Example 3.

Example 13

Production of Soluble A6 TCR with a Novel Disulphide Bond Incorporating the "Free" Cysteine in the β Chain The β chain constant regions of TCRs include a cysteine residue (residue 75 in exon 1 of TRBC1*01 and TRBC2*01) which is not involved in either inter-chain or intra-chain disulphide bond formation. All of the previous examples describe the production of soluble TCRs with a novel disulphide bond in which this "free" cysteine has been mutated to alanine in order to avoid the possible formation of any "inappropriate" disulphide bonds which could result in a reduced yield of functional TCR. The present example demonstrates that soluble TCRs incorporating this "free" cysteine can be produced.

Design of Primers and Mutagenesis of TCR β Chain

For mutating TCR β-chain alanine (residue 75 in exon 1 of TRBC1*01 and TRBC2*01) to cysteine, the following primers were designed (mutation shown in lower case):

```
                                    (SEQ ID NO:88)
5'-T GAC TCC AGA TAC tgT CTG AGC AGC CG (SEQ ID NO:89)
5'-CG GCT GCT CAG Aca GTA TCT GGA GTC A
```

PCR mutagenesis, expression and refolding of the soluble TCR was carried out as described in Example 2.

Purification of Refolded Soluble TCR:

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia) as in FIG. 98. Peak fractions were stored at 4° C. and analysed by Coomassie-stained SDS-PAGE (FIG. 99) before being pooled and concentrated.

Finally, the sTCR was purified and characterised using a Superdex 200HR gel filtration column (FIG. 100) pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

A BIAcore analysis of the binding of the disulphide-linked A6 TCR to pMHC was carried out as described in Example 3. FIG. 101 shows BIAcore analysis of the specific binding of disulphide-linked A6 soluble TCR to its cognate pMHC.

The soluble A6 TCR with a novel disulphide bond incorporating the "free" cysteine in the β chain had a $K_d$ of 21.39±3.55 μM for its cognate pMHC.

Example 14

Production of Soluble A6 TCR with a Novel Disulphide Bond Wherein "Free" Cysteine in the β Chain is Mutated to Serine The present example demonstrates that soluble TCRs with a novel disulphide bond in which the "free" cysteine in the P chain (residue 75 in exon 1 of TRBC 1*01 and TRBC2*01) is mutated to serine can be successfully produced.

Design of Primers and Mutagenesis of TCR β Chain

For mutating TCR β-chain alanine that had previously been substituted for the native cysteine (residue 75 in exon 1 of TRBC1*01 and TRBC2*01) to serine, the following primers were designed (mutation shown in lower case):

```
                                    (SEQ ID NO:90)
5'-T GAC TCC AGA TAC tCT CTG AGC AGC CG (SEQ ID NO:91)
5'-CG GCT GCT CAG AGa GTA TCT GGA GTC A
```

PCR mutagenesis (resulting in a mutated beta chain as shown in FIG. 102), expression and refolding of soluble TCR was carried out as described in Example 2.

Purification of Refolded Soluble TCR:

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia) as shown in FIG. 103. Peak fractions were stored at 4° C. and analysed by Coomassie-stained SDS-PAGE (FIG. 104) before being pooled and concentrated. Finally, the sTCR was purified and characterised using a Superdex 200HR gel filtration column (FIG. 105) pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

A BIAcore analysis of the binding of the disulphide-linked A6 TCR to pMHC was carried out as described in Example 3. FIG. 106 shows BIAcore analysis of the specific binding of disulphide-linked A6 soluble TCR to its cognate pMHC.

The soluble A6 TCR with a novel disulphide bond in which the "free" cysteine in the β chain was mutated to serine had a $K_d$ of 2.98±0.27 μM for its cognate pMHC. This value is very similar to the $K_d$ of 1.8 μM determined for the soluble A6 TCR with a novel disulphide bond in which the "free" cysteine in the P chain was mutated to alanine as determined in Example 3.

Example 15

Cloning of NY-ESO TCR α and β Chains Containing a Novel Disulphide Bond into Yeast Expression Vectors NY-ESO TCR α and β chains were fused to the C-terminus of the pre-pro mating factor alpha sequence from *Saccharomyces cerevisiae* and cloned into yeast expression vectors pYX122 and pYX112 respectively (see FIGS. 107 and 108).

The following primers were designed to PCR amplify pre-pro mating factor alpha sequence from *S. cerevisiae* strain SEY6210 (Robinson et al. (1991), *Mol Cell Biol.* 11(12): 5813-24) for fusing to the TCR α chain.

```
                                    (SEQ ID NO:94)
5'-TCT GAA TTC ATG AGA TTT CCT TCA ATT TTT AC-3'

(SEQ ID NO:95)
5'-TCA CCT CCT GGG CTT CAG CCT CTC TTT TAT C-3'
```

The following primers were designed to PCR amplify pre-pro mating factor alpha sequence from *S. cerevisiae* strain SEY6210 for fusing to the TCR β chain.

```
5'-TCT GAA TTC ATG AGA TTT CCT TCA ATT TTT AC-3'

5'-GTG TCT CGA GTT AGT CTG CTC TAC CCC AGG C-3'
```

Yeast DNA was prepared by re-suspending a colony of *S. cerevisiae* strain SEY6210 in 30 1 of 0.25% SDS in water and heating for 3 minutes at 90° C. The pre-pro mating factor alpha sequences for fusing to the TCR α and β chains were generated by PCR amplifying 0.25 μl of yeast DNA with the respective primer pairs mentioned above using the following PCR conditions. 12.5 pmoles of each primer was mixed with 200 μM dNTP, 5 μl of 10×Pfu buffer and 1.25 units of Pfu polymerase (Stratagene) in a final volume of 50 μl. After an initial denaturation step of 30 seconds at 92° C., the reaction mixture was subjected to 30 rounds of denaturation (92° C., 30 sec.), annealing (46.9° C., 60 sec.), and elongation (72° C., 2 min.) in a Hybaid PCR express PCR machine.

The following primers were designed to PCR amplify the TCR α chain to be fused to the pre-pro mating factor alpha sequence mentioned above.

```
                                    (SEQ ID NO:96)
5'-GGC TGA AGC CCA GGA GGT GAC ACA GAT TCC-3'

(SEQ ID NO:97)
5'-CTC CTC TCG AGT TAG GAA CTT TCT GGG CTG GG-3'
```

The following primers were designed to PCR amplify the TCR β chain to be fused to the pre-pro mating factor alpha sequence mentioned above.

```
                                    (SEQ ID NO:98)
5'-GGC TGA AGC CGG CGT CAC TCA GAC CCC AAA AT-3'

(SEQ ID NO:99)
5'-GTG TCT CGA GTT AGT CTG CTC TAC CCC AGG C-3'
```

The PCR conditions for amplifying the TCR α and β chains were the same as mentioned above except for the following changes: the DNA template used for amplifying the TCR α and β chains were the NY-ESO TCR α and β chains respectively (as prepared in Example 5); and the annealing temperature used was 60.1° C.

The PCR products were then used in a PCR stitching reaction utilising the complementary overlapping sequences introduced into the initial PCR products to create a full length chimeric gene. The resulting PCR products were digested with the restriction enzymes EcoR I and Xho I and cloned into either pYX122 or pYX112 digested with the same enzymes. The resulting plasmids were purified on a Qiagen™ mini-prep column according to the manufacturer's instructions, and the sequences verified by automated sequencing at the sequencing facility of Genetics Ltd, Queensway, New Milton, Hampshire, United Kingdom. FIGS. 109 and 110 show the DNA and protein sequences of the cloned chimeric products.

Example 16

Expression of Soluble NY-ESO TCR Containing a Novel Disulphide Bond in Yeast The yeast expression plasmids containing the TCR α and β chains respectively produced as described in Example 15 were co-transformed into *S. cerevisiae* strain SEY6210 using the protocol by Agatep et al. (1998) (Technical Tips Online (http://tto.trends.com) 1:51:P01525). A single colony growing on synthetic dropout (SD) agar containing Histidine and Uracil (Qbiogene, Illkirch, France) was cultured overnight at 30° C. in 10 ml SD media containing Histidine and Uracil. The overnight culture was sub-cultured 1:10 in 10 ml of the fresh SD media containing Histidine and Uracil and grown for 4 hours at 30° C. The culture was centrifuged for 5 minutes at 3800 rpm in a Heraeus Megafuge 2.0R (Kendro Laboratory Products Ltd, Bishop's Stortford, Hertfordshire, UK) and the supernatant harvested. 5 µl StratClean Resin (Stratagene) was mixed with the supernatent and kept rotating in a blood wheel at 4° C. overnight. The StrataClean resin was spun down at 3800 rpm in a Heraeus Megafuge 2.0R and the media discarded. 25 µl of reducing sample buffer (950 µl of Laemmli sample buffer (Biorad) containing 50 µl of 2M DTT) was added to the resin and the samples heated at 95° C. for 5 minutes and then cooled on ice before 20 µl of the mix was loaded on a SDS-PAGE gel at 0.8 mA constant/cm² of gel surface for 1 hour. The proteins in the gel were transferred to Immuno-Blot PVDF membranes (Bio-Rad) and probed with TCR anti α chain antibody as described in Example 17 below except for the following changes. The primary antibody (TCR anti α chain) and secondary antibodies were used at 1 in 200 and 1 in 1000 dilutions respectively. FIG. 111 shows a picture of the developed membrane. The result shows that there is a low level of TCR secretion by the yeast culture into the media.

Example 17

Disulphide A6 Tax TCR α and β Chain Expression in Baculovirus

Strategy for Cloning

The α and β chains of the disulphide A6 Tax TCR were cloned from pGMT7 into a pBlueScript KS2-based vector called the pEX172. This vector was designed for cloning different MHC class II β-chains, for insect cell expression, using the leader sequence from DRB1*0101, an AgeI site for insertion of different peptide-coding sequences, a linker region, and then MluI and SalI sites to clone the DRβ chains in front of the Jun Leucine zipper sequence. The sequence where pEX 172 differs from pBlueScript II KS–, located between the KpnI and EcoRI sites of pBlueScript II KS–, is shown in FIG. 112. For the purposes of cloning TCR chains in insect cells, this pEX172 was cut with AgeI and SalI to remove the linker region and MluI site, and the TCR chains go in where the peptide sequence would start. The TCR sequences were cloned from pGMT7 with a BspEI site at the 5' end (this had AgeI compatible sticky ends) and a SalI site at the 3' end. In order to provide the cleavage site for the removal of the DRβ leader sequence, the first three residues of the DRβ chain (GDT) were preserved. In order to prevent the Jun Leucine zipper sequence being transcribed, it was necessary to insert a stop codon before the SalI site. For a schematic of this construct, see FIG. 113. Once the TCR chains are in this plasmid, the BamHI fragment were cut out and subcloned into the pAcAB3 vector, which has homology recombination sites for Baculovirus. The pAcAB3 vector has two divergent promoters, one with a BamHI site and one with a BglII cloning site. There is a BglII site in the A6 TCR β-chain, so the A6 TCR α-chain was inserted into the BglII site, and the β-chain was then subcloned into the BamHI site.

In accordance with the above cloning strategy, the following primers were designed (homology to the vectors is in uppercase):

```
A6α:
F: 5'-gtagtccggagacaccggaCAGAAGGAAGTGGAGCAGAAC    (SEQ ID NO:100)

R: 5'-gtaggtcgacTAGGAACTTTCTGGGCTGGG              (SEQ ID NO:101)

A6β:
F: 5'-gtagtccggagacaccggaAACGCTGGTGTCACTCAGA      (SEQ ID NO:102)

R: 5'-gtaggtcgacTAGTCTGCTCTACCCCAGG               (SEQ ID NO:103)
```

PCR, Cloning and Sub-Cloning:

Expression plasmids containing the genes for the disulphide A6 Tax TCR α or β chain were used as templates in the following PCR reactions. 100 ng of α plasmid was mixed with 1 µl 10 mM dNTP, 5 µl 10×Pfu-buffer (Stratagene), 1.25 units Pfu polymerase (Stratagene), 50 µmol of the A6α primers above, and the final volume was adjusted to 50 µl with $H_2O$. A similar reaction mixture was set up for the β chain, using the β plasmid and the pair of β primers. The reaction mixtures were subjected to 35 rounds of denaturation (95° C., 60 sec.), annealing (50° C., 60 sec.), and elongation (72° C., 8 min.) in a Hybaid PCR express PCR machine. The product was then digested for 2 hours at 37° C. with 10 units of BspEI restriction enzyme then for a further 2 hours with 10 units of SalI (New England Biolabs). These digested reactions were ligated into pEX172 that had been digested with AgeI and SalI, and these were transformed into competent XL1-Blue bacteria and grown for 18 hours at 37° C. A single colony was picked from each of the α and β preps and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a QIAgen mini-prep column according to the manufacturer's instructions and the sequence was verified by automated sequencing at the sequencing facility of Genetix. The amino acid sequences of the BamHI inserts are shown in FIGS. 114 and 115 for the α chain and β chain, respectively.

These α and β disulphide A6 Tax TCR chain constructs in pEX172 were digested out for 2 hours at 37° C. with BamHI restriction enzyme (New England Biolabs). The α chain BamHI insert was ligated into pAcAB3 vector (Pharmingen-BD Biosciences: 21216P) that had been digested with BglII enzyme. This was transformed into competent XL1-Blue bacteria and grown for 18 hours at 37° C. A single colony was picked from this plate and grown overnight in 5 ml TYP+ ampicillin and the plasmid DNA was purified as before. This plasmid was then digested with BamHI and the β chain BamHI insert was ligated in, transformed into competent XL1-Blue bacteria, grown overnight, picked to TYP-ampicillin, and grown before miniprepping as before using a QIAgen mini-prep column. The correct orientation of both the α and β chains were confirmed by sequencing using the following sequencing primers:

```
pAcAB3 α forwards:
5'-gaaattatgcatttgaggatg      (SEQ ID NO:104)

pAcAB3 β forwards:
5'-attaggcctctagagatccg       (SEQ ID NO:105)
```

Transfection, Infection, Expression and Analysis of A6 TCR in Insect Cells

The expression plasmid containing the α-chain and β-chain was transfected into sf9 cells (Pharmingen-BD Biosciences: 21300C) grown in serum free medium (Pharmingen-BD Biosciences: 551411), using the Baculogold transfection kit (Pharmingen-BD Biosciences: 21100K) as per the manufacturers instructions. After 5 days at 27° C., 200 μl of the medium these transfected cells had been growing in was added to 100 ml of High Five cells at 1×10$^6$ cells/ml in serum free medium. After a further 6 days at 27° C., 1 ml of this medium was removed and centrifuged at 13,000 RPM in a Hereus microfuge for 5 minutes to pellet cell debris. 10 μl of this insect A6 disulphide linked TCR supernatant was run alongside positive controls of bacterial A6 disulphide linked TCR 5 μg and 10 μg on a pre-cast 4-20% Tris/glycine gel (Invitrogen: EC60252). Reduced samples were prepared by adding 10 μl of Reducing sample buffer (950 μl of Laemmli sample buffer (Bio-Rad: 161-0737) 50 μl of 2M DTT) and heating at 95° C. for 5 minutes, cooling at room temperature for 10 minutes then loading 20 μl. Non-reduced samples were prepared by adding 10 μl of Laemmli sample buffer, and loading 20 μl.

The gel was run at 150 volts for 1 hour in a Novex-Xcell gel tank after which the gel was stained in 50 ml of Coomassie gel stain for 1 hour with gentle agitation (1.1 g Coomassie powder in 500 ml of methanol stir for 1 hour add 100 ml acetic acid make up to 1 liter with $H_2O$ and stir for 1 hour then filter through 0.45 μM filter). The gel was de-stained three times for 30 mins with gentle agitation in 50 ml of de-stain (as Coomassie gel stain but omitting the Coomassie powder).

Western Blots were performed by running SDS-PAGE gels as before but the proteins were transferred to Immuno-Blot PVDF membranes (Bio-Rad: 162-0174) rather than staining the gels with Coomassie. Six filter papers were cut to the size of the gel and soaked in transfer buffer (2.39 g Glycine, 5.81 g of Tris Base, 0.77 g DTT dissolved in 500 mls of $H_2O$, 200 mls of methanol added then made up to 1000 mls with $H_2O$). The PVDF membrane was prepared by soaking in methanol for 1 minute and then in transfer buffer for 2 minutes. Three filter papers were placed on the anode surface of the Immunoblot apparatus (Pharmacia—Novablot) then the membrane was placed on top followed by the gel and then finally three more filter papers on the cathode side. The Immuno-blot was run for 1 hour at 0.8 mA constant/cm$^2$ of gel surface.

After blotting, the membrane was blocked in 7.5 mls of blocking buffer (4 Tris-buffered saline tablets (Sigma: T5030), 3 g non-fat dried milk (Sigma: M7409), 30 μl of Tween 20 made up to 30 mls with $H_2O$) for 60 mins with gentle agitation. The membrane was washed three times for 5 mins with TBS wash buffer (20 TBS tablets, 150 μl Tween 20 made up to 300 ml with $H_2O$). The membrane was then incubated in primary antibody 1 in 50 dilution of anti TCR α chain clone 3A8 (Serotec: MCA987) or anti TCR β chain clone 8A3 (Serotec: MCA988) in 7.5 ml blocking buffer for 1 hour with gentle agitation. The membrane was washed as before in TBS wash buffer. Next, a secondary antibody incubation of HRP labelled goat anti-mouse antibody (Santa Cruz Biotech: Sc-2005) 1 in 1000 dilution in 7.5 ml of blocking buffer was carried out for 30 min with gentle agitation. The membrane was washed as before and then washed in 30 ml of $H_2O$ with 2 TBS tablets.

The antibody binding was detected by Opti-4CN colourmetric detection (Biorad: 170-8235) (1.4 ml Opt-4CN diluent, 12.6 ml $H_2O$, 0.28 ml Opti-4CN substrate). The membranes were coloured for 30 minutes and then washed in $H_2O$ for 15 minutes. The membranes were dried at room temperature, and scanned images were aligned with an image of the coomassie stained gel (FIG. 116).

Results

It can be seen from FIG. 116 that both disulphide TCRs are formed as a heterodimer that is stable in the SDS gel. They both break into the α and β chains upon reduction. The insect disulphide TCR heterodimer has a slightly higher molecular weight that the bacterially produced version, presumably because of the glycosylation from the insect cells. It can be seen that in this instance the insect cells are producing α chain in excess, and free α chain can be seen in the non-reduced lane of the anti-α western blot.

These data clearly demonstrate that the baculovirus expression system described above provides a viable alternative to prokaryotic expression of soluble TCRs containing novel disulphide bonds.

The invention claimed is:

1. An isolated nucleic acid molecule comprising a sequence encoding all or part of a TCR α chain, except the transmembrane domain thereof,
    wherein the all or part of the TCR α chain comprises a functional variable domain and at least a part of the constant domain of the TCR α chain, and wherein the all or part of the TCR α chain comprises a cysteine residue substituted for an amino acid selected from the group consisting of:
    (a) Thr 48 of exon 1 of TRAC*01 (amino acid residue 10 of SEQ ID NO:1);
    (b) Thr 45 of exon 1 of TRAC*01 (amino acid residue 10 of SEQ ID NO:2);
    (c) Tyr 10 of exon 1 of TRAC*01 (amino acid residue 10 of SEQ ID NO:3); and
    (d) Ser 15 of exon 1 of TRAC*01 (amino acid residue 10 of SEQ ID NO:4).

2. The nucleic acid molecule of claim 1 which encodes all of the extracellular constant Ig domain of the TCR α chain.

3. A vector comprising a nucleic acid molecule comprising a sequence encoding all or part of a TCR α chain, except the transmembrane domain thereof, wherein the all or part of the TCR α chain comprises a functional variable domain and at least a part of the constant domain of the TCR α chain, and wherein the all or part of the TCR α chain comprises a cysteine residue substituted for an amino acid selected from the group consisting of
    (a) Thr 48 of exon 1 of TRAC*01 (amino acid residue 10 of SEQ ID NO:1);
    (b) Thr 45 of exon 1 of TRAC*01 (amino acid residue 10 of SEQ ID NO:2);
    (c) Tyr 10 of exon 1 of TRAC*01 (amino acid residue 10 of SEQ ID NO:3); and
    (d) Ser 15 of exon 1 of TRAC*01 (amino acid residue 10 of SEQ ID NO:4).

4. An isolated host cell comprising the vector of claim 3.

5. A method for producing a soluble TCR, said method comprising:
- (i) transforming a first host cell with a nucleic acid molecule encoding a TCR α chain comprising a non-native cysteine residue in a first position of the constant domain thereof;
- (ii) transforming a second host cell with a nucleic acid molecule encoding a TCR β chain comprising a non-native cysteine residue in a second position of the constant domain thereof;
- (iii) incubating said host cells under conditions causing expression of the TCR chains;
- (iv) refolding the TCR chains in a refolding buffer; and
- (v) isolating the refolded soluble TCR, wherein the non-native cysteine residues are substituted for native residues whose β carbon atoms are 0.6 nm or less apart in the native TCR structure and wherein the refolded soluble TCR comprises a disulfide bond formed from cysteine residues substituted for amino acid residues selected from the group consisting of:
- (a) Thr 48 of exon 1 of TRAC*01 (amino acid residue 10 of SEQ ID NO:1) and Ser 57 of exon 1 of TRBC1*01 or TRBC2*01 (amino acid residue 10 of SEQ ID NO:5);
- (b) Thr 45 of exon 1 of TRAC*01 (amino acid residue 10 of SEQ ID NO:2) and Ser 77 of exon 1 of TRBC1*01 or TRBC2*01 (amino acid residue 10 of SEQ ID NO:6);
- (c) Tyr 10 of exon 1 of TRAC*01 (amino acid residue 10 of SEQ ID NO:3) and Ser 17 of exon 1 of TRBC1*01 or TRBC2*01 (amino acid residue 10 of SEQ ID NO:7);
- (d) Thr 45 of exon 1 of TRAC*01 (amino acid residue 10 of SEQ ID NO:2) and Asp 59 of exon 1 of TRBC1*01 or TRBC2*01 (amino acid residue 10 of SEQ ID NO:8); and
- (e) Ser 15 of exon 1 of TRAC*01 (amino acid residue 10 of SEQ ID NO:4) and Glu 15 of exon 1 of TRBC1*01 or TRBC2*01 (amino acid residue 10 of SEQ ID NO:9).

6. An isolated nucleic acid molecule comprising a sequence encoding all or part of a TCR β chain, except the transmembrane domain thereof, wherein the all or part of the TCR β chain comprises a functional variable domain and at least a part of the constant domain of the TCR β chain, and wherein the all or part of the TCR β chain comprises a cysteine residue substituted for an amino acid selected from the group consisting of:
- (a) Ser 57 of exon 1 of TRBC1*01 or TRBC2*01 (amino acid residue 10 of SEQ ID NO:5);
- (b) Ser 77 of exon 1 of TRBC1*01 or TRBC2*01 (amino acid residue 10 of SEQ ID NO:6);
- (c) Ser 17 of exon 1 of TRBC1*01 or TRBC2*01 (amino acid residue 10 of SEQ ID NO:7);
- (d) Asp 59 of exon 1 of TRBC1*01 or TRBC2*01 (amino acid residue 10 of SEQ ID NO:8); and
- (e) Glu 15 of exon 1 of TRBC1*01 or TRBC2*01 (amino acid residue 10 of SEQ ID NO:9).

7. The nucleic acid molecule of claim 6 which encodes all of the extracellular constant Ig domain of the TCR β chain.

8. A vector comprising comprising a sequence encoding all or part of a TCR β chain, except the transmembrane domain thereof, wherein the all or part of the TCR β chain comprises a functional variable domain and at least a part of the constant domain of the TCR β chain, and wherein the all or part of the TCR β chain comprises a cysteine residue substituted for an amino acid selected from the group consisting of:
- (a) Ser 57 of exon 1 of TRBC1*01 or TRBC2*01 (amino acid residue 10 of SEQ ID NO:5);
- (b) Ser 77 of exon 1 of TRBC1*01 or TRBC2*01 (amino acid residue 10 of SEQ ID NO:6);
- (c) Ser 17 of exon 1 of TRBC1*01 or TRBC2*01 (amino acid residue 10 of SEQ ID NO:7);
- (d) Asp 59 of exon 1 of TRBC1*01 or TRBC2*01 (amino acid residue 10 of SEQ ID NO:8); and
- (e) Glu 15 of exon 1 of TRBC1*01 or TRBC2*01 (amino acid residue 10 of SEQ ID NO:9).

9. An isolated host cell comprising the vector of claim 8.

* * * * *

SEQUENCE LISTING

```
<160> NUMBER OF SEQ ID NOS: 183

<210> SEQ ID NO 1
<211> LENGTH: 20
<212> TYPE: PRT
<213> ORGANISM: Homo sapiens
```

```
<400> SEQUENCE: 1

Asp Ser Asp Val Tyr Ile Thr Asp Lys Thr Val Leu Asp Met Arg Ser
1               5                   10                  15

Met Asp Phe Lys
            20

<210> SEQ ID NO 2
<211> LENGTH: 20
<212> TYPE: PRT
<213> ORGANISM: Homo sapiens

<400> SEQUENCE: 2

Gln Ser Lys Asp Ser Asp Val Tyr Ile Thr Asp Lys Thr Val Leu Asp
1               5                   10                  15

Met Arg Ser Met
            20

<210> SEQ ID NO 3
<211> LENGTH: 20
<212> TYPE: PRT
<213> ORGANISM: Homo sapiens

<400> SEQUENCE: 3

Asp Ile Gln Asn Pro Asp Pro Ala Val Tyr Gln Leu Arg Asp Ser Lys
1               5                   10                  15

Ser Ser Asp Lys
            20

<210> SEQ ID NO 4
<211> LENGTH: 20
<212> TYPE: PRT
<213> ORGANISM: Homo sapiens

<400> SEQUENCE: 4

Asp Pro Ala Val Tyr Gln Leu Arg Asp Ser Lys Ser Ser Asp Lys Ser
1               5                   10                  15

Val Cys Leu Phe
            20

<210> SEQ ID NO 5
<211> LENGTH: 20
<212> TYPE: PRT
<213> ORGANISM: Homo sapiens

<400> SEQUENCE: 5

Asn Gly Lys Glu Val His Ser Gly Val Ser Thr Asp Pro Gln Pro Leu
1               5                   10                  15

Lys Glu Gln Pro
            20

<210> SEQ ID NO 6
<211> LENGTH: 20
<212> TYPE: PRT
<213> ORGANISM: Homo sapiens

<400> SEQUENCE: 6

Ala Leu Asn Asp Ser Arg Tyr Ala Leu Ser Ser Arg Leu Arg Val Ser
1               5                   10                  15

Ala Thr Phe Trp
            20
```

```
<210> SEQ ID NO 7
<211> LENGTH: 20
<212> TYPE: PRT
<213> ORGANISM: Homo sapiens

<400> SEQUENCE: 7

Pro Pro Glu Val Ala Val Phe Glu Pro Ser Glu Ala Glu Ile Ser His
1               5                   10                  15

Thr Gln Lys Ala
            20

<210> SEQ ID NO 8
<211> LENGTH: 20
<212> TYPE: PRT
<213> ORGANISM: Homo sapiens

<400> SEQUENCE: 8

Lys Glu Val His Ser Gly Val Ser Thr Asp Pro Gln Pro Leu Lys Glu
1               5                   10                  15

Gln Pro Ala Leu
            20

<210> SEQ ID NO 9
<211> LENGTH: 20
<212> TYPE: PRT
<213> ORGANISM: Homo sapiens

<400> SEQUENCE: 9

Val Phe Pro Pro Glu Val Ala Val Phe Glu Pro Ser Glu Ala Glu Ile
1               5                   10                  15

Ser His Thr Gln
            20

<210> SEQ ID NO 10
<211> LENGTH: 91
<212> TYPE: PRT
<213> ORGANISM: Mus musculus

<400> SEQUENCE: 10

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
                20                  25                  30

Ile Asn Val Pro Lys Thr Met Glu Ser Gly Thr Phe Ile Thr Asp Lys
            35                  40                  45

Thr Val Leu Asp Met Lys Ala Met Asp Ser Lys Ser Asn Gly Ala Ile
        50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro
                85                  90

<210> SEQ ID NO 11
<211> LENGTH: 126
<212> TYPE: PRT
<213> ORGANISM: Mus musculus

<400> SEQUENCE: 11

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
```

-continued

```
                    20                  25                  30

Ala Arg Gly Phe Phe Pro Asp His Val Glu Leu Ser Trp Trp Val Asn
            35                  40                  45

Gly Arg Glu Val His Ser Gly Val Ser Thr Asp Pro Gln Ala Tyr Lys
        50                  55                  60

Glu Ser Asn Tyr Ser Tyr Cys Leu Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
        115                 120                 125

<210> SEQ ID NO 12
<211> LENGTH: 20
<212> TYPE: PRT
<213> ORGANISM: Mus musculus

<400> SEQUENCE: 12

Glu Ser Gly Thr Phe Ile Thr Asp Lys Thr Val Leu Asp Met Lys Ala
1               5                   10                  15

Met Asp Ser Lys
            20

<210> SEQ ID NO 13
<211> LENGTH: 20
<212> TYPE: PRT
<213> ORGANISM: Mus musculus

<400> SEQUENCE: 13

Lys Thr Met Glu Ser Gly Thr Phe Ile Thr Asp Lys Thr Val Leu Asp
1               5                   10                  15

Met Lys Ala Met
            20

<210> SEQ ID NO 14
<211> LENGTH: 20
<212> TYPE: PRT
<213> ORGANISM: Mus musculus

<400> SEQUENCE: 14

Tyr Ile Gln Asn Pro Glu Pro Ala Val Tyr Gln Leu Lys Asp Pro Arg
1               5                   10                  15

Ser Gln Asp Ser
            20

<210> SEQ ID NO 15
<211> LENGTH: 20
<212> TYPE: PRT
<213> ORGANISM: Mus musculus

<400> SEQUENCE: 15

Ala Val Tyr Gln Leu Lys Asp Pro Arg Ser Gln Asp Ser Thr Leu Cys
1               5                   10                  15

Leu Phe Thr Asp
            20

<210> SEQ ID NO 16
<211> LENGTH: 20
```

```
<212> TYPE: PRT
<213> ORGANISM: Mus musculus

<400> SEQUENCE: 16

Asn Gly Arg Glu Val His Ser Gly Val Ser Thr Asp Pro Gln Ala Tyr
1               5                   10                  15

Lys Glu Ser Asn
            20

<210> SEQ ID NO 17
<211> LENGTH: 20
<212> TYPE: PRT
<213> ORGANISM: Mus musculus

<400> SEQUENCE: 17

Lys Glu Ser Asn Tyr Ser Tyr Cys Leu Ser Ser Arg Leu Arg Val Ser
1               5                   10                  15

Ala Thr Phe Trp
            20

<210> SEQ ID NO 18
<211> LENGTH: 20
<212> TYPE: PRT
<213> ORGANISM: Mus musculus

<400> SEQUENCE: 18

Pro Pro Lys Val Ser Leu Phe Glu Pro Ser Lys Ala Glu Ile Ala Asn
1               5                   10                  15

Lys Gln Lys Ala
            20

<210> SEQ ID NO 19
<211> LENGTH: 20
<212> TYPE: PRT
<213> ORGANISM: Mus musculus

<400> SEQUENCE: 19

Arg Glu Val His Ser Gly Val Ser Thr Asp Pro Gln Ala Tyr Lys Glu
1               5                   10                  15

Ser Asn Tyr Ser
            20

<210> SEQ ID NO 20
<211> LENGTH: 20
<212> TYPE: PRT
<213> ORGANISM: Mus musculus

<400> SEQUENCE: 20

Val Thr Pro Pro Lys Val Ser Leu Phe Glu Pro Ser Lys Ala Glu Ile
1               5                   10                  15

Ala Asn Lys Gln
            20

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
cacagacaaa tgtgtgctag acat                                          24
```

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
atgtctagca cacatttgtc tgtg                                           24

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
cagtggggtc tgcacagacc c                                              21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gggtctgtgc agaccccact g                                              21

<210> SEQ ID NO 25
<211> LENGTH: 28
<212> TYPE: DNA
<213> ORGANISM: Artificial Sequence
<220> FEATURE:
<223> OTHER INFORMATION: primer

<400> SEQUENCE: 25
atatccagaa cccggatcct gccgtgta                                       28

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
tacacggcag gaatccgggt tctggatat                                      29

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
ggagatatac atatgcaact actagaacaa                                     30

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
tacacggcag gatccgggtt ctggatatt					29

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
ggagatatac atatggtgga tggtggaatc					30

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
cccaagctta gtctgctcta ccccaggcct cggc				34

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
ggagatatac atatgcagga ggtgacacag					30

<210> SEQ ID NO 32
<211> LENGTH: 29
<212> TYPE: DNA
<213> ORGANISM: Artificial Sequence
<220> FEATURE:
<223> OTHER INFORMATION: primer

<400> SEQUENCE: 32
tacacggcag gatccgggtt ctggatatt					29

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
ggagatatac atatgggtgt cactcagacc					30

<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
cccaagctta gtctgctcta ccccaggcct cggc				34

<210> SEQ ID NO 35

```
<211> LENGTH: 30
<212> TYPE: DNA
<213> ORGANISM: Artificial Sequence
<220> FEATURE:
<223> OTHER INFORMATION: primer

<400> SEQUENCE: 35
ggagatatac atatgcagga ggtgacacag                                      30

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
cccaagctta acaggaactt tctgggctgg ggaagaa                              37

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
ggagatatac atatgggtgt cactcagacc                                      30

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
cccaagctta acagtctgct ctaccccagg cctcggc                              37

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
gggaagctta catatgaagg aggtggagca gaattctgg                            39

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40
tacacggcag gatccgggtt ctggatatt                                       29

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
```

```
ttggaattca catatgggcg tcatgcagaa cccaagacac                                40

<210> SEQ ID NO 42
<211> LENGTH: 34
<212> TYPE: DNA
<213> ORGANISM: Artificial Sequence
<220> FEATURE:
<223> OTHER INFORMATION: primer

<400> SEQUENCE: 42
cccaagctta gtctgctcta ccccaggcct cggc                                     34

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
cacagacaaa tgtgtgctag acat                                                24

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
atgtctagca cacatttgtc tgtg                                                24

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
ccctgccgtg tgccagctga gag                                                 23

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
ctctcagctg gcacacggca ggg                                                 23

<210> SEQ ID NO 47
<211> LENGTH: 28
<212> TYPE: DNA
<213> ORGANISM: Artificial Sequence
<220> FEATURE:
<223> OTHER INFORMATION: primer

<400> SEQUENCE: 47
ccgtgtacca gtgcagagac tctaaatc                                            28

<210> SEQ ID NO 48
<211> LENGTH: 28
<212> TYPE: DNA
```

```
<213> ORGANISM: Artificial Sequence
<220> FEATURE:
<223> OTHER INFORMATION: primer

<400> SEQUENCE: 48
gatttagagt ctctgcactg gtacacgg                                             28

<210> SEQ ID NO 49
<211> LENGTH: 27
<212> TYPE: DNA
<213> ORGANISM: Artificial Sequence
<220> FEATURE:
<223> OTHER INFORMATION: primer

<400> SEQUENCE: 49
cagctgagag actgtaaatc cagtgac                                              27

<210> SEQ ID NO 50
<211> LENGTH: 27
<212> TYPE: DNA
<213> ORGANISM: Artificial Sequence
<220> FEATURE:
<223> OTHER INFORMATION: primer

<400> SEQUENCE: 50
gtcactggat ttacagtctc tcagctg                                              27

<210> SEQ ID NO 51
<211> LENGTH: 27
<212> TYPE: DNA
<213> ORGANISM: Artificial Sequence
<220> FEATURE:
<223> OTHER INFORMATION: primer

<400> SEQUENCE: 51
cagtgacaag tcttgctgcc tattcac                                              27

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
gtgaataggc agcaagactt gtcactg                                              27

<210> SEQ ID NO 53
<211> LENGTH: 28
<212> TYPE: DNA
<213> ORGANISM: Artificial Sequence
<220> FEATURE:
<223> OTHER INFORMATION: primer

<400> SEQUENCE: 53
gattctgatg tgtgtatcac agacaaat                                             28

<210> SEQ ID NO 54
<211> LENGTH: 28
<212> TYPE: DNA
<213> ORGANISM: Artificial Sequence
<220> FEATURE:
<223> OTHER INFORMATION: primer

<400> SEQUENCE: 54
atttgtctgt gatacacaca tcagaatc                                             28
```

```
<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
ctgatgtgta tatctgtgac aaaactgtgc                                30

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
gcacagtttt gtcacagata tacacatcag                                30

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
agacaaaact gtgtgtgaca tgaggtct                                  28

<210> SEQ ID NO 58
<211> LENGTH: 28
<212> TYPE: DNA
<213> ORGANISM: Artificial Sequence
<220> FEATURE:
<223> OTHER INFORMATION: primer

<400> SEQUENCE: 58
agacctcatg tcacacacag ttttgtct                                  28

<210> SEQ ID NO 59
<211> LENGTH: 27
<212> TYPE: DNA
<213> ORGANISM: Artificial Sequence
<220> FEATURE:
<223> OTHER INFORMATION: primer

<400> SEQUENCE: 59
actgtgctag actgtaggtc tatggac                                   27

<210> SEQ ID NO 60
<211> LENGTH: 27
<212> TYPE: DNA
<213> ORGANISM: Artificial Sequence
<220> FEATURE:
<223> OTHER INFORMATION: primer

<400> SEQUENCE: 60
gtccatagac ctacagtcta gcacagt                                   27

<210> SEQ ID NO 61
<211> LENGTH: 25
<212> TYPE: DNA
<213> ORGANISM: Artificial Sequence
<220> FEATURE:
```

<223> OTHER INFORMATION: primer

<400> SEQUENCE: 61
cttcaagagc aactgtgctg tggcc     25

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ggccacagca cagttgctct tgaag     25

<210> SEQ ID NO 63
<211> LENGTH: 21
<212> TYPE: DNA
<213> ORGANISM: Artificial Sequence
<220> FEATURE:
<223> OTHER INFORMATION: primer

<400> SEQUENCE: 63
cagtggggtc tgcacagacc c     21

<210> SEQ ID NO 64
<211> LENGTH: 21
<212> TYPE: DNA
<213> ORGANISM: Artificial Sequence
<220> FEATURE:
<223> OTHER INFORMATION: primer

<400> SEQUENCE: 64
gggtctgtgc agaccccact g     21

<210> SEQ ID NO 65
<211> LENGTH: 27
<212> TYPE: DNA
<213> ORGANISM: Artificial Sequence
<220> FEATURE:
<223> OTHER INFORMATION: primer

<400> SEQUENCE: 65
ccgaggtcgc ttgttttgag ccatcag     27

<210> SEQ ID NO 66
<211> LENGTH: 27
<212> TYPE: DNA
<213> ORGANISM: Artificial Sequence
<220> FEATURE:
<223> OTHER INFORMATION: primer

<400> SEQUENCE: 66
ctgatggctc aaaacaagcg acctcgg     27

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
ggtcgctgtg tgtgagccat caga     24

```
<210> SEQ ID NO 68
<211> LENGTH: 24
<212> TYPE: DNA
<213> ORGANISM: Artificial Sequence
<220> FEATURE:
<223> OTHER INFORMATION: primer

<400> SEQUENCE: 68
tctgatggct cacacacagc gacc                                           24

<210> SEQ ID NO 69
<211> LENGTH: 27
<212> TYPE: DNA
<213> ORGANISM: Artificial Sequence
<220> FEATURE:
<223> OTHER INFORMATION: primer

<400> SEQUENCE: 69
gtgtttgagc catgtgaagc agagatc                                        27

<210> SEQ ID NO 70
<211> LENGTH: 27
<212> TYPE: DNA
<213> ORGANISM: Artificial Sequence
<220> FEATURE:
<223> OTHER INFORMATION: primer

<400> SEQUENCE: 70
gatctctgct tcacatggct caaacac                                        27

<210> SEQ ID NO 71
<211> LENGTH: 27
<212> TYPE: DNA
<213> ORGANISM: Artificial Sequence
<220> FEATURE:
<223> OTHER INFORMATION: primer

<400> SEQUENCE: 71
gaggtgcaca gttgtgtcag cacagac                                        27

<210> SEQ ID NO 72
<211> LENGTH: 27
<212> TYPE: DNA
<213> ORGANISM: Artificial Sequence
<220> FEATURE:
<223> OTHER INFORMATION: primer

<400> SEQUENCE: 72
gtctgtgctg acacaactgt gcacctc                                        27

<210> SEQ ID NO 73
<211> LENGTH: 23
<212> TYPE: DNA
<213> ORGANISM: Artificial Sequence
<220> FEATURE:
<223> OTHER INFORMATION: primer

<400> SEQUENCE: 73
gggtcagcac atgcccgcag ccc                                            23

<210> SEQ ID NO 74
<211> LENGTH: 23
<212> TYPE: DNA
<213> ORGANISM: Artificial Sequence
<220> FEATURE:
<223> OTHER INFORMATION: primer
```

```
<400> SEQUENCE: 74
gggctgcggg catgtgctga ccc                                         23

<210> SEQ ID NO 75
<211> LENGTH: 23
<212> TYPE: DNA
<213> ORGANISM: Artificial Sequence
<220> FEATURE:
<223> OTHER INFORMATION: primer

<400> SEQUENCE: 75
cccgcagccc tgcaaggagc agc                                         23

<210> SEQ ID NO 76
<211> LENGTH: 23
<212> TYPE: DNA
<213> ORGANISM: Artificial Sequence
<220> FEATURE:
<223> OTHER INFORMATION: primer

<400> SEQUENCE: 76
gctgctcctt gcagggctgc ggg                                         23

<210> SEQ ID NO 77
<211> LENGTH: 23
<212> TYPE: DNA
<213> ORGANISM: Artificial Sequence
<220> FEATURE:
<223> OTHER INFORMATION: primer

<400> SEQUENCE: 77
agatacgctc tgtgcagccg cct                                         23

<210> SEQ ID NO 78
<211> LENGTH: 23
<212> TYPE: DNA
<213> ORGANISM: Artificial Sequence
<220> FEATURE:
<223> OTHER INFORMATION: primer

<400> SEQUENCE: 78
aggcggctgc acagagcgta tct                                         23

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
ctctgagcag ctgcctgagg gtc                                         23

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
gaccctcagg cagctgctca gag                                         23

<210> SEQ ID NO 81
<211> LENGTH: 21
```

<212> TYPE: DNA
<213> ORGANISM: Artificial Sequence
<220> FEATURE:
<223> OTHER INFORMATION: primer

<400> SEQUENCE: 81
gctgtgtttt gtccatcaga a                                    21

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
ttctgatgga caaaacacag c                                    21

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
ggagatatac atatgggtgt cactcagaac                           30

<210> SEQ ID NO 84
<211> LENGTH: 59
<212> TYPE: DNA
<213> ORGANISM: Artificial Sequence
<220> FEATURE:
<223> OTHER INFORMATION: primer

<400> SEQUENCE: 84
ccaccggatc cgtctgctct accccaggcg gagatataca tatgaacgct ggtgtcact    59

<210> SEQ ID NO 85
<211> LENGTH: 28
<212> TYPE: DNA
<213> ORGANISM: Artificial Sequence
<220> FEATURE:
<223> OTHER INFORMATION: primer

<400> SEQUENCE: 85
ccttgttcag gtcctctgtg accgtgag                             28

<210> SEQ ID NO 86
<211> LENGTH: 28
<212> TYPE: DNA
<213> ORGANISM: Artificial Sequence
<220> FEATURE:
<223> OTHER INFORMATION: primer

<400> SEQUENCE: 86
ctcacggtca cagaggacct gaacaagg                             28

<210> SEQ ID NO 87
<211> LENGTH: 34
<212> TYPE: DNA
<213> ORGANISM: Artificial Sequence
<220> FEATURE:
<223> OTHER INFORMATION: primer

<400> SEQUENCE: 87

-continued

```
cccaagctta gtctgctcta ccccaggcct cggc                                    34

<210> SEQ ID NO 88
<211> LENGTH: 27
<212> TYPE: DNA
<213> ORGANISM: Artificial Sequence
<220> FEATURE:
<223> OTHER INFORMATION: primer

<400> SEQUENCE: 88
tgactccaga tactgtctga gcagccg                                            27

<210> SEQ ID NO 89
<211> LENGTH: 27
<212> TYPE: DNA
<213> ORGANISM: Artificial Sequence
<220> FEATURE:
<223> OTHER INFORMATION: primer

<400> SEQUENCE: 89
cggctgctca gacagtatct ggagtca                                            27

<210> SEQ ID NO 90
<211> LENGTH: 27
<212> TYPE: DNA
<213> ORGANISM: Artificial Sequence
<220> FEATURE:
<223> OTHER INFORMATION: primer

<400> SEQUENCE: 90
tgactccaga tactctctga gcagccg                                            27

<210> SEQ ID NO 91
<211> LENGTH: 27
<212> TYPE: DNA
<213> ORGANISM: Artificial Sequence
<220> FEATURE:
<223> OTHER INFORMATION: primer

<400> SEQUENCE: 91
cggctgctca gagagtatct ggagtca                                            27

<210> SEQ ID NO 92
<211> LENGTH: 32
<212> TYPE: DNA
<213> ORGANISM: Artificial Sequence
<220> FEATURE:
<223> OTHER INFORMATION: primer

<400> SEQUENCE: 92
tctgaattca tgagatttcc ttcaattttt ac                                      32

<210> SEQ ID NO 93
<211> LENGTH: 31
<212> TYPE: DNA
<213> ORGANISM: Artificial Sequence
<220> FEATURE:
<223> OTHER INFORMATION: primer

<400> SEQUENCE: 93
tcacctcctg ggcttcagcc tctcttttat c                                       31

<210> SEQ ID NO 94
<211> LENGTH: 32
<212> TYPE: DNA
<213> ORGANISM: Artificial Sequence
```

-continued

```
<220> FEATURE:
<223> OTHER INFORMATION: primer

<400> SEQUENCE: 94
tctgaattca tgagatttcc ttcaattttt ac                                    32

<210> SEQ ID NO 95
<211> LENGTH: 31
<212> TYPE: DNA
<213> ORGANISM: Artificial Sequence
<220> FEATURE:
<223> OTHER INFORMATION: primer

<400> SEQUENCE: 95
gtgtctcgag ttagtctgct ctaccccagg c                                     31

<210> SEQ ID NO 96
<211> LENGTH: 30
<212> TYPE: DNA
<213> ORGANISM: Artificial Sequence
<220> FEATURE:
<223> OTHER INFORMATION: primer

<400> SEQUENCE: 96
ggctgaagcc caggaggtga cacagattcc                                       30

<210> SEQ ID NO 97
<211> LENGTH: 32
<212> TYPE: DNA
<213> ORGANISM: Artificial Sequence
<220> FEATURE:
<223> OTHER INFORMATION: primer

<400> SEQUENCE: 97
ctcctctcga gttaggaact ttctgggctg gg                                    32

<210> SEQ ID NO 98
<211> LENGTH: 32
<212> TYPE: DNA
<213> ORGANISM: Artificial Sequence
<220> FEATURE:
<223> OTHER INFORMATION: primer

<400> SEQUENCE: 98
ggctgaagcc ggcgtcactc agaccccaaa at                                    32

<210> SEQ ID NO 99
<211> LENGTH: 31
<212> TYPE: DNA
<213> ORGANISM: Artificial Sequence
<220> FEATURE:
<223> OTHER INFORMATION: primer

<400> SEQUENCE: 99
gtgtctcgag ttagtctgct ctaccccagg c                                     31

<210> SEQ ID NO 100
<211> LENGTH: 40
<212> TYPE: DNA
<213> ORGANISM: Artificial Sequence
<220> FEATURE:
<223> OTHER INFORMATION: primer

<400> SEQUENCE: 100
gtagtccgga gacaccggac agaaggaagt ggagcagaac                            40
```

```
<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 101
gtaggtcgac taggaacttt ctgggctggg                                    30

<210> SEQ ID NO 102
<211> LENGTH: 38
<212> TYPE: DNA
<213> ORGANISM: Artificial Sequence
<220> FEATURE:
<223> OTHER INFORMATION: primer

<400> SEQUENCE: 102
gtagtccgga gacaccggaa acgctggtgt cactcaga                            38

<210> SEQ ID NO 103
<211> LENGTH: 29
<212> TYPE: DNA
<213> ORGANISM: Artificial Sequence
<220> FEATURE:
<223> OTHER INFORMATION: primer

<400> SEQUENCE: 103
gtaggtcgac tagtctgctc taccccagg                                     29

<210> SEQ ID NO 104
<211> LENGTH: 21
<212> TYPE: DNA
<213> ORGANISM: Artificial Sequence
<220> FEATURE:
<223> OTHER INFORMATION: primer

<400> SEQUENCE: 104
gaaattatgc atttgaggat g                                             21

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
attaggcctc tagagatccg                                               20

<210> SEQ ID NO 106
<211> LENGTH: 9
<212> TYPE: PRT
<213> ORGANISM: Artificial Sequence
<220> FEATURE:
<223> OTHER INFORMATION: HLA-A2 NYESO peptide

<400> SEQUENCE: 106

Ser Leu Leu Met Trp Ile Thr Gln Cys
1               5

<210> SEQ ID NO 107
<211> LENGTH: 621
<212> TYPE: DNA
<213> ORGANISM: Homo sapiens
```

<400> SEQUENCE: 107

```
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagc tgagagactc taaatccagt gacaagtctg tctgcctatt caccgatttt     420
gattctcaaa caaatgtgtc acaaagtaag gattctgatg tgtatatcac agacaaatgt     480
gtgctagaca tgaggtctat ggacttcaag agcaacagtg ctgtggcctg agcaacaaa      540
tctgactttg catgtgcaaa cgccttcaac aacagcatta ttccagaaga caccttcttc     600
cccagcccag aaagttccta a                                                621
```

<210> SEQ ID NO 108
<211> LENGTH: 741
<212> TYPE: DNA
<213> ORGANISM: Homo sapiens

<400> SEQUENCE: 108

```
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtctgca cagacccgca gcccctcaag     540
gagcagcccg ccctcaatga ctccagatac gctctgagca gccgcctgag ggtctcggcc     600
accttctggc aggaccccg caaccacttc cgctgtcaag tccagttcta cgggctctcg     660
gagaatgacg agtggaccca ggatagggcc aaacccgtca cccagatcgt cagcgccgag     720
gcctggggta gagcagacta a                                                741
```

<210> SEQ ID NO 109
<211> LENGTH: 245
<212> TYPE: PRT
<213> ORGANISM: Homo sapiens

<400> SEQUENCE: 109

```
Asn Ala Gly Val Thr Gln Thr Pro Lys Phe Gln Val Leu Lys Thr Gly
 1               5                  10                  15
Gln Ser Met Thr Leu Gln Cys Ala Gln Asp Met Asn His Glu Tyr Met
             20                  25                  30
Ser Trp Tyr Arg Gln Asp Pro Gly Met Gly Leu Arg Leu Ile His Tyr
         35                  40                  45
Ser Val Gly Ala Gly Ile Thr Asp Gln Gly Glu Val Pro Asn Gly Tyr
     50                  55                  60
Asn Val Ser Arg Ser Thr Thr Glu Asp Phe Pro Leu Arg Leu Leu Ser
```

```
                65                  70                  75                  80
Ala Ala Pro Ser Gln Thr Ser Val Tyr Phe Cys Ala Ser Arg Pro Gly
                    85                  90                  95

Leu Ala Gly Gly Arg Pro Glu Gln Tyr Phe Gly Pro Gly Thr Arg Leu
                100                 105                 110

Thr Val Thr Glu Asp Leu Lys Asn Val Phe Pro Pro Glu Val Ala Val
                115                 120                 125

Phe Glu Pro Ser Glu Ala Glu Ile Ser His Thr Gln Lys Ala Thr Leu
            130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
                180                 185                 190

Ser Arg Leu Arg Val Ser Ala Thr Phe Trp Gln Asp Pro Arg Asn His
                195                 200                 205

Phe Arg Cys Gln Val Gln Phe Tyr Gly Leu Ser Glu Asn Asp Glu Trp
            210                 215                 220

Thr Gln Asp Arg Ala Lys Pro Val Thr Gln Ile Val Ser Ala Glu Ala
225                 230                 235                 240

Trp Gly Arg Ala Asp
                245
```

<210> SEQ ID NO 110
<211> LENGTH: 621
<212> TYPE: DNA
<213> ORGANISM: Homo sapiens

<400> SEQUENCE: 110

| | | | | | |
|---|---|---|---|---|---|
| atgcagaagg | aagtggagca | gaactctgga | cccctcagtg | ttccagaggg | agccattgcc | 60 |
| tctctcaact | gcacttacag | tgaccgaggt | tcccagtcct | tcttctggta | cagacaatat | 120 |
| tctgggaaaa | gccctgagtt | gataatgtcc | atatactcca | atggtgacaa | agaagatgga | 180 |
| aggtttacag | cacagctcaa | taaagccagc | cagtatgttt | ctctgctcat | cagagactcc | 240 |
| cagcccagtg | attcagccac | ctacctctgt | gccgttacaa | ctgacagctg | ggggaaattg | 300 |
| cagtttggag | cagggaccca | ggttgtggtc | accccagata | tccagaaccc | ggatcctgcc | 360 |
| gtgtaccagc | tgagagactc | taaatccagt | gacaagtctg | tctgcctatt | caccgatttt | 420 |
| gattctcaaa | caaatgtgtc | acaaagtaag | gattctgatg | tgtatatcac | agacaaatgt | 480 |
| gtgctagaca | tgaggtctat | ggacttcaag | agcaacagtg | ctgtggcctg | agcaacaaa | 540 |
| tctgactttg | catgtgcaaa | cgccttcaac | aacagcatta | ttccagaaga | caccttcttc | 600 |
| cccagcccag | aaagttccta | a | | | | 621 |

<210> SEQ ID NO 111
<211> LENGTH: 615
<212> TYPE: DNA
<213> ORGANISM: Homo sapiens

<400> SEQUENCE: 111

| | | | | | |
|---|---|---|---|---|---|
| atgcaactac | tagaacaaag | tcctcagttt | ctaagcatcc | aagagggaga | aaatctcact | 60 |
| gtgtactgca | actcctcaag | tgttttttcc | agcttacaat | ggtacagaca | ggagcctggg | 120 |
| gaaggtcctg | tcctcctggt | gacagtagtt | acgggtggag | aagtgaagaa | gctgaagaga | 180 |

```
ctaacctttc agtttggtga tgcaagaaag gacagttctc tccacatcac tgcggcccag    240
cctggtgata caggcctcta cctctgtgca ggagcgggaa gccaaggaaa tctcatcttt    300
ggaaaaggca ctaaactctc tgttaaacca aatatccaga acccggatcc tgccgtgtac    360
cagctgagag actctaaatc cagtgacaag tctgtctgcc tattccacga ttttgattct    420
caaacaaatg tgtcacaaag taaggattct gatgtgtata tcacagacaa atgtgtgcta    480
gacatgaggt ctatggactt caagagcaac agtgctgtgg cctggagcaa caaatctgac    540
tttgcatgtg caaacgcctt caacaacagc attattccag aagacacctt cttccccagc    600
ccagaaagtt cctaa                                                     615

<210> SEQ ID NO 112
<211> LENGTH: 735
<212> TYPE: DNA
<213> ORGANISM: Homo sapiens

<400> SEQUENCE: 112
atggtggatg gtggaatcac tcagtcccca agtacctgt tcagaaagga aggacagaat    60
gtgaccctga gttgtgaaca gaatttgaac cacgatgcca tgtactggta ccgacaggac    120
ccagggcaag ggctgagatt gatctactac tcacagatag taaatgactt tcagaaagga    180
gatatagctg aagggtacag cgtctctcgg gagaagaagg aatcctttcc tctcactgtg    240
acatcggccc aaaagaaccc gacagctttc tatctctgtg ccagtagttc gaggagctcc    300
tacgagcagt acttcgggcc gggcaccagg ctcacggtca cagaggacct gaaaaacgtg    360
ttcccacccg aggtcgctgt gtttgagcca tcagaagcag agatctccca cacccaaaag    420
gccacactgg tgtgcctggc cacaggcttc taccccgacc acgtggagct gagctggtgg    480
gtgaatggga aggaggtgca cagtggggtc tgcacagacc cgcagcccct caaggagcag    540
cccgccctca tgactccaga atacagcctg agcagccgcc tgagggtctc ggccaccttc    600
tggcagaacc cccgcaacca cttccgctgt caagtccagt tctacgggct ctcggagaat    660
gacgagtgga cccaggatag ggccaaacct gtcacccaga ttgtcagcgc cgaggcctgg    720
ggtagagcag actaa                                                     735

<210> SEQ ID NO 113
<211> LENGTH: 204
<212> TYPE: PRT
<213> ORGANISM: Homo sapiens

<400> SEQUENCE: 113

Met Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
        50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ala Gly Ser Gln Gly
                85                  90                  95

Asn Leu Ile Phe Gly Lys Gly Thr Lys Leu Ser Val Lys Pro Asn Ile
                100                 105                 110
```

Gln Asn Pro Asp Pro Ala Val Tyr Gln Leu Arg Asp Ser Lys Ser Ser
            115                 120                 125

Asp Lys Ser Val Cys Leu Phe Thr Asp Phe Asp Ser Gln Thr Asn Val
130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 114
<211> LENGTH: 244
<212> TYPE: PRT
<213> ORGANISM: Homo sapiens

<400> SEQUENCE: 114

Met Val Asp Gly Gly Ile Thr Gln Ser Pro Lys Tyr Leu Phe Arg Lys
1               5                   10                  15

Glu Gly Gln Asn Val Thr Leu Ser Cys Glu Gln Asn Leu Asn His Asp
            20                  25                  30

Ala Met Tyr Trp Tyr Arg Gln Asp Pro Gly Gln Gly Leu Arg Leu Ile
        35                  40                  45

Tyr Tyr Ser Gln Ile Val Asn Asp Phe Gln Lys Gly Asp Ile Ala Glu
    50                  55                  60

Gly Tyr Ser Val Ser Arg Glu Lys Lys Glu Ser Phe Pro Leu Thr Val
65                  70                  75                  80

Thr Ser Ala Gln Lys Asn Pro Thr Ala Phe Tyr Leu Cys Ala Ser Ser
                85                  90                  95

Ser Arg Ser Ser Tyr Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ser Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 115
<211> LENGTH: 627
<212> TYPE: DNA
<213> ORGANISM: Homo sapiens

<400> SEQUENCE: 115

```
atgcaggagg ygacacagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca aacaagtgga     180
agacttaatg cctcgctgga taaatcatca ggacgtagta ctttatacat tgcagcttct     240
cagcctggtg actcagccac ctacctctgt gctgtgaggc ccacatcagg aggaagctac     300
atacctacat ttggaagagg aaccagcctt attgttcatc cgtatatcca gaaccctgac     360
cctgccgtgt accagctgag agactctaaa tccagtgaca gtctgtctg cctattcacc      420
gattttgatt ctcaaacaaa tgtgtcacaa gtaaggatt ctgatgtgta tcacagac        480
aaatgtgtgc tagacatgag gtctatggac ttcaagagca cagtgctgt ggcctggagc      540
aacaaatctg actttgcatg tgcaaacgcc ttcaacaaca gcattattcc agaagacacc     600
ttcttcccca gcccagaaag ttcctaa                                         627
```

<210> SEQ ID NO 116
<211> LENGTH: 729
<212> TYPE: DNA
<213> ORGANISM: Homo sapiens

<400> SEQUENCE: 116

```
atgggtgtca ctcagacccc aaaattccag gtcctgaaga caggacagag catgacactg      60
cagtgtgccc aggatatgaa ccatgaatac atgtcctggt atcgacaaga cccaggcatg     120
gggctgaggc tgattcatta ctcagttggt gctggtatca ctgaccaagg agaagtcccc     180
aatggctaca atgtctccag atcaaccaca gaggatttcc cgctcaggct gctgtcggct     240
gctccctccc agacatctgt gtacttctgt gccagcagtt acgtcgggaa caccggggag     300
ctgttttttg gagaaggctc taggctgacc gtactggagg acctgaaaaa cgtgttccca     360
cccgaggtcg ctgtgtttga gccatcagaa gcagagatct cccacaccca aaaggccaca     420
ctggtgtgcc tggccacagg cttctacccc gaccacgtgg agctgagctg gtgggtgaat     480
gggaaggagg tgcacagtgg ggtctgcaca gacccgcagc ccctcaagga gcagcccgcc     540
ctcaatgact ccagatacgc tctgagcagc cgcctgaggg tctcggccac cttctggcag     600
gaccccgca accacttccg ctgtcaagtc cagttctacg gctctcggga atgacgag        660
tggacccagg atagggccaa acccgtcacc cagatcgtca cgccgaggc ctggggtaga      720
gcagactaa                                                             729
```

<210> SEQ ID NO 117
<211> LENGTH: 208
<212> TYPE: PRT
<213> ORGANISM: Homo sapiens
<220> FEATURE:
<221> NAME/KEY: misc_feature
<222> LOCATION: (4)..(4)
<223> OTHER INFORMATION: X is any amino acid

<400> SEQUENCE: 117

```
Met Gln Glu Xaa Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45
```

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 118
<211> LENGTH: 244
<212> TYPE: PRT
<213> ORGANISM: Homo sapiens

<400> SEQUENCE: 118

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Glu Thr Gly Leu Arg Leu Ile His
            35                  40                  45

Tyr Ser Val Gly Ala Gly Ile Thr Asp Gln Gly Glu Val Pro Asn Gly
        50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Ser Tyr
                85                  90                  95

Val Gly Asn Thr Gly Glu Leu Phe Phe Gly Gly Gly Ser Arg Leu Thr
            100                 105                 110

Val Leu Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 119
<211> LENGTH: 630
<212> TYPE: DNA
<213> ORGANISM: Homo sapiens

<400> SEQUENCE: 119

| | | | | | |
|---|---|---|---|---|---|
| atgcaggagg | ygacacagat | tcctgcagct | ctgagtgtcc | cagaaggaga | aaacttggtt | 60 |
| ctcaactgca | gtttcactga | tagcgctatt | tacaacctcc | agtggtttag | gcaggaccct | 120 |
| gggaaaggtc | tcacatctct | gttgcttatt | cagtcaagtc | agagagagca | aacaagtgga | 180 |
| agacttaatg | cctcgctgga | taaatcatca | ggacgtagta | ctttatacat | tgcagcttct | 240 |
| cagcctggtg | actcagccac | ctacctctgt | gctgtgaggc | ccacatcagg | aggaagctac | 300 |
| atacctacat | ttggaagagg | aaccagcctt | attgttcatc | cgtatatcca | gaaccctgac | 360 |
| cctgccgtgt | accagctgag | agactctaaa | tccagtgaca | gtctgtctg | cctattcacc | 420 |
| gattttgatt | ctcaaacaaa | tgtgtcacaa | gtaaggatt | ctgatgtgta | tatcacagac | 480 |
| aaatgtgtgc | tagacatgag | gtctatggac | ttcaagagca | cagtgctgt | ggcctggagc | 540 |
| aacaaatctg | actttgcatg | tgcaaacgcc | ttcaacaaca | gcattattcc | agaagacacc | 600 |
| ttcttcccca | gcccagaaag | ttcctgttaa | | | | 630 |

<210> SEQ ID NO 120
<211> LENGTH: 732
<212> TYPE: DNA
<213> ORGANISM: Homo sapiens

<400> SEQUENCE: 120

| | | | | | |
|---|---|---|---|---|---|
| atgggtgtca | ctcagacccc | aaaattccag | gtcctgaaga | caggacagag | catgacactg | 60 |
| cagtgtgccc | aggatatgaa | ccatgaatac | atgtcctggt | atcgacaaga | cccaggcatg | 120 |
| gggctgaggc | tgattcatta | ctcagttggt | gctggtatca | ctgaccaagg | agaagtcccc | 180 |
| aatggctaca | atgtctccag | atcaaccaca | gaggatttcc | cgctcaggct | gctgtcggct | 240 |
| gctccctccc | agacatctgt | gtacttctgt | gccagcagtt | acgtcgggaa | caccggggag | 300 |
| ctgtttttg | gagaaggctc | taggctgacc | gtactggagg | acctgaaaaa | cgtgttccca | 360 |
| cccgaggtcg | ctgtgtttga | gccatcagaa | gcagagatct | cccacaccca | aaaggccaca | 420 |
| ctggtgtgcc | tggccacagg | cttctacccc | gaccacgtgg | agctgagctg | gtgggtgaat | 480 |
| gggaaggagg | tgcacagtgg | ggtctgcaca | gacccgcagc | ccctcaagga | gcagcccgcc | 540 |
| ctcaatgact | ccagatacgc | tctgagcagc | cgcctgaggg | tctcggccac | cttctggcag | 600 |
| gaccccgca | accacttccg | ctgtcaagtc | cagttctacg | gctctcggga | gaatgacgag | 660 |
| tggacccagg | atagggccaa | acccgtcacc | cagatcgtca | gcgccgaggc | ctggggtaga | 720 |
| gcagactgtt | aa | | | | | 732 |

<210> SEQ ID NO 121
<211> LENGTH: 209
<212> TYPE: PRT
<213> ORGANISM: Homo sapiens
<220> FEATURE:
<221> NAME/KEY: misc_feature
<222> LOCATION: (4)..(4)
<223> OTHER INFORMATION: X is any amino acid

<400> SEQUENCE: 121

Met Gln Glu Xaa Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Cys

<210> SEQ ID NO 122
<211> LENGTH: 243
<212> TYPE: PRT
<213> ORGANISM: Homo sapiens

<400> SEQUENCE: 122

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

```
Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
            165                 170                 175

Glu Gln Pro Ala Leu Asn Asp Ser Arg Tyr Ala Leu Ser Arg Leu
        180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp Cys

<210> SEQ ID NO 123
<211> LENGTH: 624
<212> TYPE: DNA
<213> ORGANISM: Homo sapiens

<400> SEQUENCE: 123
atgaaggagg tggagcagaa ttctggaccc tcagtgttc cagagggagc cattgcctct      60
ctcaactgca cttacagtga ccgaggttcc cagtccttct tctggtacag acaatattct    120
gggaaaagcc ctgagttgat aatgttcata tactccaatg gtgacaaaga agatggaagg    180
tttacagcac agctcaataa agccagccag tatgtttctc tgctcatcag agactcccag    240
cccagtgatt cagccaccta cctctgtgcc gtgaagggg ggtctggggg ttaccagaaa     300 gttaccctttg gaactggaac aaagctccaa gtcatcccaa atatccagaa cccggatcct   360
gccgtgtacc agctgagaga ctctaaatcc agtgacaagt ctgtctgcct attcaccgat    420
tttgattctc aaacaaatgt gtcacaaagt aaggattctg atgtgtatat cacagacaaa    480
tgtgtgctag acatgaggtc tatggacttc aagagcaaca gtgctgtggc ctggagcaac    540
aaatctgact ttgcatgtgc aaacgccttc aacaacagca ttattccaga agacaccttc    600
ttccccagcc cagaaagttc ctaa                                           624

<210> SEQ ID NO 124
<211> LENGTH: 735
<212> TYPE: DNA
<213> ORGANISM: Homo sapiens

<400> SEQUENCE: 124
atgggcgtca tgcagaaccc aagacacctg gtcaggagga ggggacagga ggcaagactg     60
agatgcagcc aatgaaaagg acacagtcat gtttactggt atcggcagct cccagaggaa    120
ggtctgaaat tcatggttta ctccagaaa gaaaatatca tagatgagtc aggaatgcca     180
aaggaacgat tttctgctga atttcccaaa gagggcccca gcatcctgag gatccagcag    240
gtagtgcgag agattcggc agcttatttc tgtgccagct caccacagac agggggcaca    300
gatacgcagt attttggccc aggcacccgg ctgacagtgc tcgaggacct gaaaaacgtg    360
ttcccacccg aggtcgctgt gtttgagcca tcagaagcag agatctccca cacccaaaag    420
gccacactgg tgtgcctggc acaggcttac ccccgacc acgtgagct gagctggtgg      480 gtgaatggga aggaggtgca cagtggggtc tgcacagacc cgcagcccct caaggagcag    540
cccgccctca tgactccag atacgctctg agcagccgcc tgggtctc ggccaccttc      600 tggcaggacc ccgcaacca cttccgctgt caagtccagt tctacgggct ctcggagaat    660
```

```
gacgagtgga cccaggatag ggccaaaccc gtcacccaga tcgtcagcgc cgaggcctgg    720
ggtagagcag actaa                                                    735
```

<210> SEQ ID NO 125
<211> LENGTH: 207
<212> TYPE: PRT
<213> ORGANISM: Homo sapiens

<400> SEQUENCE: 125

```
Met Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Lys Gly Gly Ser Gly
                85                  90                  95

Gly Tyr Gln Lys Val Thr Phe Gly Thr Gly Thr Lys Leu Gln Val Ile
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205
```

<210> SEQ ID NO 126
<211> LENGTH: 244
<212> TYPE: PRT
<213> ORGANISM: Homo sapiens

<400> SEQUENCE: 126

```
Met Gly Val Met Gln Asn Pro Arg His Leu Val Arg Arg Arg Gly Gln
1               5                   10                  15

Glu Ala Arg Leu Arg Cys Ser Pro Met Lys Gly His Ser His Val Tyr
            20                  25                  30

Trp Tyr Arg Gln Leu Pro Glu Glu Gly Leu Lys Phe Met Val Tyr Leu
        35                  40                  45

Gln Lys Glu Asn Ile Ile Asp Glu Ser Gly Met Pro Lys Glu Arg Phe
    50                  55                  60

Ser Ala Glu Phe Pro Lys Glu Gly Pro Ser Ile Leu Arg Ile Gln Gln
65                  70                  75                  80

Val Val Arg Gly Asp Ser Ala Ala Tyr Phe Cys Ala Ser Ser Pro Gln
                85                  90                  95

Thr Gly Gly Thr Asp Thr Gln Tyr Phe Gly Pro Gly Thr Arg Leu Thr
```

-continued

```
                100             105             110
Val Leu Glu Asp Leu Lys Asn Val Phe Pro Glu Val Ala Val Phe
            115                 120                 125

Gln Pro Ser Glu Ala Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
210                 215                 220

Gln Asp Arg Ala Lys Pro Val Thr Gln Ile Val Ser Ala Glu Ala Trp
225                 230                 235                 240

Gly Arg Ala Asp
```

<210> SEQ ID NO 127
<211> LENGTH: 621
<212> TYPE: DNA
<213> ORGANISM: Homo sapiens

<400> SEQUENCE: 127

```
atgcagaagg aagtggagca gaactctgga cccctcagtg ttccagaggg agccattgcc    60
tctctcaact gcacttacag tgaccgaggt tcccagtcct tcttctggta cagacaatat   120
tctgggaaaa gccctgagtt gataatgtcc atatactcca atggtgacaa agaagatgga   180
aggtttacag cacagctcaa taaagccagc cagtatgttt ctctgctcat cagagactcc   240
cagcccagtg attcagccac ctacctctgt gccgttacaa ctgacagctg ggggaaattg   300
cagtttggag cagggaccca ggttgtggtc accccagata tccagaaccc tgaccctgcc   360
gtgtaccagc tgagagactc taaatccagt gacaagtctg tctgcctatt caccgatttt   420
gattctcaaa caaatgtgtc acaaagtaag gattctgatg tgtatatcac agacaaatgt   480
gtgctagaca tgaggtctat ggacttcaag agcaacagtg ctgtggcctg agcaacaaa   540
tctgactttg catgtgcaaa cgccttcaac aacagcatta ttccagaaga caccttcttc   600
cccagcccag aaagttccta a                                              621
```

<210> SEQ ID NO 128
<211> LENGTH: 206
<212> TYPE: PRT
<213> ORGANISM: Homo sapiens

<400> SEQUENCE: 128

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
```

```
                65                  70                  75                  80
Gln Pro Ser Asp Ser Ala Thr Tyr Leu Cys Ala Val Thr Asp Ser
                    85                  90                  95

Trp Gly Lys Leu Gln Phe Gly Ala Gly Thr Gln Val Val Thr Pro
                100                 105                 110

Asp Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
                180                 185                 190

Ile Ile Pro Glu Asp Thr Phe Phe Pro Ser Pro Glu Ser Ser
                195                 200                 205

<210> SEQ ID NO 129
<211> LENGTH: 621
<212> TYPE: DNA
<213> ORGANISM: Homo sapiens

<400> SEQUENCE: 129
atgcagaagg aagtggagca gaactctgga cccctcagtg ttccagaggg agccattgcc      60
tctctcaact gcacttacag tgaccgaggt tcccagtcct tcttctggta cagacaatat    120
tctgggaaaa gccctgagtt gataatgtcc atatactcca atggtgacaa agaagatgga    180
aggtttacag cacagctcaa taaagccagc cagtatgttt ctctgctcat cagagactcc    240
cagcccagtg attcagccac ctacctctgt gccgttacaa ctgacagctg ggggaaattg    300
cagtttggag cagggaccca ggttgtggtc accccagata tccagaaccc tgaccctgcc    360
gtgtaccagc tgagagactc taaatccagt gacaagtctg tctgcctatt caccgatttt    420
gattctcaaa caaatgtgtc acaaagtaag gattctgatg tgtatatctg tgacaaaact    480
gtgctagaca tgaggtctat ggacttcaag agcaacagtg ctgtggcctg agcaacaaa    540 tctgactttg catgtgcaaa cgccttcaac aacagcatta ttccagaaga caccttcttc    600
cccagcccag aaagttccta a                                             621

<210> SEQ ID NO 130
<211> LENGTH: 206
<212> TYPE: PRT
<213> ORGANISM: Homo sapiens

<400> SEQUENCE: 130

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80
```

```
Gln Pro Ser Asp Ser Ala Thr Tyr Leu Cys Ala Val Thr Asp Ser
            85                  90                  95

Trp Gly Lys Leu Gln Phe Gly Ala Gly Thr Gln Val Val Thr Pro
            100                 105                 110

Asp Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Cys Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
            195                 200                 205

<210> SEQ ID NO 131
<211> LENGTH: 621
<212> TYPE: DNA
<213> ORGANISM: Homo sapiens

<400> SEQUENCE: 131
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagc tgagagactc taaatccagt gacaagtctg tctgcctatt caccgatttt     420
gattctcaaa caaatgtgtc acaaagtaag gattctgatg tgtatatcac agacaaaact     480
gtgctagaca tgaggtctat ggacttcaag agcaactgtg ctgtggcctg agcaacaaa     540 tctgactttg catgtgcaaa cgccttcaac aacagcatta ttccagaaga caccttcttc     600
cccagcccag aaagttccta a                                                 621

<210> SEQ ID NO 132
<211> LENGTH: 206
<212> TYPE: PRT
<213> ORGANISM: Homo sapiens

<400> SEQUENCE: 132

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95
```

```
Trp Gly Lys Leu Gln Phe Gly Ala Gly Thr Gln Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Cys Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 133
<211> LENGTH: 621
<212> TYPE: DNA
<213> ORGANISM: Homo sapiens

<400> SEQUENCE: 133
atgcagaagg aagtggagca gaactctgga cccctcagtg ttccagaggg agccattgcc     60
tctctcaact gcacttacag tgaccgaggt tcccagtcct tcttctggta cagacaatat   120
tctgggaaaa gccctgagtt gataatgtcc atatactcca atggtgacaa agaagatgga   180
aggtttacag cacagctcaa taaagccagc cagtatgttt ctctgctcat cagagactcc   240
cagcccagtg attcagccac ctacctctgt gccgttacaa ctgacagctg ggggaaattg   300
cagtttggag cagggaccca ggttgtggtc accccagata tccagaaccc tgaccctgcc   360
gtgtaccagc tgagagactc taaatccagt gacaagtctg tctgcctatt caccgatttt   420
gattctcaaa caaatgtgtc acaaagtaag gattctgatg tgtatatcac agacaaaact   480
gtgtgtgaca tgaggtctat ggactttcaag agcaacagtg ctgtggcctg agcaacaaa   540 tctgactttg catgtgcaaa cgccttcaac aacagcatta ttccagaaga caccttcttc   600
cccagcccag aaagttccta a                                             621

<210> SEQ ID NO 134
<211> LENGTH: 206
<212> TYPE: PRT
<213> ORGANISM: Homo sapiens

<400> SEQUENCE: 134

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
```

```
                    100                 105                 110
Asp Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Cys Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 135
<211> LENGTH: 621
<212> TYPE: DNA
<213> ORGANISM: Homo sapiens

<400> SEQUENCE: 135
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc agtatgtttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtgccagc tgagagactc taaatccagt gacaagtctg tctgcctatt caccgatttt     420
gattctcaaa caaatgtgtc acaaagtaag gattctgatg tgtatatcac agacaaaact     480
gtgctagaca tgaggtctat ggacttcaag agcaacagtg ctgtggcctg agcaacaaa      540 tctgactttg catgtgcaaa cgccttcaac aacagcatta ttccagaaga cacttcttc      600 cccagcccag aaagttccta a                                               621

<210> SEQ ID NO 136
<211> LENGTH: 206
<212> TYPE: PRT
<213> ORGANISM: Homo sapiens

<400> SEQUENCE: 136

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110
```

```
Asp Ile Gln Asn Pro Asp Pro Ala Val Cys Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205
```

<210> SEQ ID NO 137
<211> LENGTH: 621
<212> TYPE: DNA
<213> ORGANISM: Homo sapiens

<400> SEQUENCE: 137

| | | |
|---|---|---|
| atgcagaagg aagtggagca gaactctgga cccctcagtg ttccagaggg agccattgcc | 60 |
| tctctcaact gcacttacag tgaccgaggt tcccagtcct tcttctggta cagacaatat | 120 |
| tctgggaaaa gccctgagtt gataatgtcc atatactcca atggtgacaa gaagatgga | 180 |
| aggtttacag cacagctcaa taaagccagc cagtatgttt ctctgctcat cagagactcc | 240 |
| cagcccagtg attcagccac ctacctctgt gccgttacaa ctgacagctg ggggaaattg | 300 |
| cagtttggag cagggaccca ggttgtggtc accccagata tccagaaccc tgaccctgcc | 360 |
| gtgtaccagc tgagagactg taaatccagt gacaagtctg tctgcctatt caccgatttt | 420 |
| gattctcaaa caaatgtgtc acaaagtaag gattctgatg tgtatatcac agacaaaact | 480 |
| gtgctagaca tgaggtctat ggacttcaag agcaacagtg ctgtggcctg agcaacaaa | 540 |
| tctgactttg catgtgcaaa cgccttcaac aacagcatta ttccagaaga caccttcttc | 600 |
| cccagcccag aaagttccta a | 621 |

<210> SEQ ID NO 138
<211> LENGTH: 206
<212> TYPE: PRT
<213> ORGANISM: Homo sapiens

<400> SEQUENCE: 138

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Cys Lys
        115                 120                 125
```

```
Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 139
<211> LENGTH: 621
<212> TYPE: DNA
<213> ORGANISM: Homo sapiens

<400> SEQUENCE: 139
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagt gcagagactc taaatccagt gacaagtctg tctgcctatt caccgatttt     420
gattctcaaa caaatgtgtc acaaagtaag gattctgatg tgtatatcac agacaaaact     480
gtgctagaca tgaggtctat ggacttcaag agcaacagtg ctgtggcctg gagcaacaaa     540
tctgactttg catgtgcaaa cgccttcaac aacagcatta ttccagaaga caccttcttc     600
cccagcccag aaagttccta a                                                621

<210> SEQ ID NO 140
<211> LENGTH: 206
<212> TYPE: PRT
<213> ORGANISM: Homo sapiens

<400> SEQUENCE: 140

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Cys Arg Asp Ser Lys
        115                 120                 125

Ser Ser Asp Lys Ser Val Cys Leu Phe Thr Asp Phe Asp Ser Gln Thr
```

```
              130                 135                 140
Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
            195                 200                 205

<210> SEQ ID NO 141
<211> LENGTH: 621
<212> TYPE: DNA
<213> ORGANISM: Homo sapiens

<400> SEQUENCE: 141
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagc tgagagactc taaatccagt gacaagtctt gctgcctatt caccgatttt     420
gattctcaaa caaatgtgtc acaaagtaag gattctgatg tgtatatcac agacaaaact     480
gtgctagaca tgaggtctat ggacttcaag agcaacagtg ctgtggcctg agcaacaaa      540 tctgactttg catgtgcaaa cgccttcaac aacagcatta ttccagaaga caccttcttc     600
cccagcccag aaagttccta a                                               621

<210> SEQ ID NO 142
<211> LENGTH: 206
<212> TYPE: PRT
<213> ORGANISM: Homo sapiens

<400> SEQUENCE: 142

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Cys Cys Leu Phe Thr Asp Phe Asp Ser Gln Thr
    130                 135                 140
```

```
Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 143
<211> LENGTH: 621
<212> TYPE: DNA
<213> ORGANISM: Homo sapiens

<400> SEQUENCE: 143
atgcagaagg aagtggagca gaactctgga cccctcagtg ttccagaggg agccattgcc    60
tctctcaact gcacttacag tgaccgaggt tcccagtcct tcttctggta cagacaatat   120
tctgggaaaa gccctgagtt gataatgtcc atatactcca atggtgacaa agaagatgga   180
aggtttacag cacagctcaa taagccagca cagtatgttt ctctgctcat cagagactcc   240
cagcccagtg attcagccac ctacctctgt gccgttacaa ctgacagctg ggggaaattg   300
cagtttggag cagggaccca ggttgtggtc accccagata tccagaaccc tgaccctgcc   360
gtgtaccagc tgagagactc taaatccagt gacaagtctg tctgcctatt caccgatttt   420
gattctcaaa caaatgtgtc acaaagtaag gattctgatg tgtatatcac agacaaaact   480
gtgctagact gtaggtctat ggacttcaag agcaacagtg ctgtggcctg agcaacaaa   540 tctgactttg catgtgcaaa cgccttcaac aacagcatta ttccagaaga caccttcttc   600
cccagcccag aaagttccta a                                             621

<210> SEQ ID NO 144
<211> LENGTH: 206
<212> TYPE: PRT
<213> ORGANISM: Homo sapiens

<400> SEQUENCE: 144

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160
```

Val Leu Asp Cys Arg Ser Met Asp Phe Lys Ser Asn Ser Ala Val Ala
            165                 170                 175

Trp Ser Asn Lys Ser Asp Phe Ala Cys Ala Asn Ala Phe Asn Asn Ser
        180                 185                 190

Ile Ile Pro Glu Asp Thr Phe Phe Pro Ser Pro Glu Ser Ser
        195                 200                 205

<210> SEQ ID NO 145
<211> LENGTH: 621
<212> TYPE: DNA
<213> ORGANISM: Homo sapiens

<400> SEQUENCE: 145

```
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagc tgagagactc taaatccagt gacaagtctg tctgcctatt caccgatttt     420
gattctcaaa caaatgtgtc acaaagtaag gattctgatg tgtgtatcac agacaaaact     480
gtgctagaca tgaggtctat ggacttcaag agcaacagtg ctgtggcctg gagcaacaaa     540
tctgactttg catgtgcaaa cgccttcaac aacagcatta ttccagaaga caccttcttc     600
cccagcccag aaagttccta a                                               621
```

<210> SEQ ID NO 146
<211> LENGTH: 206
<212> TYPE: PRT
<213> ORGANISM: Homo sapiens

<400> SEQUENCE: 146

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Cys Ile Thr Asp Lys Thr
145                 150                 155                 160

Val Leu Asp Met Arg Ser Met Asp Phe Lys Ser Asn Ser Ala Val Ala

```
                         165                 170                 175
Trp Ser Asn Lys Ser Asp Phe Ala Cys Ala Asn Ala Phe Asn Asn Ser
        180                 185                 190

Ile Ile Pro Glu Asp Thr Phe Phe Pro Ser Pro Glu Ser Ser
    195                 200                 205

<210> SEQ ID NO 147
<211> LENGTH: 741
<212> TYPE: DNA
<213> ORGANISM: Homo sapiens

<400> SEQUENCE: 147
atgaacgctg gtgtcactca gaccccaaaa ttccaggtcc tgaagacagg acagagcatg      60
acactgcagt gtgcccagga tatgaaccat gaatacatgt cctggtatcg acaagaccca     120 ggcatgggge tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtctgca cagacccgca gccccttcaag    540 gagcagcccg ccctcaatga ctccagatac gctctgagca gccgcctgag ggtctcggcc     600
accttctggc aggaccccg caaccacttc cgctgtcaag tccagttcta cgggctctcg      660
gagaatgacg agtggaccca ggatagggcc aaacccgtca cccagatcgt cagcgccgag     720
gcctggggta gagcagacta a                                              741

<210> SEQ ID NO 148
<211> LENGTH: 246
<212> TYPE: PRT
<213> ORGANISM: Homo sapiens

<400> SEQUENCE: 148

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160
```

```
Trp Trp Val Asn Gly Lys Glu Val His Ser Gly Val Cys Thr Asp Pro
                165                 170                 175
Gln Pro Leu Lys Glu Gln Pro Ala Leu Asn Asp Ser Arg Tyr Ala Leu
            180                 185                 190
Ser Ser Arg Leu Arg Val Ser Ala Thr Phe Trp Gln Asp Pro Arg Asn
        195                 200                 205
His Phe Arg Cys Gln Val Gln Phe Tyr Gly Leu Ser Glu Asn Asp Glu
    210                 215                 220
Trp Thr Gln Asp Arg Ala Lys Pro Val Thr Gln Ile Val Ser Ala Glu
225                 230                 235                 240
Ala Trp Gly Arg Ala Asp
                245

<210> SEQ ID NO 149
<211> LENGTH: 741
<212> TYPE: DNA
<213> ORGANISM: Homo sapiens

<400> SEQUENCE: 149
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtcagca cagacccgca gccccctcaag     540 gagcagcccg ccctcaatga ctccagatac gctctgtgta gccgcctgag ggtctcggcc     600
accttctggc aggaccccgc caaccacttc cgctgtcaag tccagttcta cgggctctcg     660
gagaatgacg agtggaccca ggataggcc aaacccgtca cccagatcgt cagcgccgag     720
gcctggggta gagcagacta a                                                741

<210> SEQ ID NO 150
<211> LENGTH: 246
<212> TYPE: PRT
<213> ORGANISM: Homo sapiens

<400> SEQUENCE: 150

Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Gly Ala Gly Ile Thr Asp Gln Gly Glu Val Pro Asn Gly
    50                  55                  60
Tyr Asn Val Ser Arg Ser Thr Thr Glu Asp Phe Pro Leu Arg Leu Leu
65                  70                  75                  80
Ser Ala Ala Pro Ser Gln Thr Ser Val Tyr Phe Cys Ala Ser Arg Pro
                85                  90                  95
```

```
Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Cys Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 151
<211> LENGTH: 741
<212> TYPE: DNA
<213> ORGANISM: Homo sapiens

<400> SEQUENCE: 151
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg ctacaatgt ctccagatca accacagagg atttcccgct caggctgctg      240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatgtg aagcagagat ctcccacacc     420
caaaaggcca cactggtgtg cctggccaca ggcttctacc ccgaccacgt ggagctgagc     480
tggtgggtga atgggaagga ggtgcacagt ggggtcagca cagacccgca gcccctcaag     540
gagcagcccg ccctcaatga ctccagatac gctctgagca gccgcctgag ggtctcggcc     600
accttctggc aggaccccg caaccacttc cgctgtcaag tccagttcta cgggctctcg     660
gagaatgacg agtggaccca ggatagggcc aaacccgtca cccagatcgt cagcgccgag     720
gcctggggta gagcagacta a                                               741

<210> SEQ ID NO 152
<211> LENGTH: 246
<212> TYPE: PRT
<213> ORGANISM: Homo sapiens

<400> SEQUENCE: 152

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
```

```
                 35                  40                  45
Tyr Ser Val Gly Ala Gly Ile Thr Asp Gln Gly Glu Val Pro Asn Gly
 50                  55                  60

Tyr Asn Val Ser Arg Ser Thr Thr Glu Asp Phe Pro Leu Arg Leu Leu
 65                  70                  75                  80

Ser Ala Ala Pro Ser Gln Thr Ser Val Tyr Phe Cys Ala Ser Arg Pro
                 85                  90                  95

Gly Leu Ala Gly Gly Arg Pro Glu Gln Tyr Phe Gly Pro Gly Thr Arg
                100                 105                 110

Leu Thr Val Thr Glu Asp Leu Lys Asn Val Phe Pro Pro Glu Val Ala
            115                 120                 125

Val Phe Glu Pro Cys Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 153
<211> LENGTH: 741
<212> TYPE: DNA
<213> ORGANISM: Homo sapiens

<400> SEQUENCE: 153
atgaacgctg gtgtcactca gacccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgcttgtttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtcagca cagacccgca gccccctcaag    540 gagcagcccg ccctcaatga ctccagatac gctctgagca gccgcctgag ggtctcggcc     600
accttctggc aggaccccg caaccacttc cgctgtcaag tccagttcta cgggctctcg      660
gagaatgacg agtggaccca ggatagggcc aaacccgtca cccagatcgt cagcgccgag     720
gcctggggta gagcagacta a                                               741

<210> SEQ ID NO 154
<211> LENGTH: 246
<212> TYPE: PRT
```

<213> ORGANISM: Homo sapiens

<400> SEQUENCE: 154

| | | | | | | | | | | | | | | | |
|---|---|---|---|---|---|---|---|---|---|---|---|---|---|---|---|
| Met | Asn | Ala | Gly | Val | Thr | Gln | Thr | Pro | Lys | Phe | Gln | Val | Leu | Lys | Thr |
| 1 | | | | 5 | | | | | 10 | | | | | 15 | |
| Gly | Gln | Ser | Met | Thr | Leu | Gln | Cys | Ala | Gln | Asp | Met | Asn | His | Glu | Tyr |
| | | | 20 | | | | | 25 | | | | | 30 | | |
| Met | Ser | Trp | Tyr | Arg | Gln | Asp | Pro | Gly | Met | Gly | Leu | Arg | Leu | Ile | His |
| | | | 35 | | | | 40 | | | | | 45 | | | |
| Tyr | Ser | Val | Gly | Ala | Gly | Ile | Thr | Asp | Gln | Gly | Glu | Val | Pro | Asn | Gly |
| | 50 | | | | | 55 | | | | | 60 | | | | |
| Tyr | Asn | Val | Ser | Arg | Ser | Thr | Thr | Glu | Asp | Phe | Pro | Leu | Arg | Leu | Leu |
| 65 | | | | | 70 | | | | | 75 | | | | | 80 |
| Ser | Ala | Ala | Pro | Ser | Gln | Thr | Ser | Val | Tyr | Phe | Cys | Ala | Ser | Arg | Pro |
| | | | | 85 | | | | | 90 | | | | | 95 | |
| Gly | Leu | Ala | Gly | Arg | Pro | Glu | Gln | Tyr | Phe | Gly | Pro | Gly | Thr | Arg | |
| | | | 100 | | | | | 105 | | | | | 110 | | |
| Leu | Thr | Val | Thr | Glu | Asp | Leu | Lys | Asn | Val | Phe | Pro | Pro | Glu | Val | Ala |
| | | | 115 | | | | | 120 | | | | | 125 | | |
| Cys | Phe | Glu | Pro | Ser | Glu | Ala | Glu | Ile | Ser | His | Thr | Gln | Lys | Ala | Thr |
| | 130 | | | | | 135 | | | | | 140 | | | | |
| Leu | Val | Cys | Leu | Ala | Thr | Gly | Phe | Tyr | Pro | Asp | His | Val | Glu | Leu | Ser |
| 145 | | | | | 150 | | | | | 155 | | | | | 160 |
| Trp | Trp | Val | Asn | Gly | Lys | Glu | Val | His | Ser | Gly | Val | Ser | Thr | Asp | Pro |
| | | | | 165 | | | | | 170 | | | | | 175 | |
| Gln | Pro | Leu | Lys | Glu | Gln | Pro | Ala | Leu | Asn | Asp | Ser | Arg | Tyr | Ala | Leu |
| | | | 180 | | | | | 185 | | | | | 190 | | |
| Ser | Ser | Arg | Leu | Arg | Val | Ser | Ala | Thr | Phe | Trp | Gln | Asp | Pro | Arg | Asn |
| | | | 195 | | | | | 200 | | | | | 205 | | |
| His | Phe | Arg | Cys | Gln | Val | Gln | Phe | Tyr | Gly | Leu | Ser | Glu | Asn | Asp | Glu |
| | 210 | | | | | 215 | | | | | 220 | | | | |
| Trp | Thr | Gln | Asp | Arg | Ala | Lys | Pro | Val | Thr | Gln | Ile | Val | Ser | Ala | Glu |
| 225 | | | | | 230 | | | | | 235 | | | | | 240 |
| Ala | Trp | Gly | Arg | Ala | Asp | | | | | | | | | | |
| | | | | 245 | | | | | | | | | | | |

<210> SEQ ID NO 155
<211> LENGTH: 741
<212> TYPE: DNA
<213> ORGANISM: Homo sapiens

<400> SEQUENCE: 155

| | | | | | |
|---|---|---|---|---|---|
| atgaacgctg | gtgtcactca | gaccccaaaa | ttccaggtcc | tgaagacagg | acagagcatg | 60 |
| acactgcagt | gtgcccagga | tatgaaccat | gaatacatgt | cctggtatcg | acaagaccca | 120 |
| ggcatggggc | tgaggctgat | tcattactca | gttggtgctg | gtatcactga | ccaaggagaa | 180 |
| gtccccaatg | gctacaatgt | ctccagatca | accacagagg | atttcccgct | caggctgctg | 240 |
| tcggctgctc | cctcccagac | atctgtgtac | ttctgtgcca | gcaggccggg | actagcggga | 300 |
| gggcgaccag | agcagtactt | cgggccgggc | accaggctca | cggtcacaga | ggacctgaaa | 360 |
| aacgtgttcc | cacccgaggt | cgctgtgttt | gagccatcag | aagcagagat | ctcccacacc | 420 |
| caaaaggcca | cactggtgtg | cctggccaca | ggcttctacc | ccgaccacgt | ggagctgagc | 480 |
| tggtgggtga | atgggaagga | ggtgcacagt | ggggtcagca | catgcccgca | gcccctcaag | 540 |
| gagcagcccg | ccctcaatga | ctccagatac | gctctgagca | gccgcctgag | ggtctcggcc | 600 |

```
accttctggc aggacccccg caaccacttc cgctgtcaag tccagttcta cgggctctcg    660
gagaatgacg agtggaccca ggatagggcc aaacccgtca cccagatcgt cagcgccgag    720
gcctggggta gagcagacta a                                              741
```

<210> SEQ ID NO 156
<211> LENGTH: 246
<212> TYPE: PRT
<213> ORGANISM: Homo sapiens

<400> SEQUENCE: 156

```
Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Cys Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
            245
```

<210> SEQ ID NO 157
<211> LENGTH: 741
<212> TYPE: DNA
<213> ORGANISM: Homo sapiens

<400> SEQUENCE: 157

```
atgaacgctg gtgtcactca gaccccaaaa ttccaggtcc tgaagacagg acagagcatg     60
acactgcagt gtgcccagga tatgaaccat gaatacatgt cctggtatcg acaagaccca    120
ggcatggggc tgaggctgat tcattactca gttggtgctg gtatcactga ccaaggagaa    180
gtccccaatg gctacaatgt ctccagatca accacagagg atttcccgct caggctgctg    240
```

```
tcggctgctc cctcccagac atctgtgtac ttctgtgcca gcaggccggg actagcggga    300
gggcgaccag agcagtactt cgggccgggc accaggctca cggtcacaga ggacctgaaa    360
aacgtgttcc cacccgaggt cgctgtgttt gagccatcag aagcagagat ctcccacacc    420
caaaaggcca cactggtgtg cctggccaca ggcttctacc ccgaccacgt ggagctgagc    480
tggtgggtga atgggaagga ggtgcacagt ggggtcagca cagacccgca gccctcaag    540 gagcagcccg ccctcaatga ctccagatac gctctgagca gctgcctgag ggtctcggcc    600
accttctggc aggacccccg caaccacttc cgctgtcaag tccagttcta cgggctctcg    660
gagaatgacg agtggaccca ggatagggcc aaacccgtca cccagatcgt cagcgccgag    720
gcctggggta gagcagacta a    741
```

```
<210> SEQ ID NO 158
<211> LENGTH: 246
<212> TYPE: PRT
<213> ORGANISM: Homo sapiens

<400> SEQUENCE: 158
```

```
Met Asn Ala Gly Val Thr Gln Thr Pro Lys Phe Gln Val Leu Lys Thr
  1               5                  10                  15

Gly Gln Ser Met Thr Leu Gln Cys Ala Gln Asp Met Asn His Glu Tyr
             20                  25                  30

Met Ser Trp Tyr Arg Gln Asp Pro Gly Met Gly Leu Arg Leu Ile His
         35                  40                  45

Tyr Ser Val Gly Ala Gly Ile Thr Asp Gln Gly Glu Val Pro Asn Gly
     50                  55                  60

Tyr Asn Val Ser Arg Ser Thr Thr Glu Asp Phe Pro Leu Arg Leu Leu
 65                  70                  75                  80

Ser Ala Ala Pro Ser Gln Thr Ser Val Tyr Phe Cys Ala Ser Arg Pro
                 85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Cys Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245
```

```
<210> SEQ ID NO 159
<211> LENGTH: 741
<212> TYPE: DNA
<213> ORGANISM: Homo sapiens
```

<400> SEQUENCE: 159

```
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgtgt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtcagca cagacccgca gcccctcaag     540
gagcagcccg ccctcaatga ctccagatac gctctgagca gccgcctgag ggtctcggcc     600
accttctggc aggacccccg caaccacttc cgctgtcaag tccagttcta cgggctctcg     660
gagaatgacg agtggaccca ggatagggcc aaacccgtca cccagatcgt cagcgccgag     720
gcctggggta gagcagacta a                                               741
```

<210> SEQ ID NO 160
<211> LENGTH: 246
<212> TYPE: PRT
<213> ORGANISM: Homo sapiens

<400> SEQUENCE: 160

```
Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Gly Ala Gly Ile Thr Asp Gln Gly Glu Val Pro Asn Gly
    50                  55                  60
Tyr Asn Val Ser Arg Ser Thr Thr Glu Asp Phe Pro Leu Arg Leu Leu
65                  70                  75                  80
Ser Ala Ala Pro Ser Gln Thr Ser Val Tyr Phe Cys Ala Ser Arg Pro
                85                  90                  95
Gly Leu Ala Gly Gly Arg Pro Glu Gln Tyr Phe Gly Pro Gly Thr Arg
            100                 105                 110
Leu Thr Val Thr Glu Asp Leu Lys Asn Val Phe Pro Pro Glu Val Ala
        115                 120                 125
Val Cys Glu Pro Ser Glu Ala Glu Ile Ser His Thr Gln Lys Ala Thr
    130                 135                 140
Leu Val Cys Leu Ala Thr Gly Phe Tyr Pro Asp His Val Glu Leu Ser
145                 150                 155                 160
Trp Trp Val Asn Gly Lys Glu Val His Ser Gly Val Ser Thr Asp Pro
                165                 170                 175
Gln Pro Leu Lys Glu Gln Pro Ala Leu Asn Asp Ser Arg Tyr Ala Leu
            180                 185                 190
Ser Ser Arg Leu Arg Val Ser Ala Thr Phe Trp Gln Asp Pro Arg Asn
        195                 200                 205
His Phe Arg Cys Gln Val Gln Phe Tyr Gly Leu Ser Glu Asn Asp Glu
    210                 215                 220
```

```
Trp Thr Gln Asp Arg Ala Lys Pro Val Thr Gln Ile Val Ser Ala Glu
225                 230                 235                 240

Ala Trp Gly Arg Ala Asp
                245
```

<210> SEQ ID NO 161
<211> LENGTH: 741
<212> TYPE: DNA
<213> ORGANISM: Homo sapiens

<400> SEQUENCE: 161

```
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg gctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt tgtgtcagca cagacccgca gccccctcaag    540 gagcagcccg ccctcaatga ctccagatac gctctgagca gccgcctgag ggtctcggcc     600
accttctggc aggacccccg caaccacttc cgctgtcaag tccagttcta cgggctctcg     660
gagaatgacg agtggaccca ggatagggcc aaacccgtca cccagatcgt cagcgccgag     720
gcctggggta gagcagacta a                                               741
```

<210> SEQ ID NO 162
<211> LENGTH: 246
<212> TYPE: PRT
<213> ORGANISM: Homo sapiens

<400> SEQUENCE: 162

```
Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Cys Val Ser Thr Asp Pro
```

```
                    165                 170                 175
Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
            195                 200                 205

His Phe Arg Cys Gln Val Gln Phe Tyr Gly Leu Ser Glu Asn Asp Glu
            210                 215                 220

Trp Thr Gln Asp Arg Ala Lys Pro Val Thr Gln Ile Val Ser Ala Glu
225                 230                 235                 240

Ala Trp Gly Arg Ala Asp
            245

<210> SEQ ID NO 163
<211> LENGTH: 741
<212> TYPE: DNA
<213> ORGANISM: Homo sapiens

<400> SEQUENCE: 163
atgaacgctg gtgtcactca gacccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg ctacaatgt ctccagatca accacagagg atttcccgct caggctgctg      240
tcggctgctc cctcccagac atctgtgtac ttctgtgcca gcaggccggg actagcggga     300
gggcgaccag agcagtactt cgggccgggc accaggctca cggtcacaga ggaccctgaaa    360 aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtcagca cagacccgca gcctgcaag     540 gagcagcccg ccctcaatga ctccagatac gctctgagca gccgcctgag ggtctcggcc     600
accttctggc aggaccccg caaccacttc cgctgtcaag tccagttcta cgggctctcg     660
gagaatgacg agtggaccca ggatagggcc aaacccgtca cccagatcgt cagcgccgag    720
gcctggggta gagcagacta a                                              741

<210> SEQ ID NO 164
<211> LENGTH: 246
<212> TYPE: PRT
<213> ORGANISM: Homo sapiens

<400> SEQUENCE: 164

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
            35                  40                  45

Tyr Ser Val Gly Ala Gly Ile Thr Asp Gln Gly Glu Val Pro Asn Gly
        50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110
```

Leu Thr Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
        130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Cys Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
            210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 165
<211> LENGTH: 741
<212> TYPE: DNA
<213> ORGANISM: Homo sapiens

<400> SEQUENCE: 165
atgaacgctg gtgtcactca gaccccaaaa ttccaggtcc tgaagacagg acagagcatg     60
acactgcagt gtgcccagga tatgaaccat gaatacatgt cctggtatcg acaagaccca    120 ggcatgggc tgaggctgat tcattactca gttggtgctg gtatcactga ccaaggagaa    180
gtccccaatg ctacaatgt ctccagatca accacagagg atttcccgct caggctgctg    240
tcggctgctc cctcccagac atctgtgtac ttctgtgcca gcaggccggg actagcggga    300
gggcgaccag agcagtactt cgggccgggc accaggctca cggtcacaga ggacctgaaa    360
aacgtgttcc cacccgaggt cgctgtgttt tgtccatcag aagcagagat ctcccacacc    420
caaaaggcca cactggtgtg cctggccaca ggcttctacc ccgaccacgt ggagctgagc    480
tggtgggtga atgggaagga ggtgcacagt ggggtcagca cagacccgca gccctcaag    540 gagcagcccg ccctcaatga ctccagatac gctctgagca gccgcctgag ggtctcggcc    600
accttctggc aggaccccg caaccacttc cgctgtcaag tccagttcta cgggctctcg    660
gagaatgacg agtggaccca ggatagggcc aaacccgtca cccagatcgt cagcgccgag    720
gcctggggta gagcagacta a                                              741

<210> SEQ ID NO 166
<211> LENGTH: 246
<212> TYPE: PRT
<213> ORGANISM: Homo sapiens

<400> SEQUENCE: 166

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

```
Tyr Ser Val Gly Ala Gly Ile Thr Asp Gln Gly Glu Val Pro Asn Gly
 50                  55                  60

Tyr Asn Val Ser Arg Ser Thr Thr Glu Asp Phe Pro Leu Arg Leu Leu
 65                  70                  75                  80

Ser Ala Ala Pro Ser Gln Thr Ser Val Tyr Phe Cys Ala Ser Arg Pro
                 85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Cys Pro Ser Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
210                 215                 220

Trp Thr Gln Asp Arg Ala Lys Pro Val Thr Gln Ile Val Ser Ala Glu
225                 230                 235                 240

Ala Trp Gly Arg Ala Asp
                245
```

<210> SEQ ID NO 167
<211> LENGTH: 783
<212> TYPE: DNA
<213> ORGANISM: Homo sapiens

<400> SEQUENCE: 167

```
atgggtgtca ctcagacccc aaaattccag gtcctgaaga caggacagag catgacactg      60
cagtgtgccc aggatatgaa ccatgaatac atgtcctggt atcgacaaga cccaggcatg     120
gggctgaggc tgattcatta ctcagttggt gctggtatca ctgaccaagg agaagtcccc     180
aatggctaca atgtctccag atcaaccaca gaggatttcc cgctcaggct gctgtcggct     240
gctcccctcc agacatctgt gtacttctgt gccagcagtt acgtcgggaa caccggggag     300
ctgtttttg  gagaaggctc  taggctgacc  gtactggagg  acctgaaaaa  cgtgttccca    360
cccgaggtcg ctgtgtttga gccatcagaa gcagagatct cccacaccca aaaggccaca     420
ctggtgtgcc tggccacagg cttctacccc gaccacgtgg agctgagctg gtgggtgaat     480
gggaaggagg tgcacagtgg ggtctgcaca gacccgcagc ccctcaagga gcagcccgcc     540
ctcaatgact ccagatacgc tctgagcagc cgcctgaggg tctcggccac cttctggcag     600
gacccccgca accacttccg ctgtcaagtc cagttctacg ggctctcgga gaatgacgag     660
tggacccagg atagggccaa accgtcacc  cagatcgtca  gcgccgaggc  ctggggtaga    720
gcagacggat ccggtggtgg tctgaacgat atttttgaag ctcagaaaat cgaatggcat     780
taa                                                                    783
```

<210> SEQ ID NO 168
<211> LENGTH: 260
<212> TYPE: PRT

<213> ORGANISM: Homo sapiens

<400> SEQUENCE: 168

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp Gly Ser Gly Gly Leu Asn Asp Ile Phe Glu Ala Gln Lys
                245                 250                 255

Ile Glu Trp His
            260
```

<210> SEQ ID NO 169
<211> LENGTH: 762
<212> TYPE: DNA
<213> ORGANISM: Homo sapiens

<400> SEQUENCE: 169

```
atgggtgtca ctcagacccc aaaattccag gtcctgaaga caggacagag catgacactg    60
cagtgtgccc aggatatgaa ccatgaatac atgtcctggt atcgacaaga cccaggcatg   120
gggctgaggc tgattcatta ctcagttggt gctggtatca ctgaccaagg agaagtcccc   180
aatggctaca atgtctccag atcaaccaca gaggatttcc cgctcaggct gctgtcggct   240
gctccctccc agacatctgt gtacttctgt gccagcagtt acgtcgggaa caccggggag   300
ctgttttttg gagaaggctc taggctgacc gtactggagg acctgaaaaa cgtgttccca   360
cccgaggtcg ctgtgtttga gccatcagaa gcagagatct cccacaccca aaaggccaca   420
ctggtgtgcc tggccacagg cttctacccc gaccacgtgg agctgagctg gtgggtgaat   480
```

-continued

```
gggaaggagg tgcacagtgg ggtctgcaca gacccgcagc ccctcaagga gcagcccgcc      540
ctcaatgact ccagatacgc tctgagcagc cgcctgaggg tctcggccac cttctggcag      600
gacccccgca accacttccg ctgtcaagtc cagttctacg ggctctcgga gaatgacgag      660
tggacccagg atagggccaa acccgtcacc cagatcgtca cgccgaggc ctggggtaga       720 gcagacggat ccggtggtgg tcatcatcac catcatcact aa                        762
```

<210> SEQ ID NO 170
<211> LENGTH: 253
<212> TYPE: PRT
<213> ORGANISM: Homo sapiens

<400> SEQUENCE: 170

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
         35                  40                  45

Val Gly Ala Gly Ile Thr Asp Gln Gly Glu Val Pro Asn Gly Tyr Asn
     50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp Gly Ser Gly Gly Gly His His His His His His
                245                 250
```

<210> SEQ ID NO 171
<211> LENGTH: 741
<212> TYPE: DNA
<213> ORGANISM: Homo sapiens

<400> SEQUENCE: 171

```
atgaacgctg gtgtcactca gaccccaaaa ttccaggtcc tgaagacagg acagagcatg       60
acactgcagt gtgcccagga tatgaaccat gaatacatgt cctggtatcg acaagaccca      120
ggcatggggc tgaggctgat tcattactca gttggtgctg gtatcactga ccaaggagaa      180
```

| | |
|---|---|
| gtccccaatg gctacaatgt ctccagatca accacagagg atttcccgct caggctgctg | 240 |
| tcggctgctc cctcccagac atctgtgtac ttctgtgcca gcaggccggg actagcggga | 300 |
| gggcgaccag agcagtactt cgggccgggc accaggctca cggtcacaga ggacctgaac | 360 |
| aaggtgttcc cacccgaggt cgctgtgttt gagccatcag aagcagagat ctcccacacc | 420 |
| caaaaggcca cactggtgtg cctggccaca ggcttcttcc ccgaccacgt ggagctgagc | 480 |
| tggtgggtga atgggaagga ggtgcacagt ggggtctgca cagacccgca gcccctcaag | 540 |
| gagcagcccg ccctcaatga ctccagatac tctctgagca gccgcctgag ggtctcggcc | 600 |
| accttctggc aggaccccg caaccacttc cgctgtcaag tccagttcta cgggctctcg | 660 |
| gagaatgacg agtggaccca ggatagggcc aaacccgtca cccagatcgt cagcgccgag | 720 |
| gcctggggta gagcagacta a | 741 |

<210> SEQ ID NO 172
<211> LENGTH: 741
<212> TYPE: DNA
<213> ORGANISM: Homo sapiens

<400> SEQUENCE: 172

| | |
|---|---|
| atgaacgctg gtgtcactca gaccccaaaa ttccaggtcc tgaagacagg acagagcatg | 60 |
| acactgcagt gtgcccagga tatgaaccat gaatacatgt cctggtatcg acaagaccca | 120 |
| ggcatggggc tgaggctgat tcattactca gttggtgctg gtatcactga ccaaggagaa | 180 |
| gtccccaatg gctacaatgt ctccagatca accacagagg atttcccgct caggctgctg | 240 |
| tcggctgctc cctcccagac atctgtgtac ttctgtgcca gcaggccggg actagcggga | 300 |
| gggcgaccag agcagtactt cgggccgggc accaggctca cggtcacaga ggacctgaaa | 360 |
| aacgtgttcc cacccgaggt cgctgtgttt gagccatcag aagcagagat ctcccacacc | 420 |
| caaaaggcca cactggtgtg cctggccaca ggcttctacc ccgaccacgt ggagctgagc | 480 |
| tggtgggtga atgggaagga ggtgcacagt ggggtctgca cagacccgca gcccctcaag | 540 |
| gagcagcccg ccctcaatga ctccagatac tgtctgagca gccgcctgag ggtctcggcc | 600 |
| accttctggc aggaccccg caaccacttc cgctgtcaag tccagttcta cgggctctcg | 660 |
| gagaatgacg agtggaccca ggatagggcc aaacccgtca cccagatcgt cagcgccgag | 720 |
| gcctggggta gagcagacta a | 741 |

<210> SEQ ID NO 173
<211> LENGTH: 741
<212> TYPE: DNA
<213> ORGANISM: Homo sapiens

<400> SEQUENCE: 173

| | |
|---|---|
| atgaacgctg gtgtcactca gaccccaaaa ttccaggtcc tgaagacagg acagagcatg | 60 |
| acactgcagt gtgcccagga tatgaaccat gaatacatgt cctggtatcg acaagaccca | 120 |
| ggcatggggc tgaggctgat tcattactca gttggtgctg gtatcactga ccaaggagaa | 180 |
| gtccccaatg gctacaatgt ctccagatca accacagagg atttcccgct caggctgctg | 240 |
| tcggctgctc cctcccagac atctgtgtac ttctgtgcca gcaggccggg actagcggga | 300 |
| gggcgaccag agcagtactt cgggccgggc accaggctca cggtcacaga ggacctgaaa | 360 |
| aacgtgttcc cacccgaggt cgctgtgttt gagccatcag aagcagagat ctcccacacc | 420 |
| caaaaggcca cactggtgtg cctggccaca ggcttctacc ccgaccacgt ggagctgagc | 480 |

-continued

```
tggtgggtga atgggaagga ggtgcacagt ggggtctgca cagacccgca gcccctcaag      540
gagcagcccg ccctcaatga ctccagatac tctctgagca gccgcctgag ggtctcggcc      600
accttctggc aggaccccg caaccacttc cgctgtcaag tccagttcta cgggctctcg       660
gagaatgacg agtggaccca ggatagggcc aaacccgtca cccagatcgt cagcgccgag     720
gcctggggta gagcagacta a                                                741
```

<210> SEQ ID NO 174
<211> LENGTH: 6671
<212> TYPE: DNA
<213> ORGANISM: Artificial Sequence
<220> FEATURE:
<223> OTHER INFORMATION: Expression vector pYX112

<400> SEQUENCE: 174

```
gaattcacca tggatcctag ggcccacaag cttacgcgtc gacccgggta tccgtatgat      60
gtgcctgact acgcatgata tctcgagctc agctagctaa ctgaataagg aacaatgaac     120 gttttttcctt tctcttgttc ctagtattaa tgactgaccg atacatccct ttttttttt     180 gtctttgtct agctccagct tttgttccct ttagtgaggg ttaattcaat tcactggccg     240
tcgttttaca acgtcgtgac tgggaaaacc ctggcgttac ccaacttaat cgccttgcag     300
cacatccccc tttcgccagc tggcgtaata gcgaagaggc ccgcaccgat cgcccttccc     360
aacagttgcg cagcctgaat ggcgaatggc gcgacgcgcc ctgtagcggc gcattaagcg     420
cggcgggtgt ggtggttacg cgcagcgtga ccgctacact tgccagcgcc ctagcgcccg     480
ctcctttcgc tttcttccct tcctttctcg ccacgttcgc cggctttccc cgtcaagctc     540
taaatcgggg gctcccttta gggttccgat ttagtggttt acggcacctc gaccccaaaa     600
aacttgatta gggtgatggt tcacgtagtg gccatcgcc ctgatagacg ttttttcgcc      660
ctttgacgtt ggagtccacg ttctttaata gtggactctt gttccaaact ggaacaacac     720
tcaaccctat ctcggtctat tcttttgatt tataagggat tttgccgatt tcggcctatt     780
ggttaaaaaa tgagctgatt taacaaaaat ttaacgcgaa ttttaacaaa atattaacgt     840
ttacaatttc ctgatgcggt attttctcct tacgcatctg tgcggtattt cacaccgcat     900
agggtaataa ctgatataat taaattgaag ctctaatttg tgagtttagt atacatgcat     960
ttacttataa tacagttttt tagttttgct ggccgcatct tctcaaatat gcttcccagc    1020 ctgctttttct gtaacgttca ccctgtacct tagcatccct tcccttttgca aatagtcctc   1080 ttccaacaat aataatgtca gatcctgtag agaccacatc atccacggtt ctatactgtt    1140
gacccaatgc gtctcccttg tcatctaaac ccacaccggg tgtcataatc aaccaatcgt    1200
aaccttcatc tcttccaccc atgtctcttt gagcaataaa gccgataaca aaatctttgt    1260
cgctcttcgc aatgtcaaca gtaccttag tatattctcc agtagatagg gagcccttgc     1320
atgacaattc tgctaacatc aaaaggcctc taggttcctt tgttacttct tctgccgcct    1380
gcttcaaacc gctaacaata cctggcccca gcacaccgtg tgcattcgta atgtctgccc    1440
attctgctat tctgtataca cccgcagagt actgcaattt gactgtatta ccaatgtcag    1500
caaattttct gtcttcgaag agtaaaaaat tgtacttggc ggataatgcc tttagcggct    1560
taactgtgcc ctccatcgaa aaatcagtca atatatccac atgtgttttt agtaaacaaa    1620
ttttgggacc taatgcttca actaactcca gtaattcctt ggtggtacga acatccaatg    1680
aagcacacaa gtttgtttgc ttttcgtgca tgatattaaa tagcttggca gcaacaggac    1740
taggatgagt agcagcacgt tccttatatg tagctttcga catgatttat cttcgtttcc    1800
```

```
tgcaggtttt tgttctgtgc agttgggtta agaatactgg gcaatttcat gtttcttcaa    1860
cactacatat gcgtatatat accaatctaa gtctgtgctc cttccttcgt tcttccttct    1920
gttcggagat taccgaatca aaaaaatttc aaagaaaccg aaatcaaaaa aagaataaa     1980
aaaaaaatga tgaattgaat tgaaaagctg tggtatggtg cactctcagt acaatctgct    2040
ctgatgccgc atagttaagc cagccccgac acccgccaac acccgctgac gcgccctgac    2100
gggcttgtct gctcccggca tccgcttaca gacaagctgt gaccgtctcc gggagctgca    2160
tgtgtcagag gttttcaccg tcatcaccga acgcgcgag acgaaagggc ctcgtgatac     2220
gcctatttt ataggttaat gtcatgataa taatggtttc ttaggacgga tcgcttgcct     2280
gtaacttaca cgcgcctcgt atcttttaat gatggaataa tttgggaatt tactctgtgt    2340
ttatttattt ttatgttttg tatttggatt ttagaaagta aataaagaag gtagaagagt    2400
tacggaatga agaaaaaaaa ataaacaaag gtttaaaaaa tttcaacaaa aagcgtactt    2460
tacatatata tttattagac aagaaaagca gattaaatag atatacattc gattaacgat    2520
aagtaaaatg taaaatcaca ggattttcgt gtgtggtctt ctacacagac aagatgaaac    2580
aattcggcat taatacctga gagcaggaag agcaagataa aaggtagtat ttgttggcga    2640
tcccctaga gtcttttaca tcttcggaaa acaaaaacta ttttttcttt aatttctttt     2700
tttactttct attttaatt tatatattta tattaaaaaa tttaaattat aattattttt     2760
atagcacgtg atgaaaagga cccaggtggc acttttcggg gaaatgtgcg cggaacccct    2820
atttgtttat ttttctaaat acattcaaat atgtatccgc tcatgagaca ataaccgtga    2880
taaatgcttc aataatattg aaaaggaag agtatgagta ttcaacattt ccgtgtcgcc    2940
cttattccct tttttgcggc attttgcctt cctgttttg ctcacccaga aacgctggtg     3000
aaagtaaaag atgctgaaga tcagttgggt gcacgagtgg gttacatcga actggatctc    3060
aacagcggta agatccttga gagttttcgc cccgaagaac gttttccaat gatgagcact    3120
tttaaagttc tgctatgtgg cgcggtatta tcccgtattg acgccgggca agagcaactc    3180
gctcgccgca tacactattc tcagaatgac ttggttgagt actcaccagt cacagaaaag    3240
catcttacgg atggcatgac agtaagagaa ttatgcagtg ctgccataac catgagtgat    3300
aacactgcgg ccaacttact tctgacaacg atcggaggac cgaaggagct aaccgctttt    3360
ttggacaaca tgggggatca tgtaactcgc cttgatcgtt gggaaccgga gctgaatgaa    3420
gccataccaa acgacgagcg tgacaccacg atgcctgtag caatggcaac aacgttgcgc    3480
aaactattaa ctggcgaact acttactcta gcttcccggc aacaattaat agactggatg    3540
gaggcggata aagttgcagg accacttctg cgctcggccc ttccggctgg ctggtttatt    3600
gctgataaat ctggagccgg tgagcgtggg tctcgcggta tcattgcagc actggggcca    3660
gatggtaagc cctcccgtat cgtagttatc tacacgacgg ggagtcaggc aactatggat    3720
gaacgaaata gacagatcgc tgagataggt gcctcactga ttaagcattg gtaactgtca    3780
gaccaagttt actcatatat actttagatt gatttaaaac ttcatttta atttaaaagg     3840
atctaggtga agatccttt tgataatctc atgaccaaaa tcccttaacg tgagttttcg    3900
ttccactgag cgtcagaccc cgtagaaaag atcaaaggat cttcttgaga tcctttttt     3960
ctgcgcgtaa tctgctgctt gcaaacaaaa aaaccaccgc taccagcggt ggtttgtttg    4020
ccggatcaag agctaccaac tcttttccg aaggtaactg gcttcagcag agcgcagata    4080
ccaaatactg tccttctagt gtagccgtag ttaggccacc acttcaagaa ctctgtagca    4140
```

```
ccgcctacat acctcgctct gctaatcctg ttaccagtgg ctgctgccag tggcgataag      4200
tcgtgtctta ccgggttgga ctcaagacga tagttaccgg ataaggcgca gcggtcgggc      4260
tgaacggggg gttcgtgcac acagcccagc ttggagcgaa cgacctacac cgaactgaga      4320
tacctacagc gtgagctatg agaaagcgcc acgcttcccg aagggagaaa ggcggacagg      4380
tatccggtaa gcggcagggt cggaacagga gagcgcacga gggagcttcc agggggaaac      4440
gcctggtatc tttatagtcc tgtcgggttt cgccacctct gacttgagcg tcgattttg       4500
tgatgctcgt caggggggcg gagcctatgg aaaaacgcca gcaacgcggc ctttttacgg      4560
ttcctggcct tttgctggcc ttttgctcac atgttctttc ctgcgttatc ccctgattct      4620
gtggataacc gtattaccgc ctttgagtga gctgataccg tcgccgcag ccgaacgacc       4680
gagcgcagcg agtcagtgag cgaggaagcg gaagagcgcc caatacgcaa accgcctctc      4740
cccgcgcgtt ggccgattca ttaatgcagc tggcacgaca ggtttcccga ctggaaagcg      4800
ggcagtgagc gcaacgcaat taatgtgagt tacctcactc attaggcacc ccaggcttta      4860
cactttatgc ttccggctcc tatgttgtgt ggaattgtga gcggataaca atttcacaca      4920
ggaaacagct atgaccatga ttacgccaag ctcgaaatac gactcactat agggcgaatt      4980
gggtaccggg ccggccgtcg agcttgatgg catcgtggtg tcacgctcgt cgtttggtat      5040
ggcttcattc agctccggtt cccaacgatc aaggcgagtt acatgatccc ccatgttgtg      5100
aaaaaaagcg gttagctctt cggtcctccg atcgttgtca gaagtaagtt ggccgcagtg      5160
ttatcactca tggttatggc aggaactgca taattctctt actgtcatgc catccgtaag      5220
atgcttttct gtgactggtg tactcaacca agtcattctg agaatagtgt atgcggcgac      5280
cgagttgctc ttgcccggcg tcaacacggg ataataccgc gccacatagc agaactttaa      5340
aagtgctcat cattggaaaa cgttcttcgg ggcgaaaact ctcaaggatc ttaccgctgt      5400
tgagatccag ttcgatgtaa cccactcgtg cacccaactg atcttcagca tcttttactt      5460
tcaccagcgt ttctgggtga gcaaaaacag gaaggcaaaa tgccgcaaaa aagggaataa      5520
gggcgacacg gaaatgttga atactcatac tcttcctttt tcaatattat tgaagcattt      5580
atcagggtta ttgtctcatg agcgatacat atttgaatgt atttagaaaa ataaacaaat      5640
aggggttccg cgcacatttc cccgaaaagt gccacctgac gtctaagaaa ccattattat      5700
catgacatta acctataaaa ataggcgtat cacgaggccc tttcgtcttc aagaattggg      5760
gatctacgta tggtcattct tcttcagatt ccctcatgga gaagtgcggc agatgtatat      5820
gacagagtcg ccagtttcca agagacttta ttcaggcact tccatgatag gcaagagaga      5880
agacccagag atgttgttgt cctagttaca catggtattt attccagagt attcctgatg      5940
aaatggttta gatggacata cgaagagttt gaatcgttta ccaatgttcc taacgggagc      6000
gtaatggtga tggaactgga cgaatccatc aatagatacg tcctgaggac cgtgctaccc      6060
aaatggactg attgtgaggg agacctaact acatagtgtt taaagattac ggatatttaa      6120
cttacttaga ataatgccat tttttgagt tataataatc ctacgttagt gtgagcggga      6180
tttaaactgt gaggacctca atacattcag acacttctga cggtatcacc ctacttattc      6240
ccttcgagat tatatctagg aacccatcag gttggtggaa gattacccgt tctaagactt      6300
ttcagcttcc tctattgatg ttacactcgg acaccccttt tctggcatcc agttttaat    6360
cttcagtggc atgtgagatt ctccgaaatt aattaaagca atcacacaat tctctcggat      6420
accacctcgt tgaaactga caggtggttt gttacgcatg ctaatgcaaa ggagcctata       6480
tacctttggc tcggctgctg taacagggaa tataaagggc agcataattt aggagtttag      6540
```

```
tgaacttgca acatttacta ttttcccttc ttacgtaaat atttttcttt ttaattctaa    6600
atcaatcttt ttcaattttt tgtttgtatt cttttcttgc ttaaatctat aactacaaaa    6660
aacacataca g                                                          6671

<210> SEQ ID NO 175
<211> LENGTH: 6683
<212> TYPE: DNA
<213> ORGANISM: Artificial Sequence
<220> FEATURE:
<223> OTHER INFORMATION: Expression vector pYX122

<400> SEQUENCE: 175
gtgcctgact acgcatgata tctcgagctc agctagctaa ctgaataagg aacaatgaac      60 gttttttcctt tctcttgttc ctagtattaa tgactgaccg atacatccct ttttttttt    120 gtctttgtct agctccagct tttgttccct ttagtgaggg ttaattcaat tcactggccg    180
tcgttttaca acgtcgtgac tgggaaaacc ctggcgttac ccaacttaat cgccttgcag    240
cacatccccc tttcgccagc tggcgtaata gcgaagaggc ccgcaccgat cgcccttccc    300
aacagttgcg cagcctgaat ggcgaatggc gcgacgcgcc ctgtagcggc gcattaagcg    360
cggcgggtgt ggtggttacg cgcagcgtga ccgctacact tgccagcgcc ctagcgcccg    420
ctcctttcgc tttcttccct tcctttctcg ccacgttcgc cggctttccc cgtcaagctc    480
taaatcgggg gctcccttta gggttccgat ttagtggttt acggcacctc gaccccaaaa    540
aacttgatta gggtgatggt tcacgtagtg gccatcgcc tgatagacg ttttttcgcc     600 ctttgacgtt ggagtccacg ttctttaata gtggactctt gttccaaact ggaacaacac    660
tcaaccctat ctcggtctat tcttttgatt tataagggat tttgccgatt tcggcctatt    720
ggttaaaaaa tgagctgatt taacaaaaat ttaacgcgaa ttttaacaaa atattaacgt    780
ttacaatttc ctgatgcggt attttctcct tacgcatctg tgcggtattt cacaccgcat    840
agatccgtcg agttcaagag aaaaaaaaag aaaagcaaa agaaaaaaag gaaagcgcgc    900
ctcgttcaga atgacacgta tagaatgatg cattaccttg tcatcttcag tatcatactg    960
ttcgtataca tacttactga cattcatagg tatacatata tacacatgta tatatatcgt   1020
atgctgcagc tttaaataat cggtgtcact acataagaac acctttggtg gagggaacat   1080
cgttggttcc attgggcgag gtggcttctc ttatggcaac cgcaagagcc ttgaacgcac   1140
tctcactacg gtgatgatca ttcttgcctc gcagacaatc aacgtggagg gtaattctgc   1200
ttgcctctgc aaaactttca agaaaatgcg ggatcatctc gcaagagaga tctcctactt   1260
tctccctttg caaaccaagt tcgacaactg cgtacggcct gttcgaaaga tctaccaccg   1320
ctctggaaag tgcctcatcc aaaggcgcaa atcctgatcc aaacctttt actccacgcg   1380 ccagtagggc ctctttaaat gcttgaccga gagcaatccc gcagtcttca gtggtgtgat   1440
ggtcgtctat gtgtaagtca ccaatgcact caacgattag cgaccagccg gaatgcttgg   1500
ccagagcatg tatcatatgg tccagaaacc ctatacctgt gtggacgtta atcacttgcg   1560
attgtgtggc ctgttctgct actggttctg cctctttttc tgggaagatc gagtgctcta   1620
tcgctagggg accagccttt aaagagatcg caatctgaat cttggtttca tttgtaatac   1680
gctttactag ggctttctgc tctgtcatct ttgccttcgt ttatcttgcc tgctcatttt   1740
ttagtatatt cttcgaagaa atcacattac tttatataat gtaaattca ttatgtgata   1800 atgccaatcg ctaagaaaaa aaagagtca tccgctaggg gaaaaaaaa aatgaaaatc   1860
```

```
attaccgagg cataaaaaaa tatagagtgt actagaggag gccaagagta atagaaaaag    1920
aaaattgcgg gaaaggactg tgttatgact tccctgacta atgccgtgtt caaacgatac    1980
ctggcagtga ctcctagcgc tcaccaagct cttaaaacgg gaatttatgg tgcactctca    2040
gtacaatctg ctctgatgcc gcatagttaa gccagccccg acacccgcca acacccgctg    2100
acgcgccctg acgggcttgt ctgctcccgg catccgctta cagacaagct gtgaccgtct    2160
ccgggagctg catgtgtcag aggttttcac cgtcatcacc gaaacgcgcg agacgaaagg    2220
gcctcgtgat acgcctattt ttataggtta atgtcatgat aataatggtt tcttaggacg    2280
gatcgcttgc ctgtaactta cacgcgcctc gtatctttta atgatggaat aatttgggaa    2340
tttactctgt gtttatttat ttttatgttt tgtatttgga ttttagaaag taaataaaga    2400
aggtagaaga gttacggaat gaagaaaaaa aaataaacaa aggtttaaaa aatttcaaca    2460
aaaagcgtac tttacatata tatttattag acaagaaaag cagattaaat agatatacat    2520
tcgattaacg ataagtaaaa tgtaaaatca caggattttc gtgtgtggtc ttctacacag    2580
acaagatgaa acaattcggc attaatacct gagagcagga agagcaagat aaaaggtagt    2640
atttgttggc gatcccccta gagtctttta catcttcgga aaacaaaaac tatttttttct   2700 ttaatttctt tttttacttt ctatttttaa tttatatatt tatattaaaa aatttaaatt    2760
ataattattt ttatagcacg tgatgaaaag gacccaggtg gcacttttcg gggaaatgtg    2820
cgcggaaccc ctatttgttt attttttctaa atacattcaa atatgtatcc gctcatgaga    2880
caataaccgt gataaatgct tcaataatat tgaaaaagga agagtatgag tattcaacat    2940
ttccgtgtcg cccttattcc cttttttgcg gcattttgcc ttcctgtttt tgctcaccca    3000
gaaacgctgg tgaaagtaaa agatgctgaa gatcagttgg gtgcacgagt gggttacatc    3060
gaactggatc tcaacagcgg taagatcctt gagagttttc gccccgaaga acgttttcca    3120
atgatgagca ctttttaaagt tctgctatgt ggcgcggtat tatcccgtat tgacgccggg    3180
caagagcaac tcggtcgccg catacactat tctcagaatg acttggttga gtactcacca    3240
gtcacagaaa agcatcttac ggatggcatg acagtaagag aattatgcag tgctgccata    3300
accatgagtg ataacactgc ggccaactta cttctgacaa cgatcggagg accgaaggag    3360
ctaaccgctt ttttggacaa catgggggat catgtaactc gccttgatcg ttgggaaccg    3420
gagctgaatg aagccatacc aaacgacgag cgtgacacca cgatgcctgt agcaatggca    3480
acaacgttgc gcaaactatt aactggcgaa ctacttactc tagcttcccg gcaacaatta    3540
atagactgga tggaggcgga taaagttgca ggaccacttc tgcgctcggc ccttccggct    3600
ggctggttta ttgctgataa atctggagcc ggtgagcgtg ggtctcgcgg tatcattgca    3660
gcactggggc cagatggtaa gccctcccgt atcgtagtta tctacacgac ggggagtcag    3720
gcaactatgg atgaacgaaa tagacagatc gctgagatag gtgcctcact gattaagcat    3780
tggtaactgt cagaccaagt ttactcatat atactttaga ttgatttaaa acttcatttt    3840
taatttaaaa ggatctaggt gaagatcctt tttgataatc tcatgaccaa atcccttaa    3900 cgtgagtttt cgttccactg agcgtcagac cccgtagaaa agatcaaagg atcttcttga    3960
gatccttttt ttctgcgcgt aatctgctgc ttgcaaacaa aaaaaccacc gctaccagcg    4020
gtggtttgtt tgccggatca agagctacca actctttttc cgaaggtaac tggcttcagc    4080
agagcgcaga taccaaatac tgtccttcta gtgtagccgt agttaggcca ccacttcaag    4140
aactctgtag caccgcctac atacctcgct ctgctaatcc tgttaccagt ggctgctgcc    4200
agtggcgata agtcgtgtct taccgggttg gactcaagac gatagttacc ggataaggcg    4260
```

```
cagcggtcgg gctgaacggg gggttcgtgc acacagccca gcttggagcg aacgacctac    4320
accgaactga gatacctaca gcgtgagcta tgagaaagcg ccacgcttcc cgaagggaga    4380
aaggcggaca ggtatccggt aagcggcagg gtcggaacag gagagcgcac gagggagctt    4440
ccagggggaa acgcctggta tctttatagt cctgtcgggt ttcgccacct ctgacttgag    4500
cgtcgatttt tgtgatgctc gtcaggggg cggagcctat ggaaaaacgc cagcaacgcg    4560
gcctttttac ggttcctggc cttttgctgg ccttttgctc acatgttctt cctgcgtta    4620 tcccctgatt ctgtggataa ccgtattacc gcctttgagt gagctgatac cgctcgccgc    4680
agccgaacga ccgagcgcag cgagtcagtg agcgaggaag cggaagagcg cccaatacgc    4740
aaaccgcctc tccccgcgcg ttggccgatt cattaatgca gctggcacga caggtttccc    4800
gactggaaag cgggcagtga gcgcaacgca attaatgtga gttacctcac tcattaggca    4860
ccccaggctt tacactttat gcttccggct cctatgttgt gtggaattgt gagcggataa    4920
caatttcaca caggaaacag ctatgaccat gattacgcca agctcgaaat acgactcact    4980
atagggcgaa ttgggtaccg gccggccgt cgagcttgat ggcatcgtgg tgtcacgctc    5040
gtcgtttggt atggcttcat tcagctccgg ttcccaacga tcaaggcgag ttacatgatc    5100
ccccatgttg tgaaaaaaag cggttagctc ttcggtcctc cgatcgttgt cagaagtaag    5160
ttggccgcag tgttatcact catggttatg gcaggaactg cataattctc ttactgtcat    5220
gccatccgta agatgctttt ctgtgactgg tgtactcaac caagtcattc tgagaatagt    5280
gtatgcggcg accgagttgc tcttgcccgg cgtcaacacg ggataatacc gcgccacata    5340
gcagaacttt aaaagtgctc atcattggaa aacgttcttc ggggcgaaaa ctctcaagga    5400
tcttaccgct gttgagatcc agttcgatgt aacccactcg tgcacccaac tgatcttcag    5460
catcttttac tttcaccagc gtttctgggt gagcaaaaac aggaaggcaa aatgccgcaa    5520
aaaagggaat aagggcgaca cggaaatgtt gaatactcat actcttcctt tttcaatatt    5580
attgaagcat ttatcagggt tattgtctca tgagcgatac atatttgaat gtatttagaa    5640
aaataaacaa ataggggttc cgcgcacatt tccccgaaaa gtgccacctg acgtctaaga    5700
aaccattatt atcatgacat taacctataa aaataggcgt atcacgaggc cctttcgtct    5760
tcaagaattg gggatctacg tatggtcatt cttcttcaga ttccctcatg gagaagtgcg    5820
gcagatgtat atgacagagt cgccagtttc caagagactt tattcaggca cttccatgat    5880
aggcaagaga gaagacccag agatgttgtt gtcctagtta cacatggtat ttattccaga    5940
gtattcctga tgaaatggtt tagatggaca tacgaagagt ttgaatcgtt taccaatgtt    6000
cctaacggga gcgtaatggt gatggaactg gacgaatcca tcaatagata cgtcctgagg    6060
accgtgctac ccaaatggac tgattgtgag ggagacctaa ctacatagtg tttaaagatt    6120
acggatattt aacttactta gaataatgcc atttttttga gttataataa tcctacgtta    6180
gtgtgagcgg gatttaaact gtgaggacct caatacattc agacacttct gacggtatca    6240
ccctacttat tcccttcgag attatatcta ggaacccatc aggttggtgg aagattaccc    6300
gttctaagac ttttcagctt cctctattga tgttacactc ggacacccct ttctggcat    6360 ccagttttta atcttcagtg gcatgtgaga ttctccgaaa ttaattaaag caatcacaca    6420
attctctcgg ataccacctc ggttgaaact gacaggtggt tgttacgca tgctaatgca    6480 aaggagccta tataccttg gctcggctgc tgtaacaggg aatataaagg gcagcataat    6540
ttaggagttt agtgaacttg caacatttac tatttttccct tcttacgtaa atattttct    6600
```

```
ttttaattct aaatcaatct ttttcaattt tttgtttgta ttcttttctt gcttaaatct    6660
ataactacaa aaaacacata cag                                            6683
```

<210> SEQ ID NO 176
<211> LENGTH: 296
<212> TYPE: PRT
<213> ORGANISM: Homo sapiens

<400> SEQUENCE: 176

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Gln Glu Val Thr Gln Ile Pro
                85                  90                  95

Ala Ala Leu Ser Val Pro Glu Gly Glu Asn Leu Val Leu Asn Cys Ser
            100                 105                 110

Phe Thr Asp Ser Ala Ile Tyr Asn Leu Gln Trp Phe Arg Gln Asp Pro
        115                 120                 125

Gly Lys Gly Leu Thr Ser Leu Leu Leu Ile Gln Ser Ser Gln Arg Glu
    130                 135                 140

Gln Thr Ser Gly Arg Leu Asn Ala Ser Leu Asp Lys Ser Ser Gly Arg
145                 150                 155                 160

Ser Thr Leu Tyr Ile Ala Ala Ser Gln Pro Gly Asp Ser Ala Thr Tyr
                165                 170                 175

Leu Cys Ala Val Arg Pro Thr Ser Gly Gly Ser Tyr Ile Pro Thr Phe
            180                 185                 190

Gly Arg Gly Thr Ser Leu Ile Val His Pro Tyr Ile Gln Asn Pro Asp
        195                 200                 205

Pro Ala Val Tyr Gln Leu Arg Asp Ser Lys Ser Ser Asp Lys Ser Val
    210                 215                 220

Cys Leu Phe Thr Asp Phe Asp Ser Gln Thr Asn Val Ser Gln Ser Lys
225                 230                 235                 240

Asp Ser Asp Val Tyr Ile Thr Asp Lys Cys Val Leu Asp Met Arg Ser
                245                 250                 255

Met Asp Phe Lys Ser Asn Ser Ala Val Ala Trp Ser Asn Lys Ser Asp
            260                 265                 270

Phe Ala Cys Ala Asn Ala Phe Asn Asn Ser Ile Ile Pro Glu Asp Thr
        275                 280                 285

Phe Phe Pro Ser Pro Glu Ser Ser
    290                 295
```

<210> SEQ ID NO 177
<211> LENGTH: 903
<212> TYPE: DNA
<213> ORGANISM: Homo sapiens

<400> SEQUENCE: 177

```
gaattcatga gatttccttc aattttact gcagttttat tcgcagcatc ctccgcatta    60
```

-continued

```
gctgctccag tcaacactac aacagaagat gaaacggcac aaattccggc tgaagctgtc    120
atcggttact tagatttaga aggggatttc gatgttgctg ttttgccatt ttccaacagc    180
acaaataacg ggttattgtt tataaatact actattgcca gcattgctgc taaagaagaa    240
ggggtatctt tggataaaag agaggctgaa gcccaggagg tgacacagat tcctgcagct    300
ctgagtgtcc cagaaggaga aaacttggtt ctcaactgca gtttcactga tagcgctatt    360
tacaacctcc agtggtttag gcaggaccct gggaaaggtc tcacatctct gttgcttatt    420
cagtcaagtc agagagagca aacaagtgga agacttaatg cctcgctgga taaatcatca    480
ggacgtagta ctttatacat tgcagcttct cagcctggtg actcagccac ctacctctgt    540
gctgtgaggc ccacatcagg aggaagctac atacctacat ttggaagagg aaccagcctt    600
attgttcatc cgtatatcca gaacccggat cctgccgtgt accagctgag agactctaaa    660
tccagtgaca gtctgtctg cctattcacc gatttgatt ctcaaacaaa tgtgtcacaa    720
agtaaggatt ctgatgtgta tatcacagac aaatgtgtgc tagacatgag gtctatggac    780
ttcaagagca acagtgctgt ggcctggagc aacaaatctg actttgcatg tgcaaacgcc    840
ttcaacaaca gcattattcc agaagacacc ttcttcccca gcccagaaag ttcctaactc    900
gag                                                                 903
```

<210> SEQ ID NO 178
<211> LENGTH: 330
<212> TYPE: PRT
<213> ORGANISM: Homo sapiens
<400> SEQUENCE: 178

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Gly Val Thr Gln Thr Pro Lys
                85                  90                  95

Phe Gln Val Leu Lys Thr Gly Gln Ser Met Thr Leu Gln Cys Ala Gln
            100                 105                 110

Asp Met Asn His Glu Tyr Met Ser Trp Tyr Arg Gln Asp Pro Gly Met
        115                 120                 125

Gly Leu Arg Leu Ile His Tyr Ser Val Gly Ala Gly Ile Thr Asp Gln
    130                 135                 140

Gly Glu Val Pro Asn Gly Tyr Asn Val Ser Arg Ser Thr Thr Glu Asp
145                 150                 155                 160

Phe Pro Leu Arg Leu Leu Ser Ala Ala Pro Ser Gln Thr Ser Val Tyr
                165                 170                 175

Phe Cys Ala Ser Ser Tyr Val Gly Asn Thr Gly Glu Leu Phe Phe Gly
            180                 185                 190

Glu Gly Ser Arg Leu Thr Val Leu Glu Asp Leu Lys Asn Val Phe Pro
        195                 200                 205

Pro Glu Val Ala Val Phe Glu Pro Ser Glu Ala Glu Ile Ser His Thr
    210                 215                 220
```

```
Gln Lys Ala Thr Leu Val Cys Leu Ala Thr Gly Phe Tyr Pro Asp His
225                 230                 235                 240

Val Glu Leu Ser Trp Trp Val Asn Gly Lys Glu Val His Ser Gly Val
            245                 250                 255

Cys Thr Asp Pro Gln Pro Leu Lys Glu Gln Pro Ala Leu Asn Asp Ser
        260                 265                 270

Arg Tyr Ala Leu Ser Ser Arg Leu Arg Val Ser Ala Thr Phe Trp Gln
    275                 280                 285

Asp Pro Arg Asn His Phe Arg Cys Gln Val Gln Phe Tyr Gly Leu Ser
        290                 295                 300

Glu Asn Asp Glu Trp Thr Gln Asp Arg Ala Lys Pro Val Thr Gln Ile
305                 310                 315                 320

Val Ser Ala Glu Ala Trp Gly Arg Ala Asp
                325                 330

<210> SEQ ID NO 179
<211> LENGTH: 1005
<212> TYPE: DNA
<213> ORGANISM: Homo sapiens

<400> SEQUENCE: 179
gaattcatga gatttccttc aattttttact gcagttttat tcgcagcatc ctccgcatta        60
gctgctccag tcaacactac aacagaagat gaaacggcac aaattccggc tgaagctgtc       120
atcggttact tagatttaga agggatttc gatgttgctg ttttgccatt ttccaacagc       180
acaaataacg ggttattgtt tataaatact actattgcca gcattgctgc taaagaagaa       240
ggggtatctt tggataaaag agaggctgaa gccggcgtca ctcagacccc aaaattccag       300
gtcctgaaga caggacagag catgacactg cagtgtgccc aggatatgaa ccatgaatac       360
atgtcctggt atcgacaaga cccaggcatg gggctgaggc tgattcatta ctcagttggt       420
gctggtatca ctgaccaagg agaagtcccc aatggctaca atgtctccag atcaaccaca       480
gaggatttcc cgctcaggct gctgtcggct gctccctccc agacatctgt gtacttctgt       540
gccagcagtt acgtcgggaa caccggggag ctgttttttg gagaaggctc taggctgacc       600
gtactggagg acctgaaaaa cgtgttccca cccgaggtcg ctgtgtttga gccatcagaa       660
gcagagatct cccacacccca aaaggccaca ctggtgtgcc tggccacagg cttctacccc       720
gaccacgtgg agctgagctg gtgggtgaat gggaaggagg tgcacagtgg ggtctgcaca       780
gacccgcagc ccctcaagga gcagcccgcc ctcaatgact ccagatacgc tctgagcagc       840
cgcctgaggg tctcggccac cttctggcag gaccccgca accacttccg ctgtcaagtc       900
cagttctacg gctctcgga gaatgacgag tggacccagg ataggccaa acccgtcacc       960 cagatcgtca gcgccgaggc ctggggtaga gcagactaac tcgag                     1005

<210> SEQ ID NO 180
<211> LENGTH: 317
<212> TYPE: DNA
<213> ORGANISM: Artificial Sequence
<220> FEATURE:
<223> OTHER INFORMATION: pEX172 Plasmid

<400> SEQUENCE: 180
ggatccagca tggtgtgtct gaagctccct ggaggctcct gcatgacagc gctgacagtg        60
acactgatgg tgctgagctc cccactggct ttgtccggag acaccggtgg cggatctcta       120
gttccacgcg gtagtggagg cggtggttcc ggagacacgc gttagtaggt cgacggaggc       180
```

```
ggtgggggta gaatcgcccg gctggaggaa aaagtgaaaa ccttgaaagc tcagaactcg    240
gagctggcgt ccacggccaa catgctcagg gaacaggtgg cacagcttaa acagaaagtc    300
atgaactact aggatcc                                                   317

<210> SEQ ID NO 181
<211> LENGTH: 884
<212> TYPE: DNA
<213> ORGANISM: Homo sapiens

<400> SEQUENCE: 181
ggatccagca tggtgtgtct gaagctccct ggaggctcct gcatgacagc gctgacagtg     60
acactgatgg tgctgagctc cccactggct ttgtccggag acaccggaga caccggacag    120
aaggaagtgg agcagaactc tggaccctc agtgttccag agggagccat tgcctctctc    180
aactgcactt acagtgaccg aggttcccag tccttcttct ggtacagaca atattctggg    240
aaaagccctg agttgataat gtccatatac tccaatggtg acaaagaaga tggaaggttt    300
acagcacagc tcaataaagc cagccagtat gtttctctgc tcatcagaga ctcccagccc    360
agtgattcag ccacctacct ctgtgccgtt acaactgaca gctgggggaa attgcagttt    420
ggagcaggga cccaggttgt ggtcaccca gatatccaga accctgaccc tgccgtgtac    480
cagctgagag actctaaatc cagtgacaag tctgtctgcc tattcaccga ttttgattct    540
caaacaaatg tgtcacaag taaggattct gatgtgtata tcacagacaa atgtgtgcta    600
gacatgaggt ctatgggactt caagagcaac agtgctgtgg cctggagcaa caaatctgac    660
tttgcatgtg caaacgcctt caacaacagc attattccag aagacacctt cttcccagc    720 ccagaaagtt cctaagtcga cggaggcggt ggggtagaa tcgcccggct ggaggaaaaa    780
gtgaaaacct tgaaagctca gaactcggag ctggcgtcca cggccaacat gctcagggaa    840
caggtggcac agcttaaaca gaaagtcatg aactactagg atcc                    884

<210> SEQ ID NO 182
<211> LENGTH: 1004
<212> TYPE: DNA
<213> ORGANISM: Homo sapiens

<400> SEQUENCE: 182
ggatccagca tggtgtgtct gaagctccct ggaggctcct gcatgacagc gctgacagtg     60
acactgatgg tgctgagctc cccactggct ttgtccggag acaccggaga caccggaaac    120
gctggtgtca ctcagacccc aaaattccag gtcctgaaga caggacagag catgacactg    180
cagtgtgccc aggatatgaa ccataataca tgtcctggt atcgacaaga cccaggcatg    240
gggctgaggc tgattcatta ctcagttggt gctggtatca ctgaccaagg agaagtcccc    300
aatggctaca atgtctccag atcaaccaca gaggatttcc cgctcaggct gctgtcggct    360
gctccctccc agacatctgt gtacttctgt gccagcaggc cgggactagc ggggagggcga    420 ccagagcagt acttcgggcc gggcaccagg ctcacggtca cagaggacct gaaaaacgtg    480
ttcccacccg aggtcgctgt gtttgagcca tcagaagcag agatctccca cacccaaaag    540
gccacactgg tgtgcctggc cacaggcttc taccccgacc acgtggagct gagctggtgg    600
gtgaatggga aggaggtgca cagtggggtc tgcacagacc cgcagcccct caaggagcag    660
cccgccctca tgactccag atacgctctg agcagccgcc tgagggtctc ggccaccttc    720
tggcaggacc ccgcaaacca cttccgctgt caagtccagt tctacgggct ctcggagaat    780
```

```
gacgagtgga cccaggatag ggccaaaccc gtcacccaga tcgtcagcgc cgaggcctgg    840
ggtagagcag actaagtcga cggaggcggt gggggtagaa tcgcccggct ggaggaaaaa    900
gtgaaaacct tgaaagctca gaactcggag ctggcgtcca cggccaacat gctcagggaa    960
caggtggcac agcttaaaca gaaagtcatg aactactagg atcc                   1004
```

<210> SEQ ID NO 183
<211> LENGTH: 206
<212> TYPE: PRT
<213> ORGANISM: Homo sapiens

<400> SEQUENCE: 183

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205
```